United States Patent
Brown et al.

(10) Patent No.: US 9,018,384 B2
(45) Date of Patent: *Apr. 28, 2015

(54) N-LINK HYDROXAMIC ACID DERIVATIVES USEFUL AS ANTIBACTERIAL AGENTS

(71) Applicant: Pfizer Inc., New York, NY (US)

(72) Inventors: Matthew Frank Brown, Stonington, CT (US); Ye Che, Groton, CT (US); Anthony Marfat, Mystic, CT (US); Michael Joesph Melnick, Portage, MI (US); Justin Ian Montgomery, Ledyard, CT (US); Usa Reilly, West Haven, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,788

(22) Filed: Jul. 31, 2014

(65) Prior Publication Data

US 2014/0343031 A1 Nov. 20, 2014

Related U.S. Application Data

(63) Continuation of application No. 14/154,239, filed on Jan. 14, 2014, now Pat. No. 8,846,933, which is a continuation of application No. 12/515,607, filed as application No. PCT/IB2010/055596 on Dec. 6, 2010, now Pat. No. 8,664,401.

(60) Provisional application No. 61/287,035, filed on Dec. 16, 2009.

(51) Int. Cl.
| | | |
|---|---|---|
| *A61K 31/44* | (2006.01) |
| *C07D 401/00* | (2006.01) |
| *C07D 213/64* | (2006.01) |
| *C07D 401/04* | (2006.01) |
| *C07D 401/08* | (2006.01) |
| *C07D 401/10* | (2006.01) |
| *C07D 401/12* | (2006.01) |
| *C07D 405/04* | (2006.01) |
| *C07D 405/10* | (2006.01) |
| *C07D 409/04* | (2006.01) |
| *C07D 413/10* | (2006.01) |
| *C07D 413/12* | (2006.01) |
| *C07D 417/04* | (2006.01) |
| *C07D 417/10* | (2006.01) |
| *C07D 417/12* | (2006.01) |
| *C07D 211/86* | (2006.01) |
| *C07D 403/04* | (2006.01) |
| *C07D 401/14* | (2006.01) |

(52) U.S. Cl.
CPC ............ *C07D 213/64* (2013.01); *C07D 401/04* (2013.01); *C07D 401/08* (2013.01); *C07D 401/10* (2013.01); *C07D 401/12* (2013.01); *C07D 405/04* (2013.01); *C07D 405/10* (2013.01); *C07D 409/04* (2013.01); *C07D 413/10* (2013.01); *C07D 413/12* (2013.01); *C07D 417/04* (2013.01); *C07D 417/10* (2013.01); *C07D 417/12* (2013.01); *C07D 211/86* (2013.01); *C07D 403/04* (2013.01); *C07D 401/14* (2013.01)

(58) Field of Classification Search
None
See application file for complete search history.

(56) References Cited

U.S. PATENT DOCUMENTS

| | | | |
|---|---|---|---|
| 4,769,461 A | 9/1988 | Musser et al. |
| 5,110,831 A | 5/1992 | Magolda et al. |
| 6,673,965 B1 | 1/2004 | Ward et al. |
| 8,664,401 B2 * | 3/2014 | Brown et al. ............ 546/268.1 |
| 2002/0119962 A1 | 8/2002 | Jacobs et al. |
| 2005/0119305 A1 | 6/2005 | Naka et al. |
| 2005/0171148 A1 | 8/2005 | Mjalli et al. |
| 2006/0247271 A1 | 11/2006 | Bruton |
| 2006/0276409 A1 | 12/2006 | Hunter et al. |
| 2008/0085893 A1 | 4/2008 | Yang et al. |
| 2008/0234297 A1 | 9/2008 | Qian et al. |
| 2011/0178042 A1 | 7/2011 | Brown et al. |
| 2012/0232083 A1 | 9/2012 | Reilly et al. |
| 2012/0258948 A1 | 10/2012 | Brown et al. |

FOREIGN PATENT DOCUMENTS

| | | |
|---|---|---|
| CN | 101016270 | 8/2007 |
| EP | 1437349 | 7/2004 |
| WO | 0130747 | 5/2001 |
| WO | 2004062601 | 7/2004 |
| WO | 2004067502 | 8/2004 |
| WO | 2006063281 | 6/2006 |
| WO | 2006118155 | 11/2006 |
| WO | 2006124897 | 11/2006 |
| WO | 2007069020 | 6/2007 |
| WO | 2007093904 | 8/2007 |
| WO | 2008045671 | 4/2008 |
| WO | 2008105515 | 9/2008 |
| WO | 2008115262 | 9/2008 |
| WO | 2009008905 | 1/2009 |
| WO | 2010017060 | 2/2010 |

(Continued)

OTHER PUBLICATIONS

Machine Translation of WO 2010/024356 published Mar. 4, 2010.

(Continued)

*Primary Examiner* — Heidi Reese
(74) *Attorney, Agent, or Firm* — John A. Wichtowski

(57) ABSTRACT

The present invention is directed to a new class of hydroxamic acid derivatives, their use as LpxC inhibitors, and more specifically their use to treat bacterial infections.

14 Claims, No Drawings

(56) References Cited

FOREIGN PATENT DOCUMENTS

| WO | 2010024356 | 3/2010 |
|---|---|---|
| WO | 2010031750 | 3/2010 |
| WO | 2010032147 | 3/2010 |
| WO | 2010100475 | 9/2010 |
| WO | 2011073845 | 6/2011 |
| WO | 2012120397 | 9/2012 |
| WO | 2012137094 | 10/2012 |
| WO | 2012137099 | 10/2012 |

OTHER PUBLICATIONS

Barlaam, B., et al., "New Alpha-Substituted Succinate-Based Hydroxamic Acids As TNFALPHA Convertase Inhibitors", Journal of Medicinal Chemistry, Jan. 1, 1999, pp. 4890-4908, 42(23).

Dube, Peter H., et al., "Protective Role of Interleukin-6 During *Yersinia enterocolitica* Infection Is Mediated through the Modulation of Inflammatory Cytokines", Infection and Immunity, Jun. 2004, pp. 3561-3570, 72(6).

Hennigan, Stephanie, et al., "Interleukin-6 Inhibitors in the Treatment of Rheumatoid Arthritis", Therapeutics and Clinical Risk Management, 2008, pp. 767-775, 4(4).

Imanishi, Jiro, "Expression of Cytokines in Bacterial and Viral Infections and Their Biochemical Aspects", The Japanese Biochemical Society, 2000, pp. 525-530, 127(4).

International Patent Application No. PCT/IB2009/053809, PCT International Search Report (ISR), mailed Apr. 4, 2010, 7 pages.

International Patent Application No. PCT/IB2009/053809, PCT International Written Opinion, mailed Apr. 4, 2010, 7 pages.

International Patent Application No. PCT/IB2012/050812 PCT International Search Report (ISR) and Written Opinion mailed Apr. 23, 2012, 4 pages.

Product Label—Actemra* (toclizumab) Injection, for intravenous infusion; revised Apr. 2013, pp. 1-35.

Apfel, Christian et al., "Hydroxamic Acid Derivatives as Potent Peptide Deformylase Inhibitors and Antibacterial Agents", Journal of Medicinal Medicinal Chemistry, Jun. 15, 2000, pp. 2324-2331, 43(12).

Brown, Matthew F., et al., "Potent Inhibitors of LpxC for the Treatment of Gram-Negative Infections", Journal of Medicinal Chemistry, Dec. 18, 2011, pp. 914-923, 55(18).

International Patent Application No. PCT/IB2012/051406 PCT International Search Report ISR and Written Opinion mailed Oct. 7, 2012, 5 pages.

International Patent Application No. PCT/IB2010/055596, publication No. WO 2011/073845, Search Report and Written Opinion mailed Mar. 23, 2011, 15 pages.

English Translation of International Patent Application WO 2008/105515 publication date Sep. 4, 2008.

Clements, J.M., et al., "Antimicrobial Activities and Characterization of Novel Inhibitors of LpxC", Antimicrobial Agents and Chemotherapy, American Society for Microbiology, Jun. 1, 2002, pp. 1793-1799, 46(6).

Antinfective Therapy, Antiboitics and Antibacterial Drugs, "455710" (Vicuron Pharmaceuticals), Drug Data Report, Jul./Aug. 2007, p. 629, 29(7).

IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook. Last update: Feb. 4, 2014; version: 2.3.3.

Rice, Louis B., "Unmet Medical Needs in Antibacterial Therapy", Biochemical Pharmacology, Mar. 30, 2006, pp. 991-995, 71(7).

Raetz, Christian, H., et al., "Lipid A Modification Systems in Gram-Negative Bacteria", Annual Review Biochemistry, 2007, pp. 295-329, vol. 76.

Gennadios, H.A., et al., "Mechanistic Inferences from the Binding of Ligands to LpxC, a Metal-Dependent Deacetylase", Biochemistry, 2006, pp. 7940-7948, 45(26).

Conreaux, D., et l., "A practical procedure for the selective N-alkylation of 4-alkoxy-2-pyridones and its use in a sulfone-mediated synthesis of N-methyl-4-methoxy-2-pyridone", Tetrahedron Letters, 2005, pp. 7917-7920, 46(46).

Gipstein, E., et al., "Synthesis and Polymerization of Alkyl.α-(Alkylsulfonyl)acrylates1a", Journal of Organic Chemistry, 1980, pp. 1486-1489, 45(8).

Kwok, A., et al., "*Helicobacter pylori* Eradication Therapy: Indications, efficacy and Safety", Expert Opinion Drug Safety, May 2008, pp. 271-281, 7(3).

Qu, W., et al., "Quick Assembly of 1,4-Diphenyltriazoles as Probes Targeting β-Amyloid Aggregates in Alzheimer's Disease", Journal of Medicinal Chemistry, 2007, pp. 3380-3387, 50(14).

Kirsch, P., et al., "Super-Fluorinated Liquid Crystals: Towards the Limits of Polarity", European Journal Organic Chemistry, Jul. 2008, pp. 3479-3487, 2008(20).

Wang, Y., et al., "A novel and efficient synthesis of terminal arylacetylenes via Sonogashira coupling reactions catalysed by MCM-41-supported bidentate phosphine palladium (0) complex", Journal of Chemical Research, Dec. 2007, pp. 728-732, 2007(12).

Chinese Application No. 201280016114.4 Office Action and search report dated Aug. 26, 2014, 17 pages.

Guangjian Du et al., "Synthesis and Antibacterial Activity of 3-(morpholinopyridyl)-5-substituted Isoxazole Derivatives", Chinese Journal of Organic Chemistry, Dec. 31, 2009, pp. 1575-1581, 29(10).

Du, Guangjian et al., "Synthesis and Antibacterial Activity of 3-(morpholinopyridyl)-5-substituted Isoxazole Derivatives", Chinese Journal of Organic Chemistry, Dec. 31, 2009, pp. 1575-1581, 29(10).

Singapore Patent Application No. 2013061643, Search Report dated Feb. 17, 2015, 22 pages.

* cited by examiner

N-LINK HYDROXAMIC ACID DERIVATIVES USEFUL AS ANTIBACTERIAL AGENTS

This application is a continuation application under 35 U.S.C. §120 of U.S. patent application Ser. No. 14/154,239 filed Jan. 14, 2014 which is a continuation application under 35 U.S.C. §120 of U.S. patent application Ser. No. 13/515,607, filed on Jun. 13, 2012, which claims priority to PCT/IB2010/055596 filed Dec. 6, 2010, which claims priority to U.S. Provisional Patent Application No. 61/287,035 filed Dec. 16, 2009, the disclosures of which are hereby incorporated by reference in its entirety.

FIELD OF THE INVENTION

This invention relates to novel hydroxamic acid derivatives that are useful for the treatment of bacterial infections, especially Gram-negative infections. The invention also relates to methods of using such compounds in the treatment of bacterial infections in mammals, and to pharmaceutical compositions containing such compounds.

BACKGROUND OF THE INVENTION

Infection by Gram-negative bacteria such as *Pseudomonas aeruginosa*, Extended Spectrum β-lactamase producing (ESBL) Enterobacteriaceae, and *Acinetobacter baumannii* is a major health problem, especially in the case of hospital-acquired infections. In addition, there is an increasing level of resistance to current antibiotic therapies, which severely limits treatment options. For example, in 2002, 33% of *Pseudomonas aeruginosa* infections from intensive care units were resistant to fluoroquinolones, while resistance to imipenem was 22% (CID 42: 657-68, 2006). In addition, multi-drug resistant (MDR) infections are also increasing; in the case of *Pseudomonas aeruginosa*, MDR increased from 4% in 1992 to 14% in 2002 (Biochem Pharm 71: 991, 2006).

Gram-negative bacteria are unique in that their outer membrane contains lipopolysaccharide (LPS), which is crucial for maintaining membrane integrity, and is essential for bacterial viability (reviewed in Ann. Rev. Biochem 76: 295-329, 2007). The major lipid component of LPS is Lipid A, and inhibition of Lipid A biosynthesis is lethal to bacteria. Lipid A is synthesized on the cytoplasmic surface of the bacterial inner membrane via a pathway that consists of nine different enzymes. These enzymes are highly conserved in most gram-negative bacteria. LpxC is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$-dependent enzyme that has no mammalian homologue, making it a good target for the development of novel antibiotics. Several inhibitors of LpxC [UDP-3-O—(R-3-hydroxymyristoyl)-GlcNAc deacetylase] with low nM affinity have been reported (Biochemistry 45: 7940-48, 2006).

SUMMARY OF THE INVENTION

A new class of LpxC inhibitors has been discovered. These compounds, or their pharmaceutical salts, can be represented by Formula I below:

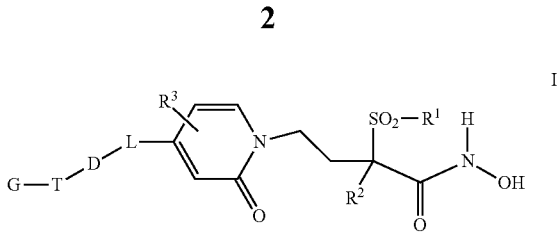

in which:
$R^1$ is represented by $C_1$-$C_3$ alkyl;
$R^2$ is represented by hydrogen or $C_1$-$C_3$ alkyl;
$R^3$ is represented by hydrogen, halogen, $C_1$-$C_3$alkyl, $C_1$-$C_3$alkoxy, trifluoromethyl, or trifluoromethoxy;
L is absent, or is represented by a moiety selected from the group consisting of $C_1$-$C_6$ alkylene which may be optionally substituted, $C_2$-$C_6$ alkenylene, $C_2$-$C_6$ alkynylene,
—$(CH_2)_p$—O—$(CH_2)_n$,
—$(CH_2)_p$—O—$(CH_2)_z$—O—$(CH_2)_n$—;
n is represented by an integer ranging from 0 to 4;
p is represented by an integer ranging from 0 to 4;
q is represented by an integer ranging from 0 to 6;
z is represented by an integer ranging from 1 to 4;
D is represented by a substituent selected from the group consisting of:
  i) ($C_3$-$C_{10}$)cycloalkyl, optionally substituted,
  ii) ($C_6$-$C_{10}$)aryl, optionally substituted,
  iii) heteroaryl, optionally substituted,
  iv) heterocyclic, optionally substituted,
T is absent, or is represented by —S—$(CH_2)_z$—O—$(CH_2)_n$, —O—$(CH_2)_z$—S—$(CH_2)_n$, —$(CH_2)_q$—, —$(CH_2)_n$—C(O)—$(CH_2)_p$—, —$(CH_2)_n$—O—$(CH_2)_q$—, —$(CH_2)_n$—S—$(CH_2)_p$, —O—$(CH_2)_p$—C(O)—$(CH_2)_n$—, —$(CH_2)_p$—C(O)—$(CH_2)_q$—O—$(CH_2)_n$—, —O—$(CH_2)_z$—O—$(CH_2)_n$—, —O—$C_1$-$C_6$ alkylene optionally substituted, —S—$C_1$-$C_6$ alkylene optionally substituted, —O—$(CH_2)_z$—O—$(CH_2)_z$—O—$(CH_2)_n$—, —S—$(CH_2)_z$—S—$(CH_2)_n$—,
—$(CH_2)_n$—SH, or —$(CH_2)_n$—OH, and;
G is absent, or is represented by a substituent selected from the group consisting of:
  i) ($C_3$-$C_{10}$)cycloalkyl, optionally substituted;
  ii) ($C_6$-$C_{10}$)aryl optionally substituted;
  iii) heteroaryl, optionally substituted, and;
  iv) heterocyclic, optionally substituted.

The compounds of Formula I exhibit antibacterial activity, especially against Gram-negative organisms. They may be used to treat bacterial infections in mammals, especially humans. The compounds may also be used for veterinary applications, such as treating infections in livestock and companion animals.

The compounds of Formula I are useful for treating a variety of infections; especially Gram-negative infections including nosocomial pneumonia, urinary tract infections, systemic infections (bacteremia and sepsis), skin and soft tissue infections, surgical infections, intraabdominal infections, lung infections (including those in patients with cystic fibrosis), *Helicobacter pylori* (and relief of associated gastric complications such as peptic ulcer disease, gastric carcinogenesis, etc.), endocarditis, diabetic foot infections, osteomyelitis, and central nervous system infections.

In order to simplify administration, the compounds will typically be admixed with at least one excipient and formulated into a pharmaceutical dosage form. Examples of such dosage forms include tablets, capsules, solutions/suspensions for injection, aerosols for inhalation and solutions/suspensions for oral ingestion.

DETAILED DESCRIPTION OF THE INVENTION

The headings within this document are only being utilized to expedite its review by the reader. They should not be construed as limiting the invention or claims in any manner.

DEFINITIONS AND EXEMPLIFICATION

As used throughout this application, including the claims, the following terms have the meanings defined below, unless specifically indicated otherwise. The plural and singular should be treated as interchangeable, other than the indication of number:

a. "$C_1$-$C_3$ alkyl" refers to a branched or straight chained alkyl group containing from 1 to 3 carbon atoms, such as methyl, ethyl, n-propyl, or isopropyl, etc.

b. "$C_1$-$C_3$ alkoxy" refers to a straight or branched chain alkoxy group containing from 1 to 3 carbon atoms, such as methoxy, ethoxy, n-propoxy, isopropoxy, etc.

c. "halogen" refers to a chlorine, fluorine, iodine, or bromine atom.

d. "$C_1$-$C_6$ alkylene" refers to a branched or straight chained alkyl group containing from 1 to 6 carbon atoms, having single bonds for attachment to other groups at two different carbon atoms. Examples of such alkylene groups include methylene, ethylene, n-propylene, isopropylene, n-butylene, isobutylene, pentylene, etc. This alkylene moiety may be optionally substituted in which up to 6 hydrogen atoms are replaced by a substituent selected from the group consisting of halogen, cyano, sulfonamide, imino, iminohydroxy, iminoalkoxy, iminoalkyl, —O—$R^a$, —$SR^a$, and —$NR^aR^b$ in which $R^a$ and $R^b$ are each independently represented by hydrogen or $C_1$-$C_6$ alkyl which may be optionally substituted.

e. "$C_2$-$C_6$ alkenylene" refers to a branched or straight chained alkene group containing from 2 to 6 carbon atoms and having single bonds for attachment to other groups at two different carbon atoms. Examples of such groups include —$CH_2$—CH=CH—$CH_2$—, —$CH_2$—CH=CH—CH=CH—, etc.

f. "$C_2$-$C_6$ alkynylene" refers to a branched or straight chained alkyne group containing from 2 to 6 carbon atoms and having single bonds for attachment to other groups at two different carbon atoms. Examples of such groups include —$CH_2$—C≡C—$CH_2$—, —$CH_2$—CH=CH—CH=CH—, etc.

g. "$C_1$-$C_6$ alkyl" refers to a branched or straight chained alkyl group containing from 1 to 6 carbon atoms, such as methyl, ethyl, n-propyl, isopropyl, n-butyl, isobutyl, pentyl, etc.

h. "$C_1$-$C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are replaced by a substituent selected from the group consisting of halogen, cyano, sulfonamide, imino, iminoalkoxy, iminohydroxy, iminoalkyl, —O—$R^a$, —$SR^a$, and —$NR^aR^b$ in which $R^a$ and $R^b$ are each independently represented by hydrogen or $C_1$-$C_6$lkyl which may be optionally substituted as described above.

i. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc; which may be unsubstituted or optionally further substituted with halogen, hydroxy, thiol or amino(—$NH_2$).

j. "($C_3$-$C_{10}$) cycloalkyl" refers to a saturated or partially saturated monocyclic, bicyclic, bridged bicyclic or tricyclic alkyl radical wherein each cyclic moiety has 3 to 10 carbon atoms. Examples of such cycloalkyl radicals include cyclopropyl, cyclobutyl, cyclopentyl, cyclohexyl, cyclooctyl, and the like.

k. "($C_3$-$C_{10}$) cycloalkyl" optionally substituted refers to a ($C_3$-$C_{10}$) cycloalkyl moiety as described above. Such a cycloalkyl group may be optionally substituted, in which up to 4 hydrogen atoms are replaced by a substituent selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, oxo, —$SO_2NR^4R^5$, —$(CH_2)_m$—$NR^5$—C(O)—$R^4$, —$(CH_2)_m$—C(O)—N—$R^4R^5$, —C(O)—$R^4$, —C(O)—O—$R^4$, —$SR^4$, —$SO_2R^4$ and —$NR^4R^5$, in which $R^4$ and $R^5$ are each independently represented by hydrogen or $C_1$-$C_6$ alkyl, which may be optionally substituted as defined above, and m is 0-4. These substituents may be the same or different and may be located at any position of the ring, that is chemically permissible.

l. "($C_6$-$C_{10}$)aryl" means a cyclic, aromatic hydrocarbon containing from 6 to 10 carbon atoms. Examples of such aryl groups include phenyl, naphthyl, etc.

m. "($C_6$-$C_{10}$)aryl optionally substituted" means a cyclic, aromatic hydrocarbon as defined above. Such an aryl moiety may be optionally substituted with up to 4 non-hydrogen substituents, each substituent is independently selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, —$SO_2NR^4R^5$, —$(CH_2)_m$—$NR^5$—C(O)—$R^4$, —$(CH_2)_m$—C(O)—N—$R^4R^5$, —C(O)—$R^4$, —C(O)—O—$R^4$, —$SR^4$, —$SO_2R^4$ and —$NR^4R^5$, in which m, $R^4$ and $R^5$ are as defined above. These substituents may be the same or different and may be located at any position of the ring, that is chemically permissible. "Phenyl optionally substituted" refers to a phenyl ring substituted as described above.

n. "heteroaryl" refers to an aromatic ring having one, or more, heteroatoms selected from oxygen, nitrogen and sulfur. More specifically, it refers to a 5- or 6-membered ring containing 1, 2, 3, or 4 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds. The term heteroaryl also includes bicyclic groups in which the heteroaryl ring is fused to a benzene ring, heterocyclic ring, a cycloalkyl ring, or another heteroaryl ring. Examples of such heteroaryl ring systems include, but are not limited to, pyrrolyl, furanyl, thienyl, imidazolyl, oxazolyl, indolyl, thiazolyl, pyrazolyl, pyridinyl, pyrimidinyl, purinyl, quinolinyl, benzofuran, tetrazole, isoquinolinyl, oxadiazolyl, thiadiazolyl, isothiazolyl, isoxazolyl, triazolyl, benzo[b]thienyl, 2-, 4-, 5-, 6-, or 7-benzoxazolyl, 7-benzimidazolyl, or benzothiazolyl.

o. "heteroaryl, optionally substituted," refers to a heteroaryl moiety as defined immediately above, in which up to 4 carbon atoms of the heteroaryl moiety may be substituted with a substituent, each substituent is independently selected from the group consisting of halogen, cyano, nitro, hydroxy, $(C_1-C_6)$alkyl optionally substituted, $(C_1-C_6)$alkoxy optionally substituted, trifluoromethyl, trifluoromethoxy, phosphate, $SO_2NR^4R^5$, $-(CH_2)_m-N-C(O)-R^4$, $-(CH_2)_m-C(O)-N-R^4R^5$, $-C(O)-R^4$, $-C(O)-O-R^4$, $-SR^4$, $-SO_2R^4$ and $-NR^4R^5$, in which m, $R^4$ and $R^5$ are as defined above. These substituents may be the same or different and may be located at any position of the ring, that is chemically permissible.

p. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolidinyl, tetrahydrofuranyl, tetrahydrothiophenyl, piperidinyl, piperazinyl, azepane, azocane, morpholinyl, isochromyl, quinolinyl, tetrahydrotriazine, tetrahydropyrazole, dihydro-oxathiol-4-yl, dihydro-1H-isoindole, tetrahydro-oxazolyl, tetrahydro-oxazinyl, thiomorpholinyl, tetrahydropyrimidinyl, dioxolinyl, octahydrobenzofuranyl, octahydrobenzimidazolyl, and octahydrobenzothiazolyl.

q. "heterocyclic, optionally substituted" refers to a heterocyclic moiety as defined immediately above, in which up to 4 carbon atoms of the heterocycle moiety may be substituted with a substituent, each substituent is independently selected from the group consisting of halogen, cyano, nitro, hydroxy, $(C_1-C_6)$alkyl optionally substituted, $(C_1-C_6)$alkoxy optionally substituted, trifluoromethyl, trifluoromethoxy, phosphate, oxo, $SO_2NR^4R^5$, $-(CH_2)_m-N-C(O)-R^4$, $-(CH_2)_m-C(O)-N-R^4R^5$, $-C(O)-R^4$, $-C(O)-O-R^4$, $-SR^4$, $-SO_2R^4$ and $-NR^4R^5$, in which m, $R^4$ and $R^5$ are as defined above. These substituents may be the same or different and may be located at any position of the ring that is chemically permissible. Any nitrogen atom within such a heterocyclic ring may optionally be substituted with $(C_1-C_6)$ alkyl, or any other substituent listed above, if such a substitution is chemically permissible. Any sulfur atom in the ring may be further substituted with 1 or 2 oxygen atoms.

r. "therapeutically effective amount" refers to an amount of a compound of Formula I that, when administered to a patient, provides the desired effect; i.e., lessening in the severity of the symptoms associated with a bacterial infection, decreasing the number of bacteria in the affected tissue, and/or preventing bacteria in the affected tissue from increasing in number.

s. "patient" refers to warm blooded animals such as, for example, guinea pigs, mice, rats, gerbils, cats, rabbits, dogs, monkeys, chimpanzees, and humans.

t. "treat" refers to the ability of the compounds to relieve, alleviate or slow the progression of the patient's bacterial infection (or condition) or any tissue damage associated with the disease.

u. "pharmaceutically acceptable" indicates that the substance or composition must be compatible chemically and/or toxicologically, with the other ingredients comprising a formulation, and/or the mammal being treated therewith.

v. "isomer" means "stereoisomer" and "geometric isomer" as defined below.

w. "stereoisomer" means compounds that possess one or more chiral centers and each center may exist in the R or S configuration. Stereoisomers include all diastereomeric, enantiomeric and epimeric forms as well as racemates and mixtures thereof.

v. "geometric isomer" means compounds that may exist in cis, trans, anti, entgegen (E), and zusammen (Z) forms as well as mixtures thereof.

w. Compounds of "Formula I", "formula I" and "compounds of the invention" are being used interchangeably thru-out the application and should be treated as synonyms.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

The invention also relates to base addition salts of the compounds of the invention. The chemical bases that may be used as reagents to prepare these pharmaceutically acceptable base salts are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002). Methods for making pharmaceutically acceptable salts of compounds of the invention are known to one of skill in the art.

Certain of the compounds of the formula (I) may exist as geometric isomers. The compounds of the formula (I) may possess one or more asymmetric centers, thus existing as two, or more, stereoisomeric forms. The present invention includes all the individual stereoisomers and geometric isomers of the compounds of formula (I) and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples below, by substituting a readily available isotopically-labeled reagent for a non-isotopically-labeled reagent.

All of the compounds of Formula I contain a sulfonyl moiety as depicted below:

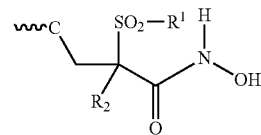

This sulfonyl moiety will always be substituted with a lower alkyl moiety. Typically it will be methyl. The carbon atom adjacent to the sulfonyl may optionally be substituted, as represented by $R^2$. Typically both $R^1$ and $R^2$ will be methyl.

As is readily apparent to one skilled in the art, the carbon adjacent to the sulfonyl moiety is a chiral center. Therefore the compounds can exist as the racemate, as the S enantiomer, or as the R enantiomer. In a further embodiment, the compounds may be prepared and administered as the R-enantiomer, as depicted below:

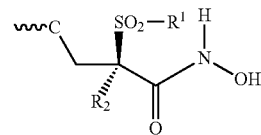

As is readily apparent to one skilled in the art, the compound as synthesized will rarely be present exclusively as a single enantiomer. The opposite enantiomer (i.e the S-enantiomer) may be present in minor amounts (i.e. "substantially pure"). This minor amount can be up to 10 w/w %, more typically no greater than 5 w/w % and in a further embodiment no greater than 1 w/w %.

All of the compounds of Formula I contain a pyridinone as depicted below:

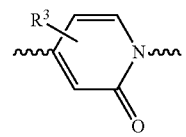

This pyridinone ring will be connected to the rest of the molecule via the 1- and 4-positions as depicted above. The pyridinone moiety may be optionally substituted, as depicted by the $R^3$ moiety. $R^3$ may represent one non-hydrogen substituent, as defined above. This non-hydrogen substituent may be located at any of positions 3, 4 or 5 of the pyridinone ring. Typically $R^3$ will represent hydrogen.

While the presence of L, T and G are optional, all of the compounds of Formula I will contain one of the substituents as defined by D. D may be any of aryl, cycloalkyl, heteroaryl or heterocyclic, as defined above. These ring systems may also be optionally substituted, as defined above. Any chemically permissible position of D may be bonded to the 4-position of the pyridine ring or D may be connected to the pyridinone via the linker as defined by L.

The molecule may contain one of the substituents defined by G. G, if present, may be bonded directly to D. Alternatively, the linker T may connect G and D. G may be any of aryl, cycloalkyl, heteroaryl or heterocyclic as defined above. These ring systems may also be optionally substituted, as defined above.

If G is absent, the molecule may terminate with either T or D as the tail. If the molecule terminates with T, then one skilled in the art will recognize that any of the linkers specified above will have an additional hydrogen atom on the terminal atom of that specific substituent, due to the lack of a bond to G.

More specific embodiments of the invention include compounds of Formula I in which:

a) $R^1$ is methyl;
b) $R^1$ and $R^2$ are each methyl;
c) $R^3$ is hydrogen;
d) L is absent;
e) the compound is present as the R-enantiomer (i.e. substantially pure);
f) $R^1$ and $R^2$ are each methyl, D is represented by optionally substituted phenyl and the compound is present as the R-enantiomer (i.e. substantially pure);
g) $R^1$ and $R^2$ are each methyl, L, G and T are all absent, D is represented by optionally substituted phenyl, and the compound is present as the R-enantiomer (i.e. substantially pure);
h) $R^1$ and $R^2$ are each methyl, L is absent, D is represented by phenyl optionally substituted, T is absent, G is represented by heteroaryl, optionally substituted and the compound is present as the R-enantiomer (i.e. substantially pure).

In a further embodiment, the invention is directed to a subgenus represented by formula Ia below. As depicted below, L, T and G are all absent. D is phenyl optionally substituted, $R^3$ is hydrogen and the compound is present as the R-enantiomer (i.e. the S-enantiomer may optionally be present as a minor impurity, typically no more than 5 w/w %, more typically no more than 1 w/w %). In a further embodiment, the phenyl ring is substituted with up to 3 substituents selected from the group consisting of halogen, hydroxy, $C_1$-$C_3$ alkyl, $C_1$-$C_3$ alkoxy, trifluoromethyl, trifluoromethoxy, and $C_1$-$C_3$ alkyl, optionally substituted with hydroxy or halogen.

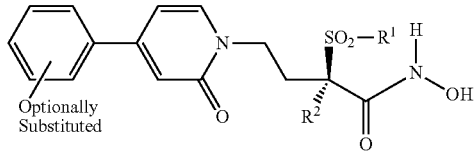

In a further embodiment, the invention is directed to a subgenus represented by formula Ib below As depicted, L and T are both absent, D is phenyl bonded directly to G which is optionally substituted heteroaryl. $R^3$ is hydrogen and the compound is present as the R-enantiomer (i.e. the S-enantiomer may optionally be present as a minor impurity, typically no more than 5 w/w %, more typically no more than 1 w/w %.

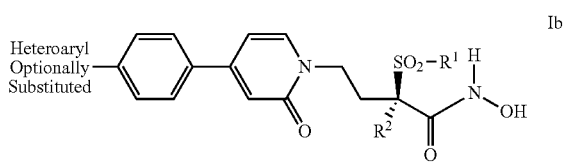

Synthesis

The compounds of Formula I can be prepared by a variety of methods that are analogously known in the art. The reaction schemes presented below illustrate one method for preparing these compounds. Others, including modifications thereof, will be readily apparent to one skilled in the art.

Scheme A below illustrates how to prepare the compounds of Formula I. The initial step in the synthesis, as depicted in Step A, is to conduct an N-alkylation reaction between the pyridinone of structure 1 and the sulfonyl derivative of structure 2, generating the sulfonyl-pyridinone derivative of structure 3. In Step B, which is further illustrated in Scheme B, the terminal carboxylate of structure 3 is converted to a hydroxamic acid derivative as is depicted in structure 4. In Step C, which is further illustrated in Scheme C, the terminal moiety, L-D-T-G, is attached to the 4-position of the pyridinone moiety, generating the desired compound of Formula I.

As is readily apparent to one skilled in the art, the order in which Step B and Step C are carried out is not critical. If desired, the terminal moiety represented by L-D-T-G may be attached to the pyridinone and then the hydroxamic moiety may be incorporated into the molecule. Likewise, the synthetic team may partially complete either Step B or Step C and return to this portion of the molecule after completing the modifications required at the other end of the molecule. Such variations are readily apparent to one of skilled in the art.

SCHEME A

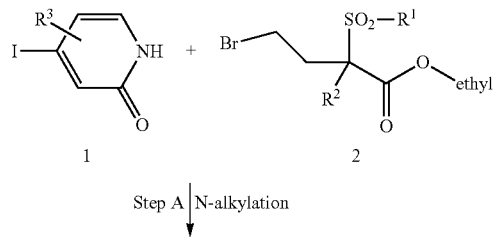

Step A | N-alkylation

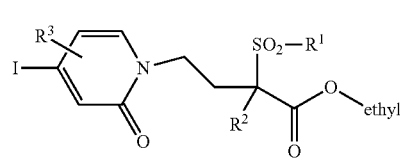

Step B | Hydroxamic Acid formation (See Scheme B)

-continued

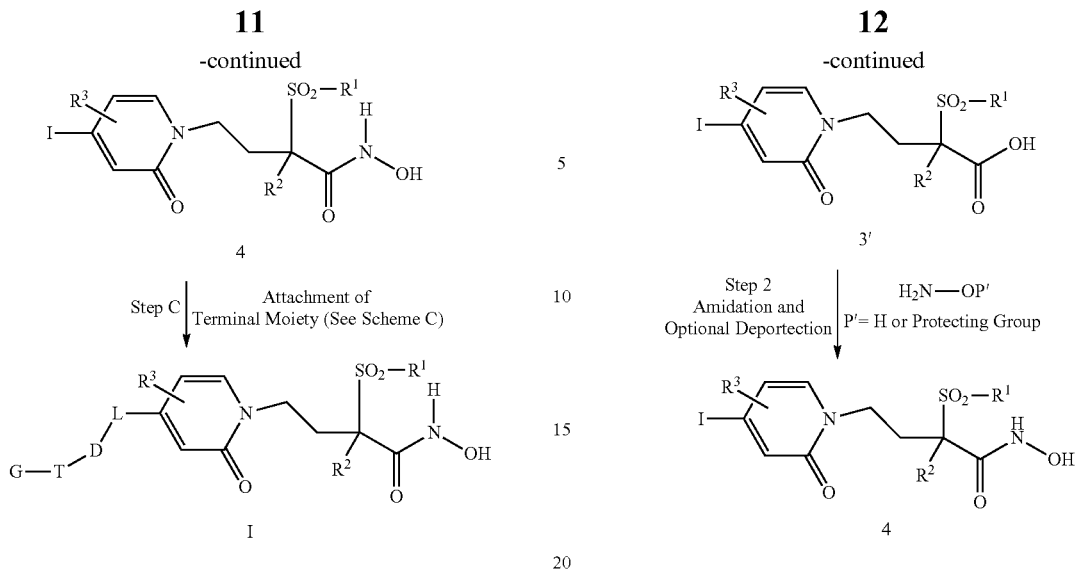

The N-alkylation depicted above in Step A can be carried out using techniques well known to medicinal chemists. One of the starting materials is the 2-pyridinone derivative of structure 1. In this pyridinone, $R^3$ should be represented by the same moiety as is desired in the final product, or a protected variation thereof. Many of these pyridinone derivatives are known in the art and the remainder can be produced using synthetic techniques analogously known in the art. The reader's attention is directed to *Tet. Lett.* (2005) Vol 46, 7917 for a description of such techniques. Preparation 2A infra, also illustrates their preparation.

The other reactant is the protected alkyl sulfonate of structure 2. $R^1$ and $R^2$ should both be represented by the same moiety as is desired in the final product. An ethyl protecting group is depicted, but any standard protecting group may be substituted. These alkyl sulfonates are also known in the art. The reader's attention is directed to *JOC*, (1980) Vol 45, 8, 1486-89 for a description of their preparation. Preparation 1A infra, also illustrates their preparation.

The N-alkylation can be carried out as is known in the art. Typically equivalent amounts of the compounds of structure 1 and 2 are contacted in an aprotic solvent such as tetrahydrofuran in the presence of a weak base such as potassium carbonate, cesium carbonate, sodium carbonate, etc. The reactants are typically heated and the reaction is continued until completed. The desired product of structure 3 can be recovered and isolated as is known in the art. If desired, it can be purified, or alternatively the crude can be used in the next step of the reaction.

Scheme B illustrates how to incorporate the hydroxamic acid moiety into the molecules. As is depicted in Step 1, the protecting group is removed from the carboxylic acid, thereby generating the intermediate of structure 3'. The manner in which this is accomplished will vary with the identity of the actual protecting group and is well known to those skilled in the art.

In Step 2, the hydroxamic acid moiety, as depicted, is incorporated into the molecule. This can also be carried out as is known in the art. If desired, a protected hydroxylamine may be used, followed by a subsequent deprotection reaction. Alternatively hydroxylamine may be directly incorporated. In either case the hydroxamic acid functionality is incorporated into the molecule using standard amidation reactions. For example, the compound of structure 3' may be contacted with an excess of oxalyl chloride, in an aprotic solvent such as dichloromethane to allow formation of the corresponding acid chloride, followed by the addition of an excess of either the hydroxylamine or protected hydroxylamine. The reaction is then allowed to proceed to completion and the compound of structure 4 or its corresponding protected intermediate is isolated from the reaction medium and purified as is known in the art. As mentioned above, any deprotection, if required, may be carried out as is known in the art. Alternatively the amide can be formed using the amide coupling reagent, 1,1'-carbonyliimidazole or 1-ethyl-3-(3-dimethylaminopropyl)carbodiimide) ("EDCI"), as is known in the art.

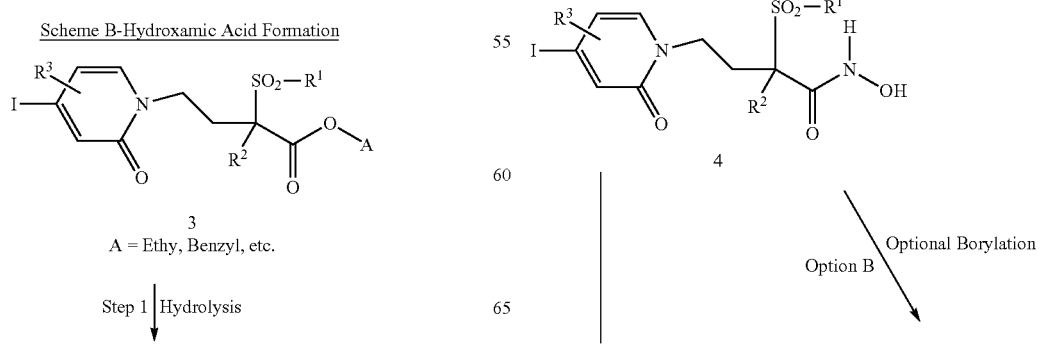

Scheme B-Hydroxamic Acid Formation

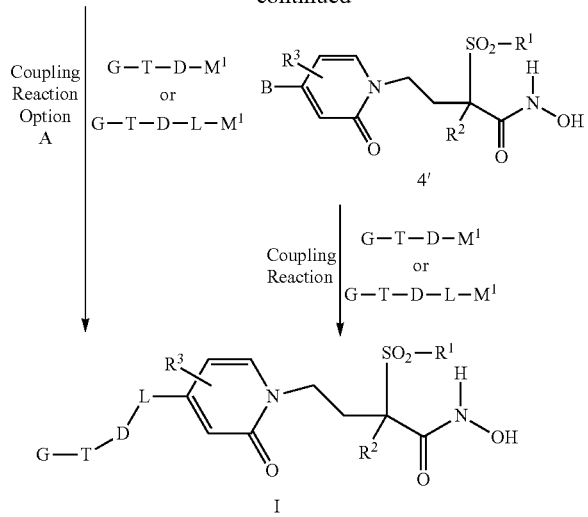

In Scheme C, as shown above, the tail of the molecule, i.e L-D-T-G, is attached to the 4-position of the N-hydroxylated pyridinone intermediate generated in Step B. The coupling reaction depicted in Scheme C can be carried out by two alternative methods.

In Option A, the halide function at the 4-position is directly displaced by the desired tail group. In Option B, the halide moiety is converted to a boronate ester which is subsequently displaced by the desired tail group. Either strategy may be utilized.

If Option B is chosen, the boronation can be carried out using techniques well known to those skilled in the art. For example, the intermediate of structure 4 is placed in an aprotic solvent (such as tetrahydrofuran or dioxane) and then contacted with an organobornane (such as neopentyl diboron, bis(pinolacto)diborane, etc.,) in the presence of both a transition metal catalyst (i.e. palladium) and a base (potassium acetate, cesium carbonate, etc.). The reaction is allowed to proceed to completion. The borylated intermediate describe by structure 4' may be isolated and purified as is known in the art, or the crude may be used directly in the next step of the reaction.

Regardless of whether Option A or Option B is chosen, a coupling reaction is ultimately carried out to attach the terminal moiety, G-T-D-L, to the 4-position of the pyridinone intermediate. In Scheme C above, the co-reactant is depicted as G-T-D-L-M$^1$. However the reader is reminded that the presence of G, T, and L are all optional. Only D is required. Thus, the co-reactant with the pyridinone may be any of D-M$^1$, T-D-M$^1$, G-T-D-M$^1$, G-T-D-L-M$^1$, T-D-L-M$^1$ or D-L-M$^1$. Therefore, G-T-D-L-M$^1$ will be represented by the same moiety as desired in the final product, except that it will be substituted by a halogen atom, a metal such as magnesium, copper, or a boronate ester, etc. at the desired point of attachment to the pyridinone intermediate (i.e. the other reactant). The tails encompassed by Formula I, i.e G-T-D-L, are either known in the art or can be prepared by methods analogously known in the art.

The manner in which the coupling reaction is carried out varies with the type of bond being formed, i.e. (carbon-carbon, carbon-nitrogen, carbon-oxygen, carbon-sulfur, etc.). If a carbon-carbon bond is desired, then a Suzuki-Miyaura strategy may be used. In such a reaction M$^1$ will be represented by a boronic acid/ester or a halogen atom. Equivalent molar amounts of the reactants will be contacted in a solvent such as THF, dioxane, water, toluene, or an admixture thereof; in the presence of a transition metal catalyst such as palladium, or nickel (or resin bound catalyst) along with a base such as sodium carbonate, potassium carbonate, cesium fluoride or cesium carbonate. The reactants will be heated by microwave or other conventional technique till completed. Once completed the desired product may be isolated and recovered from the reaction and further purified as is known in the art.

Alternatively an Ullmann coupling strategy may be used. In such a reaction, M$^1$ will be copper or nickel and the 4-position of the pyridinone will be substituted with an iodine atom (i.e. Option A will be chosen). Equivalent amounts of the reactants will be contacted in an aprotic solvent such as ether, DMF, or DME and the reactants are heated till the reaction is completed. The desired product of formula I may be isolated and purified as is known in the art.

If a carbon-oxygen or carbon-sulfur linkage is desired, then a Willamson/Ullmann ether coupling or Mitsunobu reaction may be utilized to produce these derivatives. G-T-D-L-M$^1$ will be represented by the same moiety as desired in the final product, except that it will be substituted by a hydroxyl function at the desired point of attachment to the pyridinone. If a thioether is desired, G-T-D-L-M$^2$ will be an appropriately substituted disulfide moiety.

The Ullmann ether reaction can be carried out in the presence of copper salts. If a Williamson ether approach is used, then equivalent amounts of the reactants will be contacted in an aprotic solvent such as dioxane in the presence or absence of a phase transfer catalyst such as 18-crown-6. A base such as potassium hydroxide, sodium t-butoxide or sodium methoxide will typically be added as well. The reactants will be heated by microwave or other conventional technique to reaction completion. The desired product may be isolated and purified as is known in the art.

If a carbon-nitrogen bond is desired, then a Buchwald-Hartwig cross-coupling or Ullmann strategy, similar to that described above, may be utilized. Equivalent amounts of the reactants will be contacted in an aprotic solvent such as ether, dimethylformamide, or dimethoxyethane in the presence of a source of copper, such as copper acetate, and a base such as pyridine or catalyst such as a palladium complex. The reaction will be allowed to proceed to completion and the desired product may be isolated and purified as is known in the art.

The reaction schemes depicted above for producing the compound of Formula I, are merely illustrative. As is readily apparent to one skilled in the art, they may be modified depending upon the specific compound, availability of reagents, etc.

Medical and Veterinary Uses

The compounds may be used for the treatment or prevention of infectious disorders, especially those caused by susceptible and multi-drug resistant (MDR) Gram-negative bacteria. Examples of such Gram-negative bacteria include *Acinetobacter baumannii, Acinetobacter* spp., *Achromobacter* spp., *Aeromonas* spp., *Bacteroides fragilis, Bordetella* spp., *Borrelia* spp., *Brucella* spp., *Campylobacter* spp., *Citrobacter diversus (koseri), Citrobacter freundii, Enterobacter aerogenes, Enterobacter cloacae, Escherichia coli, Francisella tularensis, Fusobacterium* spp., *Haemophilus influenzae* (β-lactamase positive and negative), *Helicobacter pylori, Klebsiella oxytoca, Klebsiella pneumoniae* (including those encoding extended-spectrum β-lactamases (hereinafter "ESBLs"), *Legionella pneumophila, Moraxella catarrhalis* (β-lactamase positive and negative), *Morganella morganii, Neisseria gonorrhoeae, Neisseria meningitidis, Proteus vulgaris, Porphyromonas* spp., *Prevotella* spp., members of the Enterobacteriaceae that express ESBLs KPCs, CTX-M, metallo-β-lactamases, and AmpC-type beta-lactamases that confer resistance to currently available cephalosporins, cephamycins, carbapenems, and beta-lactam/beta-lactamase inhibitor combinations, *Mannheimia haemolyticus, Pasteurella* spp., *Proteus mirabilis, Providencia* spp., *Pseudomonas aeruginosa, Pseudomonas* spp., *Salmonella* spp., *Shigella* spp., *Serratia marcescens, Treponema* spp., *Burkholderia cepacia, Vibrio* spp., *Yersinia* spp., and *Stenotrophomonas malophilia.*

In a more specific embodiment, the Gram-negative bacteria are selected from the group consisting of *Acinetobacter baumannii, Acinetobacter* spp., *Enterobacter aerogenes, Enterobacter cloacae, Escherichia coli, Klebsiella oxytoca, Klebsiella pneumoniae, Serratia marcescens, Pseudomonas aeruginosa* and members of the Enterobacteriaceae and *Pseudomonas* that express ESBLs, KPCs, CTX-M, metallo-β-lactamases, and AmpC-type beta-lactamases that confer resistance to currently available cephalosporins, cephamycins, carbapenems, and beta-lactam/beta-lactamase inhibitor combinations.

Examples of infections that may be treated with the compounds of Formula I include nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In addition, the compounds can be used to treat *Helicobacter pylori* infections in the GI tract of humans (and other mammals). Elimination of these bacteria is associated with improved health outcomes including fewer dyspeptic symptoms, reduced peptic ulcer recurrence and rebleeding, reduced risk of gastric cancer, etc. A more detailed discussion of eradicating *H. pylori* and its impact on gastrointestinal illness may be found at: www.informahealthcare.com, Expert Opin. Drug Saf. (2008) 7(3).

In order to exhibit this anti-infective activity, the compounds need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 5000 mg/kg/day in single or in divided doses. Typically, dosages for humans will range from about 10 mg to about 3000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, and intraocular, intranasal, intravetricular injections or infusions techniques. Topical administrations include the treatment of areas readily accessibly by local application, such as, for example, eyes, ears including external and middle ear infections, vaginal, open wound, skin including the surface skin and the underneath dermal structures, or other lower intestinal tract. Transmucosal administration includes nasal aerosol or inhalation applications.

Formulations

Compounds of the invention can be formulated for administration in any way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, ophthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods will known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 60% by weight, of the active material, depending on the method of administration. Where the compositions comprise dosage units, each unit will contain, for example, from about 5-500 mg of the active ingredient. The dosage as employed for adult human treatment will range, for example, from about 10 to 3000 mg per day, depending on the route and frequency of administration.

If desired, the compounds of the invention may be administered in combination with one or more additional anti-bacterial agents ("the additional active agent"). Such use of compounds of the invention in combination with an additional active agent may be for simultaneous, separate or sequential use.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Experimental Procedures

Experiments were generally carried out under an inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS) or atmospheric pressure chemical ionization (APCI). Chemical shifts for nuclear magnetic resonance (NMR) data are expressed in parts per million (ppm, δ) referenced to residual peaks from the deuterated solvents employed. Melting points are uncorrected. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20-25° C.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate $R_f$s or retention times.

In the discussion above and in the examples below, the following abbreviations have the following meanings. If an abbreviation is not defined, it has its generally accepted meaning.

Aq.=aqueous
bm=broad multiplet
BOC=tert-butoxycarbonyl
bd=broad doublet
bs=broad singlet
CDI=1,1'-carbonyldiimidazole
d=doublet
dd=doublet of doublets
dq=doublet of quartets
dt=doublet of triplets
DIAD=diisopropyl azocarboxylate
DMF=dimethylformamide
DMA=dimethylacetamide
DMAP=dimethylaminopyridine
DMSO=dimethyl sulfoxide
eq.=equivalents
g=grams
h=hours
HPLC=high pressure liquid chromatography
LG=leaving group
m=multiplet
M=molar
M %=mole percent
max=maximum
meq=milliequivalent
mg=milligram
mL=milliliter
mm=millimeter
mmol=millimol
q=quartet
s=singlet
t or tr=triplet
TBS=tert-butyldimethylsilyl
TFA=trifluoroacetic acid
THF=tetrahydrofuran
TLC=thin layer chromatography
p-TLC=preparative thin layer chromatography
μL=microliter
N=normality
MeOH=methanol
DCM=dichloromethane
HCl=hydrochloric acid
ACN=acetonitrile
MS=mass spectrometry
rt=room temperature
EtOAc=ethyl acetate
EtO=ethoxy
Ac=acetate
NMP=1-methyl-2-pyrrolidinone
μL=microliter
J=coupling constant
NMR=nuclear magnetic resonance
MHz=megahertz
Hz=hertz
m/z=mass to charge ratio
min=minutes
ppt=precipitate
CBZ=benzyloxycarbonyl
DCC=1,3-dicyclohexylcarbodiimide PyBop=benzotriazole-1-yl-oxy-trispyrrolidinophosphonium hexafluorophosphate
Pd(dppf)Cl$_2$=bis(diphenylphosphino)ferrocenepalladium (II) chloride
Pd(dppf)Cl$_2$ DCM complex
Pd tetrakis=Tetrakis(triphenylphosphine)palladium(0)
Pd (II) EnCat=Pd (II) EnCat™ BINAP 30
LDA=lithium diisopropylamide
mCPBA=meta-chloroperbenzoic acid
MTBE=methyl tert butyl ether
CDMT=2-chloro-4,6-dimethoxy-1,3,5-triazine
NMM=N-methyl morphiline
TMS=trimethyl silyl
TPP=triphenyl phosphine
TPPO=triphenyl phosphine oxide
DME=dimethyl ether
IPA=isopropanol
Et$_2$O=diethyl ether
LiHMDS=lithium hexamethyldisilazide/lithium bis(trimethylsilyl)amide
9-BBN=9-Borabicyclo[3.3.1]nonane
sat.=saturated
MeTHF=2-methyltetrahydrofuran Preparation of Starting Materials Preparation 1

Preparation 1A (+/−)-Ethyl 4-bromo-2-methyl-2-(methylsulfonyl) butanoate and individual enantiomers (R) and (S)

Step A) Ethyl 2-(methylsulfonyl)propanoate

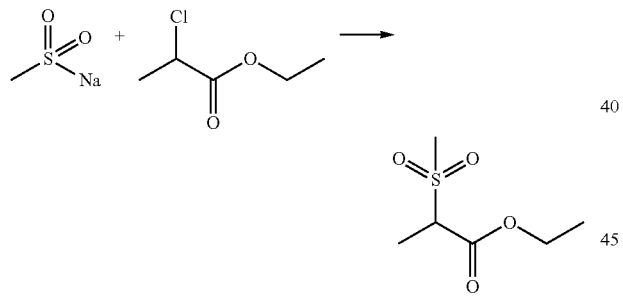

Sodium methyl sulfinate (103 g, 937 mmol) was combined with the ethyl 2-chloropropionate (109 g, 892 mmol) in ethanol (350 mL) in a 500 mL one neck round bottom flask. The reaction was warmed to 77° C. for 20 hours, and then allowed to cool to room temperature. Solids were removed by filtration through celite, and the filter pad was washed with ethanol and the combined filtrates were concentrated in vacuo. The crude product was suspended in diethyl ether (250 mL), and solids were removed by filtration. The filtrate was concentrated in vacuo to afford the title compound as a pale yellow oil (51 g, 73%). $^1$H NMR (400 MHz, CHLOROFORM-d) δ ppm 1.32 (t, J=7.05 Hz, 3H) 1.67 (d, J=7.47 Hz, 3H) 3.05 (s, 3H) 3.83-3.92 (m, 1H) 4.18-4.37 (m, 2H).

Step B) (+/−)-Ethyl 4-bromo-2-methyl-2-(methylsulfonyl)butanoate

Sodium hydride (60% dispersion in mineral oil, 2.33 g, 58.3 mmol) was washed with hexane (2×10 mL) in a 100 mL two neck round bottom flask under nitrogen then suspended in DMF (30 mL). The suspension was treated dropwise with ethyl 2-(methylsulfonyl)propanoate (10.0 g, 55.49 mmol) in DMF (10 mL). The mixture was stirred 30 min at RT, cooled to 0° C., and treated dropwise with 1,2-dibromoethane (5.17 mL, 58.8). The mixture was allowed to warm to room temperature while stirring overnight. The mixture was quenched with saturated ammonium chloride (100 mL) and the mixture was extracted with diethyl ether (4×50 mL). Combined organics were washed with 50% saturated sodium chloride (4×50 mL), dried (MgSO$_4$), filtered and the filtrate concentrated in vacuo. Crude material was chromatographed over silica gel (350 g, 230-400 mesh) eluting with 10-20% EtOAc/hexane to afford the title compound as a pale yellow oil (7.9 g, 50%). $^1$H NMR (400 MHz, CHLOROFORM-d) δ ppm 1.33 (t, J=7.05 Hz, 3H) 1.64 (s, 3H) 2.49-2.59 (m, 1H) 2.78 (ddd, J=13.89, 10.16, 6.64 Hz, 1H) 3.05 (s, 3H) 3.33-3.41 (m, 1H) 3.46-3.54 (m, 1H) 4.22-4.37 (m, 2H).

Step C) Chiral separation of (+/−)-Ethyl 4-bromo-2-methyl-2-(methylsulfonyl)butanoate Crude (+/−)-ethyl 4-bromo-2-methyl-2-(methylsulfonyl) butanoate (1.82 kg) was purified via flash chromatography using an LP-600 column and toluene as the eluant to afford pure (+/−)-ethyl 4-bromo-2-methyl-2-(methylsulfonyl)butanoate (1.63 kg). The purified material was dissolved in ethanol (75 g/L) and resolved via chiral multi-column chromatography (condition listed in Table 1) on MCC-2 to afford enantiomer 1 (738.4 g, rt=4.719 min, $[\alpha]_{589}^{20}$=+14.1°) at 99% enantiomeric purity and enantiomer #2 (763.8 g, rt=4.040 min) at 95% enantiomeric purity. Purity of the enantiomers was determined via chiral HPLC, 4.6×250 mm Chiralpak AD, 10µ column, 215 nm wavelength, mobile phase: ethanol, isocratic elution at 1 mL/min at ambient temperature.

TABLE 1

| Stationary Phase | ChiralPak AD, 20 µ |
|---|---|
| Column Dimension/Temp | 5 × 10 cm/30° C. |
| Mobile Phase | 100% ethanol |
| Feed Concentration | 75 g/L in mobile phase |
| Feed Rate | 4.0 mL/min |
| Eluant Rate | 90.5 mL/min |
| Raffinate Rate | 35.6 mL/min |
| Extract Rate | 58.9 mL/min |
| Recycling Rate | 262 mL/min |
| Period Time | 1.0 min |

Enantiomer 1 was determined to be Ethyl (2R)-4-bromo-2-methyl-2-(methylsulfonyl)butanoate.

Preparation 1B

Benzyl (+/−)-4-bromo-2-methyl-2-(methylsulfonyl) butanoate and individual enantiomers (R) and (S)

Step A) Benzyl 2-chloropropanoate

Benzyl alcohol (242 mL, 253 g, 2.34 mol) and pyridine (204 mL, 204 g, 2.57 mol) were dissolved in methylene chloride (2.5 L) and cooled to 0° C. 2-Chloropropanoyl chloride (250 mL, 327 g, 2.57 mol) was added dropwise keeping the temperature between 0° C. and 5° C. After addition the mixture was allowed to warm to RT overnight. The mixture was washed with 20% aqueous citric acid (2.5 L), saturated aqueous NaHCO$_3$ (2.5 L), brine (2.5 L), dried (MgSO$_4$), filtered and concentrated in vacuo. The resulting brown liquid (450 g) was dissolved in a small amount of methylene chloride and filtered through a short path of silica gel. After concentration, the crude was purified via bulb-to-bulb distillation (2*10−2 mbar, 90-95° C.) affording the title compound as a pale yellow liquid (420 g, 90%). ¹H-NMR: (CDCl₃, 300 MHz): δ ppm 1.75 (d, 3H, CH₃), 4.45 (q, 1H, CHCl), 5.25 (s, 2H, CH2Ar), 7.40 (m, 5H, ArH).

Step B) Benzyl 2-(methylsulfonyl)propanoate

Benzyl 2-chloropropanoate was converted to the title compound following the general procedure outlined for ethyl 2-(methylsulfonyl)propanoate in Preparation 1A. The title compound was obtained as a yellow liquid (389 g, 70%). ¹H-NMR: (CDCl₃, 300 MHz): δ ppm 1.65 (dt, 3H, CHCH₃), 3.00 (s, 3H, SO₂CH₃), 3.95 (q, 1H, CH), 5.25 (m, 2H, CO2CH2Ar), 7.40 (m, 5H, ArH).

Step C) Benzyl (+/−)-4-bromo-2-methyl-2-(methylsulfonyl)butanoate

Benzyl 2-(methylsulfonyl)propanoate was converted to the title compound following the general procedure outlined for ethyl (+/−)-4-bromo-2-methyl-2-(methylsulfonyl)butanoate in Preparation 1A. The title compound was obtained as a pale yellow liquid (300 g, 58%). 1H-NMR: (CDCl₃, 300 MHz): δ ppm 1.70 (s, 3H, CH₃), 2.60 (m, 1H, CH₂CH₂Br), 2.80 (m, 1H, CH₂CH₂Br), 3.00 (s, 3H, SO₂CH₃), 3.35 (m, 1H, CH₂CH₂Br), 3.50 (m, 1H, CH₂CH₂Br), 5.30 (m, 2H, CO₂CH₂Ar), 7.40 (m, 5H, ArH)

Step D) Chiral separation of Benzyl (+/−)-4-bromo-2-methyl-2-(methylsulfonyl)butanoate

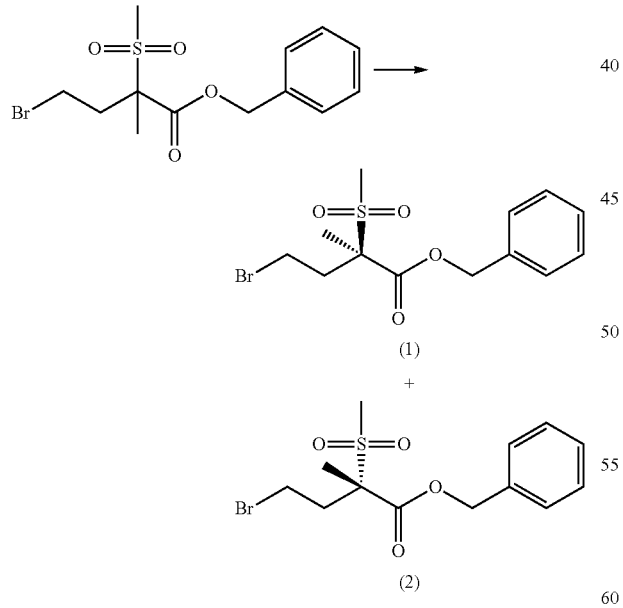

Benzyl (+/−)-4-bromo-2-methyl-2-(methylsulfonyl)butanoate (275 g) was dissolved in isopropanol/acetonitrile (900 mL) and resolved using an Analytical SFC-4 instrument, AS-H column (30×250), a CO₂/Propanol (90/10) mobile phase, with a flow rate of 120 g/min to afford enantiomer 1 (98 g, rt=3.09 min, [α]₅₈₉²⁰=−13.9°) at 99.94% enantiomeric purity and enantiomer 2 (101.5 g, rt=4.18 min, [α]₅₈₉²⁰=+11.61°) at 97.77% enantiomeric purity.

(S)-benzyl 4-bromo-2-methyl-2-(methylsulfonyl)butanoate

¹H NMR (400 MHz, CHLOROFORM-d) δ ppm 1.65 (s, 3H) 2.48-2.60 (m, 1H) 2.74-2.86 (m, 1H) 2.95 (s, 3H) 3.25-3.37 (m, 1H) 3.40-3.52 (m, 1H) 5.16-5.31 (m, 2H) 7.31-7.40 (m, 5H)

[α]₅₈₉²⁰=−13.9°

(R)-benzyl 4-bromo-2-methyl-2-(methylsulfonyl)butanoate

¹H NMR (400 MHz, CHLOROFORM-d) δ ppm 1.67 (s, 3H) 2.51-2.61 (m, 1H) 2.75-2.87 (m, 1H) 2.97 (s, 3H) 3.28-3.37 (m, 1H) 3.40-3.60 (m, 1H) 5.15-5.36 (m, 2H) 7.30-7.48 (m, 5H)

[α]₅₈₉²⁰=+11.61°

Preparation 2

Scheme 2 below illustrates the preparation of 4-(4-iodo-2-oxopyridin-1(2H)-yl)-2-methyl-2-(methylsulfonyl)-N-(tetrahydro-2H-pyran-2-yloxy)butanamide and its corresponding R-enantiomer. The reaction sequence in Preparation 2B, is the same with the exception that benzyl (2R)-4-bromo-2-methyl-2-(methylsulfonyl)butanoate is used as a starting material in order to arrive at the desired enantiomer.

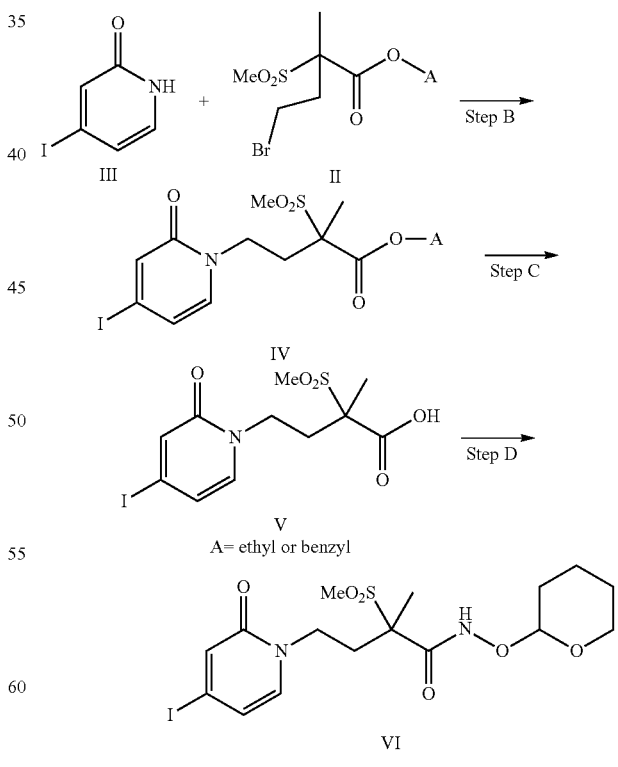

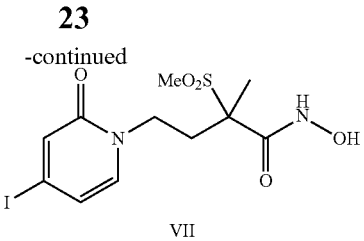

VII

Preparation 2A

Synthesis of Compound VI (T3): 4-(4-iodo-2-oxopyridin-1(2H)-yl)-2-methyl-2-(methylsulfonyl)-N-(tetrahydro-2H-pyran-2-yloxy)butanamide as a mixture of diastereoisomers

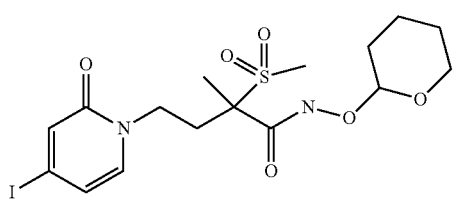 [SMILES: CC(CCn1ccc(I)cc1=O)(C(=O)NOC1CCCCO1)S(C)(=O)=O]

Step A) 4-iodopyridin-2(1H)-one (compound III)

2-fluoro-4-iodopyridine (2.21 kg, 9.91 mol) was suspended in a mixture of acetic acid (7 L) and $H_2O$ (3.5 L) with mechanical stirring. The mixture was heated at reflux overnight. After cooling to room temperature the solid was filtered off and concentrated in vacuo. The residue was stirred in $Et_2O$ (3 L), the title compound (1.72 kg, 7.78 mol) was collected by filtration as a pale yellow solid. $^1$H-NMR: (DMSO-$d_6$, 300 MHz): δ 6.50 (d, 1H), 6.85 (s, 1H), 7.15 (d, 1H), 11.80 (s, 1H)

Step B) Compound IV (T1): ethyl 4-(4-iodo-2-oxopyridin-1(2H)-yl)-2-methyl-2-(methylsulfonyl)butanoate (A=Et)

To a mixture of 4-iodopyridin-2(1H)-one (3.9 g, 18 mmol), which may be produced in Step A above, and cesium carbonate (11.9 g, 35.3 mmol) in tetrahydrofuran (176 mL) at ambient temperature was added ethyl 4-bromo-2-methyl-2-(methylsulfonyl)butanoate (6.08 g, 21.2 mmol) (Compound II). The mixture was heated to 50° C. and stirred overnight. The mixture was allowed to cool to ambient temperature and filtered through a celite pad. The pad was washed with methylene chloride and the filtrate was concentrated in vacuo. The crude oil was purified via silica gel chromatography, eluting with heptanes/ethyl acetate. The desired fractions were isolated, the solvent removed via rotary evaporation ethyl 4-(4-iodo-2-oxopyridin-1(2H)-yl)-2-methyl-2-(methylsulfonyl)butanoate as a solid. 4.73 g. LCMS: (M+1) 428.2

Step C) Compound (V) T2: 4-(4-iodo-2-oxopyridin-1(2H)-yl)-2-methyl-2-(methylsulfonyl)butanoic acid To a solution of ethyl 4-(4-iodo-2-oxopyridin-1(2H)-yl)-2-methyl-2-(methylsulfonyl)butanoate (3.26 g, 7.63 mmol), which may be produced in Step B above, in tetrahydrofuran/methanol (4:1, 60 mL) at ambient temperature was added a solution of lithium hydroxide monohydrate (0.9 M in water, 15.3 mmol). The resulting mixture was stirred at ambient temperature for 3 hours. The mixture was acidified with aqueous hydrochloric acid (1N, 16 mL) and extracted three times with methylene chloride. The combined organic extracts were dried over magnesium sulfate, filtered and concentrated in vacuo to afford 4-(4-iodo-2-oxopyridin-1(2H)-yl)-2-methyl-2-(methylsulfonyl)butanoic acid as a solid. 3.05 g.
LCMS: (M+1) 400.1

Step D) Compound (VI) T3: 4-(4-iodo-2-oxopyridin-1(2H)-yl)-2-methyl-2-(methylsulfonyl)-N-(tetrahydro-2H-pyran-2-yloxy)butanamide To a solution of 4-(4-iodo-2-oxopyridin-1(2H)-yl)-2-methyl-2-(methylsulfonyl)butanoic acid (3.01 g, 7.54 mmol), which may be produced as in Step C above, in methylene chloride (75 mL) at ambient temperature was added 1-(3-dimethylaminopropyl)-3-ethylcarbodiimide hydrochloride (2.02 g, 10.6 mmol), 1-hydroxy benzotriazole monohydrate (2.08 g, 13.6 mmol), triethyl amine (1.89 mL, 13.6 mmol) and O-tetrahydro-2H-pyran-2-yl-hydroxylamine (1.33 g, 11.3 mmol). The resulting mixture was stirred at ambient temperature overnight. The mixture was diluted with methylene chloride and water. The phases were separated and the aqueous extracted with methylene chloride two times. The organic extracts were combined and dried over magnesium sulfate, filtered and concentrated in vacuo to a crude residue. The crude residue was purified via silica gel chromatography eluting with methylene chloride and methanol. The fractions containing desired product were combined and concentrated to afford 4-(4-iodo-2-oxopyridin-1(2H)-yl)-2-methyl-2-(methylsulfonyl)-N-(tetrahydro-2H-pyran-2-yloxy)butanamide as a solid. 3.62 g LCMS: (M−1) 497

Preparation 2B

Synthesis of T6: (2R)-4-(4-iodo-2-oxopyridin-1(2H)-yl)-2-methyl-2-(methylsulfonyl)-N-(tetrahydro-2H-pyran-2-yloxy)butanamide

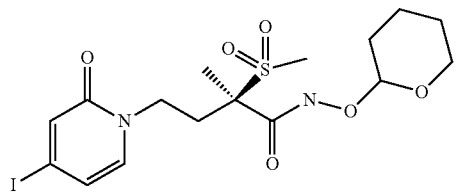 [SMILES: C[C@@](CCn1ccc(I)cc1=O)(C(=O)NOC1CCCCO1)S(C)(=O)=O]

Step A) T4: Benzyl (2R)-4-(4-iodo-2-oxopyridin-1(2H)-yl)-2-methyl-2-(methylsulfonyl)butanoate To a mixture of 4-iodopyridin-2(1H)-one which may be produced as in Step A of Preparation 2A (32.9 g, 149 mmol) and cesium carbonate (102 g, 312 mmol) in tetrahydrofuran (400 mL) at ambient temperature was added benzyl (2R)-4-bromo-2-methyl-2-(methylsulfonyl)butanoate (62.3 g, 178.4 mmol). The mixture was heated to 60° C. and stirred overnight. The mixture was allowed to cool to ambient temperature and filtered through a celite pad. The pad was washed with ethyl acetate (500 mL), the filtrates combined and concentrated in vacuo to afford an orange oil. The crude oil was purified via filtration through a silica gel pad, eluting with heptanes/ethyl acetate. The desired fractions were isolated and the solvent was removed via rotary evaporation affording benzyl (2R)-4-(4-iodo-2-oxopyridin-1(2H)-yl)-2-methyl-2-(methylsulfonyl)butanoate as a white solid. 44.91 g.
$^1$NMR (CDCl$_3$): 7.39-7.36 (5H, m), 7.03 (1H, d, J=1.76 Hz), 6.77 (1H, d, J=7.03 Hz), 6.41 (1H, dd, J=1.76 Hz, J=7.03 Hz), 5.21 (2H, d, J=1.56 Hz), 4.19-4.12 (1H, m), 3.82-3.75 (1H, m), 2.97 (3H, s), 2.47-2.42 (2H, m), 1.73 (3H, s) ppm.

Step B) T5: (2R)-4-(4-iodo-2-oxopyridin-1(2H)-yl)-2-methyl-2-(methylsulfonyl)butanoic acid To a solution of benzyl (2R)-4-(4-iodo-2-oxopyridin-1(2H)-yl)-2-methyl-2-(methylsulfonyl)butanoate (44.91 g, 91.7 mmol), which may be produced as in Step A above, in tetrahydrofuran (300 mL) and methanol (300 mL) at ambient temperature was added potassium hydroxide (3.76 M in water, 564 mmol). The resulting mixture was stirred at ambient temperature for 16 hours. The solvent was removed via rotary evaporation and the residue was dissolved in water. The aqueous layer was washed with diethyl ether and then acidified with concentrated hydrochloric acid (~pH 2) which afforded a white precipitate. The precipitate was collected via filtration, washed with water and dried in vacuo to a constant weight affording (2R)-4-(4-iodo-2-oxopyridin-1(2H)-yl)-2-methyl-2-(methylsulfonyl)butanoic acid as a white solid. 33.2 g. LCMS: (M+1) 400.4 $^1$NMR (CD$_3$OD): 7.34 (1H, d, J=7.23), 7.03 (1H, d, J=1.76), 6.69 (1H, dd, J=1.95, J=7.23), 4.24-4.16 (1H, m), 4.05-3.98 (1H, m), 3.14 (3H, s), 2.57-2.50 (1H, m), 2.35-2.28 (1H, m), 1.68 (3H, s) ppm.

Step C) T6: (2R)-4-(4-iodo-2-oxopyridin-1(2H)-yl)-2-methyl-2-(methylsulfonyl)-N-(tetrahydro-2H-pyran-2-yloxy)butanamide To a solution of (2R)-4-(4-iodo-2-oxopyridin-1(2H)-yl)-2-methyl-2-(methylsulfonyl)butanoic acid, which may be produced as in Step B above, (33.18 g, 83.12 mmol) in methylene chloride (400 mL) at ambient temperature was added 1-ethyl-3-(3-dimethylaminopropyl)carbodiimide hydrochloride (22.3 g, 116 mmol), 1-hydroxy benzotriazole monohydrate (22.9 g, 150 mmol), triethyl amine (20.9 mL, 150 mmol) and O-tetrahydro-2H-pyran-2-yl-hydroxylamine (14.6 g, 125 mmol). The resulting mixture was stirred at ambient temperature overnight. The mixture was diluted with methylene chloride and water. The phases separated and the aqueous extracted with methylene chloride two times. The organic extracts were combined and dried over magnesium sulfate, filtered and concentrated to a crude residue. The crude residue was dissolved in methylene chloride (~150 mL) with minimal methanol. To this solution was added heptanes (450 mL) and the mixture was concentrated in vacuo to 150 mL and filtered. The solid was washed with heptanes and dried in vacuo to give (2R)-4-(4-iodo-2-oxopyridin-1(2H)-yl)-2-methyl-2-(methylsulfonyl)-N-(tetrahydro-2H-pyran-2-yloxy)butanamide. 26.1 g LCMS: (M−1) 497.6

Preparation 3

Synthesis of T8: (2R)-4-(4-(5,5-dimethyl-1,3,2-dioxaborinan-2-yl)-2-oxopyridin-1(2H)-yl)-2-methyl-2-(methylsulfonyl)-N-(tetrahydro-2H-pyran-2-yloxy)butanamide

Step A) T7: (R)-4-(4-(5,5-dimethyl-1,3,2-dioxaborinan-2-yl)-2-oxopyridin-1(2H)-yl)-2-methyl-2-(methylsulfonyl)butanoic acid Neopentyl diboron (9.4 g, 28 mmol), KOAc (7.1 g, 69 mmol, 3 eq.) and Pd(dppf)Cl$_2$ (532 mg, 0.69 mmol, 0.03 eq.) was added into a 200 mL round bottom flask equipped with a magnetic stirrer and a 120 mL addition funnel. The product of Step B of Preparation 2B, (2R)-4-(4-iodo-2-oxopyridin-1(2H)-yl)-2-methyl-2-(methylsulfonyl)butanoic acid T5 (9.2 g, 23 mmol, 1.0 equiv.) was added into the addition funnel. The system was purged with nitrogen/vacuum and kept under nitrogen. Degassed DMSO (45 mL) was added into the addition funnel. The system was again purged with N$_2$ for 5 mins. The T5 solution was added to the reaction mixture over 2 mins at room temperature then heated to 80° C. and maintained at that temperature for a further hour. The reaction mixture was cooled to RT and poured into 100 mL water. Mixture was adjusted to pH 3 with 6 N HCl and refrigerated for 30 min. A dark solid formed and was collected via filtration and dried under high vacuum over P$_2$O$_5$ for 3 days to yield 13 g of solid product. The solid was suspended in 100 mL MeOH, 16 g silica gel was added and mixture was concentrated in vacuo. The preabsorbed material was packed into a cartridge, loaded onto an 80 g silica gel column and purified using 0 to 20% MeOH in DCM (product eluted out at ~8% MeOH) in 45 min at 60 mL/min flow rate. The desired fractions were concentrated to furnish 6.3 g off white solid (71%). LCMS m/z 318.0 (M−neopentyl+H), 396.1 (M−neopentyl+DMSO+H); $^1$H NMR (400 MHz, DMSO-d$_6$) δ ppm 0.93 (s, 6H) 1.54 (s, 3H) 2.14 (ddd, J=13.04, 10.69, 4.79 Hz, 1H) 2.38 (ddd, J=13.18, 10.45, 5.86 Hz, 1H) 3.16 (s, 3H) 3.73 (s, 4H) 3.77-3.92 (m, 1H) 4.05 (ddd, J=12.40, 10.74, 4.98 Hz, 1H) 6.33 (dd, J=6.74, 1.27 Hz, 1H) 6.62 (s, 1H) 7.59 (d, J=6.84 Hz, 1H) 13.87 (br. s., 1H).

Step B) T8: (2R)-4-(4-(5,5-dimethyl-1,3,2-dioxaborinan-2-yl)-2-oxopyridin-1(2H)-yl)-2-methyl-2-(methylsulfonyl)-N-(tetrahydro-2H-pyran-2-yloxy)butanamide To a suspension of the product of Step A above, T 7, (5.0 g, 13 mmol) in 200 mL THF was added N-methyl morpholine (2.0 g, 20 mmol) and 2-chloro-4,6-dimethoxy-1,3,5-triazine (2.6 g, 14 mmol). The reaction mixture was stirred at room temperature for 2 h. O-tetrahydro-2H-pyran-2-yl-hydroxylamine was added to the resulting mixture and was stirred at RT for 3 hrs. The solids were filtered and the filtrate was concentrated in vacuo to low volume ~20 mL, 20 mL EtOAc was added to the liquid and the resulting mixture was kept in refrigerator for 20 h. The resulting white solid was collected via filtration and dried to furnish 2.82 g of the title compound. LCMS m/z 341.71 (M−neopentyl+H).

Preparation 4

4-(4-bromo-2-oxopyridin-1(2H)-yl)-2-methyl-2-(methylsulfonyl)-N-(tetrahydro-2H-pyran-2-yloxy)butanamide (Mixture of diastereoisomers)

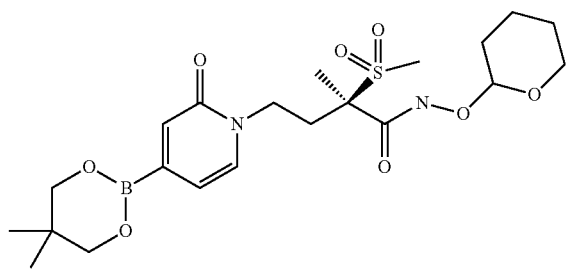 [SMILES: CC1(C)COB(c2ccn(CC[C@](C)(C(=O)NOC3CCCCO3)S(C)(=O)=O)c(=O)c2)OC1]

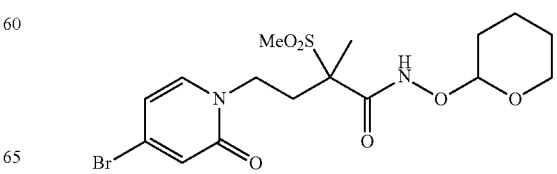

T9: 4-(4-bromo-2-oxopyridin-1(2H)-yl)-2-methyl-2-(methylsulfonyl)-N-(tetrahydro-2H-pyran-2-yloxy)butanamide The title compound was made via a method analogous to the preparation of T3 in Preparation 2A, Step D, except that 4-bromopyridin-2(1H)-one was used instead of 4-iodopyridin-2(1H)-one with comparable yields.
m/z+ was 367

Example 1

(2R)—N-hydroxy-2-methyl-2-(methylsulfonyl)-4-{2-oxo-4-[4-(1H-pyrazol-1-yl)phenyl]pyridin-1(2H)-yl}butanamide

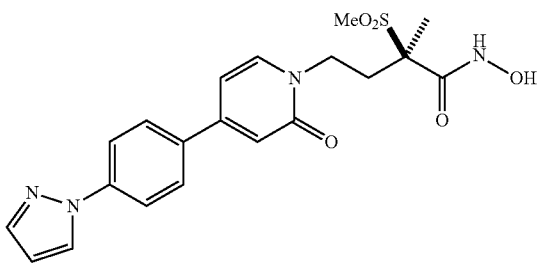 [SMILES: C[C@@](CCn1ccc(-c2ccc(-n3cccn3)cc2)cc1=O)(C(=O)NO)S(C)(=O)=O]

Step A) 1-[4-(4,4,5,5-tetramethyl-1,3,2-dioxaborolan-2-yl)phenyl]-1H-pyrazole 1-(4-bromophenyl)-1H-pyrazole (0.34 g, 1.5 mmol), bis(pinacolato)diborane (0.53 g, 2.1 mmol) and potassium acetate (446 mg, 4.5 mmol) were combined in a 4 dram vial in 10 mL dioxane. The reaction mixture was bubbled with nitrogen for 10 minutes then Pd(dppf)Cl$_2$ (110 mg, 0.15 mmol) was added. The reaction was heated at 100° C. overnight. The reaction was diluted with 20 mL of EtOAc and 20 mL of 1:1 saturated sodium bicarbonate/water. The organic layer was isolated and the aqueous layer was back-extracted once with 10 mL of EtOAc. The organic layers were combined, dried over solid magnesium sulfate, filtered and concentrated. The crude material was purified by eluting the material through a short pad of silica gel with EtOAc to provide a dark solid (0.42 g, 100%). MS (LCMS) m/z 271.4 (M+1). $^1$H NMR (400 MHz, CHLOROFORM-d) δ ppm 1.35 (s, 12H) 6.46 (dd, J=2.54, 1.76 Hz, 1H) 7.68-7.72 (m, 2H) 7.72 (d, J=1.76 Hz, 1H) 7.85-7.90 (m, 2H) 7.96 (d, J=1.76 Hz, 1H).

Step B) (2R)-2-methyl-2-(methylsulfonyl)-4-{2-oxo-4-[4-(1H-pyrazol-1-yl)phenyl]pyridin-1(2H)-yl}-N-(tetrahydro-2H-pyran-2-yloxy)butanamide Trisdibenzylidine dipalladium (29 mg, 0.049 mmol) was added to a mixture of potassium carbonate (343 mg, 2.46 mmol), 1-[4-(4,4,5,5-tetramethyl-1,3,2-dioxaborolan-2-yl)phenyl]-1H-pyrazole (133 mg, 0.49 mmol) and (2R)-4-(4-iodo-2-oxopyridin-1(2H)-yl)-2-methyl-2-(methylsulfonyl)-N-(tetrahydro-2H-pyran-2-yloxy)butanamide (245 mg, 0.49 mmol), which may be synthesized as described in Preparation 2B in 1,2-dimethoxyethane-methanol (5.0 mL, 1:1). The reaction was heated to 80° C. and allowed to stir overnight. The reaction was diluted with ethyl acetate (10 mL), filtered through a pad of Celite, and concentrated under reduced pressure. The crude material was purified by flash chromatography (1:0-9:1 ethyl acetate/methanol) to provide a colorless residue (58 mg, 23%). MS (LCMS) m/z 513.7 (M−1).

Step C) (2R)—N-hydroxy-2-methyl-2-(methylsulfonyl)-4-{2-oxo-4-[4-(1H-pyrazol-1-yl)phenyl]pyridin-1(2H)-yl}butanamide A solution of hydrochloric acid (3.0 mL, 4.0 M in 1,4-dioxane) was added dropwise to a solution of (2R)-2-methyl-2-(methylsulfonyl)-4-{2-oxo-4-[4-(1H-pyrazol-1-yl)phenyl]pyridin-1(2H)-yl}-N-(tetrahydro-2H-pyran-2-yloxy)butanamide (58 mg, 0.11 mmol) in dichloromethane (3.0 mL) and methanol (0.6 mL) at 0° C. After 2 h, the reaction was concentrated under reduced pressure. The resulting residue was triturated with diethyl ether, filtered, washed with heptane, and dried under reduced pressure to provide a light yellow solid (47 mg, 98%). MS (APCI) m/z 431.3 (M+1). $^1$H NMR (400 MHz, CD$_3$OD) δ ppm 1.71 (s, 3H), 2.36-2.43 (m, 1H), 2.59-2.68 (m, 1H), 3.09 (s, 3H), 3.96-4.05 (m 1H), 4.30-4.40 (m, 1H), 6.56 (dd, J=1.8, 2.3 Hz, 1H), 6.93-6.95 (m, 2H), 7.76 (d, J=1.8 Hz, 1H), 7.82-7.92 (m, 5H), 8.31 (d, J=2.3, 1H).

Example 2

(2R)—N-hydroxy-2-methyl-2-(methylsulfonyl)-4-{2-oxo-4-[(E)-2-phenylvinyl]pyridin-1(2H)-yl}butanamide

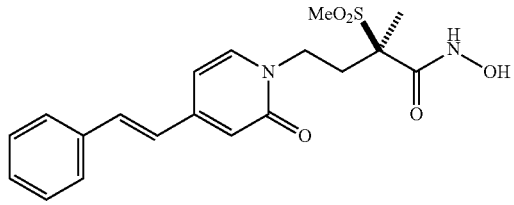 [SMILES: C[C@@](CCn1ccc(/C=C/c2ccccc2)cc1=O)(C(=O)NO)S(C)(=O)=O]

Step A) (2R)-2-methyl-2-(methylsulfonyl)-4-{2-oxo-4-[(E)-2-phenylvinyl]pyridin-1(2H)-yl}-N-(tetrahydro-2H-pyran-2-yloxy)butanamide Pd EnCat™ (133 mg, 0.04 mmol, 0.1 equiv), was added to a mixture of potassium carbonate (166 mg, 1.2 mmol, 3.0 equiv), [(E)-2-phenylvinyl]boronic acid (65 mg, 0.44 mmol, 1.1 equiv), and (2R)-4-(4-iodo-2-oxopyridin-1(2H)-yl)-2-methyl-2-(methylsulfonyl)-N-(tetrahydro-2H-pyran-2-yloxy)butanamide (200 mg, 0.40 mmol), which may be synthesized as described Preparation 2B, in 2:1 1,4-dioxane-water (3.6 mL). The reaction was heated to 80° C. and allowed to stir overnight. The reaction was diluted with ethyl acetate (10 mL), filtered through a pad of Celite, and concentrated under reduced pressure. The crude material was purified by flash chromatography ((1:1-0:1 heptane/ethyl acetate) to provide a white residue (90 mg, 47%). MS (LCMS) m/z 473.7 (M−1).

Step B) (2R)—N-hydroxy-2-methyl-2-(methylsulfonyl)-4-{2-oxo-4-[(E)-2-phenylvinyl]pyridin-1(2H)-yl}butanamide A solution of hydrochloric acid (2.5 mL, 4.0 M in 1,4-dioxane) was added to a solution of (2R)-2-methyl-2-(methylsulfonyl)-4-{2-oxo-4-[(E)-2-phenylvinyl]pyridin-1(2H)-yl}-N-(tetrahydro-2H-pyran-2-yloxy)butanamide (40 mg, 0.084 mmol) in 5:1 dichloromethane-methanol (2.5 mL) at 0°

C. After 4 h, the reaction was concentrated under reduced pressure. The resulting residue was triturated with 1:1 pentane-diethyl ether, filtered, washed with pentane and dried under reduced pressure to provide a light yellow solid (33 mg, 76%). MS (LCMS) m/z 391.4 (M+1). ¹H NMR (400 MHz, METHANOL-d₄) δ ppm 1.69 (s, 3H) 2.30-2.42 (m, 1H) 2.56-2.69 (m, 1H) 3.08 (s, 3H) 3.93-4.06 (m, 1H) 4.32 (td, J=11.76, 4.98 Hz, 1H) 6.75 (s, 1H) 7.00 (d, J=6.24 Hz, 1H) 7.11 (d, J=16.39 Hz, 1H) 7.30-7.42 (m, 3H) 7.47 (d, J=16.39 Hz, 1H) 7.62 (d, J=7.02 Hz, 2H) 7.75 (s, 1H)

Example 3

(2R)-2-methyl-2-(methylsulfonyl)-4-[2-oxo-4-(2-phenylethyl)pyridin-1(2H)-yl]-Netrahydro-2H-pyran-2-yloxy)butanamide

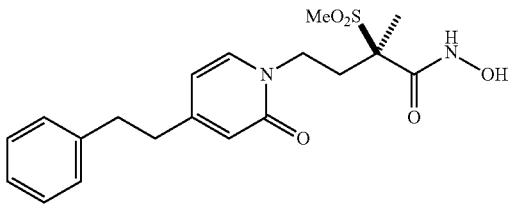 [SMILES: C[C@@](CCn1ccc(CCc2ccccc2)cc1=O)(C(=O)NO)S(C)(=O)=O]

Step A) (2R)-2-methyl-2-(methylsulfonyl)-4-[2-oxo-4-(2-phenylethyl)pyridin-1(2H)-yl]-Netrahydro-2H-pyran-2-yloxy)butanamide Palladium (20 mg, 5% on activated carbon) was added to a nitrogen-purged solution of (2R)-2-methyl-2-(methylsulfonyl)-4-{2-oxo-4-[(E)-2-phenylvinyl]pyridin-1(2H)-yl}-N-(tetrahydro-2H-pyran-2-yloxy)butanamide (50 mg, 0.10 mmol), which may be produced as in Example 2, Step A, and 1,4-cyclohexadiene (0.20 mL, 2.1 mmol, 20.0 equiv) in ethanol (2 mL) at room temperature. The reaction was allowed to stir for 3 days. The mixture was filtered through a plug of silica, washed with ethyl acetate, and the resulting filtrate was concentrated under reduced pressure. The crude material was purified by flash chromatography ((1:1-0:1 heptane/ethyl acetate) to provide a colorless oil (14 mg, 28%). MS (LCMS) m/z 475.7 (M−1).

Step B) (2R)—N-hydroxy-2-methyl-2-(methylsulfonyl)-4-[2-oxo-4-(2-phenylethyl)pyridin-1(2H)-yl]butanamide A solution of hydrochloric acid (1.0 mL, 4.0 M in 1,4-dioxane) was added to a solution of (2R)-2-methyl-2-(methylsulfonyl)-4-[2-oxo-4-(2-phenylethyl)pyridin-1(2H)-yl]-Netrahydro-2H-pyran-2-yloxy)butanamide (14 mg, 0.029 mmol) in 5:1 dichloromethane-methanol (1.2 mL) at 0° C. After 2 h, the reaction was concentrated under reduced pressure. The resulting residue was triturated with 1:1 pentane-dichloromethane, filtered, washed with pentane, and dried under reduced pressure to provide a light pink solid (8 mg, 70%). MS (APCI) m/z 393.3 (M+1). ¹H NMR (400 MHz, DMSO-d₆) δ ppm 1.51 (s, 3H) 2.00-2.14 (m, 1H) 2.24-2.36 (m, 1H) 2.63-2.74 (m, 2H) 2.78-2.88 (m, 2H) 3.06 (s, 3H) 3.58-3.73 (m, 1H) 3.94-4.08 (m, 1H) 6.16-6.26 (m, 2H) 7.11-7.32 (m, 5H) 7.55 (d, J=7.41 Hz, 1H) 11.14 (br s, 1H).

Example 4

(+/−)-4-[4-{4-[3-(4,4-Difluoropiperidin-1-yl)propoxy]phenyl}-2-oxopyridin-1(2H)-yl]-N-hydroxy-2-methyl-2-(methylsulfonyl)butanamide hydrochloride

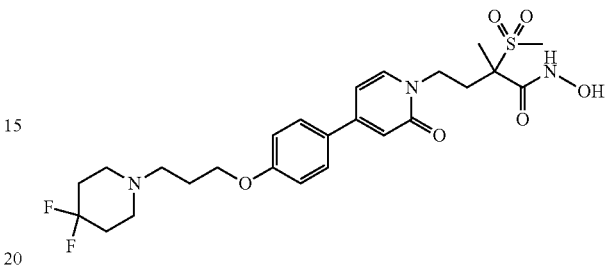

Step A) 1-bromo-4-(3-bromopropoxy)benzene

A suspension of 4-bromophenol (10.0 g, 58 mmol), 1,3-dibromopropane (14.0 g, 69.4 mmol) and potassium carbonate (16.0 g, 116 mmol) in DMF/THF (1:1, 200 mL) was heated to 60° C. over night. The reaction was poured into water and extracted with ether (2×200 mL). The organic layers were combined and washed with water (4×200 mL) and brine (2×200 mL). The organic layer was dried (Na₂SO₄), filtered and concentrated. Upon concentration a white solid precipitated, the solid was removed by filtration. The filtrate was concentrated and purified by flash column chromatography on an Anaolgix SF65-200 g column (hexanes/ethyl acetate 95:5) to afford the title compound as clear oil (6.28 g, 37%). ¹H NMR (400 MHz, CHLOROFORM-d) δ ppm 2.24-2.42 (m, 2H) 3.50-3.64 (m, 2H) 4.08 (t, J=5.66 Hz, 2H) 6.74-6.86 (m, 2H) 6.75-6.84 (m, 2H).

Step B) 1-[3-(4-bromophenoxy)propyl]-4,4-difluoropiperidine

A suspension of 1-bromo-4-(3-bromopropoxy)benzene (1.85 g, 6.29 mmol), 4,4-difluoropiperidine hydrochloride (1.0 g, 6.34 mmol) and potassium carbonate (2.17 g, 15.7 mmol) in acetonitrile (100 mL) was heated to 60° C. overnight, then concentrated in vacuo. The residue was partitioned between ether and saturated aqueous sodium bicarbonate. The layers were separated; the organic layer was washed with saturated aqueous sodium bicarbonate, water and brine. The organic layer was dried (Na₂SO₄), filtered and concentrated. Purification by flash column chromatography on an analogix SF40-80g column (hexanes/ethyl acetate=7:3) afforded the title compound as a clear oil (1.07 g, 50%). LCMS m/z 334.3 (M+1). ¹H NMR (400 MHz, CHLOROFORM-d) δ ppm 1.90-2.08 (m, 6H) 2.47-2.64 (m, 6H) 3.99 (t, J=6.34 Hz, 2H) 6.75-6.81 (m, 2H) 7.34-7.40 (m, 2H).

Step C) 4-[4-{4-[3-(4,4-difluoropiperidin-1-yl)propoxy]phenyl}-2-oxopyridin-1(2H)-yl]-2-methyl-2-(methylsulfonyl)-N-(tetrahydro-2H-pyran-2-yloxy)butanamide Potassium acetate (1.26 g, 12.8 mmol) was added to a suspension of 1-[3-(4-bromophenoxy)propyl]-4,4-difluoropiperidine (1.07 g, 3.20 mmol) in DMF (10 mL). After 10 minutes, bis(pinacolato)diborane (1.220 g, 4.80 mmol) and dichloro 1,1'-bis(diphenylphosphino)ferrocene palladium (II) (261 mg, 0.32 mmol) were added. The resulting suspension was heated to 100° C. After 1 hour the reaction was concentrated and the residue was diluted with ethyl acetate (100 mL) and filtered through celite. The filtrate was washed with saturated aqueous sodium bicarbonate (2×50 mL). The organic layer was dried (Na$_2$SO$_4$), filtered and concentrated. The residue was dissolved in 1,4-dioxane (20 mL). Potassium carbonate (553 mg, 1.00 mmol), (+/−)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2A (500 mg, 1.00 mmol) were added, followed by water (2.0 mL). A clear solution resulted, Pd EnCat™ (513 mg, 0.20 mmol) was added and the resulting suspension was heated overnight at 80° C. After 16 hours the reaction was diluted with ethyl acetate (100 mL) and filtered through celite. The filtrate was concentrated the residue was triturated at room temperature for 1 hour in ethyl acetate/DCM 1:1 and filtered through celite. The filtrate was dried (Na$_2$SO$_4$) and concentrated.

Purification by flash column chromatography on an Analogix SF40-80 g column (DCM/MeOH 98:2-95:5) afforded the title compound as clear oil (213 mg, 34%). LCMS m/z 627.0/542.8 (M+1)

Step D) (+/−)-4-[4-{4-[3-(4,4-difluoropiperidin-1-yl)propoxy]phenyl}-2-oxopyridin-1(2H)-yl]-N-hydroxy-2-methyl-2-(methylsulfonyl)butanamide hydrochloride HCl (4.0 M in 1,4-dioxane, 1.0 mL) was added to a solution of 4-[4-{4-[3-(4,4-difluoropiperidin-1-yl)propoxy]phenyl}-2-oxopyridin-1(2H)-yl]-2-methyl-2-(methylsulfonyl)-N-(tetrahydro-2H-pyran-2-yloxy)butanamide (209 mg, 0.334 mmol) in 1,4-dioxane/water (1:1, 5 mL). After 10 minutes the reaction was concentrated to give a white solid, the solid was triturated with 2-propanol at 50° C. for 1 h. The title compound was isolated by filtration as a white solid (146 mg, the hydrochloride salt, 75%). LCMS m/z 542.8 (M+1)$^1$H NMR (400 MHz, DMSO-d$_6$) δ ppm 1.57 (s, 3H) 2.22 (br. s., 3H) 2.38 (br. s., 5H) 3.11 (s, 3H) 3.13-3.26 (m, 2H) 3.31 (br. s., 2H) 3.74 (br. s., 3H) 4.14 (t, J=5.76 Hz, 3H) 6.59-6.72 (m, 2H) 7.05 (d, J=8.78 Hz, 2H) 7.63-7.79 (m, 3H) 11.03 (br. s., 1H) 11.18 (br. s., 1H)

Example 5

(2R)—N-hydroxy-4-{4-[4-(cis-3-hydroxycyclobutyl)phenyl}-2-oxopyridin-1(2H)-yl]-2-methyl-2-(methylsulfonyl)butanamide

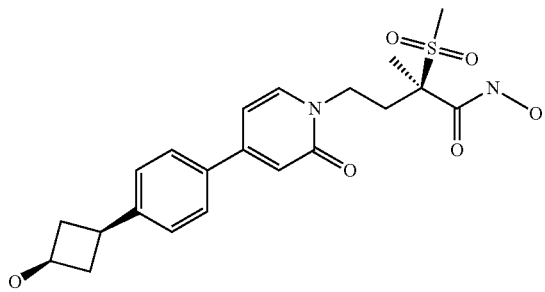 [SMILES: C[C@@](CCn1ccc(-c2ccc([C@H]3C[C@@H](O)C3)cc2)cc1=O)(C(=O)NO)S(C)(=O)=O]

Step A) Cis-3-[4-(4,4,5,5-tetramethyl-1,3,2-dioxaborolan-2-yl)phenyl]cyclobutanol A solution of cis-3-(4-bromophenyl)cyclobutanol (0.500 g, 2.20 mmol), bis(pinacolato)diborane (0.671 g, 2.64 mmol), potassium acetate (0.864 g, 8.81 mmol) and palladium dppf (89.9 mg, 0.110 mmol) in 1,4-dioxane (20 mL) was heated to reflux. After 2 hours the reaction was cooled to room temperature, diluted with ethyl acetate and filtered through celite. The filtrate was concentrated the resulting residue was partitioned between ether and water, an emulsion was removed by filtration. The layers were separated; the organic layer was washed with water (2×) then brine (1×). The organic layer was dried (Na$_2$SO$_4$), filtered and concentrated. Purification by flash column chromatography on a Biotage SNAP cartridge Kp-sil 25 g column (hexanes/ethyl acetate=8:2) afforded the title compound (430 mg) as a clear oil contaminated with 10% cis-3-(4-bromophenyl)cyclobutanol.

Step B) (2R)-4-{4-[4-(cis-3-hydroxycyclobutyl)phenyl]-2-oxopyridin-1(2H)-yl}-2-methyl-2-(methylsulfonyl)-N-(tetrahydro-2H-pyran-2-yloxy)butanamide Water (1.0 mL) was added to a suspension of potassium carbonate (388 mg, 2.81 mmol), (2R)-4-(4-iodo-2-oxopyridin-1(2H)-yl)-2-methyl-2-(methylsulfonyl)-N-[(2R)-tetrahydro-2H-pyran-2-yloxy]butanamide, which may be produced as in Preparation 2B (700 mg, 1.40 mmol), and cis-3-[4-(4,4,5,5-tetramethyl-1,3,2-dioxaborolan-2-yl)phenyl]cyclobutanol (385 mg, 1.40 mmol) in 1,4-dioxane (10 mL). A clear solution resulted. Pd EnCat™ (380 mg, 0.15 mmol) was added and the resulting suspension was heated to 100° C. After 2 hours, the reaction was cooled to room temperature, diluted with ethyl acetate (50 mL) and filtered through celite eluting with ethyl acetate (50 mL). The filtrate was concentrated and the residue was partitioned between dichloromethane and water. The layers were separated, and the aqueous layer was extracted with dichloromethane (3×). The organic layers were combined, dried (Na$_2$SO$_4$), filtered and concentrated. Purification by flash column chromatography on an Analogix SF25-40 g (hexanes/ethyl acetate 1:1-05:95) afforded the title compound as a solid (625 mg, 86%). LCMS m/z 519.2/435.2 (M+1).

Step C) (2R)—N-hydroxy-4-{4-[4-(cis-3-hydroxycyclobutyl)phenyl]-2-oxopyridin-1(2H)-yl}-2-methyl-2-(methylsulfonyl)butanamide HCl (1.0 N in water, 3.58 mL) was added to a solution of (2R)-4-{4-[4-(cis-3-hydroxycyclobutyl)phenyl]-2-oxopyridin-1(2H)-yl}-2-methyl-2-(methylsulfonyl)-N-(tetrahydro-2H-pyran-2-yloxy)butanamide (620 mg, 1.20 mmol) in 1,4-dioxane (10 mL). After 2 hours the reaction was concentrated to give a brown solid. The solid was triturated with ethanol at 50° C., for 30 minutes. After cooling, filtration afforded the title compound as a white solid (384 mg, 74%). LCMS m/z 435.6 (M+1). 1H NMR (400 MHz, DMSO-d$_6$) δ ppm 1.58 (s, 3H) 1.83-1.98 (m, 2H) 2.11-2.24 (m, 1H) 2.44 (d, J=17.95 Hz, 1H) 2.54-2.69 (m, 2H) 2.83-3.00 (m, 1H) 3.11 (s, 3H) 3.65-3.84 (m, 1H) 3.98-4.18 (m, 2H) 6.65 (dd, J=7.02, 2.15 Hz, 1H) 6.69 (d, J=1.95 Hz, 1H) 7.34 (d, J=8.20 Hz, 2H) 7.62-7.71 (m, 2H) 7.74 (d, J=7.02 Hz, 1H) 11.17 (br. s., 1H)

Example 6

(2R)—N-hydroxy-4-{4-[4-(trans-3-hydroxycyclobu-tyl)phenyl]-2-oxopyridin-1(2H)-yl}-2-methyl-2-(methylsulfonyl)butanamide

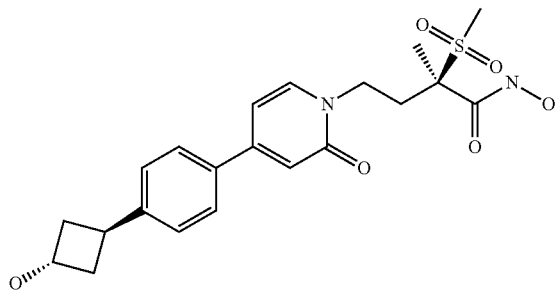 [SMILES: C[C@@](CCn1ccc(-c2ccc([C@H]3C[C@H](O)C3)cc2)cc1=O)(C(=O)NO)S(C)(=O)=O]

Step A) Trans-3-[4-(4,4,5,5-tetramethyl-1,3,2-dioxaborolan-2-yl)phenyl]cyclobutanol A solution of trans-3-(4-bromophenyl)cyclobutanol (0.500 g, 2.20 mmol), bis(pinacolato)diborane (0.671 g, 2.64 mmol), potassium acetate (0.864 g, 8.81 mmol) and [1,1'-bis-(diphenylphosphino)ferrocene]-dichloropalladium (II) dcm complex (89.9 mg, 0110 mmol) in 1,4-dioxane (20 mL) was heated to reflux overnight. After 16 hours the reaction was cooled to room temperature, diluted with ethyl acetate and filtered through celite. The filtrate was concentrated, the resulting residue was partitioned between ether and water, and an emulsion was removed by filtration. The layers in the filtrate were separated; the organic layer was washed with water (2×) then brine (1×). The organic layer was dried (Na$_2$SO$_4$), filtered and concentrated. Purification on a Biotage SNAP cartridge Kp-sil 25 g column (hexanes/ethyl acetate=8:2) afforded the title compound as a clear oil (508 mg, 84%).

$^1$H NMR (400 MHz, CHLOROFORM-d) δ ppm 1.35 (s, 12H) 2.35-2.62 (m, 4H) 3.54-3.71 (m, 1H) 4.49-4.62 (m, 1H) 7.23-7.29 (m, 3H) 7.74-7.80 (m, 2H).

Step B) (2R)-4-{4-[4-(trans-3-hydroxycyclobutyl)phenyl]-2-oxopyridin-1(2H)-yl}-2-methyl-2-(methylsulfonyl)-N-(tetrahydro-2H-pyran-2-yloxy)butanamide Water (1.0) was added to a suspension of potassium carbonate (499 mg, 3.61 mmol), (2R)-4-(4-iodo-2-oxopyridin-1(2H)-yl)-2-methyl-2-(methylsulfonyl)-N-[(2R)-tetrahydro-2H-pyran-2-yloxy]butanamide, which may be produced as in Preparation 2B (900 mg, 1.81 mmol), and trans-3-[4-(4,4,5,5-tetramethyl-1,3,2-dioxaborolan-2-yl)phenyl]cyclobutanol (495 mg, 1.81 mmol) in 1,4-dioxane (10 mL). A clear solution resulted. Pd EnCat™ (482 mg, 0.19 mmol) was added and the resulting suspension was heated to 100° C. After 2 hrs the reaction was cooled to room temperature, diluted with ethyl acetate (50 mL) and filtered through celite eluting with ethyl acetate (50 mL). The filtrate concentrated and the residue was partitioned between dichloromethane and water. The layers were separated and the aqueous layer was extracted with dichloromethane (3×). The organic layers were combined, dried (Na$_2$SO$_4$), filtered and concentrated. Purification on an Analogix SF25-40 g (hexanes/ethyl acetate 1:1-05:95) afforded the title compound as a solid (383 mg, 40%). LCMS m/z 517.8 (M−1).

Step C) (2R)—N-hydroxy-4-{4-[4-(trans-3-hydroxycyclobutyl)phenyl]-2-oxopyridin-1(2H)-yl}-2-methyl-2-(methylsulfonyl)butanamide HCl (1.0 N in water, 2.17 mL) was added to a solution of (2R)-4-{4-[4-(trans-3-hydroxycyclobutyl)phenyl]-2-oxopyridin-1(2H)-yl}-2-methyl-2-(methylsulfonyl)-N-(tetrahydro-2H-pyran-2-yloxy)butanamide (375 mg, 0.723 mmol) in 1,4-dioxane (5 mL). After 1 hour, the reaction was concentrated to give a brown solid. The solid was triturated with 2-propanol at 50° C., for 30 minutes. After cooling, filtration afforded the title compound as a white solid (187 mg, 60%). LCMS m/z 435.6 (M+1). $^1$H NMR (400 MHz, DMSO-d$_6$) δ ppm 1.57 (s, 3H) 2.11-2.23 (m, 1H) 2.26-2.38 (m, 4H) 2.38-2.48 (m, 1H) 3.11 (s, 3H) 3.42-3.60 (m, 1H) 3.74 (td, J=12.00, 4.68 Hz, 1H) 4.00-4.21 (m, 1H) 4.25-4.42 (m, 1H) 6.58-6.72 (m, 2H) 7.36 (d, J=8.20 Hz, 2H) 7.61-7.71 (m, 2H) 7.74 (d, J=7.22 Hz, 1H) 11.17 (br. s., 1H)

Example 7

(2R)—N-hydroxy-4-[4-{4-[(4-hydroxycyclohexyl)oxy]phenyl}-2-oxopyridin-1(2H)-yl]-2-methyl-2-(methylsulfonyl)butanamide

Step A) 8-(4-bromophenoxy)-1,4-dioxaspiro[4.5]decane 1,4-dioxaspiro[4.5]decan-8-ol[ref 1] (3.6 g, 20.8 mmol) was added to a solution of 4-bromophenol (3.00 g, 18.96 mmol) in THF (20 mL). Triphenylphosphine (4.96 g, 18.9 mmol) and triethylamine (1.92 g, 18.9 mmol) were added. The resulting solution was cooled to 0° C. and DIAD (3.83 g, 18.9 mmol) was added by dropwise addition. The reaction was maintained at 0° C. for 30 minutes then warmed to room temperature and stirred over night. The reaction was quenched by addition of water and extracted with ether (2×100 mL). The organic layers were combined and washed with 1N NaOH (2×100 mL), then water (2×100 mL). The organic layer was dried (Na$_2$SO$_4$), filtered and concentrated. Purification by flash column chromatography on an Analogix SF40-150 g column (hexanes/ethyl acetate 8:2) afforded the title compound as a white waxy solid (2.83 g, 47%). $^1$H NMR (400 MHz, CHLOROFORM-d) δ ppm 1.58-1.69 (m, 2H) 1.85-1.98 (m, 6H) 3.92-4.02 (m, 4H) 4.33-4.41 (m, 1H) 6.76-6.84 (m, 2H) 7.33-7.40 (m, 2H)

Ref 1: Journal of Organic Chemistry, 71(22), 8424-8430; 2006

Step B) 4-(4-bromophenoxy)cyclohexanone

1 N HCl$_{(aq)}$ (45 mL) was added to a solution of 8-(4-bromophenoxy)-1,4-dioxaspiro[4.5]decane (2.8 g, 8.94 mmol) in THF (100 mL). The reaction was heated to 50° C. After 1 hour the reaction was cooled to room temperature and neutralized by addition of solid sodium bicarbonate. The reaction was extracted with ether (1×), the resulting organic layer was washed with water, dried (Na$_2$SO$_4$), filtered and concentrated. Purification on a Biotage SNAP cartridge KP Sil 100 g (hexanes/ethyl acetate=9:1) afforded the title compound as a white solid (2.09 g, 87%). $^1$H NMR (400 MHz, CHLOROFORM-d) δ ppm 2.02-2.13 (m, 2H) 2.21-2.41 (m, 4H) 2.61-2.74 (m, 2H) 4.62-4.71 (m, 1H) 6.81-6.89 (m, 2H) 7.37-7.44 (m, 2H)

Step C) 4-(4-bromophenoxy)cyclohexanol

Sodium borohydride (77.3 mg, 2.04 mmol) was added to a solution of 4-(4-bromophenoxy)cyclohexanone (500 mg, 1.86 mmol) in ethanol (10 mL) at room temperature. After 20 minutes the reaction was cooled to 0° C. and quenched by the addition of 1N HCl (aq). The reaction was concentrated and the resulting residue was partitioned between ether and 1N HCl (aq). The layers were separated, the organic layer was washed with water then dried ($Na_2SO_4$), filtered and concentrated. Purification on an Analogix SF15-12g column (hexanes/ethyl acetate=8:2) afforded the title compound as a white solid (360 mg, 72%).

Step D) 4-[4-(4,4,5,5-tetramethyl-1,3,2-dioxaborolan-2-yl)phenoxy]cyclohexanol

A solution of 4-(4-bromophenoxy)cyclohexanol (345 mg, 1.27 mmol), bis(pinacolato)diborane (0.388 g, 1.53 mmol), potassium acetate (0.499 g, 5.09 mmol) and palladium dppf (52.3 mg, 0.064 mmol) in 1,4-dioxane (10 mL) was heated to reflux. After 2 hours the reaction was cooled to room temperature, diluted with ethyl acetate and filtered through celite. The filtrate was concentrated, the resulting residue was partitioned between ether and water, and an emulsion was removed by filtration. The layers in the filtrate were separated and the organic layer was washed with water (2×) then brine (1×). The organic layer was dried ($Na_2SO_4$), filtered and concentrated. Purification on an Analogix SF15-12g column (hexanes/ethyl acetate=8:2) afforded the title compound as a white solid (400 mg, 99%). LCMS m/z 319.6/301.6 (M+1).

Step E) (2R)-4-[4-{4-[(4-hydroxycyclohexyl)oxy]phenyl}-2-oxopyridin-1(2H)-yl]-2-methyl-2-(methylsulfonyl)-N-(tetrahydro-2H-pyran-2-yloxy)butanamide Water (1.0) was added to a suspension of potassium carbonate (352 mg, 2.55 mmol), (2R)-4-(4-iodo-2-oxopyridin-1(2H)-yl)-2-methyl-2-(methylsulfonyl)-N-[(2R)-tetrahydro-2H-pyran-2-yloxy]butanamide, which may be produced as in preparation 2B (634 mg, 1.27 mmol), and 4-[4-(4,4,5,5-tetramethyl-1,3,2-dioxaborolan-2-yl)phenoxy]cyclohexanol (405 mg, 1.27 mmol) in 1,4-dioxane (10 mL). A clear solution resulted. Pd EnCat™ (344 mg, 0.13 mmol) was added and the resulting suspension was heated to 80° C. After 2 hours the reaction was cooled to room temperature, diluted with ethyl acetate (50 mL) and filtered through celite eluting with ethyl acetate (50 mL). The filtrate was concentrated and the residue was partitioned between dichloromethane and water. The layers were separated and the aqueous layer was extracted with dichloromethane (3×). The organic layers were combined, dried ($Na_2SO_4$), filtered and concentrated. Purification by flash column chromatography on an Analogix SF25-40 g (hexanes/ethyl acetate 1:1-05:95) afforded the title compound as solid (444 mg, 62%). LCMS m/z 563.8/479.7 (M+1)

Step F) (2R)—N-hydroxy-4-[4-{4-[(4-hydroxycyclohexyl)oxy]phenyl}-2-oxopyridin-1(2H)-yl]-2-methyl-2-(methylsulfonyl)butanamide HCl (1.0 N in water, 2.37 mL) was added to a solution of the (2R)-4-[4-{4-[(4-hydroxycyclohexyl)oxy]phenyl}-2-oxopyridin-1(2H)-yl]-2-methyl-2-(methylsulfonyl)-N-(tetrahydro-2H-pyran-2-yloxy)butanamide (444 mg, 0.789 mmol) in 1,4-dioxane (5 mL). After 1 hour the reaction was concentrated to give a brown solid. The solid was triturated with ethanol at 50° C., for 30 minutes. After cooling, filtration afforded the title compound as a white solid (203 mg, 54%). LCMS m/z 479.7 (M+1)

Example 8

(2R)—N-hydroxy-4-[4-{4-[(cis-4-hydroxycyclohexyl]methoxyl phenyl}-2-oxopyridin-1(2H)-yl]-2-methyl-2-(methylsulfonyl)butanamide Step A) Ethyl 4-(tetrahydro-2H-pyran-2-yloxy)cyclohexanecarboxylate Pyridinium-4-toluenesulfonate (2.57 g, 10.2 mmol) was added to a solution of ethyl 4-hydroxycyclohexanecarboxylate (8.8 g, 51.10 mmol) and 3,4-dihydro-2H-pyran (8.60 g, 102 mmol) in DCM (200 mL). After 16 hours the reaction was quenched with saturated aqueous sodium bicarbonate. The layers were separated and the organic layer was washed with water. The organic layer was dried ($Na_2SO_4$), filtered and concentrated. Purification by flash column chromatography on an Analogix SF65-200 g column (hexanes/ethyl acetate 95:05-9:1) afforded the title compound (clear oil) as a mixture of isomers (11.1 g, 85%).

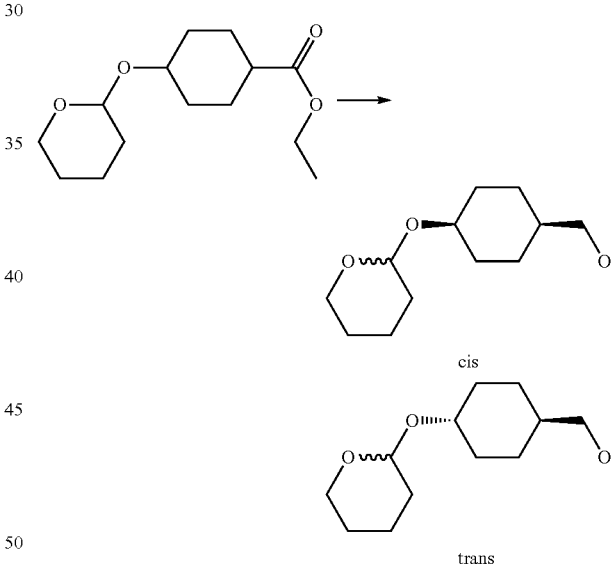

cis trans

Step B) (+/−)-[cis-4-(tetrahydro-2H-pyran-2-yloxy)cyclohexyl]methanol and (+/−)-[trans-4-(tetrahydro-2H-pyran-2-yloxy)cyclohexyl]methanol Sodium borohydride (3.69 g, 97.5 mmol) was added to a solution of ethyl 4-(tetrahydro-2H-pyran-2-yloxy)cyclohexanecarboxylate (2.50 g, 9.75 mmol) in ethanol (100 mL) at 0° C. The reaction was allowed to warm to room temperature as the ice bath expired. After 2 days the reaction was cooled to 0° C. and quenched by addition of 1N HCl until the effervescence ceased (pH 5-6). The reaction was concentrated and the resulting residue was partitioned between ethyl acetate and water. The layers were separated and the aqueous layer was extracted with ethyl acetate (1×). The organic layers were combined, dried (MgSO$_4$), filtered and concentrated. Purification on a Biotage SNAP cartridge Kp-sil 100 g column (hexanes/ethyl acetate=9:1-6:4) afforded the cis and trans cyclohexylmethanols as clear oils.

(+/−)-[cis-4-(tetrahydro-2H-pyran-2-yloxy)cyclohexyl]methanol (387 mg, 18%)

$^1$H NMR (400 MHz, CHLOROFORM-d) δ ppm 1.30-1.65 (m, 12H) 1.64-1.76 (m, 1H) 1.76-1.94 (m, 3H) 3.33-3.64 (m, 3H) 3.80-4.01 (m, 2H) 4.59-4.75 (m, 1H).

(+/−)-[trans-4-(tetrahydro-2H-pyran-2-yloxy)cyclohexyl]methanol $^1$H NMR (400 MHz, CHLOROFORM-d) δ ppm 0.86-1.11 (m, 2H) 1.16-1.31 (m, 1H) 1.31-1.64 (m, 7H) 1.64-1.77 (m, 1H) 1.78-1.93 (m, 3H) 1.99-2.14 (m, 2H) 3.35-3.67 (m, 4H) 3.80-4.04 (m, 1H) 4.63-4.79 (m, 1H).

Step C) (+/−)-2-({cis-4-[(4-bromophenoxy)methyl]cyclohexyl}oxy)tetrahydro-2H-pyran 4-Bromophenol (0.344 g, 2.0 mmol) was added to a solution of (+/−)-[cis-4-(tetrahydro-2H-pyran-2-yloxy)cyclohexyl]methanol (0.387 g, 1.81 mmol) in THF (10 mL). Triphenylphosphine (0.474 g, 1.81 mmol) and triethylamine (0.183 g, 1.81 mmol) were added. The resulting solution was cooled to 0° C. and DIAD (0.365 g, 1.81 mmol) was added by dropwise addition. After 18 hours the reaction was quenched by addition of water and extracted with ether (2×100 mL). The organic layers were combined and washed with 1N NaOH (2×100 mL) then water (2×100 mL). The organic layer was dried (MgSO$_4$), filtered and concentrated to give a clear oil. Purification by flash column chromatography on a Biotage SNAP cartridge Kp-sil 100 g column (hexanes/ethyl acetate 9:1) afforded the title compound as a white solid (324 mg, 48%). $^1$H NMR (400 MHz, CHLOROFORM-d) δ ppm 1.41-1.75 (m, 11H) 1.75-1.98 (m, 4H) 3.39-3.54 (m, 1H) 3.70-3.80 (m, 2H) 3.83-3.97 (m, 2H) 4.55-4.69 (m, 1H) 6.66-6.82 (m, 2H) 7.29-7.42 (m, 2H).

Step D) (+/−)-2-[(cis-4-{[4-(4,4,5,5-tetramethyl-1,3,2-dioxaborolan-2-yl)phenoxy]methyl}cyclohexyl)oxy]tetrahydro-2H-pyran A solution of (+/−)-2-({cis-4-[(4-bromophenoxy)methyl]cyclohexyl}oxy)tetrahydro-2H-pyran (0.3 g, 0.812 mmol), bis(pinacolato)diborane (0.247 g, 0.974 mmol), potassium acetate (0.319 g, 3.25 mmol) and [1,1'-bis-(diphenylphosphino)ferrocene]-dichloropalladium (II) dcm complex (33.5 mg, 0.041 mmol) in 1,4-dioxane (10 mL) was heated to reflux. After 28 hours the reaction was concentrated. The residue was partitioned between ether and water, an emulsion was removed by filtration. The layers in the filtrate were separated. The organic layer was washed with water (2×) then brine (1×). The organic layer was dried (Na$_2$SO$_4$), filtered and concentrated. Purification on a Biotage SNAP cartridge Kp-sil 10 g column (hexanes/ethyl acetate 95:5) afforded the title compound as a white solid (190 mg, 56%). $^1$H NMR (400 MHz, CHLOROFORM-d) δ ppm 1.30-1.38 (m, 12H) 1.39-1.78 (m, 11H) 1.78-1.97 (m, 4H) 3.44-3.56 (m, 1H) 3.84 (dd, J=6.74, 1.66 Hz, 2H) 3.88-4.00 (m, 2H) 4.61-4.75 (m, 1H) 6.85-6.94 (m, 2H) 7.67-7.80 (m, 2H)

Step E) (2R)-2-methyl-2-(methylsulfonyl)-4-[2-oxo-4-(4-{[cis-4-(tetrahydro-2H-pyran-2-yloxy)cyclohexyl]methoxy}phenyl)pyridin-1(2H)-yl]-Netrahydro-2H-pyran-2-yloxy)butanamide Water (1.0) was added to a suspension of potassium carbonate (116 mg, 0.842 mmol), (2R)-4-(4-iodo-2-oxopyridin-1(2H)-yl)-2-methyl-2-(methylsulfonyl)-N-[(2R)-tetrahydro-2H-pyran-2-yloxy]butanamide, which may be produced as in Preparation 2B (210.0 mg, 4.21 mmol), and (+/−)-2-[(cis-4-{[4-(4,4,5,5-tetramethyl-1,3,2-dioxaborolan-2-yl)phenoxy]methyl}cyclohexyl)oxy]tetrahydro-2H-pyran (175 mg, 4.21 mmol) in 1,4-dioxane (10 mL). A clear solution resulted. Pd EnCat™ (113 mg, 0.044 mmol) was added and the resulting suspension was heated to 100° C. After 1 hour the reaction was cooled to room temperature, diluted with ethyl acetate (50 mL) and filtered through celite eluting with ethyl acetate (50 mL). The filtrate was concentrated and the residue was partitioned between ethyl acetate and brine. The layers were separated and the aqueous layer was extracted with ethyl acetate (3×). The organic layers were combined, dried (Na$_2$SO$_4$), filtered and concentrated. Purification on an Analogix SF15-12 g column (hexanes/ethyl acetate=1:9) afforded the title compound as solid (140 mg, 50%). LCMS m/z 659.8 (M−1).

Step F) (2R)—N-hydroxy-4-[4-{4-[(cis-4-hydroxycyclohexyl)methoxy]phenyl}-2-oxopyridin-1(2H)-yl]-2-methyl-2-(methylsulfonyl)butanamide HCl (1.0 N in water, 1.02 mL) was added to a solution of (2R)-2-methyl-2-(methylsulfonyl)-4-[2-oxo-4-(4-{[cis-4-(tetrahydro-2H-pyran-2-yloxy)cyclohexyl]methoxy}phenyl)pyridin-1(2H)-yl]-Netrahydro-2H-pyran-2-yloxy)butanamide (135 mg, 0.204 mmol) in 1,4-dioxane (5.0 mL). After 1 hour the reaction was concentrated to give a white solid. The solid was triturated with ethanol at 50° C., for 30 minutes. After cooling, filtration afforded the title compound as a white solid (90 mg, 90%). LCMS m/z 493.7 (M+1). $^1$H NMR (400 MHz, DMSO-d$_6$) δ ppm 1.38-1.70 (m, 12H) 1.79 (br. s., 1H) 2.09-2.24 (m, 1H) 2.42 (ddd, J=13.07, 11.12, 4.68 Hz, 1H) 3.12 (s, 3H) 3.68-3.83 (m, 2H) 3.87 (d, J=6.63 Hz, 2H) 4.10 (d, J=6.44 Hz, 1H) 6.55-6.75 (m, 2H) 6.94-7.10 (m, 2H) 7.61-7.80 (m, 3H) 11.15 (br. s., 1H)

Example 9

(2R)—N-hydroxy-4-[4-{4-[(trans-4-hydroxycyclohexyl)methoxy]phenyl}-2-oxopyridin-1(2H)-yl]-2-methyl-2-(methylsulfonyl)butanamide

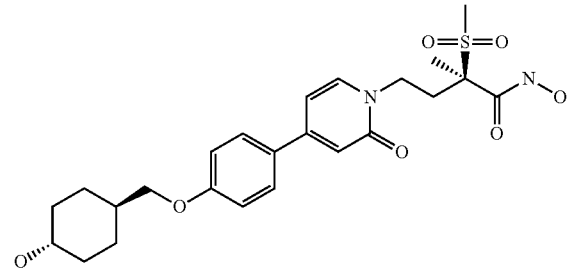 [SMILES: C[C@@](CCn1ccc(-c2ccc(OC[C@H]3CC[C@H](O)CC3)cc2)cc1=O)(C(=O)NO)S(C)(=O)=O]

Step A) (+/−)-2-({trans-4-[(4-bromophenoxy)methyl]cyclohexyl}oxy)tetrahydro-2H-pyran The title compound (987 mg, 70.3%) was prepared from (+/−)-[trans-4-(tetrahydro-2H-pyran-2-yloxy)cyclohexyl] methanol (815 mg, 3.80 mmol) and 4-bromophenol (0.724 g, 4.18 mmol) by a procedure analogous to that described for (+/−)-2-({cis-4-[(4-bromophenoxy)methyl]cyclohexyl}oxy)tetrahydro-2H-pyran, Example 8, Step C. $^1$H NMR (400 MHz, CHLOROFORM-d) δ ppm 1.02-1.35 (m, 3H) 1.36-1.64 (m, 5H) 1.66-1.90 (m, 3H) 1.90-2.01 (m, 2H) 2.02-2.18 (m, 2H) 3.51 (dt, J=11.02, 5.22 Hz, 1H) 3.61 (tt, J=10.98, 4.24 Hz, 1H) 3.68-3.78 (m, 2H) 3.88-4.00 (m, 1H) 4.68-4.79 (m, 1H) 6.71-6.82 (m, 2H) 7.31-7.42 (m, 2H)

Step B) (+/−)2-[(trans-4-{[4-(4,4,5,5-tetramethyl-1,3,2-dioxaborolan-2-yl)phenoxy]methyl}cyclohexyl)oxy]tetrahydro-2H-pyran The title compound (624 mg, 61.5 mmol) was prepared from (+/−)-2-({trans-4-[(4-bromophenoxy)methyl]cyclohexyl}oxy)tetrahydro-2H-pyran (900 mg, 2.44 mmol) and bis(pinacolato)diborane (742 mg, 2.92 mmol) by a procedure analogous to that described for (+/−)-2-[(cis-4-{[4-(4,4,5,5-tetramethyl-1,3,2-dioxaborolan-2-yl)phenoxy]methyl}cyclohexyl)oxy]tetrahydro-2H-pyran, Example 8, Step D. $^1$H NMR (400 MHz, CHLOROFORM-d) δ ppm 1.03-1.63 (m, 20H) 1.65-1.90 (m, 3H) 1.90-2.01 (m, 2H) 2.03-2.15 (m, 2H) 3.45-3.55 (m, 1H) 3.55-3.67 (m, 1H) 3.72-3.85 (m, 2H) 3.89-3.97 (m, 1H) 4.70-4.79 (m, 1H) 6.88 (d, J=8.78 Hz, 2H) 7.74 (d, J=8.78 Hz, 2H)

Step C) (2R)-2-methyl-2-(methylsulfonyl)-4-[2-oxo-4-(4-{[trans-4-(tetrahydro-2H-pyran-2-yloxy)cyclohexyl]methoxy}phenyl)pyridin-1(2H)-yl]-N-tetrahydro-2H-pyran-2-yloxy)butanamide The title compound (489 mg, 49.7%) was prepared from (2R)-4-(4-iodo-2-oxopyridin-1(2H)-yl)-2-methyl-2-(methylsulfonyl)-N-[(2R)-tetrahydro-2H-pyran-2-yloxy]butanamide (742 mg, 1.49 mmol) and 2-[(trans-4-{[4-(4,4,5,5-tetramethyl-1,3,2-dioxaborolan-2-yl)phenoxy]methyl}cyclohexyl)oxy]tetrahydro-2H-pyran (620 mg, 1.49 mmol) by a procedure analogous to that described for (2R)-2-methyl-2-(methylsulfonyl)-4-[2-oxo-4-(4-{[cis-4-(tetrahydro-2H-pyran-2-yloxy)cyclohexyl]methoxy}phenyl)pyridin-1(2H)-yl]-N-tetrahydro-2H-pyran-2-yloxy)butanamide, Example 8, Step E. LCMS m/z 659.8 (M−1).

Step D) (2R)—N-hydroxy-4-[4-{4-[(trans-4-hydroxycyclohexyl)methoxy]phenyl}-2-oxopyridin-1(2H)-yl]-2-methyl-2-(methylsulfonyl)butanamide The title compound (300 mg, 83%) was prepared from (2R)-2-methyl-2-(methylsulfonyl)-4-[2-oxo-4-(4-{[trans-4-(tetrahydro-2H-pyran-2-yloxy)cyclohexyl]methoxy}phenyl)pyridin-1(2H)-yl]-N-tetrahydro-2H-pyran-2-yloxy)butanamide (480 mg, 0.726 mmol) by a procedure analogous to that described for (2R)—N-hydroxy-4-[4-{4-[(cis-4-hydroxycyclohexyl)methoxy]phenyl}-2-oxopyridin-1(2H)-yl]-2-methyl-2-(methylsulfonyl)butanamide Example 8, Step F. LCMS m/z 493.7 (M+1) $^1$H NMR (400 MHz, DMSO-d$_6$) δ ppm 0.92-1.23 (m, 4H) 1.54 (s, 3H) 1.58-1.72 (m, 1H) 1.81 (br. s., 4H) 2.06-2.21 (m, 1H) 2.41 (s, 1H) 3.08 (s, 3H) 3.25-3.41 (m, 1H) 3.74 (br. s., 1H) 3.80 (d, J=6.44 Hz, 2H) 3.98-4.17 (m, 1H) 6.48-6.71 (m, 2H) 6.85-7.06 (m, 2H) 7.52-7.78 (m, 3H) 11.15 (s, 1H)

Example 10

(2R)-4-[4-{2-Fluoro-4-[(trans-4-hydroxycyclohexyl)methoxy]phenyl}-2-oxopyridin-1(2H)-yl]-N-hydroxy-2-methyl-2-(methylsulfonyl)butanamide

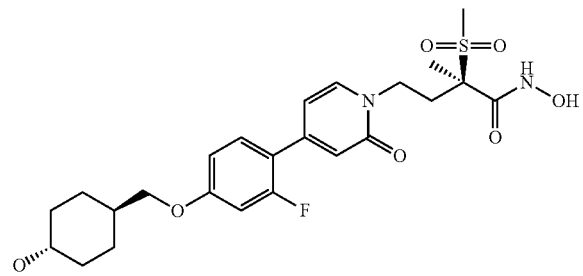 [SMILES: C[C@@](CCn1ccc(-c2ccc(OC[C@H]3CC[C@H](O)CC3)cc2F)cc1=O)(C(=O)NO)S(C)(=O)=O]

Step A) (+/−)-2-({trans-4-[(4-bromo-3-fluorophenoxy)methyl]cyclohexyl}oxy)tetrahydro-2H-pyran The title compound (885 mg, 81.6%) was prepared from (+/−)-[trans-4-(tetrahydro-2H-pyran-2-yloxy)cyclohexyl] methanol (600 mg, 2.80 mmol) and 4-bromo-3-fluorophenol (588 mg, 3.08 mmol) by a procedure analogous to that described for (+/−)-2-({cis-4-[(4-bromophenoxy)methyl]cyclohexyl}oxy)tetrahydro-2H-pyran in Example 8, Step C. $^1$H NMR (400 MHz, CHLOROFORM-d) δ ppm 1.03-1.21 (m, 2H) 1.21-1.36 (m, 1H) 1.35-1.50 (m, 1H) 1.49-1.66 (m, 4H) 1.65-1.99 (m, 5H) 2.03-2.17 (m, 2H) 3.44-3.55 (m, 1H) 3.60 (tt, J=10.98, 4.24 Hz, 1H) 3.72 (d, J=6.24 Hz, 2H) 3.86-4.00 (m, 1H) 4.70-4.80 (m, 1H) 6.59 (ddd, J=8.88, 2.83, 0.98 Hz, 1H) 6.68 (dd, J=10.54, 2.73 Hz, 1H) 7.35-7.44 (m, 1H)

Step B) (+/−)-2-[(trans-4-{[3-fluoro-4-(4,4,5,5-tetramethyl-1,3,2-dioxaborolan-2-yl)phenoxy]methyl}cyclohexyl)oxy]tetrahydro-2H-pyran The title compound (366 mg, 37.1%) was prepared from (+/−)-2-({trans-4-[(4-bromo-3-fluorophenoxy)methyl]cyclohexyl}oxy)tetrahydro-2H-pyran (0.88 g, 2.27 mmol) and bis(pinacolato)diborane (0.692 g, 2.73 mmol) by a procedure analogous to that described for (+/−)-2-[(cis-4-{[4-(4,4,5,5-tetramethyl-1,3,2-dioxaborolan-2-yl)phenoxy]methyl}cyclohexyl)oxy]tetrahydro-2H-pyran in Example 8, Step D. $^1$H NMR (400 MHz, CHLOROFORM-d) δ ppm 1.03-1.31 (m, 3H) 1.35 (s, 12H) 1.37-1.47 (m, 1H) 1.47-1.64 (m, 4H) 1.65-1.90 (m, 3H) 1.94 (dd, J=13.27, 2.93 Hz, 2H) 2.04-2.15 (m, 2H) 3.41-3.55 (m, 1H) 3.55-3.66 (m, 1H) 3.76 (d, J=6.44 Hz, 2H) 3.88-3.99 (m, 1H) 4.70-4.78 (m, 1H) 6.55 (dd, 1H) 6.67 (dd, J=8.39, 2.34 Hz, 1H) 7.64 (dd, J=8.29, 7.32 Hz, 1H)

Step C) (2R)-4-[4-(2-fluoro-4-{[trans-4-(tetrahydro-2H-pyran-2-yloxy)cyclohexyl]methoxy}phenyl)-2-oxopyridin-1(2H)-yl]-2-methyl-2-(methylsulfonyl)-N-(tetrahydro-2H-pyran-2-yloxy)butanamide The title compound (366 mg, 65.5 mmol) was prepared from (2R)-4-(4-iodo-2-oxopyridin-1(2H)-yl)-2-methyl-2-

(methylsulfonyl)-N-[(2R)-tetrahydro-2H-pyran-2-yloxy]butanamide (0.410 g, 8.23 mmol) and (+/−)-2-[(trans-4-{[3-fluoro-4-(4,4,5,5-tetramethyl-1,3,2-dioxaborolan-2-yl)phenoxy]methyl}cyclohexyl)oxy]tetrahydro-2H-pyran (0.358 g, 8.23 mmol) by a procedure analogous to that described for (2R)-2-methyl-2-(methylsulfonyl)-4-[2-oxo-4-(4-{[cis-4-(tetrahydro-2H-pyran-2-yloxy)cyclohexyl]methoxy}phenyl)pyridin-1(2H)-yl]-Netrahydro-2H-pyran-2-yloxy)butanamide Example 8, Step E. LCMS m/z 677.8 (M−1)

Step D) Preparation of (2R)-4-[4-{2-fluoro-4-[(trans-4-hydroxycyclohexyl)methoxy]phenyl}-2-oxopyridin-1(2H)-yl]-N-hydroxy-2-methyl-2-(methylsulfonyl) butanamide The title (0.16 g, 62.6%) compound was prepared from (2R)-4-[4-{2-fluoro-4-{[trans-4-(tetrahydro-2H-pyran-2-yloxy)cyclohexyl]methoxy}phenyl)-2-oxopyridin-1(2H)-yl]-2-methyl-2- (methylsulfonyl)-N-(tetrahydro-2H-pyran-2-yloxy)butanamide (0.35 g, 0.516 mmol) by a procedure analogous to that described for (2R)—N-hydroxy-4-[4-{4-[(cis-4-hydroxycyclohexyl)methoxy]phenyl}-2-oxopyridin-1(2H)-yl]-2-methyl-2-(methylsulfonyl)butanamide, Example 8, Step F. LCMS m/z 511.7 (M+1) $^1$H NMR (400 MHz, DMSO-d$_6$) δ ppm 0.94-1.25 (m, 4H) 1.57 (s, 3H) 1.60-1.75 (m, 1H) 1.83 (br. s., 4H) 2.08-2.24 (m, 1H) 2.35-2.48 (m, 1H) 3.11 (s, 3H) 3.28-3.44 (m, 1H) 3.65-3.80 (m, 1H) 3.84 (d, J=6.64 Hz, 2H) 4.01-4.22 (m, 1H) 6.47 (dt, J=7.18, 1.88 Hz, 1H) 6.53 (s, 1H) 6.87 (dd, J=8.79, 2.54 Hz, 1H) 6.94 (dd, J=13.38, 2.44 Hz, 1H) 7.51 (t, J=8.98 Hz, 1H) 7.71 (d, J=7.23 Hz, 1H) 9.24 (br. s., 1H) 11.15 (s, 1H)

Examples 10A-10N

The following compounds can be prepared by the procedures described in Example 6 through Example 10 where the appropriate alcohol or protected derivative thereof is employed. Methods used to describe the synthesis of the precursor are analogously known to those skilled in the art.

TABLE 2

| Example number | IUPACNAME | Retention Time | Mass ion[1] | Purity | NMR |
|---|---|---|---|---|---|
| 10-A | (2R)-N-hydroxy-4-[4-{4-[(4-hydroxy-4-methylcyclohexyl)oxy]phenyl}-2-oxopyridin-1(2H)-yl]-2-methyl-2-(methylsulfonyl)butanamide | Purity <80% UV-215 m/z Impurity: 467.0 0.46 | 493 | 79 | $^1$H NMR (400 MHz, DMSO-d$_6$) d ppm 1.10 (s, 3 H) 1.36-1.46 (m, 2 H) 1.54 (s, 3 H) 1.57-1.62 (m, 2 H) 1.68-1.76 (m, 2 H) 2.08-2.15 (m, 1 H) 2.32-2.40 (m, 1 H) 3.08 (s, 3 H) 3.33-3.42 (m, 1 H) 3.66-3.75 (m, 1 H) 3.95-4.04 (m, 1 H) 4.04-4.13 (m, 1 H) 4.27-4.36 (m, 1 H) 6.61 (s, 2 H) 7.00 (s, 2 H) 7.51-7.60 (m, 1 H) 7.67-7.68 (m, 1 H) 7.69-7.75 (m, 1 H) |
| 10-B | (2R)-N-hydroxy-4-[4-{4-[(3-hydroxy-3-methylcyclobutyl)methoxy]phenyl}-2-oxopyridin-1(2H)-yl[-2-methyl-2-(methylsulfonyl)butanamide | 0.46 | 479 | 90 | 1H NMR (CD3OD, 400MHz), 7.65 (1H, d), 7.62 (1H, d), 7.00 (1H, d), 6.74-6.72 (2H, m), 4.30-4.23 (1H, m), 4.00 (2H, d), 3.93-3.86 (1H, m), 3.09 (3H, s), 2.59-2.51 (1H, m), 2.40-2.28 (2H, m), 2.18-2.13 (2H, m), 1.99-1.93 (2H, m), 1.69 (3H, s), 1.36 (3H, s) ppm. |
| 10-C | (2R)-4-{4-[4-(3-cyanopropoxy)phenyl]-2-oxopyridin-1(2H)-y}-N-hydroxy-2-methyl-2-(methylsulfonyl)butanamide | Purity <80% UV-215 m/z Impurity: 279.1 0.45 | 448 | 77 | 1H NMR (400 MHz, DMSO-d6) d ppm 1.57 (s, 3 H) 2.00 - 2.09 (m, J = 6.54, 6.54, 6.54, 6.54 Hz, 2 H) 2.17 (td, J = 12.20, 5.46 Hz, 1 H) 2.42 (td, J = 12.44, 4.59 Hz, 1 H) 2.67 (t, J = 7.12 Hz, 2 H) 3.11 (s, 3 H) 3.74 (dd, J = 11.42, 7.51 Hz, 1 H) 4.10 (t, J = 6.05 Hz, 4 H) 6.60-6.67 (m, 2 H) 7.05 (d, J = 8.59 Hz, 2 H) 7.56 (dd, J = 7.22, 3.71 Hz, 1 H) 7.58-7.66 (m, 1 H) 7.62 (d, J = 4.88 Hz, 1 H) 7.70 (d, J = 8.59 Hz, 2 H) |
| 10-D | (2R)-N-hydroxy-4-[4-(4-{[3-(hydroxymethyl)cyclobutyl]methoxy}phenyl)-2-oxopyridin-1(2H)-yl]-2-methyl-2-(methylsulfonyl)butanamide | 0.46 | 479 | 100 | 1H NMR (400 MHz, DMSO-d6) d ppm 1.56 (s, 3 H) 1.75-1.92 (m, 2 H) 2.01-2.09 (m, 1 H) 2.09-2.22 (m, 1 H) 2.24-2.45 (m, 2 H) 2.52-2.69 (m, 1 H) 3.10 (s, 2 H) 3.37-3.46 (m, 1 H) 3.65-3.78 (m, 1 H) 3.89-3.98 (m, 1 H) 4.02 (d, J = 0.78 Hz, 2 H) 4.05-4.16 (m, 1 H) 4.38-4.54 (m, 1 H) 6.64 (s, 2 H) 7.01 (s, 2 H) 7.65 (s, 3 H) 9.14-9.32 (m, 1 H) |

TABLE 2-continued

| Example number | IUPACNAME | Retention Time | Mass ion[1] | Purity | NMR |
|---|---|---|---|---|---|
| 10-E | N-hydroxy-4-[4-{4-[(4-hydroxy-4-methylpentyl)oxy]phenyl}-2-oxopyridin-1(2H)-yl]-2-methyl-2-(methylsulfonyl)butanamide | Purity <80% UV-215 m/z Impurity: 499.1 0.45 | 481 | 80 | $^1$H NMR (400 MHz, METHANOL-$d_4$) d ppm 1.21 (s, 6 H) 1.60-1.69 (m, 2 H) 1.70 (s, 3 H) 1.82-2.03 (m, 2 H) 2.34-2.46 (m, 1 H) 2.60-2.74 (m, 1 H) 4.00-4.13 (m, 3 H) 4.31-4.44 (m, 1 H) 6.97 (s, 1 H) 7.01-7.12 (m, 3 H) 7.71 (d, J = 8.79 Hz, 2 H) 7.89 (d, J = 7.03 Hz, 1 H) |
| 10-F | N-hydroxy-4-(4-{[3-(hydroxymethyl)cyclobutyl]oxy}phenyl)-2-oxopyridin-1(2H)-yl]-2-methyl-2-(methylsulfonyl)butanamide | 0.41 | 465 | 100 | $^1$H NMR (400 MHz, METHANOL-$d_4$) d ppm 1.71 (s, 3 H) 2.20-2.55 (m, 7 H) 2.66-2.77 (m, 1 H) 3.07 (s, 3 H) 3.62 (d, J = 6.44 Hz, 2 H) 4.07-4.19 (m, 1 H) 4.36-4.48 (m, 1 H) 4.76-4.84 (m, 1 H) 6.95 (d, J = 8.59 Hz, 2 H) 7.05 (s, 1 H) 7.20 (d, J = 6.63 Hz, 1 H) 7.72 (d, J = 8.78 Hz, 2 H) 7.98 (d, J = 6.83 Hz, 1 H) |
| 10-G | (2R)-N-hydroxy-4-[4-{4-[(4-hydroxy-4-methylcyclohexyl)oxy]phenyl}-2-oxopyridin-1(2H)-yl]-2-methyl-2-(methylsulfonyl)butanamide | 0.47 | 493 | 100 | $^1$H NMR (400 MHz, DMSO-$d_6$) d ppm 1.07 (br. s., 4 H) 1.54 (s, 3 H) 1.59-1.70 (m, 1 H) 1.72-1.92 (m, 4 H) 2.05-2.24 (m, 1 H) 2.31-2.43 (m, 1 H) 3.06 (s, 3 H) 3.23-3.41 (m, 1 H) 3.61-3.74 (m, 1 H) 3.80 (s, 3 H) 4.01-4.16 (m, 1 H) 6.60 (ddd, 2 H) 6.97 (dd, 2 H) 7.56-7.74 (m, 3 H) 11.16 (s, 1 H) |
| 10-H | (2R)-N-hydroxy-4-[4-(4-{[3-(1-hydroxy-1-methylethyl)cyclobutyl]oxy}phenyl)-2-oxopyridin-1(2H)-yl]-2-methyl-2-(methylsulfonyl)butanamide | 0.51 | 493 | 100 | 1H NMR (400 MHz, DMSO-d6) d ppm 1.01 (s, 3 H) 1.06 (s, 3 H) 1.56 (s, 3 H) 1.80-2.22 (m, 3 H) 2.23-2.48 (m, 3 H) 3.10 (s, 3 H) 3.67-3.80 (m, 1 H) 4.04-4.15 (m, 1 H) 4.17-4.37 (m, 1 H) 4.49-4.74 (m, 1 H) 6.55-6.70 (m, 2 H) 6.81-7.01 (m, 2 H) 7.56-7.78 (m, 3 H) |
| 10-I | (2R)-4-[4-{3-fluoro-4-[(4-hydroxy-4-methylcyclohexyl)oxy]phenyl}-2-oxopyridin-1(2H)-yl]-N-hydroxy-2-methyl-2-(methylsulfonyl)butanamide | 0.48 | 511 | 100 | 1H NMR (CD3OD, 400 HHZ), 7.77 (1H, d), 7.49-7.43 (2H, m), 7.20 (1H, t), 6.74-6.70 (2H,m), 4.64-4.59 (1H, m), 4.31-4.23 (1H, m), 3.94-3.87 (1H, m), 3.09 (3H, s), 2.60-2.52 (1H, m), 2.39-2.32 (1H, m), 2.03-1.95 (2H, m), 1.81-1.74 (4H, m), 1.69 (3H, s), 1.54-1.48 (2H, m), 1.32-1.26 (1H, m), 1.24 (3H, s) ppm. |
| 10-J | N-hydroxy-4-{4-[4-(2-hydroxy-2-methylpropoxy)phenyl]-2-oxopyridin-1(2H)-yl}-2-methyl-2-(methylsulfonyl)butanamide | 0.4 | 453 | 100 | $^1$H NMR (400 MHz, METHANOL-$d_4$) d ppm 1.32 (s, 6 H) 1.70 (s, 3 H) 2.32-2.47 (m, 1 H) 2.60-2.74 (m, 1 H) 3.08 (s, 3 H) 3.85 (s, 2 H) 4.00-4.13 (m, 1 H) 4.31-4.45 (m, 1 H) 6.97 (s, 1 H) 7.03-7.14 (m, 3 H) 7.72 (d, J = 8.79 Hz, 2 H) 7.89 (d, J = 6.83 Hz, 1 H) |
| 10-K | (2R)-4-[4-{4-[(3,4-dihydroxy-4-methylpentyl)oxy]phenyl}-2-oxopyridin-1(2H)-yl]-N-hydroxy-2-methyl-2-(methylsulfonyl)butanamide | 0.42 | 497 | 100 | $^1$H NMR (400 MHz, DMSO-$d_6$) d ppm 1.03 (s, 3 H) 1.09 (s, 3 H) 1.50-1.64 (m, 1 H) 1.57 (s, 3 H) 1.99-2.10 (m, 1 H) 2.12-2.22 (m, 1 H) 2.36-2.46 (m, 1 H) 3.11 (s, 3 H) 3.27-3.41 (m, 2 H) 3.73 (td, J = 11.95, 4.59 Hz, 1 H) 4.04-4.20 (m, 3 H) 4.53 (br. s., 1 H) 6.61-6.67 (m, 2 H) 7.02 (d, J = 8.78 Hz, 2 H) 7.65-7.74 (m, 3 H) 9.24 (br. s., 1 H) 11.19 (s, 1 H) |

TABLE 2-continued

| Example number | IUPACNAME | Retention Time | Mass ion[1] | Purity | NMR |
|---|---|---|---|---|---|
| 10-L | (2R)-4-[4-{2-fluoro-4-[(cis-4-hydroxycyclohexyl)methoxy]phenyl}-2-oxopyridin-1(2H)-yl]-N-hydroxy-2-methyl-2-(methylsulfonyl)butanamide | 0.51 | 511 | 100 | 1H NMR (CD3OD, 400 HHZ), 7.66 (1H, d), 7.47 (1H, t), 6.86 (1H, dd), 6.81 (1H, dd), 6.71 (1H, s), 6.64 (1H, d), 4.33-4.25 (1H, m), 3.96-3.90 (2H, m), 3.87 (2H, d), 3.10 (3H, s), 2.61-2.52 (1H, m), 2.41-2.32 (1H, m), 1.90-1.81 (1H, m), 1.78-1.72 (2H, m), 1.69 (3H, s), 1.65-1.55 (6H, m) ppm. |

Foot note
[1]-Mass Spec.-See Method A as described in Table 5 infra.

Example 11

(2R)—N-Hydroxy-2-methyl-2-(methylsulfonyl)-4-(2-oxo-4-phenylpyridin-1(2H)-yl)butanamide

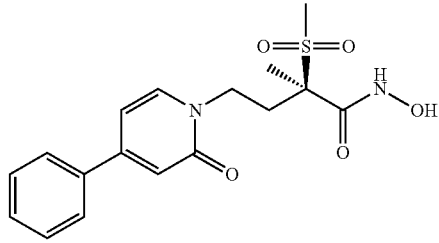 [SMILES: C[C@@](CCn1ccc(-c2ccccc2)cc1=O)(C(=O)NO)S(C)(=O)=O]

Step A) Ethyl 2-methyl-2-(methylsulfonyl)-4-(2-oxo-4-phenylpyridin-1(2H)-yl)butanoate Ethyl 4-bromo-2-methyl-2-(methylsulfonyl)butanoate (25.02 g, 87.1 mmol) was added to a mixture of 4-phenylpyridin-2-ol (12.40 g, 72.43 mmol) and cesium carbonate (49.70 g, 152.5 mmol) in THF (150 mL). The reaction was stirred and heated at 60° C. overnight. The reaction was diluted with ethyl acetate (200 mL) and water (200 mL); the organics were separated and the aqueous layer was extracted with ethyl acetate (2×150 mL). The combined organics were dried (MgSO$_4$), filtered, and concentrated to afford a crude solid. The crude was purified via flash chromatography using an Analogix SF65-400 g column and eluted with ethyl acetate in heptane (30-80%) to afford the title compound as a white solid (16.79 g, 61.4%). LC-MS m/z 378.6 (M+1). $^1$H NMR (400 MHz, CHLOROFORM-d) δ ppm 1.31 (t, J=7.12 Hz, 3H) 1.58 (s, 2H) 2.41-2.62 (m, 2H) 3.09 (s, 3H) 3.90-4.01 (m, 1H) 4.20-4.32 (m, 3H) 6.40-6.45 (m, 1H) 6.73 (d, J=1.56 Hz, 1H) 7.31 (d, J=7.03 Hz, 1H) 7.37-7.46 (m, 2H) 7.50-7.55 (m, 2H).

Step B) (+/−)-2-Methyl-2-(methylsulfonyl)-4-(2-oxo-4-phenylpyridin-1(2H)-yl)butanoic acid (+/−)-Ethyl 2-methyl-2-(methylsulfonyl)-4-(2-oxo-4-phenylpyridin-1(2H)-yl)butanoate was converted to the title product following the general procedure outlined for (2R)-4-(4-iodo-2-oxopyridin-1(2H)-yl)-2-methyl-2-(methylsulfonyl)butanoic acid, Preparation 2B, Step B. The title compound was obtained as a white solid (69.83 g, 95.24%). LC-MS m/z 350.5 (M+1). $^1$H NMR (400 MHz, DMSO-d$_6$) δ ppm 1.57 (s, 3H) 2.13-2.24 (m, 1H) 2.39-2.47 (m, 1H) 3.17 (s, 3H) 3.83-3.99 (m, 1H) 4.02-4.16 (m, 1H) 6.59-6.63 (m, 1H) 6.66 (d, J=1.76 Hz, 1H) 7.35-7.56 (m, 3H) 7.64-7.87 (m, 3H) 13.87 (br. s., 1H).

Step C) Chiral separation to provide (2R)-2-Methyl-2-(methylsulfonyl)-4-(2-oxo-4-phenylpyridin-1(2H)-yl)butanoic acid (+/−)-2-Methyl-2-(methylsulfonyl)-4-(2-oxo-4-phenylpyridin-1(2H)-yl)butanoic acid (69.83 g) was dissolved in methylene chloride/ethanol (2 L) and resolved using an Analytical SFC-4 instrument, AS-H column (30×250), a CO2/Propanol (85/15) mobile phase with isopropylamine as the modifier, with a flow rate of 128 g/min to afford enantiomer 1 (22.5 g, rt=3.09 min, $[\alpha]_{589}^{20}$=+35.96°) at 96.46% enantiomeric purity and enantiomer 2 (26.63 g, rt=4.18 min) at 98.48% enantiomeric purity. It was determined that enantiomer 2 was the title compound

Step D) Preparation of (2R)-2-Methyl-2-(methylsulfonyl)-4-(2-oxo-4-phenylpyridin-1(2H)-yl)-N-(tetrahydro-2H-pyran-2-yloxy)butanamide (2R)-2-Methyl-2-(methylsulfonyl)-4-(2-oxo-4-phenylpyridin-1(2H)-yl)butanoic acid was converted to the title product following the general procedure outlined for 4-(4-iodo-2-oxopyridin-1(2H)-yl)-2-methyl-2-(methylsulfonyl)-N-(tetrahydro-2H-pyran-2-yloxy)butanamide Preparation 2 A, Step D, using N,N-diisopropylethylamine in place of triethylamine. The title compound was obtained as a white solid (5.15 g, 80.24%) LC-MS m/z 449.7 (M+1).

Step E) (2R)—N-Hydroxy-2-methyl-2-(methylsulfonyl)-4-(2-oxo-4-phenylpyridin-1(2H)-yl)butanamide HCl (4.0 N in 1,4-dioxane, 20 mL) was added to a solution of (2R)-2-Methyl-2-(methylsulfonyl)-4-(2-oxo-4-phenylpyridin-1(2H)-yl)-N-(tetrahydro-2H-pyran-2-yloxy)butanamide (5.15 g, 11.5 mmol) in 1,4-dioxane (100 mL) and water (20 mL). The reaction was continued for 2 hours. The reaction was concentrated in vacuo, upon concentration a white solid precipitated. The solid was triturated with 2-propanol (150 mL) at 50° C. for 30 minutes then collected by filtration. The title compound was obtained as a white solid (3.85 g, 92%) LC-MS m/z 365.5 (M+1). $^1$H NMR (400 MHz, DMSO-d$_6$) δ ppm 1.58 (s, 3H) 2.10-2.23 (m, 1H) 2.37-2.48 (m, 1H) 3.11 (s, 3H) 3.69-3.82 (m, 1H) 4.04-4.19 (m, 1H) 6.63-6.68 (m, 1H)

6.70 (d, J=1.76 Hz, 1H) 7.41-7.55 (m, 3H) 7.68-7.75 (m, 2H) 7.77 (d, J=6.83 Hz, 1H) 11.17 (br. s., 1H). [α]$_{589}^{20}$=+33.21°.

Example 12

(2R)-4-[4-(2-fluoro-4-hydroxy-3-methylphenyl)-2-oxopyridin-1(2H)-yl]-N-hydroxy-2-methyl-2-(methylsulfonyl)butanamide

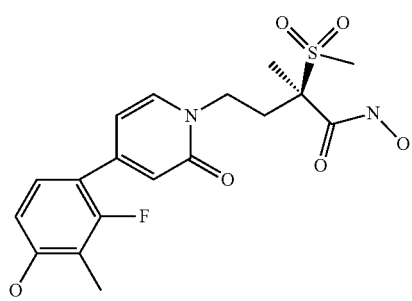 [SMILES: Cc1c(O)ccc(-c2ccn(CC[C@](C)(C(=O)NO)S(C)(=O)=O)c(=O)c2)c1F]

Step A)
2-(4-bromo-3-fluorophenoxy)tetrahydro-2H-pyran

Pyridinium p-toluene sulfonic acid (789 mg, 3.1 mmol) was added to a solution of 4-bromo-3-fluorophenol (4.00 g, 20.9 mmol) and 3,4-dihydro-2H-pyran (3.52 g, 41.9 mmol) in dichloromethane (105 mL, 0.2M). After 2 h the reaction was quenched with saturated aqueous sodium bicarbonate and the layers were separated. The aqueous layer was extracted with dichloromethane (2×). The organic layers were combined, dried (Na$_2$SO$_4$), filtered and concentrated to give a colorless oil. The material was loaded onto a 25 g silica guard column and run on a 330 g column with 0-5% EtOAc in heptane. Desired material was concentrated down yielding 1900 mg (33%) of a clear colorless oil. $^1$H NMR (400 MHz, CHLOROFORM-d) δ ppm 1.56-1.77 (m, 3H) 1.82-1.89 (m, 2H) 1.89-2.07 (m, 1H) 3.62 (m, J=11.37, 4.07, 4.07, 1.37 Hz, 1H) 3.85 (ddd, J=11.32, 10.05, 3.02 Hz, 1H) 5.38 (dd, J=3.12 Hz, 1H) 6.76 (ddd, J=8.88, 2.73, 1.07 Hz, 1H) 6.89 (dd, J=10.34, 2.73 Hz, 1H) 7.35-7.46 (m, 1H).

Step B) 2-(4-bromo-3-fluoro-2-methylphenoxy)tetrahydro-2H-pyran 2-(4-bromo-3-fluorophenoxy)tetrahydro-2H-pyran (1200 mg, 4.4 mmol) was dissolved in tetrahydrofuran (22 mL, 0.2M) under nitrogen and cooled to −78° C. To this was added (600 mg, 5.6 mmol) lithium diisopropylamide in solution dropwise over 5 minutes. The reaction mixture was stirred for 1 h at −78° C. Methyl iodide (948 mg, 6.5 mmol) was then added dropwise. The reaction was stirred at −78° C. for 30 min and allowed to warm to RT overnight. The mixture was quenched with water and 10 mL of saturated aqueous ammonium chloride solution. The reaction was extracted with diethyl ether (3×). The organic layer was dried over sodium sulfate, filtered and evaporated to yield 1.17 g (93%) of a light yellow mix of solid and oil. $^1$H NMR (400 MHz, CHLOROFORM-d) δ ppm 1.57-1.78 (m, 3H) 1.85-1.93 (m, 2H) 1.95-2.08 (m, 1H) 2.21 (d, J=2.34 Hz, 3H) 3.61 (m, J=11.27, 3.98, 3.98, 1.46 Hz, 1H) 3.78-3.88 (m, 1H) 5.41 (t, J=3.12 Hz, 1H) 6.81 (dd, J=8.98, 1.37 Hz, 1H) 7.27 (d, J=16.98 Hz, 1H)

Step C) 2-[3-fluoro-2-methyl-4-(4,4,5,5-tetramethyl-1,3,2-dioxaborolan-2-yl)phenoxy]tetrahydro-2H-pyran Potassium acetate (810 mg, 8.1 mmol) was added to a suspension of 2-(4-bromo-3-fluoro-2-methylphenoxy)tetrahydro-2H-pyran (1170 mg, 4.0 mmol) in p-dioxane (41 mL, 0.1M). After 10 minutes, bis(pinacolato)diborane (1230 mg, 4.9 mmol) and dichloro 1,1'-bis(diphenylphosphino)ferrocene palladium (II) (96 mg, 0.13 mmol) were added. The resulting suspension was heated to 100° C. 18 h. An additional 100 mg of catalyst was added. After another 24 h, an additional 100 mg of catalyst was added. After another 24 h (66 h total) the material was filtered through celite, concentrated and loaded onto a 120 g silica column (0-10% ethyl acetate in hexanes). The product was concentrated to yield 677 mg (50%) as a golden brown oil. Contains some bis(pinacolato)diborane impurity. Partial NMR $^1$H NMR (400 MHz, CHLOROFORM-d) δ ppm 1.35 (s, 12H) 1.56-1.78 (m, 3H) 1.82-1.95 (m, 2H) 1.96-2.07 (m, 1H) 2.16 (d, J=2.15 Hz, 3H) 3.57-3.68 (m, 1H) 3.70-3.92 (m, 1H) 5.50 (t, J=2.93 Hz, 1H) 6.88 (d, J=8.39 Hz, 1H) 7.51 (t, J=7.71 Hz, 1H)

Step D) (2R)-4-{4-[2-fluoro-3-methyl-4-(tetrahydro-2H-pyran-2-yloxy)phenyl]-2-oxopyridin-1(2H)-yl}-2-methyl-2-(methylsulfonyl)-N-(tetrahydro-2H-pyran-2-yloxy)butanamide Pd EnCat™ (150 mg, 0.05 mmol) was added to a mixture of potassium carbonate (370 mg, 2.7 mmol) the 2-[3-fluoro-2-methyl-4-(4,4,5,5-tetramethyl-1,3,2-dioxaborolan-2-yl)phenoxy]tetrahydro-2H-pyran (150 mg, 0.45 mmol) and (2R)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2B, Step C, (267 mg, 0.54 mmol) in 1,4-dioxane (3.5 mL, 0.1M) and water (0.5 mL). The resulting suspension was heated to 100° C. and left to stir 66 h. The material was cooled, filtered through celite and concentrated yielding 256 mg (99% TY) of white solid. LCMS m/z 579.8 (M−1) Partial NMR capturing aromatic and dietheric THP protons. $^1$H NMR (400 MHz, DMSO-d$_6$) δ ppm 4.97 (br. s., 1H) 5.58-5.64 (m, 1H) 6.46 (dt, J=7.02, 1.85 Hz, 1H) 6.52 (s, 1H) 7.01 (d, J=8.78 Hz, 1H) 7.36 (t, J=8.98 Hz, 1H) 7.68 (d, J=7.02 Hz, 1H)

Step E) (2R)-4-[4-(2-fluoro-4-hydroxy-3-methylphenyl)-2-oxopyridin-1(2H)-yl]-N-hydroxy-2-methyl-2-(methylsulfonyl)butanamide (2R)-4-{4-[2-fluoro-3-methyl-4-(tetrahydro-2H-pyran-2-yloxy)phenyl]-2-oxopyridin-1(2H)-yl}-2-methyl-2-(methylsulfonyl)-N-(tetrahydro-2H-pyran-2-yloxy)butanamide (335 mg, 0.58 mmol) was dissolved in 3 mL of dioxane. To this solution was added 1 mL of 4M HCl in dioxane 1 mL of water. The resulting solution was stirred at RT for 10 minutes. The material was diluted up with methanol and concentrated (3×). Dichloromethane was added and the mixture was stirred for 18 h. The solution retained color and a fine particulate was suspended. The mixture was filtered leaving 13.3 mg (6%) of white solid. LCMS m/z 413.6 (M+1) $^1$H NMR (400 MHz, METHANOL-d$_4$) δ ppm 1.71 (s, 3H) 2.14 (d, J=1.56 Hz, 3H) 2.33-2.46 (m, 1H) 2.54-2.68 (m, 1H) 3.10 (s, 3H) 3.91-4.05

(m, 1H) 4.24-4.40 (m, 1H) 6.70 (d, J=8.59 Hz, 1H) 6.75-6.86 (m, 2H) 7.23 (t, J=8.68 Hz, 1H) 7.75 (d, J=6.83 Hz, 1H)

Example 13

(2R)-4-[4-(2-fluoro-4-methylphenyl)-2-oxopyridin-1 (2H)-yl]-2-methyl-2-(methylsulfonyl)-N-(tetrahydro-2H-pyran-2-yloxy)butanamide

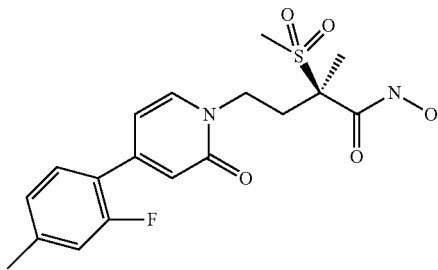 [SMILES: Cc1ccc(-c2ccn(CC[C@](C)(C(=O)NO)S(C)(=O)=O)c(=O)c2)c(F)c1]

Pd EnCat™ (0.1 eq) was added to a mixture of potassium carbonate (3.0 eq), (2-fluoro-4-methylphenyl)boronic acid (201 mg, 1.3 mmol) and (2R)-4-(4-iodo-2-oxopyridin-1 (2H)-yl)-2-methyl-2-(methylsulfonyl)-N-(tetrahydro-2H-pyran-2-yloxy)butanamide, which may be produced as in Preparation 2B (1.0 eq) in dioxane:water (0.1 M, 5:1 mixture). The reaction mixture was heated overnight at 80° C. The reaction was cooled to ambient temperature and filtered through celite and eluted with ethyl acetate. The filtrate was concentrated in vacuo, then subjected to the standard THP-deprotection step as described for the formation of (2R)-4-[4-(2-fluoro-4-hydroxy-3-methylphenyl)-2-oxopyridin-1 (2H)-yl]-N-hydroxy-2-methyl-2-(methylsulfonyl) butanamide in Example 12, Step E. LCMS m/z 397.6 (M+1). $^1$H NMR (400 MHz, DMSO-d$_6$) δ ppm 1.58 (s, 3H) 2.17 (td, J=12.20, 5.07 Hz, 1H) 2.36 (s, 3H) 2.44 (td, J=12.15, 4.98 Hz, 1H) 3.11 (s, 3H) 3.75 (td, J=12.00, 4.68 Hz, 1H) 4.12 (td, J=11.90, 5.07 Hz, 1H) 6.43-6.52 (m, 1H) 6.56 (s, 1H) 7.05-7.24 (m, 2H) 7.47 (t, J=8.10 Hz, 1H) 7.73 (d, J=7.02 Hz, 1H) 9.25 (br. s., 1H) 11.14 (s, 1H)

Example 14

(2R)-4-[4-(2,3-difluorophenyl)-2-oxopyridin-1(2H)-yl]-N-hydroxy-2-methyl-2-(methylsulfonyl)butanamide

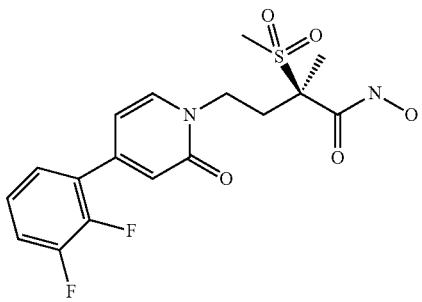 [SMILES: C[C@@](CCn1ccc(-c2cccc(F)c2F)cc1=O)(C(=O)NO)S(C)(=O)=O]

Title compound was prepared using (2,3-difluorophenyl) boronic acid (114 mg, 0.72 mmol) following the general methodology of Example 13. Yield 99 mg (41%) of yellow solid. LCMS m/z 401.5 (M+1). $^1$H NMR (400 MHz, DMSO-d$_6$) δ ppm 1.58 (s, 3H) 2.18 (td, J=12.20, 4.88 Hz, 1H) 2.38-2.48 (m, 1H) 3.11 (s, 3H) 3.77 (td, J=12.00, 4.88 Hz, 1H) 4.13 (td, J=11.90, 5.07 Hz, 1H) 6.50 (dt, J=7.02, 1.85 Hz, 1H) 6.61 (s, 1H) 7.28-7.37 (m, 1H) 7.37-7.44 (m, 1H) 7.54 (m, J=10.17, 8.13, 8.13, 1.66 Hz, 1H) 7.79 (d, J=7.02 Hz, 1H) 9.25 (s, 1H) 11.12 (s, 1H)

Example 15

(2R)-4-[4-(4-chlorophenyl)-2-oxopyridin-1(2H)-yl]-N-hydroxy-2-methyl-2-(methylsulfonyl)butanamide

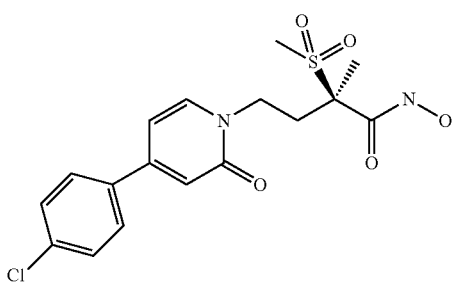 [SMILES: C[C@@](CCn1ccc(-c2ccc(Cl)cc2)cc1=O)(C(=O)NO)S(C)(=O)=O]

Title compound was prepared using (4-chlorophenyl)boronic acid (113 mg, 0.72 mmol) following the general methodology of Example 13. The product was purified using 35-50% acetonitrile in water. Yield 112 mg (47%) of yellow solid. LCMS m/z 399.5 (M+1). $^1$H NMR (400 MHz, DMSO-d$_6$) δ ppm 1.57 (s, 3H) 2.09-2.23 (m, 1H) 2.38-2.48 (m, 1H) 3.11 (s, 3H) 3.75 (td, J=11.95, 4.78 Hz, 1H) 4.12 (td, J=11.81, 5.07 Hz, 1H) 6.65 (dd, J=7.12, 2.05 Hz, 1H) 6.72 (d, J=1.95 Hz, 1H) 7.52-7.57 (m, 2H) 7.72-7.80 (m, 3H) 9.24 (br. s., 1H) 11.14 (s, 1H)

Example 16

(2R)—N-hydroxy-2-methyl-4-[4-(4-methylphenyl)-2-oxopyridin-1(2H)-yl]-2-(methylsulfonyl)butanamide

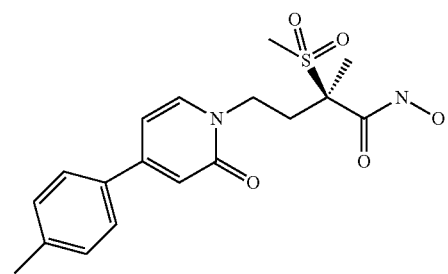 [SMILES: Cc1ccc(-c2ccn(CC[C@](C)(C(=O)NO)S(C)(=O)=O)c(=O)c2)cc1]

Title compound was prepared using (4-methylphenyl)boronic acid (98 mg, 0.72 mmol) following the general methodology of Example 13. Yield 79 mg (35%) of yellow solid. LCMS m/z 379.6 (M+1) $^1$H NMR (400 MHz, DMSO-d$_6$) δ ppm 1.57 (s, 3H) 2.11-2.22 (m, 1H) 2.35 (s, 3H) 2.37-2.47 (m, 1H) 3.11 (s, 3H) 3.74 (td, J=11.95, 4.78 Hz, 1H) 4.11 (td, J=11.90, 5.07 Hz, 1H) 6.64 (dd, J=7.12, 2.05 Hz, 1H) 6.68 (d,

Example 17

(2R)—N-hydroxy-4-[4-(4-methoxyphenyl)-2-oxopyridin-1(2H)-yl]-2-methyl-2-(methylsulfonyl)butanamide

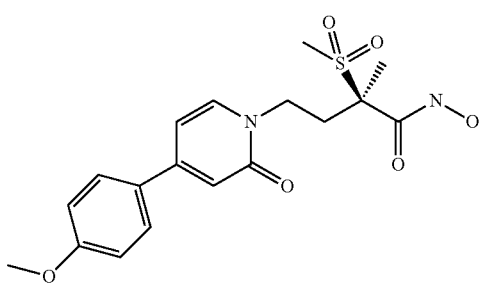 [SMILES: COc1ccc(-c2ccn(CC[C@](C)(C(=O)NO)S(C)(=O)=O)c(=O)c2)cc1]

Title compound was prepared from (4-methoxyphenyl) boronic acid (110 mg, 0.72 mmol) using the general methodology of Example 13. Yield 35 mg (15%) of yellow solid. LCMS m/z 395.6 (M+1). $^1$H NMR (400 MHz, DMSO-$d_6$) δ ppm 1.57 (s, 3H) 2.11-2.23 (m, 1H) 2.35-2.47 (m, 1H) 3.11 (s, 3H) 3.68-3.79 (m, 1H) 3.81 (s, 3H) 4.10 (td, J=11.85, 5.17 Hz, 1H) 6.60-6.68 (m, 2H) 7.03 (d, J=8.98 Hz, 2H) 7.60-7.76 (m, 3H) 9.25 (s, 1H) 11.18 (s, 1H)

Example 18

(2R)-4-[4-(2,3-dihydro-1,4-benzodioxin-6-yl)-2-oxopyridin-1(2H)-yl]-N-hydroxy-2-methyl-2-(methylsulfonyl)butanamide

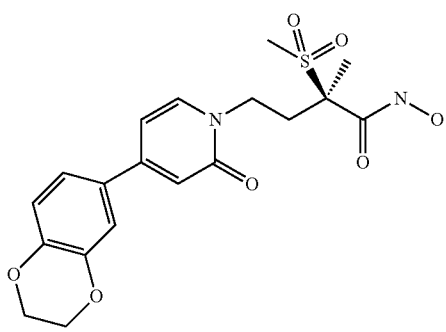 [SMILES: C[C@@](CCn1ccc(-c2ccc3c(c2)OCCO3)cc1=O)(C(=O)NO)S(C)(=O)=O]

Step A) (2R)-4-[4-(2,3-dihydro-1,4-benzodioxin-6-yl)-2-oxopyridin-1(2H)-yl]-2-methyl-2-(methylsulfonyl)-N-(tetrahydro-2H-pyran-2-yloxy)butanamide Pd EnCat™ (200 mg, 0.6 mmol) was added to a mixture of potassium carbonate (250 mg, 1.8 mmol), 2,3-dihydro-1,4-benzodioxin-6-ylboronic acid (130 mg, 0.72 mmol), and (2R)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2B, Step C, (300 mg, 0.6 mmol) in dioxane:water (5 mL, 5:1 mixture). The reaction mixture was heated overnight at 80° C. The reaction was cooled to ambient temperature, filtered through celite and washed with ethyl acetate. The crude material was concentrated and loaded onto a 12 g silica column and run using 0-100% ethyl acetate in hexanes. (Some material was lost during purification). The material was concentrated yielding 44 mg (15%) of a light yellow glass. LCMS m/z 505.7 (M−1)

Step B) (2R)-4-[4-(2,3-dihydro-1,4-benzodioxin-6-yl)-2-oxopyridin-1(2H)-yl]-N-hydroxy-2-methyl-2-(methylsulfonyl)butanamide (2R)-4-[4-(2,3-dihydro-1,4-benzodioxin-6-yl)-2-oxopyridin-1(2H)-yl]-2-methyl-2-(methylsulfonyl)-N-(tetrahydro-2H-pyran-2-yloxy)butanamide (581 mg, 1 mmol) was dissolved in 3 mL of dichloromethane. To this solution was added 1 mL of 4M HCl in dioxane 1 mL of water. The reaction was monitored for completion by LCMS. After standing overnight, a solid precipitated. The solid was collected by filteration and dried in vacuo yielding 25 mg (68%) of light yellow solid. LCMS m/z 423.5 (M+1) 1H NMR (400 MHz, DMSO-$d_6$) δ ppm 1.57 (s, 3H) 2.09-2.22 (m, 1H) 2.36-2.46 (m, 1H) 3.10 (s, 3H) 3.65-3.79 (m, 1H) 4.03-4.15 (m, 1H) 4.28 (s, 4H) 6.59-6.66 (m, 2H) 6.94 (d, J=8.20 Hz, 1H) 7.19-7.26 (m, 2H) 7.67-7.73 (m, 1H)

Example 19

(2R)—N-hydroxy-2-methyl-4-[4-(2-methyl-1H-indol-5-yl)-2-oxopyridin-1(2H)-yl]-2-(methylsulfonyl)butanamide

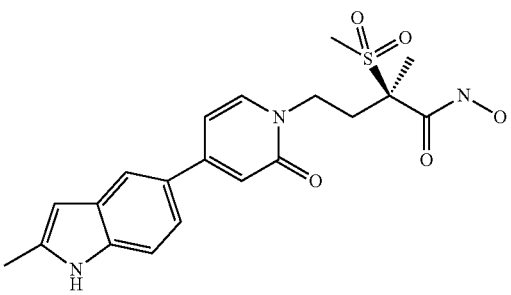 [SMILES: Cc1cc2cc(-c3ccn(CC[C@](C)(C(=O)NO)S(C)(=O)=O)c(=O)c3)ccc2[nH]1]

Step A) (2R)—N-hydroxy-4-(4-iodo-2-oxopyridin-1(2H)-yl)-2-methyl-2-(methylsulfonyl)butanamide (2R)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2B, Step C (300 mg, 0.6 mmol) was dissolved in 3 mL of p-dioxane. To this solution was added 1 mL of water and 0.5 mL of 4M HCl in water. The reaction was monitored for completion by LCMS. Upon completion (10 minutes), the reaction mixture was concentrated and recrystallized from methanol. 115 mg (46%) of white solid was isolated by filtration. LCMS m/z 415.3 (M+1). 1H NMR (400 MHz, DMSO-$d_6$) δ ppm 1.54 (s, 3H) 2.04-2.14 (m, 1H) 2.34-2.44 (m, 1H) 3.08 (s, 3H) 3.62-3.72 (m, 1H) 3.96-4.06 (m, 1H) 6.62 (dd, J=7.13, 1.86 Hz, 1H) 6.94 (d, J=1.76 Hz, 1H) 7.44 (d, J=7.03 Hz, 1H) 9.23 (br. s., 1H) 11.04 (s, 1H)

Step B) 2-Methyl-5-(4,4,5,5-tetramethyl-1,3,2-dioxaborolan-2-yl)-1H-indole

Potassium acetate (477 mg, 4.76 mmol) was added to a solution of 5-bromo-2-methylindole (500 mg, 2.4 mmol), bis(pinacolato)diboron (725 mg, 2.86 mmol), and [1,1'-bis-(diphenylphosphino)ferrocene]-dichloropalladium (II) dcm complex (178 mg, 0.24 mmol) in 1,4-dioxane (25 mL) in a 20 mL vial. The vial was capped and heated to 80° C., reaction was heated at this temperature with stirring overnight. The reaction mixture was concentrated, dissolved in EtOAc, and filtered through a 5 g silica plug. This filtrate was concentrated and purified on an 80 g silica column using 0-10% ethyl acetate in hexanes to furnish 202 mg (33%) of a clear colorless oil. LCMS m/z 258.3 (M+1) 1H NMR (400 MHz, CHLOROFORM-d) δ ppm 1.39 (s, 21H) 2.40 (s, 3H) 6.24 (s, 1H) 7.25 (d, J=8.20 Hz, 1H) 7.60 (d, J=8.20 Hz, 1H) 7.94 (br. s., 1H) 8.08 (s, 1H)

Step C) (2R)—N-hydroxy-2-methyl-4-[4-(2-methyl-1H-indol-5-yl)-2-oxopyridin-1(2H)-yl]-2-(methylsulfonyl)butanamide Pd EnCat™ (93 mg, 0.03 mmol) was added to a mixture of potassium carbonate (115 mg, 0.83 mmol), 2-methyl-5-(4,4,5,5-tetramethyl-1,3,2-dioxaborolan-2-yl)-1H-indole (86 mg, 0.33 mmol), and (2R)—N-hydroxy-4-(4-iodo-2-oxopyridin-1(2H)-yl)-2-methyl-2-(methylsulfonyl)butanamide (115 mg, 0.28 mmol) in dioxane:water (2.5 mL, 5:1 mixture). The reaction mixture was heated overnight at 80° C. The reaction was cooled to ambient temperature, filtered through a nylon filter and concentrated. The material was dissolved in a minimal amount of DMSO and loaded onto a 13 g c18 column. The gradient was run from 25-45% acetonitrile in water. The desired material was concentrated yielding 25 mg (22%) of a light brown solid. LCMS m/z 418.5 (M+1) 1H NMR (400 MHz, DMSO-$d_6$) δ ppm 1.58 (s, 3H) 2.13-2.24 (m, 1H) 2.32-2.46 (m, 1H) 2.39 (s, 3H) 3.12 (s, 3H) 3.69-3.78 (m, 1H) 4.06-4.16 (m, 1H) 6.20 (s, 1H) 6.65 (d, J=1.95 Hz, 1H) 6.70 (dd, J=7.22, 1.95 Hz, 1H) 7.31-7.39 (m, 2H) 7.70 (d, J=7.22 Hz, 1H) 7.79 (s, 1H) 9.25 (br. s., 1H) 11.11 (br. s., 1H) 11.23 (br. s., 1H)

Example 20

(2R)-4-[4-(4-chloro-2-fluorophenyl)-2-oxopyridin-1(2H)-yl]-N-hydroxy-2-methyl-2-(methylsulfonyl)butanamide

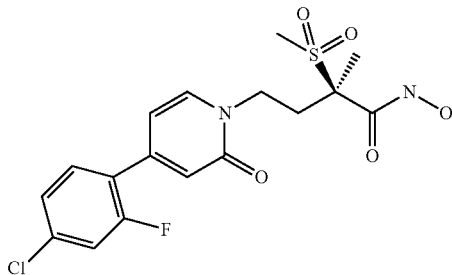 [SMILES: C[C@@](CCn1ccc(-c2ccc(Cl)cc2F)cc1=O)(C(=O)NO)S(C)(=O)=O]

Step A) (2R)-4-[4-(4-chloro-2-fluorophenyl)-2-oxopyridin-1(2H)-yl]-2-methyl-2-(methylsulfonyl)-N-(tetrahydro-2H-pyran-2-yloxy)butanamide Pd EnCat™ (333 mg, 0.1 mmol) was added to a mixture of potassium carbonate (832 mg, 6.0 mmol), (2-fluoro-4-chlorophenyl)boronic acid (227 mg, 1.3 mmol), and (2R)-4-(4-iodo-2-oxopyridin-1(2H)-yl)-2- methyl-2-(methylsulfonyl)-N-(tetrahydro-2H-pyran-2-yloxy)butanamide, which may be produced as in Preparation 2B, Step C (500 mg, 1.0 mmol) in dioxane:water (8 mL, 5:1 mixture). The reaction mixture was heated overnight at 80° C. The reaction was cooled to ambient temperature, filtered through celite and washed with ethyl acetate. The crude material was concentrated yielding 1188 mg (236%) of impure light yellow solid. LCMS m/z 499.7 (M−1)

Step B) (2R)-4-[4-(4-chloro-2-fluorophenyl)-2-oxopyridin-1(2H)-yl]-N-hydroxy-2-methyl-2-(methylsulfonyl)butanamide (2R)-4-[4-(4-chloro-2-fluorophenyl)-2-oxopyridin-1(2H)-yl]-2-methyl-2-(methylsulfonyl)-N-(tetrahydro-2H-pyran-2-yloxy)butanamide (1188 mg impure material, 1 mmol) was dissolved in 3 mL of dichloromethane. To this solution was added 1 mL of 4M HCl in dioxane and 1 mL of water. The reaction was monitored for completion by LCMS. Upon completion, the reaction mixture was concentrated and redissolved in a minimal amount of dimethylsulfoxide and water and loaded onto a 5 g c18 guard-column. This material was purified on a 75 g c18 column with 10-40% acetonitrile in water with 0.1% trifluoroacetic acid. The desired material was concentrated yielding 434 mg (88%) of a light yellow solid. LCMS m/z 417.5 (M+1). $^1$H NMR (400 MHz, DMSO-$d_6$) δ ppm 1.58 (s, 3H) 2.10-2.23 (m, 1H) 2.37-2.47 (m, 1H) 3.11 (s, 3H) 3.69-3.82 (m, 1H) 4.04-4.19 (m, 1H) 6.44-6.52 (m, 1H) 6.58 (s, 1H) 7.42 (dd, J=8.29, 1.85 Hz, 1H) 7.56-7.67 (m, 2H) 7.77 (d, J=7.02 Hz, 1H) 11.12 (br. s., 1H)

Example 21

(2R)-4-[4-(2-fluoro-4-methoxyphenyl)-2-oxopyridin-1(2H)-yl]-N-hydroxy-2-methyl-2-(methylsulfonyl)butanamide

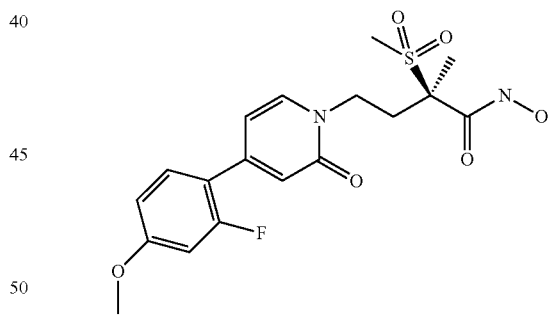

Step A: (2R)-4-[4-(2-Fluoro-4-methoxyphenyl)-2-oxopyridin-1(2H)-yl]-2-methyl-2-(methylsulfonyl)butanoic acid (2-Fluoro-4-methoxyphenyl)boronic acid (3.89 g, 22.43 mmol), ethyl (2R)-4-(4-iodo-2-oxopyridin-1(2H)-yl)-2-methyl-2-(methylsulfonyl)butanoate (7.68 g, 17.98 mmol), (which may be produced as in the preparation of 2A compound IV Step B except that (R)-ethyl 4-bromo-2-methyl-2-(methylsulfonyl)butanoate was used), and Pd(dppf)Cl$_2$; DCM complex (0.60 g, 0.73 mmol) were charged into a round bottom flask, flushed with nitrogen, and dissolved in methyltetrahydrofuran (75 mL). Potassium phosphate, tribasic (11.45 g, 53.94 mmol) in water (37 mL) was added to the flask and the reaction was heated to 65° C. for 45 minutes. The reaction was allowed to cool and the aqueous layer was separated. The organics were transferred back in the flask and lithium hydroxide (1.31 g, 53.88 mmol) in water (25 mL) was added to the organics and the mixture was heated to 55° C. for 1 hour. The mixture was allowed to cool and the aqueous layer was separated. The organics were extracted with 1N aqueous sodium hydroxide (2×25 mL). The combined aqueous layers were washed with ethyl acetate (3×25 mL), treated with celite (3 g) and filtered. The filter pad was washed with water (25 mL) and the combined filtrates were treated dropwise with 6N aqueous HCl to afford a pH of 3 and a cream colored precipitate. The solid was collected via filtration and dried under vacuum to afford the title compound as a tan solid (6.50 g, 90.99%).

HPLC/MS m/z 398 (M+1)

$^1$H NMR (d-6-DMSO) σ 7.70 (d, J=7.43 Hz, 1H), 7.51 (t, J=9.37 Hz, 1H), 6.95 (dd, J=13.27, 2.34 Hz, 1H), 6.87 (dd, J=8.59, 2.73 Hz, 1H), 6.49 (s, 1H), 6.95 (dt, J=6.42, 1.95 Hz, 1H), 4.10-4.02 (m, 1H), 3.94-3.84 (m, 1H), 2.46-2.37 (m, 1H), 2.22-2.13 (m, 1H), 1.55 (s, 3H).

Step B: (2R)-4-[4-(2-fluoro-4-methoxyphenyl)-2-oxopyridin-1(2H)-yl]-2-methyl-2-(methylsulfonyl)-N-(tetrahydro-2H-pyran-2-yloxy)butanamide (2R)-4-[4-(2-fluoro-4-methoxyphenyl)-2-oxopyridin-1(2H)-yl]-2-methyl-2-(methylsulfonyl)butanoic acid (2.38 g, 5.99 mmol) and 2-chloro-4,6-dimethoxy-1,3,5-triazine (1.38 g, 7.86 mmol) were charged into a round bottom flask, flushed with nitrogen, and dissolved in 2-methyltetrahydrofuran (20 mL). The mixture was treated with N-methylmorpholine (0.92 mL, 8.39 mmol) and stirred for 85 minutes. THP-hydroxylamine (0.94 g, 8.07 mmol) in MeTHF (3.0 mL) was added dropwise via syringe and the reaction was stirred for 45 minutes. The aqueous layer was separated and extracted with MeTHF (20 mL). The combined organics were washed with brine (15 mL), dried (Na$_2$SO$_4$), filtered, and concentrated to afford the title compound as a solid glass (3.67 g) which contains impurities. LCMS m/z 495.7 (M−1) Used as is in the next step.

Step C: (2R)-4-[4-(2-fluoro-4-methoxyphenyl)-2-oxopyridin-1(2H)-yl]-N-hydroxy-2-methyl-2-(methylsulfonyl)butanamide (2R)-4-[4-(2-Fluoro-4-methoxyphenyl)-2-oxopyridin-1(2H)-yl]-2-methyl-2-(methylsulfonyl)-N-(tetrahydro-2H-pyran-2-yloxy)butanamide (34.7 mg, 69.9 mmol) and pyridinium p-toluenesulfonic acid (8.8 mg, 34.9 mmol) were dissolved in ethanol (277.6 uL) and immersed in a 75° C. oil bath. The reaction was stirred at this temperature for 1 hour and allowed to cool. Water (600 uL) was added to the solution and the reaction was stirred overnight. A solid was collected via filtration and dried under vacuum to afford the title compound as an off-white powder (22 mg, 76.33%). LCMS m/z 413.5 (M+1). 1H NMR (400 MHz, DMSO-d$_6$) δ ppm 1.57 (s, 3H) 2.11-2.22 (m, 1H) 2.37-2.47 (m, 1H) 3.10 (s, 3H) 3.68-3.79 (m, 1H) 3.82 (s, 3H) 4.05-4.16 (m, 1H) 6.44-6.50 (m, 1H) 6.54 (s, 1H) 6.89 (dd, J=8.68, 2.44 Hz, 1H) 6.97 (dd, J=13.37, 2.44 Hz, 1H) 7.54 (dd, J=8.98, 8.98 Hz, 1H) 7.71 (d, J=7.02 Hz, 1H) 11.14 (br. s., 1H).

Example 22

(2R)—N-hydroxy-2-methyl-2-(methylsulfonyl)-4-[2-oxo-4-(2,3,6-trifluorophenyl)pyridin-1(2H)-yl]butanamide

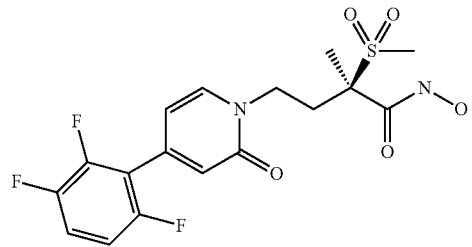 [SMILES: C[C@@](CCn1ccc(-c2c(F)ccc(F)c2F)cc1=O)(C(=O)NO)S(C)(=O)=O]

Step A) (2R)—N-hydroxy-2-methyl-2-(methylsulfonyl)-4-[2-oxo-4-(2,3,6-trifluorophenyl)pyridin-1(2H)-yl]butanamide To an 8 mL tube was added 0.15 mmol of 2-bromo-1,3,4-trifluorobenzene (32 mg), a 1.0 mL DMF solution of (2R)-4-(4-(5,5-dimethyl-1,3,2-dioxaborinan-2-yl)-2-oxopyridin-1(2H)-yl)-2-methyl-2-(methylsulfonyl)-N-(tetrahydro-2H-pyran-2-yloxy)butanamide, which may be produced as in Preparation 3 (73 mg, 0.15 mmol), a 0.10 mL aqueous solution of K$_2$CO$_3$ (62 mg, 0.45 mmol), and Pd EnCat™ (75 mg). The resulting suspension was shaken at 80° C. for 14 hr. Complete consumption of starting material was confirmed by LCMS, with the major peak confirmed as desired coupling product by ionization. The mixture was then diluted with 2 mL dioxane and 350 mg celite was added. The resulting mixture was shaken at room temperature for 15 min and then filtered. To the filtrate was added 0.5 mL 1N HCl (aq.) and resulting mixture shaken at room temperature for 4 hrs. The reaction mixture was then concentrated in the Genevac. The residue was then dissolved in 2 mL DMSO, filtered and purified using a Sunfire C18 ODB 5u 19×100 mm column, 1 to 60% ACN in water with 0.01% TFA at 22 mL/min flow rate over a 12 min run time. Pure desired product was obtained, 10 mg off white solid (16%). LCMS m/z 419.2 (M+H), 837.3 (2M+H); $^1$H NMR (400 MHz, DMSO-d6) d ppm 1.54 (s, 3H) 2.14 (td, J=12.26, 5.18 Hz, 1H) 2.39-2.44 (m, 1H) 2.46 (s, 3H) 3.72 (td, J=12.01, 4.88 Hz, 1H) 4.09 (td, J=11.96, 4.79 Hz, 1H) 6.37 (d, J=7.03 Hz, 1H) 6.54 (s, 1H) 7.27 (t, J=9.18 Hz, 1H) 7.59 (qd, J=9.38, 4.88 Hz, 1H) 7.77 (d, J=7.03 Hz, 1H) 11.08 (br. s., 1H).

Example 23

(2R)—N-hydroxy-2-methyl-4-{4-[4-(2-methylpyrimidin-4-yl)phenyl]-2-oxopyridin-1(2H)-yl}-2-(methylsulfonyl)butanamide

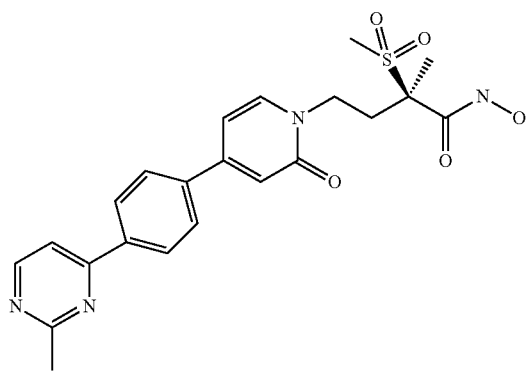 [SMILES: Cc1nccc(-c2ccc(-c3ccn(CC[C@](C)(C(=O)NO)S(C)(=O)=O)c(=O)c3)cc2)n1]

Example 23 was carried out using the general methodology described in Example 22. Title compound was made from the corresponding bromide (0.15 mmol): 4-(4-bromophenyl)-2-methylpyrimidine. Product isolated is an off white solid, 21 mg (31%). LCMS m/z 457.3 (M+1); 1H NMR (400 MHz, DMSO-d6) d ppm 0.94 (s, 3H) 1.59 (ddd, J=13.23, 11.18, 5.08 Hz, 1H) 1.81 (ddd, J=13.23, 11.18, 5.08 Hz, 1H) 2.07 (s, 3H) 2.41 (s, 3H) 3.10-3.21 (m, 1H) 3.52 (ddd, J=12.55, 11.08, 5.27 Hz, 1H) 6.07 (dd, J=7.13, 2.05 Hz, 1H) 6.14 (d, J=2.15 Hz, 1H) 7.08 (d, J=7.23 Hz, 1H) 7.20 (m, J=8.79 Hz, 2H) 7.32 (d, J=5.66 Hz, 1H) 7.64 (m, J=8.79 Hz, 2H) 8.12 (d, J=5.66 Hz, 1H).

Example 24

(2R)—N-hydroxy-2-methyl-4-{4-[4-(1-methyl-1H-pyrazol-5-yl)phenyl]-2-oxopyridin-1(2H)-yl}-2-(methylsulfonyl)butanamide

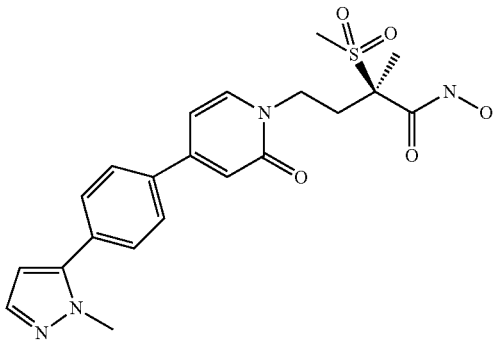 [SMILES: Cn1nccc1-c1ccc(-c2ccn(CC[C@](C)(C(=O)NO)S(C)(=O)=O)c(=O)c2)cc1]

Example 24 was carried out using the general methodology described in Example 22. Title compound was made from the corresponding bromide (0.15 mmol): 5-(4-bromophenyl)-1-methyl-1H-pyrazole. Product isolated is an off white solid, 11 mg (16%). LCMS m/z 445.3 (M+1); 1H NMR (400 MHz, DMSO-d6) d ppm 0.94 (s, 3H) 1.58 (ddd, J=13.23, 11.38, 5.47 Hz, 1H) 1.75-1.84 (m, 1H) 2.41 (s, 3H) 3.14 (td, J=12.01, 4.69 Hz, 1H) 3.21 (s, 3H) 3.45-3.58 (m, 1H) 6.02 (d, J=2.15 Hz, 1H) 6.04 (dd, J=7.13, 2.05 Hz, 1H) 6.08 (d, J=1.95 Hz, 1H) 6.97 (d, J=2.15 Hz, 1H) 7.02-7.07 (m, 3H) 7.20 (d, J=8.59 Hz, 2H).

Example 25

(2R)—N-hydroxy-2-methyl-4-{4-[4-(2-methyl-1,3-oxazol-4-yl)phenyl]-2-oxopyridin-1(2H)-yl}-2-(methylsulfonyl)butanamide

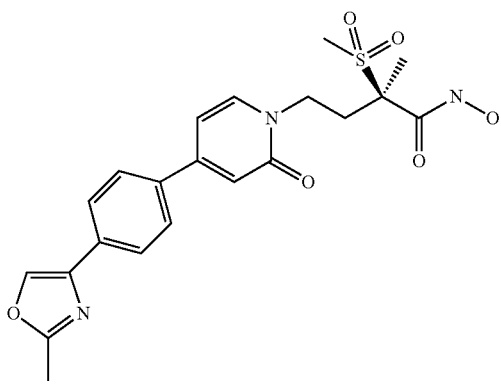 [SMILES: Cc1nc(-c2ccc(-c3ccn(CC[C@](C)(C(=O)NO)S(C)(=O)=O)c(=O)c3)cc2)co1]

Example 25 was carried out using the general methodology described in Example 22. Title compound was made from the corresponding bromide (0.15 mmol): 4-(4-bromophenyl)-2-methyloxazole. Product isolated is an off white solid, 7 mg (10%). LCMS m/z 446.1 (M+1); 1H NMR (400 MHz, DMSO-d6) d ppm 1.55 (s, 3H) 2.14 (td, J=12.21, 5.08 Hz, 1H) 2.34-2.45 (m, 1H) 2.65 (s, 3H) 3.08 (s, 3H) 3.73 (td, J=11.91, 4.69 Hz, 1H) 4.09 (td, J=11.91, 5.08 Hz, 1H) 6.68 (dd, J=7.23, 2.15 Hz, 1H) 6.76 (d, J=2.15 Hz, 1H) 7.77 (d, J=7.03 Hz, 1H) 7.85-7.92 (m, 2H) 8.02-8.08 (m, 2H) 9.18-9.31 (m, 1H) 11.13 (s, 1H).

Example 26

(2R)—N-hydroxy-2-methyl-4-{4-[4-(5-methyl-1,2,4-oxadiazol-3-yl)phenyl]-2-oxopyridin-1(2H)-yl}-2-(methylsulfonyl)butanamide

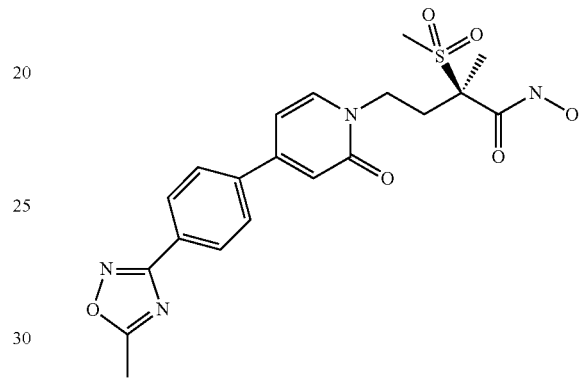

Example 26 was carried out using the general methodology described in Example 22. Title compound was made from the corresponding bromide (0.15 mmol): 3-(4-bromophenyl)-5-methyl-1,2,4-oxadiazole Product isolated is a white solid, 14 mg (17%). LCMS m/z 447.2; 1H NMR (400 MHz, DMSO-d6) d ppm 1.58 (s, 3H) 2.11-2.25 (m, 1H) 2.37-2.48 (m, 1H) 2.68 (s, 3H) 3.12 (s, 3H) 3.44 (br. s., 1H) 3.76 (td, J=11.91, 4.69 Hz, 1H) 4.13 (td, J=11.91, 5.08 Hz, 1H) 6.72 (dd, J=7.23, 2.15 Hz, 1H) 6.79 (d, J=2.15 Hz, 1H) 7.81 (d, J=7.03 Hz, 1H) 7.92 (d, J=8.59 Hz, 2H) 8.08 (d, J=8.59 Hz, 2H) 9.29 (br. s., 1H) 11.17 (s, 1H).

Example 27

(2R)—N-hydroxy-2-methyl-4-{4-[4-(2-methylpyrimidin-5-yl)phenyl]-2-oxopyridin-1(2H)-yl}-2-(methylsulfonyl)butanamide

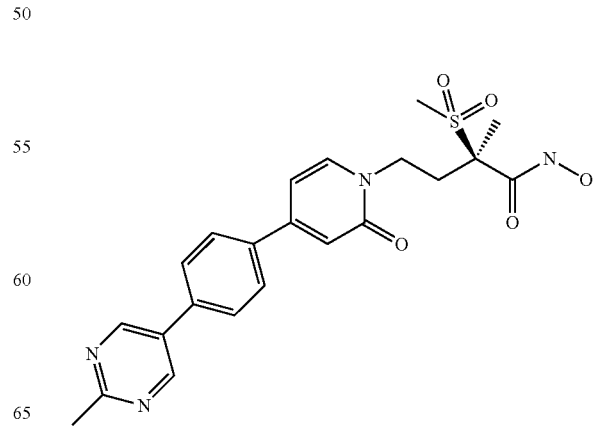

Example 27 was carried out using the general methodology described in Example 22. Title compound was made from the corresponding bromide (0.15 mmol): 5-(4-bromophenyl)-2-methylpyrimidine. Product isolated is an off white solid, 19 mg (28%). LCMS m/z 457.2 (M+1); 1H NMR (400 MHz, DMSO-d6) d ppm 1.58 (s, 3H) 2.13-2.24 (m, 1H) 2.39-2.48 (m, 1H) 2.68 (s, 3H) 3.12 (s, 3H) 3.76 (td, J=12.06, 4.79 Hz, 1H) 4.13 (td, J=11.91, 4.88 Hz, 1H) 6.74 (dd, J=7.13, 2.05 Hz, 1H) 6.80 (d, J=2.15 Hz, 1H) 7.79 (d, J=7.03 Hz, 1H) 7.85-7.96 (m, 4H) 9.10 (s, 2H).

Example 28

(2R)-4-{4-[4-(difluoromethoxy)-2-fluorophenyl]-2-oxopyridin-1(2H)-yl}-N-hydroxy-2-methyl-2-(methylsulfonyl)butanamide

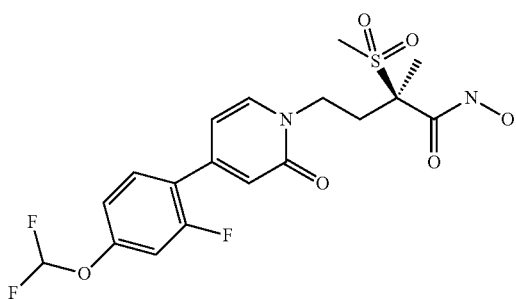 [SMILES: C[C@@](CCn1ccc(-c2ccc(OC(F)F)cc2F)cc1=O)(C(=O)NO)S(C)(=O)=O]

Step A)
1-Bromo-4-difluoromethoxy-2-fluoro-benzene

To a solution of 4-bromo-3-fluoro-phenol (962 mg, 5.037 mmol) in acetonitrile (25 mL) was added a solution of potassium carbonate (28.3 g, 181 mmol) dissolved in water (25 mL) all under nitrogen. To the reaction mixture was added 2-chloro-2,2-difluoroacetophenone (5 g, 25 mmol) and the reaction was heated to 80° C. for 4 hours. The reaction was cooled to room temperature and extracted with ethyl acetate (3×50 mL). The organic layer was dried with sodium sulfate, filtered and concentrated onto silica gel. Silica gel chromotography (5% ethyl acetate 95% heptane to 100% ethyl acetate over 55 minutes) furnished a clear oil (950 mg, 78%). LCMS m/z 531.7 (M−1) $^1$H NMR (400 MHz, METHANOL-d$_4$) δ ppm 6.85 (s, 1H) 6.92 (dd, J=8.88, 2.63 Hz, 1H) 7.05 (t, 1H) 7.38 (t, 1H)

Step B) (2R)-4-{4-[4-(difluoromethoxy)-2-fluorophenyl]-2-oxopyridin-1(2H)-yl}-2-methyl-2-(methylsulfonyl)-N-(tetrahydro-2H-pyran-2-yloxy)butanamide (2R)-4-(4-(5,5-Dimethyl-1,3,2-dioxaborinan-2-yl)-2-oxopyridin-1(2H)-yl)-2-methyl-2-(methylsulfonyl)-N-(tetrahydro-2H-pyran-2-yloxy)butanamide, which may be produced as in Preparation 3 (240 mg, 0.495 mmol), 1-bromo-4-difluoromethoxy-2-fluoro-benzene, (159 mg, 0.990 mmol), potassium carbonate (274 mg, 1.98 mmol), and dioxane (3 mL) were added to a 5 mL microwave vial with a stir bar, followed by the addition of water (0.30 mL) and Pd II Encat (128 mg, 0.050 mmol). The reaction was irradiated at 120° C. for 45 minutes in a microwave reactor. The reaction was filtered through a thin film of celite, rinsed with ethyl acetate then concentrated. Purification via silica gel chromatography (15% ethyl acetate 85% heptane to 100% ethyl acetate over 45 minutes) and then (5% MeOH 95% ethyl acetate for an additional 5 minutes) afforded the product as a white solid (120 mg, 45%). LC-MS m/z 531.7 (M−1).

Step C) (2R)-4-{4-[4-(difluoromethoxy)-2-fluorophenyl]-2-oxopyridin-1(2H)-yl}-N-hydroxy-2-methyl-2-(methylsulfonyl)butanamide To a stirred solution of (2R)-4-{4-[4-(difluoromethoxy)-2-fluorophenyl]-2-oxopyridin-1(2H)-yl}-2-methyl-2-(methylsulfonyl)-N-(tetrahydro-2H-pyran-2-yloxy)butanamide (120 mg, 0.225 mmol) in DCM (3 mL) was added a solution of 4M hydrogen chloride in dioxane (1.7 mL, 6.75 mmol). After 30 minutes the reaction was quenched through the addition of methanol 0.5 mL. The reaction was concentrated then purified via reverse phase chromatography (Method: 95% water/5% methanol (initial conditions) linear gradient to 5% water/95% methanol for 10.0 min, then HOLD 0% water/100% methanol for 1.0 min. Flow rate, 1.5 mL/min Column: Phenomenex Luna (2) C18 4.6×150 mm, 5 um) white solid was isolated (25 mg, 25%)

LC-MS m/z 449.5 (M+1) retention time 1.82 $^1$H NMR (400 MHz, METHANOL-d$_4$) d ppm 1.68-1.75 (m, 3H) 2.38 (ddd, J=13.42, 11.07, 5.17 Hz, 2H) 2.59 (ddd, J=13.46, 10.83, 5.17 Hz, 2H) 3.09-3.13 (m, 3H) 3.94 (ddd, J=12.83, 11.07, 5.17 Hz, 1H) 4.31 (ddd, J=12.93, 10.88, 5.27 Hz, 1H) 6.64 (dt, J=7.07, 1.93 Hz, 1H) 6.73 (s, 1H) 6.93-6.99 (m, 1H) 7.05-7.09 (m, 1H) 7.09-7.13 (m, 1H) 7.59-7.64 (m, 1H) 7.71 (d, J=7.02 Hz, 1H)

Example 29

N-Hydroxy-2-methyl-2-(methylsulfonyl)-4-{2-oxo-4-[4-(pyridin-2-yloxy)phenyl]pyridin-1(2H)-yl}butanamide

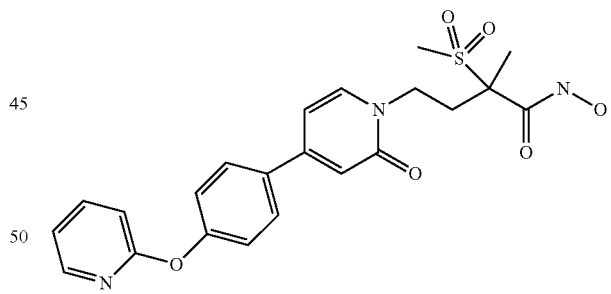

Step A) 2-(4-Bromophenoxy)pyridine

A solution of copper powder (6.4 mg, 0.1 mmol, 0.1 equiv), copper (I) iodide (19 mg, 0.1 mmol, 0.1 equiv), potassium carbonate (484 mg, 3.5 mmol, 3.5 equiv), 4-bromophenol (190 mg, 1.1 mmol, 1.1 equiv), and 2-bromopyridine (158 mg, 1.0 mmol, 1.0 equiv) in 1-methyl-2-pyrrolidinone (1.0 mL) was heated to 140° C. for 5 days. A solution of 1M sodium hydroxide (15 mL) was added, and the mixture was extracted with ethyl acetate (1×30 mL). The organic phase was washed with 1 M sodium hydroxide (15 mL), dried over anhydrous sodium sulfate, filtered, and concentrated under reduced pressure. The crude material was purified by flash chromatography (30% ethyl acetate in heptane) to provide a colorless oil (190 mg, 76%). MS (LCMS) m/z 250.4 (M+1).

Step B) 2-[4-(4,4,5,5-Tetramethyl-1,3,2-dioxaborolan-2-yl)phenoxy]pyridine

The title compound (0.23 g, 100%) was prepared from 2-(4-bromophenoxy)pyridine (266 mg, 1.1 mmol) and bis(pinacolato)diborane (190 mg, 0.76 mmol) by a general procedure analogous to that described for the preparation of 2-[3-fluoro-2-methyl-4-(4,4,5,5-tetramethyl-1,3,2-dioxaborolan-2-yl)phenoxy]tetrahydro-2H-pyran, Example 12, step C. MS (LCMS) m/z 298.5 (M+1).

Step C) 2-Methyl-2-(methylsulfonyl)-4-{2-oxo-4-[4-(pyridin-2-yloxy)phenyl]pyridin-1(2H)-yl}-N-(tetrahydro-2H-pyran-2-yloxy)butanamide The title compound (212 mg, 58%) can be prepared from 2-[4-(4,4,5,5-tetramethyl-1,3,2-dioxaborolan-2-yl)phenoxy]pyridine (239 mg, 0.8 mmol) by a procedure analogous to that described for the preparation of (2R)-2-methyl-2-(methylsulfonyl)-4-{2-oxo-4-[4-(1H-pyrazol-1-yl)phenyl]pyridin-1(2H)-yl}-N-(tetrahydro-2H-pyran-2-yloxy)butanamide Example 1, Step B. MS (LCMS) m/z 540.8 (M−1).

Step D) N-Hydroxy-2-methyl-2-(methylsulfonyl)-4-{2-oxo-4-[4-(pyridin-2-yloxy)phenyl]pyridin-1(2H)-yl}butanamide Methanol (25 mL) was added to a solution of 2-methyl-2-(methylsulfonyl)-4-{2-oxo-4-[4-(pyridin-2-yloxy)phenyl]pyridin-1(2H)-yl}-N-(tetrahydro-2H-pyran-2-yloxy)butanamide (212 mg, 0.39 mmol) in 4.0 M hydrochloric acid in 1,4-dioxane (4.9 mL) at room temperature. After 1 h, the reaction was concentrated under reduced pressure. The resulting residue was triturated with 10:1 diethyl ether-methanol, filtered, and dried under reduced pressure to provide a white solid (168 mg, 88%). LCMS m/z 458.6 (M+1). $^1$H NMR (400 MHz, CD$_3$OD) δ ppm 1.73 (s, 3H), 2.41 (ddd, J=13, 10.5, 5 Hz, 1H), 2.67 (ddd, J=13, 10.5, 5 Hz, 1H), 3.11 (s, 3H), 4.06 (ddd, J=13, 11, 5 Hz, 1H), 4.39 (ddd, J=13, 11, 5 Hz, 1H), 6.97-7.00 (m, 2H), 7.25 (br d, J=8.7 Hz, 1H), 7.47 (d, J=8.8 Hz, 2H), 7.56 (ddd, J=7.4, 5.8, 0.9 Hz, 1H), 7.90-7.94 (m, 3H), 8.33 (ddd, J=8.7, 7.4, 1.9 Hz, 1H), 8.47 (ddd, J=5.8, 1.9, 0.6 Hz, 1H).

Example 30

N-hydroxy-4-{4-[4-(3-hydroxypropoxy)phenyl]-2-oxopyridin-1(2H)-yl}-2-methyl-2-(methylsulfonyl)butanamide

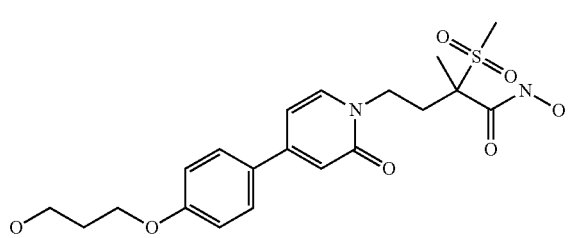 [SMILES: CC(CCn1ccc(-c2ccc(OCCCO)cc2)cc1=O)(C(=O)NO)S(C)(=O)=O]

Step A) 3-[4-(4,4,5,5-tetramethyl-1,3,2-dioxaborolan-2-yl)phenoxy]propan-1-ol

To a flask containing 3-(4-iodophenoxy)propan-1-ol (316 mg, 1.14 mmol) (see Qu, W. et. al. Journal of Medicinal Chemistry (2007), 50, 3380-3387), bis(pinacolato)diboron (397 mg, 1.56 mmol), potassium acetate (338 mg, 3.41 mmol), and [1,1'-bis-(diphenylphosphino)ferrocene]-dichloropalladium (II)dichloromethane complex (83.4 mg, 0.114 mmol) was added degassed 1,4-dioxane (9.0 mL). The reaction was heated at 80° C. under nitrogen overnight. The reaction was cooled and diluted with ethyl acetate and water. The organic layer was separated, dried over magnesium sulfate, filtered, and concentrated in vacuo to give a black solid. Chromatography on silica gel with heptane-ethyl acetate (40% ethyl acetate) gave 3-[4-(4,4,5,5-tetramethyl-1,3,2-dioxaborolan-2-yl)phenoxy]propan-1-ol as a clear oil (212.5 mg, 67.2%). $^1$H NMR (400 MHz, CDCl$_3$, δ ppm 1.24 (s, 12H), 2.02 (m, 2H), 3.84 (m, 2H), 4.06 (t, J=6.05, 2H), 6.66 (d, J=8.59, 2H), 7.53 (d, J=8.98, 2H).

Step B) 4-(4-(4-(3-hydroxypropoxy)phenyl)-2-oxopyridin-1(2H)-yl)-2-methyl-2-(methylsulfonyl)-N-(tetrahydro-2H-pyran-2-yloxy)butanamide 4-(4-iodo-2-oxopyridin-1(2H)-yl)-2-methyl-2-(methylsulfonyl)-N-(tetrahydro-2H-pyran-2-yloxy)butanamide, which may be prepared as in Preparation 2A (301 mg, 0.622 mmol), 3-[4-(4,4,5,5-tetramethyl-1,3,2-dioxaborolan-2-yl)phenoxy]propan-1-ol (212 mg, 0.762 mmol), potassium carbonate (434 mg, 3.11 mmol), and tris(dibenzylideneacetone)dipalladium(0) (56.8 mg, 0.062 mmol) were combined into a flask, placed under vacuum and opened to nitrogen. Degassed dimethoxyethane (2.0 mL) and methanol (2.0 mL) were added and the reaction was heated at 80° C. under nitrogen for 16 hours. The reaction was cooled and diluted with ethyl acetate and water. The aqueous layer was extracted with ethyl acetate and the combined organics were dried over magnesium sulfate, filtered and evaporated in vacuo onto silica gel. Chromatography on silica gel with a dichloromethane-methanol gradient (1%-25%) eluted 4-(4-(4-(3-hydroxypropoxy)phenyl)-2-oxopyridin-1(2H)-yl)-2-methyl-2-(methylsulfonyl)-N-(tetrahydro-2H-pyran-2-yloxy)butanamide as a yellow oil (120 mg, 36.9%). LCMS 521 (M−1).

Step C) N-hydroxy-4-{4-[4-(3-hydroxypropoxy)phenyl]-2-oxopyridin-1(2H)-yl}-2-methyl-2-(methylsulfonyl)butanamide To 4-(4-(4-(3-hydroxypropoxy)phenyl)-2-oxopyridin-1(2H)-yl)-2-methyl-2-(methylsulfonyl)-N-(tetrahydro-2H-pyran-2-yloxy)butanamide (120 mg, 0.230 mmol) was added 4 N hydrogen chloride in dioxane (5.0 mL) and methanol (0.50 mL). The reaction was stirred for 30 minutes and then evaporated in vacuo onto silica gel. Chromatography on silica gel with a dichloromethane-methanol gradient (1%-25%) gave the title compound as a white foam (20.8 mg, 20.1%). 1H NMR: 400 MHz, (CD$_3$OD) δ ppm 1.71 (s, 3H), 2.06 (m, 2H), 2.38 (ddd, J=13.2, 10.8, 4.8 Hz, 1H), 2.53-2.62 (m, 1H), 3.11 (s, 3H), 3.76 (t, J=6.2 Hz, 2H), 3.88-3.96 (m, 1H), 4.14

(t, J=6.3 Hz, 2H), 4.29 (ddd, J=12.5, 10.8, 4.9 Hz, 1H), 6.75 (m, 2H), 7.04 (d, J=8.7 Hz, 2H), 7.62-7.69 (m, 3H). LCMS: 437.2 (M−1).

Example 31

N-Hydroxy-4-{4-[4-(3-hydroxypropyl)phenyl]-2-oxopyridin-1(2H)-yl}-2-methyl-2-(methylsulfonyl)butanamide

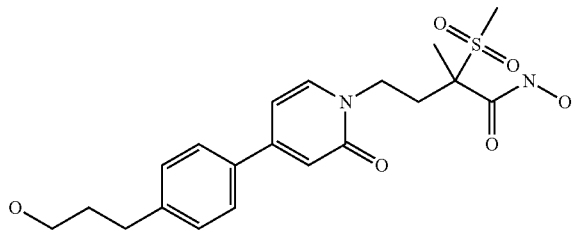 [SMILES: CC(CCn1ccc(-c2ccc(CCCO)cc2)cc1=O)(C(=O)NO)S(C)(=O)=O]

Step A) 4-{4-[4-(3-hydroxypropyl)phenyl]-2-oxopyridin-1(2H)-yl}-2-methyl-2-(methylsulfonyl)-N-(tetrahydro-2H-pyran-2-yloxy)butanamide 4-(4-iodo-2-oxopyridin-1(2H)-yl)-2-methyl-2-(methylsulfonyl)-N-(tetrahydro-2H-pyran-2-yloxy)butanamide, which may be prepared as in Preparation 2A (320 mg, 0.640 mmol), 3-[4-(4,4,5,5-tetramethyl-1,3,2-dioxaborolan-2-yl)phenyl]propan-1-ol (202 mg, 0.770 mmol) (See Takashima, H. et. al. WO 2008105515), potassium carbonate (448 mg, 3.20 mmol), and tris(dibenzylideneacetone)dipalladium(0) (56.8 mg, 0.064 mmol) were combined into a flask, placed under vacuum and opened to nitrogen. Degassed dimethoxyethane (2.0 mL) and methanol (2.0 mL) were added and the reaction was heated at 80° C. under nitrogen for 16 hours. The reaction was cooled and then diluted with ethyl acetate and water. The aqueous layer was extracted with ethyl acetate and the combined organics were dried over magnesium sulfate, filtered and evaporated in vacuo onto silica gel. Chromatography on silica gel with a dichloromethane-methanol gradient (1%-25%) gave 4-{4-[4-(3-hydroxypropyl)phenyl]-2-oxopyridin-1(2H)-yl}-2-methyl-2-(methylsulfonyl)-N-(tetrahydro-2H-pyran-2-yloxy)butanamide as a white foam (213.3 mg, 65.6%). LCMS 507.5 (M+1).

Step B) N-hydroxy-4-{4-[4-(3-hydroxypropyl)phenyl]-2-oxopyridin-1(2H)-yl}-2-methyl-2-(methylsulfonyl)butanamide To 4-{4-[4-(3-hydroxypropyl)phenyl]-2-oxopyridin-1(2H)-yl}-2-methyl-2-(methylsulfonyl)-N-(tetrahydro-2H-pyran-2-yloxy)butanamide (213 mg, 0.420 mmol) was added 4 N hydrogen chloride in dioxane (5.0 mL) and methanol (0.50 mL). The reaction was stirred for 30 minutes and then evaporated to dryness. The residue was dissolved in minimal dichloromethane (2.0 mL) and diluted with ether to produce a precipitate. The suspension was stirred overnight at room temperature. The resulting solid was allowed to settle and the liquid was decanted off. The solid was rinsed twice with ether and dried on a vacuum pump to give the title compound as a white solid (164 mg, 92.4%).

$^1$H NMR (400 MHz, CD$_3$OD, δ ppm 1.72 (s, 3H), 1.83-1.91 (m, 2H), 2.41 (ddd, J=13.4, 10.9, 5.4 Hz, 1H), 2.66 (ddd, J=13.6, 10.8, 5.4 Hz, 1H), 2.76 (m, 2H), 3.10 (s, 3H), 3.59 (t, J=6.4 Hz, 2H), 4.05 (ddd, J=12.5, 10.5, 5.2 Hz, 1H), 4.38 (ddd, J=12.9, 10.7, 5.0 Hz, 1H), 6.95 (d, J=1.8 Hz, 1H), 7.00 (m, 1H), 7.38 (br d, J=8.3 Hz, 2H), 7.66 (br d, J=8.3 Hz, 2H), 7.87 (d, J=7.1 Hz, 1H). LCMS: 423.3 (M+1).

Example 32

(2R)—N-hydroxy-4-[4-{4-[2-(3-hydroxycyclobutyl)ethoxy]phenyl}-2-oxopyridin-1(2H)-yl]-2-methyl-2-(methylsulfonyl)butanamide

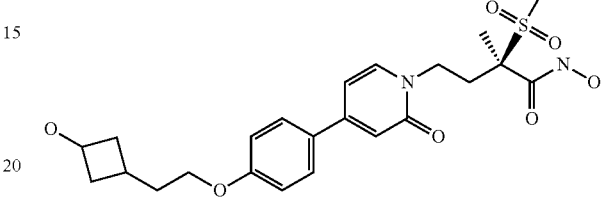

Step A) 3-(2-{[Tert-butyl(diphenyl)silyl]oxy}ethyl)cyclobutanol 3-(2-{[Tert-butyl(diphenyl)silyl]oxy}ethyl)cyclobutanone (5.11 g, 14.5 mmol) (WO 2006063281) was dissolved in tetrahydrofuran (120 mL). Sodium borohydride (548 mg, 14.5 mmol) was added and the reaction was stirred overnight at room temperature. The reaction was quenched with water and saturated aqueous sodium bicarbonate and stirred for 20 min until the bubbling ceased. The reaction mixture was diluted with ether and the aqueous layer was extracted with ether. The combined organic layers were washed with brine, dried over magnesium sulfate, filtered and evaporated in vacuo to give 3-(2-{[tert-butyl(diphenyl)silyl]oxy}ethyl)cyclobutanol (3.58 g, 69.6%) as a clear oil. Partial $^1$H NMR indicated a ~3.5:1 mix of cis-trans isomers. (CDCl$_3$, δ ppm, key peaks are 4.08 (quintet, J=7.42, 0.78H) and 4.34 (quintet, J=6.83, 0.22H).

Step B) Tert-butyl(diphenyl){2-[3-(tetrahydro-2H-pyran-2-yloxy)cyclobutyl]ethoxy}silane 3-(2-{[Tert-butyl(diphenyl)silyl]oxy}ethyl)cyclobutanol (3.58 g, 10.1 mmol) was dissolved in dry tetrahydrofuran (50 mL) and 2,3-dihydro-4H-pyran and 4-toluenesulfonic acid pyridine salt were added and the reaction was stirred at room temperature for 48 hours. The reaction was concentrated in vacuo and purified on silica gel with a heptane-ethyl acetate gradient (5% ethyl acetate, then 20% ethyl acetate) to give crude tert-butyl(diphenyl){2-[3-(tetrahydro-2H-pyran-2-yloxy)cyclobutyl]ethoxy}silane (4.66 g, 105%) as a milky oil. Partial $^1$H NMR indicated a ~4:1 mix of unknown cis-trans isomers. (CDCl$_3$, δ ppm, key peaks are 4.05 (m, 0.80H), 4.30 (m, 0.20H), 4.52 (m, 0.20H), 4.56 (m, 0.80H).

Step C) 2-[3-(Tetrahydro-2H-pyran-2-yloxy)cyclobutyl]ethanol

Tert-butyl(diphenyl){2-[3-(tetrahydro-2H-pyran-2-yloxy)cyclobutyl]ethoxy}silane (4.66 g, 10.6 mmol) was dissolved in tetrahydrofuran (50 mL) and tetrabutylammonium fluoride (1.0 N in tetrahydrofuran, 1.66 mL, 10.6 mmol). The reaction was stirred at room temperature overnight. The reaction was evaporated in vacuo and purified on silica gel with a heptane-ethyl acetate gradient (10% ethyl acetate, then 50% ethyl acetate) to give 2-[3-(tetrahydro-2H-pyran-2-yloxy)cyclobutyl]ethanol (2.14 g, 100%) as a yellow oil. Partial ¹H NMR indicated a ~4:1 mix of unknown cis-trans isomers. (CDCl₃, δ ppm, key peaks are 4.07 (m, 0.80H), 4.35 (m, 0.20H), 4.54 (m, 0.20H), 4.56 (m, 0.80H).

Step D) 2-({3-[2-(4-Bromophenoxy)ethyl]cyclobutyl}oxy)tetrahydro-2H-pyran

2-[3-(Tetrahydro-2H-pyran-2-yloxy)cyclobutyl]ethanol (1.08 g, 5.39 mmol) was dissolved in tetrahydrofuran (20 mL) and was cooled in an ice bath. Triphenylphosphine (2.12 g, 8.09 mmol) and 4-bromo-phenol (1.12 g, 6.47 mmol) were added and the reaction was stirred until dissolved. Diethylazodicarboxylate (1.45 g, 8.09 mmol) was added dropwise to the reaction and the reaction was then warmed to room temperature and stirred for 48 hours. The reaction was diluted with ethyl acetate and washed with 1 N aqueous sodium hydroxide. The organic layer was dried over magnesium sulfate, filtered and evaporated in vacuo to give a clear oil. Purification on silica gel with heptane-ethyl acetate (15% ethyl acetate) gave 2-({3-[2-(4-bromophenoxy)ethyl]cyclobutyl}oxy)tetrahydro-2H-pyran (622 mg, 32.4%) as a clear oil. Partial ¹H NMR indicated a ~4:1 mix of unknown cis-trans isomers. (CDCl₃, δ ppm, key peaks are 4.08 (m, 0.80H), 4.38 (m, 0.20H), 6.74 (d, J=8.98, 2H), 7.34 (d, J=9.18, 2H).

Step E) 2-[(3-{2-[4-(4,4,5,5-tetramethyl-1,3,2-dioxaborolan-2-yl)phenoxy]ethyl}cyclobutyl)oxy]tetrahydro-2H-pyran To a flask containing 2-({3-[2-(4-bromophenoxy)ethyl]cyclobutyl}oxy)tetrahydro-2H-pyran (622 mg, 1.75 mmol), bis(pinacolato)diboron (612 mg, 2.41 mmol), potassium acetate (521 mg, 5.25 mmol), and [1,1'-bis-(diphenylphosphino)ferrocene]-dichloropalladium (II)dichloromethane complex (128 mg, 0.175 mmol) was added deoxygenated 1,4-dioxane (8.0 mL). The reaction was heated at 80° C. under nitrogen overnight. The reaction was cooled, diluted with ether and filtered through a pad of celite. The filtrate was evaporated in vacuo to give a black oil. Chromatography on silica gel with heptane-ethyl acetate (33% ethyl acetate) gave 2-[(3-{2-[4-(4,4,5,5-tetramethyl-1,3,2-dioxaborolan-2-yl)phenoxy]ethyl}cyclobutyl)oxy]tetrahydro-2H-pyran as a clear oil (845 mg, 120%). Partial ¹H NMR indicated a ~3.5:1 mix of unknown cis-trans isomers. (CDCl₃, δ ppm, key peaks are 1.31 (s, 12H), 4.08 (m, 0.78H), 4.38 (m, 0.22H), 6.85 (d, J=8.59, 2H), 7.72 (d, J=8.79, 2H).

Step F) (2R)-2-methyl-2-(methylsulfonyl)-4-[2-oxo-4-(4-{2-[3-(tetrahydro-2H-pyran-2-yloxy)cyclobutyl]ethoxy}phenyl)pyridin-1(2H)-yl]-Netrahydro-2H-pyran-2-yloxy)butanamide (2R)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2 B (334 mg, 0.670 mmol), 2-[(3-{2-[4-(4,4,5,5-tetramethyl-1,3,2-dioxaborolan-2-yl)phenoxy]ethyl}cyclobutyl)oxy]tetrahydro-2H-pyran (324 mg, 0.804 mmol), potassium carbonate (463 mg, 3.35 mmol), and palladium II EnCat (172 mg, 0.067 mmol) were combined into a flask, placed under vacuum and opened to nitrogen. Deoxygenated 1,4-dioxane (2.0 mL) and water (0.50 mL) were added and the reaction was heated at 80° C. under nitrogen overnight. The reaction was cooled, diluted with ethyl acetate and filtered through celite. The celite was washed with ethyl acetate and the filtrate was evaporated in vacuo onto silica gel. Chromatography on silica gel with a dichloromethane-methanol gradient (1%-25%) gave (2R)-2-methyl-2-(methylsulfonyl)-4-[2-oxo-4-(4-{2-[3-(tetrahydro-2H-pyran-2-yloxy)cyclobutyl]ethoxy}phenyl)pyridin-1(2H)-yl]-Netrahydro-2H-pyran-2-yloxy)butanamide as a tan foam (386 mg, 89.1%. LCMS 645.8 (M−1).

Step G) (2R)—N-hydroxy-4-[4-{4-[2-(3-hydroxycyclobutyl)ethoxy]phenyl}-2-oxopyridin-1(2H)-yl]-2-methyl-2-(methylsulfonyl)butanamide To (2R)-2-methyl-2-(methylsulfonyl)-4-[2-oxo-4-(4-{2-[3-(tetrahydro-2H-pyran-2-yloxy)cyclobutyl]ethoxy}phenyl)pyridin-1(2H)-yl]-Netrahydro-2H-pyran-2-yloxy)butanamide (386 mg, 0.597 mmol) was added 4 N hydrogen chloride in dioxane (6.0 mL) and methanol (0.60 mL). The reaction was stirred for 30 minutes and then evaporated in vacuo to give a yellow oil. The residue was dissolved in a minimal amount of methanol (0.50 mL) and diluted with ether to give a yellow precipitate. This suspension was stirred overnight at room temperature. The solid was allowed to settle and the liquid was decanted off. The solid was rinsed twice with ether and dried on a vacuum pump to give the title compound as a white solid (229 mg, 80.5%). ¹H NMR (poor resolution in spectra) (400 MHz, METHANOL-d₄) δ ppm 1.55-1.63 (m, 2H) 1.69-1.73 (m, 3H) 1.87-1.97 (m, 3H) 2.11 (t, J=6.83 Hz, 0H) 2.36-2.50 (m, 3H) 2.61-2.72 (m, 1H) 3.08-3.11 (m, 3H) 3.99-4.10 (m, 4H) 4.32-4.42 (m, 1H) 6.89-6.97 (m, 1H) 7.00-7.07 (m, 3H) 7.67-7.73 (m, 2H) 7.87 (t, J=10.54 Hz, 1H). LCMS 479.6 (M+1).

Example 33

(+/−)-4-[4-(1-benzofuran-2-yl)-2-oxopyridin-1(2H)-yl]-N-hydroxy-2-methyl-2-(methylsulfonyl)butanamide

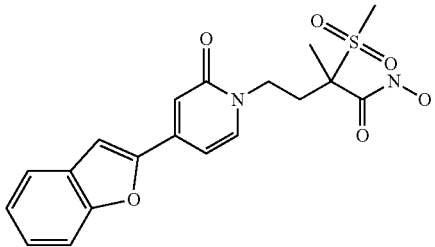 [SMILES: CC(CCn1ccc(-c2cc3ccccc3o2)cc1=O)(C(=O)NO)S(C)(=O)=O]

Step A) (+/−)-4-[4-(1-benzofuran-2-yl)-2-oxopyridin-1(2H)-yl]-2-methyl-2-(methylsulfonyl)-N-(tetrahydro-2H-pyran-2-yloxy)butanamide Pd EnCat™ (130 mg, 0.051 mmol) was added to a mixture of potassium carbonate (221 mg, 1.60 mmol), 1-benzofuran-2-ylboronic acid (271 mg, 0.954 mmol), and 4-(4-iodo-2-oxopyridin-1(2H)-yl)-2-methyl-2-(methylsulfonyl)-N-(tetrahydro-2H-pyran-2-yloxy)butanamide, which may be produced as in Preparation 2A (240 mg, 0.63 mmol) in dioxane:water (5 mL, 4:1) in a 2-5 mL microwave vial and the reaction was heated at 90° C. overnight. The reaction was filtered and the resin was washed with ethyl acetate (50 mL) and water (50 mL). The filtrate was concentrated to dryness and the crude was purified via flash chromatography on an Analogix SF15-12g column and eluted with ethyl acetate in heptane (0-80%) to afford the title compound as a white solid (105 mg, 42.8%). LC-MS m/z 487.7 (M−1).

Step B) (+/−)-4-[4-(1-Benzofuran-2-yl)-2-oxopyridin-1(2H)-yl]-N-hydroxy-2-methyl-2-(methylsulfonyl)butanamide A 4.0 M solution of HCl in 1,4-dioxane (5 mL) was added slowly to a solution of (+/−)-4-[4-(1-benzofuran-2-yl)-2-oxopyridin-1(2H)-yl]-2-methyl-2-(methylsulfonyl)-N-(tetrahydro-2H-pyran-2-yloxy)butanamide (105 mg, 0.22 mmol) in dichloromethane (5 mL) with water (1.0 mL) at 0° C. The ice bath was removed and the reaction was allowed to warm to rt. After 30 min (complete by TLC), the reaction was concentrated to afford a crude white solid. The crude was triturated in isopropanol (5 mL) overnight. The solid was collected via filtration, washed with isopropanol (5 mL), isopropanol:heptane (1:1, 5 mL), heptane (5 mL), and ether (5 mL). The solid was collected by filtration and dried under vacuum to afford a white solid (86.1 mg, 99%). LC-MS m/z 405.5 (M+1). $^1$H NMR (400 MHz, DMSO-$d_6$) δ ppm 1.57 (s, 3H) 2.10-2.23 (m, 1H) 2.39-2.48 (m, 1H) 3.11 (s, 3H) 3.71-3.81 (m, 1H) 4.05-4.15 (m, 1H) 6.78-6.89 (m, 2H) 7.27-7.35 (m, 1H) 7.37-7.45 (m, 1H) 7.63-7.82 (m, 4H).

Example 34

(+/−)-N-hydroxy-4-[4-(6-methoxy-2-naphthyl)-2-oxopyridin-1(2H)-yl]-2-methyl-2-(methylsulfonyl)butanamide

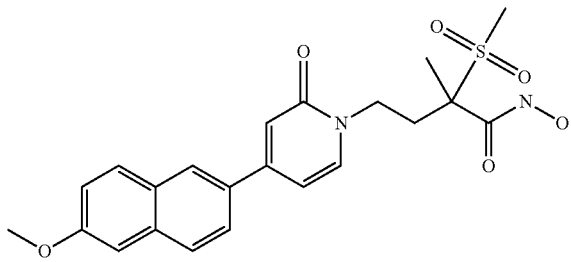 [SMILES: COc1ccc2cc(-c3ccn(CCC(C)(C(=O)NO)S(C)(=O)=O)c(=O)c3)ccc2c1]

Step A) (+/−)-4-[4-(6-methoxy-2-naphthyl)-2-oxopyridin-1(2H)-yl]-2-methyl-2-(methylsulfonyl)-N-(tetrahydro-2H-pyran-2-yloxy)butanamide (+/−)-4-(4-Iodo-2-oxopyridin-1(2H)-yl)-2-methyl-2-(methylsulfonyl)-N-(tetrahydro-2H-pyran-2-yloxy)butanamide, which may be produced as in Preparation 2A and (6-methoxy-2-naphthyl)boronic acid were converted to the title product following the general procedure outlined for (+/−)-4-[4-(1-benzofuran-2-yl)-2-oxopyridin-1(2H)-yl]-2-methyl-2-(methylsulfonyl)-N-(tetrahydro-2H-pyran-2-yloxy)butanamide (Example 33, Step A). The title compound was obtained as a white solid (452.7 mg, 85.3%) LC-MS m/z 529.7 (M+1).

Step B) N-hydroxy-4-[4-(6-methoxy-2-naphthyl)-2-oxopyridin-1(2H)-yl]-2-methyl-2-(methylsulfonyl)butanamide (+/−)-4-[4-(6-Methoxy-2-naphthyl)-2-oxopyridin-1(2H)-yl]-2-methyl-2-(methylsulfonyl)-N- (tetrahydro-2H-pyran-2-yloxy)butanamide was converted to the title product following the general procedure outlined for (+/−)-4-[4-(1-Benzofuran-2-yl)-2-oxopyridin-1(2H)-yl]-N-hydroxy-2-methyl-2-(methylsulfonyl)butanamide (Example 33, Step B). The title compound was obtained as a white solid (101.2 mg, 69.9%) LC-MS m/z 445.3 (M+1). $^1$H NMR (400 MHz, DMSO-$d_6$) δ ppm 1.59 (s, 3H) 2.13-2.27 (m, 1H) 2.37-2.49 (m, 1H) 3.12 (s, 3H) 3.70-3.84 (m, 1H) 3.90 (s, 3H) 4.06-4.25 (m, 1H) 6.77-6.89 (m, 2H) 7.18-7.26 (m, 1H) 7.38 (d, J=2.54 Hz, 1H) 7.76-7.86 (m, 2H) 7.87-7.97 (m, 2H) 8.29 (d, J=1.76 Hz, 1H) 11.18 (br. s., 1H).

Example 35

N-Hydroxy-2-methyl-2-(methylsulfonyl)-4-[2-oxo-4-(4-pyridin-4-ylphenyl)pyridin-1(2H)-yl]butanamide

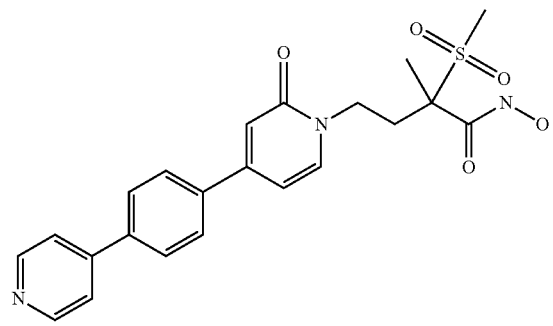 [SMILES: CC(CCn1ccc(-c2ccc(-c3ccncc3)cc2)cc1=O)(C(=O)NO)S(C)(=O)=O]

Step A) (+/−)-2-Methyl-2-(methylsulfonyl)-4-[2-oxo-4-(4-pyridin-4-ylphenyl)pyridin-1(2H)-yl]-N-tetrahydro-2H-pyran-2-yloxy)butanamide (+/−)-4-(4-Iodo-2-oxopyridin-1(2H)-yl)-2-methyl-2-(methylsulfonyl)-N-(tetrahydro-2H-pyran-2-yloxy)butanamide, which may be prepared as in Preparation 2A and 4-[4-(4,4,5,5-tetramethyl-1,3,2-dioxaborolan-2-yl)phenyl]pyridine were converted to the title product following the general procedure outlined for (+/−)-4-[4-(1-benzofuran-2-yl)-2-oxopyridin-1(2H)-yl]-2-methyl-2-(methylsulfonyl)-N-(tetrahydro-2H-pyran-2-yloxy)butanamide in Example 33, Step A. The title compound was obtained as a white solid (161 mg, 61%) LC-MS m/z 526.7 (M+1).

Step B) (+/−)-N-hydroxy-2-methyl-2-(methylsulfonyl)-4-[2-oxo-4-(4-pyridin-4-ylphenyl)pyridin-1 (2H)-yl]butanamide (+/−)-2-Methyl-2-(methylsulfonyl)-4-[2-oxo-4-(4-pyridin-4-ylphenyl)pyridin-1(2H)-yl]-N-tetrahydro-2H-pyran-2-yloxy)butanamide was converted to the title product following the general procedure outlined for (+/−)-4-[4-(1-benzofuran-2-yl)-2-oxopyridin-1(2H)-yl]-N-hydroxy-2-methyl-2-(methylsulfonyl)butanamide in Example 33, Step B. The title compound was obtained as a white solid (90 mg, 62%) LC-MS m/z 442.3 (M+1). $^1$H NMR (400 MHz, DMSO-$d_6$) δ ppm 1.58 (s, 3H) 2.09-2.24 (m, 1H) 2.44 (m, 1H) 3.11 (s, 3H) 3.72-3.82 (m, 1H) 4.07-4.22 (m, 1H) 6.69-6.78 (m, 1H) 6.84 (d, J=1.95 Hz, 1H) 7.82 (d, J=7.03 Hz, 1H) 7.98 (d, J=8.59 Hz, 2H) 8.12 (d, J=8.59 Hz, 2H) 8.36 (d, J=5.86 Hz, 2H) 8.93 (d, J=6.25 Hz, 2H) 11.15 (br. s., 1H)

Example 36

N-hydroxy-2-methyl-2-(methylsulfonyl)-4-(2-oxo-4-quinolin-7-ylpyridin-1(2H)-yl)butanamide

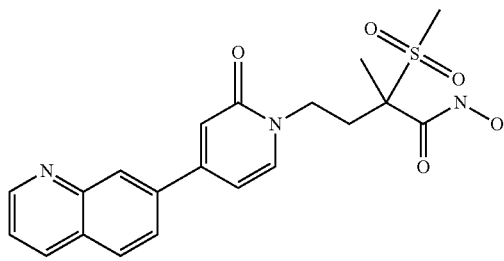 [SMILES: CC(CCn1ccc(-c2ccc3cccnc3c2)cc1=O)(C(=O)NO)S(C)(=O)=O]

Step A) Quinolin-7-yl trifluoromethanesulfonate

Trifluoromethanesulfonic anhydride (1.40 mL, 8.32 mmol) was added dropwise via a syringe to a solution of quinolin-7-ol (930 mg, 6.41 mmol), and pyridine (1.05 mL, 13.0 mmol) in anhydrous dichloromethane (50 mL) at 0° C. After addition the ice bath was removed and the reaction was allowed to warm to room temperature and stirred overnight. The reaction was concentrated and purified via flash chromatography using an Analogix SF25-40g column and eluant of ethyl acetate in heptane (0-40%) to afford the title compound as an orange-white solid (1.54 g, 86.7%). LC-MS m/z 278.4 (M+1). $^1$H NMR (400 MHz, CHLOROFORM-d) δ ppm 7.42-7.57 (m, 2H) 7.95 (d, J=8.98 Hz, 1H) 8.05 (d, J=2.54 Hz, 1H) 8.20-8.29 (m, 1H) 8.97-9.06 (m, 1H).

Step B) 7-(4,4,5,5-Tetramethyl-1,3,2-dioxaborolan-2-yl)quinoline

Potassium acetate (391 mg, 3.98 mmol) was added to a solution of quinolin-7-yl trifluoromethanesulfonate (370 mg, 1.32 mmol), 4,4,4',4',5,5,5',5'-octamethyl-2,2'-bi-1,3,2-dioxaborolane (405 mg, 1.60 mmol), and [1,1'-bis-(diphenylphosphino)ferrocene]-dichloropalladium (II) dcm complex (325 mg, 0.40 mmol) in 1,4-dioxane (5.0 mL) in a 20 mL vial. The vial was capped and heated to 80° C. and stirred at this temperature overnight. The reaction was allowed to cool, diluted with ethyl acetate (25 mL) and water (25 mL), filtered through celite (~1 inch) and the filter pad was washed with ethyl acetate (10 mL). The organic layer was separated, and the aqueous layer was extracted with ethyl acetate (2×30 mL). The combined organics were dried (MgSO$_4$), filtered, and concentrated. Crude material was purified via flash chromatography using an Analogix SF15-24g column and ethyl acetate in heptane (0-50%) as the eluent to afford the title compound as a white solid (277 mg, 81.3%). LC-MS m/z 256.5 (M+1). $^1$H NMR (400 MHz, CHLOROFORM-d) δ ppm 1.40 (s, 12H) 7.40-7.45 (m, 1H) 7.81 (d, J=8.01 Hz, 1H) 7.88-7.95 (m, 1H) 8.12-8.18 (m, 1H) 8.62 (d, J=0.78 Hz, 1H) 8.83-9.01 (m, 1H)

Step C) (+/−)-2-Methyl-2-(methylsulfonyl)-4-(2-oxo-4-quinolin-7-ylpyridin-1(2H)-yl)-N-(tetrahydro-2H-pyran-2-yloxy)butanamide (+/−)-4-(4-Iodo-2-oxopyridin-1(2H)-yl)-2-methyl-2-(methylsulfonyl)-N-(tetrahydro-2H-pyran-2 -yloxy)butanamide, which may be produced as in Preparation 2A and 7-(4,4,5,5-tetramethyl-1,3,2-dioxaborolan-2-yl)quinoline were converted to the title product following the general procedure outlined for (+/−)-4-[4-(1-benzofuran-2-yl)-2-oxopyridin-1 (2H)-yl]-2-methyl-2-(methylsulfonyl)-N-(tetrahydro-2H-pyran-2-yloxy)butanamide in Example 33, Step A. The title compound was obtained as a white solid (221 mg, 88.1%) LC-MS m/z 500.7 (M+1).

Step D) N-hydroxy-2-methyl-2-(methylsulfonyl)-4-(2-oxo-4-quinolin-7-ylpyridin-1(2H)-yl)butanamide, hydrochloride salt 2-Methyl-2-(methylsulfonyl)-4-(2-oxo-4-quinolin-7-ylpyridin-1(2H)-yl)-N-(tetrahydro-2H-pyran-2-yloxy)butanamide was converted to the title product following the general procedure outlined for (+/−)-4-[4-(1-benzofuran-2-yl)-2-oxopyridin-1(2H)-yl]-N-hydroxy-2-methyl-2-(methylsulfonyl)butanamide in Example 33, Step B. Purification was performed using preparatory HPLC to afford the title compound as a white solid (65.5 mg, 32.8%) LC-MS m/z 416.6 (M+1). $^1$H NMR (400 MHz, DMSO-d$_6$) δ ppm $^1$H NMR (400 MHz, DMSO-d$_6$) δ ppm 1.60 (s, 3H) 2.14-2.26 (m, 1H) 2.41-2.48 (m, 1H) 3.12 (s, 3H) 3.72-3.86 (m, 1H) 4.09-4.22 (m, 1H) 6.84-6.88 (m, 1H) 6.90 (d, J=2.15 Hz, 1H) 7.56-7.65 (m, 1H) 7.83 (d, J=7.23 Hz, 1H) 7.93-8.02 (m, 1H) 8.10 (d, J=8.40 Hz, 1H) 8.35 (d, J=1.76 Hz, 1H) 8.40-8.47 (m, 1H) 8.94-9.02 (m, 1H) 9.27 (d, J=1.56 Hz, 1H) 11.17 (s, 1H).

Example 37

N-hydroxy-2-methyl-2-(methylsulfonyl)-4-{2-oxo-4-[4-(2-pyridin-4-ylethoxy)phenyl]pyridin-1(2H)-yl}butanamide

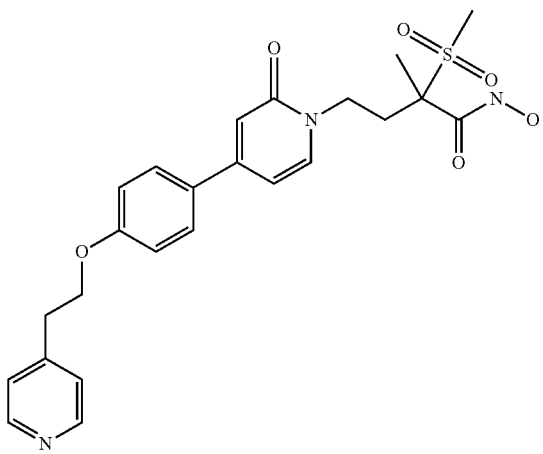 [SMILES: CC(CCn1ccc(-c2ccc(OCCc3ccncc3)cc2)cc1=O)(C(=O)NO)S(C)(=O)=O]

Step A) 4-[2-(4-Bromophenoxy)ethyl]pyridine

Diethyl azodicarboxylate (4.44 mL, mmol, 40%) was slowly added to a solution of 2-pyridin-4-yl-ethanol (1.00 g, 8.12 mmol), triphenylphosphine (2.56 g, 9.74 mmol), and 4-bromophenol (1.40 g, 8.12 mmol) in THF (40.6 mL) at 0° C. under nitrogen. The reaction was allowed to warm to room temperature and stirred overnight. The reaction mixture was quenched with water (150 mL) and extracted with ethyl acetate (200 mL). The organics were washed with 1N aqueous NaOH (100 mL) and brine (100 mL). The organics were dried (Na₂SO₄), filtered, and concentrated. The crude material was crystallized with ether:heptanes (1:1, ~25 mL) and the solid was removed via filtration and washed with ether:heptanes. The combined filtrates were concentrated and further purified via flash chromatography using an Analogix SF25-40 g column and ethyl acetate in heptane (0-30%) as the eluant to afford the title compound as a clear liquid (1.20 g, 46.2%). LC-MS m/z 278.4 (M+1). ¹H NMR (400 MHz, CHLOROFORM-d) δ ppm 3.11 (t, 2H) 4.19 (t, J=6.44 Hz, 2H) 6.77 (d, J=8.98 Hz, 2H) 7.22-7.26 (m, 2H) 7.38 (d, J=4.69 Hz, 2H) 8.54-8.57 (m, 3H)

Step B) 4-{2-[4-(4,4,5,5-Tetramethyl-1,3,2-dioxaborolan-2-yl)phenoxy]ethyl}pyridine Potassium acetate (391 mg, 3.98 mmol) was added to a solution of 4-[2-(4-bromophenoxy)ethyl]pyridine (370 mg, 1.33 mmol), 4,4,4',4',5,5,5',5'-octamethyl-2,2'-bi-1,3,2-dioxaborolane (405 mg, 1.60 mmol), and [1,1'-bis-(diphenylphosphino)ferrocene]-dichloropalladium (II) dcm complex (325 mg, 0.40 mmol) in 1,4-dioxane (5.0 mL) in a 20 mL vial. The vial was capped and heated to 80° C. and stirred at this temperature overnight. [1,1'-bis-(diphenylphosphino)ferrocene]-dichloropalladium (II) dcm complex (325 mg, 0.40 mmol) was added to the reaction and the mixture was reheated to 80° C. and stirring was continued at this temperature overnight. The reaction was cooled, diluted with ethyl acetate (25 mL) and water (25 mL), filtered through celite (~1 inch) and the filter pad was washed with ethyl acetate (10 mL). The organic layer was separated, and the aqueous layer was extracted with ethyl acetate (2×30 mL). The combined organics were dried (MgSO₄), filtered, and concentrated. The crude was purified via flash chromatography using an Analogix SF15-24g column and ethyl acetate in heptane (30-80%) as the eluant to afford the title compound as an orange-solid (547 mg, 85.3%). LC-MS m/z 326.6 (M+1).

Step C) (+/−)-2-Methyl-2-(methylsulfonyl)-4-{2-oxo-4-[4-(2-pyridin-4-ylethoxy)phenyl]pyridin-1(2H)-yl}-N-(tetrahydro-2H-pyran-2-yloxy)butanamide (+/−)-4-(4-Iodo-2-oxopyridin-1(2H)-yl)-2-methyl-2-(methylsulfonyl)-N-(tetrahydro-2H-pyran-2-yloxy)butanamide which may be produced as in Preparation 2A and 4-{2-[4-(4, 4,5,5-tetramethyl-1,3,2-dioxaborolan-2-yl)phenoxy] ethyl}pyridine were converted to the title product following the general procedure outlined for (+/−)-4-[4-(1-benzofuran-2-yl)-2-oxopyridin-1(2H)-yl]-2-methyl-2-(methylsulfonyl)-N-(tetrahydro-2H-pyran-2-yloxy)butanamide in Example 33, Step A. The title compound was obtained as a white solid (44.1 mg, 15.4%) LC-MS m/z 568.8 (M−1).

Step D) N-hydroxy-2-methyl-2-(methylsulfonyl)-4-{2-oxo-4-[4-(2-pyridin-4-ylethoxy)phenyl]pyridin-1(2H)-yl}butanamide, hydrochloride salt (+/−)-2-Methyl-2-(methylsulfonyl)-4-{2-oxo-4-[4-(2-pyridin-4-ylethoxy)phenyl]pyridin-1(2H)-yl}-N-(tetrahydro-2H-pyran-2-yloxy)butanamide was converted to the title compound following the general procedure outlined for (+/−)-4-[4-(1-benzofuran-2-yl)-2-oxopyridin-1(2H)-yl]-N-hydroxy-2-methyl-2-(methylsulfonyl)butanamide in Example 33, Step B. The title compound was obtained as a white solid (11.2 mg, 30%) LC-MS m/z 486.6 (M+1). ¹H NMR (400 MHz, METHANOL-d₄) δ ppm 1.70 (s, 3H) 2.28-2.46 (m, 1H) 2.49-2.69 (m, 1H) 3.11 (s, 3H) 3.48 (t, J=5.47 Hz, 2H) 3.93 (dt, 1H) 4.20-4.37 (m, 1H) 4.47 (t, J=5.76 Hz, 2H) 6.75 (br. s., 1H) 7.04 (d, J=8.20 Hz, 1H) 7.67 (m, J=8.20 Hz, 3H) 8.12 (d, J=5.86 Hz, 2H) 8.78 (d, J=5.66 Hz, 2H).

Example 38

(2R)—N-hydroxy-2-methyl-4-{4-[4-(5-methyl-1,3-oxazol-2-yl)phenyl]-2-oxopyridin-1(2H)-yl}-2-(methylsulfonyl)butanamide

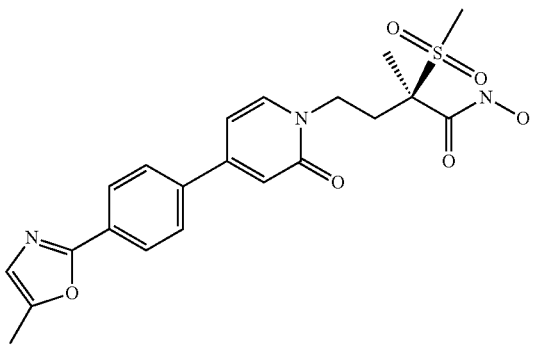 [SMILES: Cc1cnc(-c2ccc(-c3ccn(CC[C@](C)(C(=O)NO)S(C)(=O)=O)c(=O)c3)cc2)o1]

Step A) 5-Methyl-2-[4-(4,4,5,5-tetramethyl-1,3,2-dioxaborolan-2-yl)phenyl]-1,3-oxazole 2-(4-Bromophenyl)-5-methyl-1,3-oxazole was converted to the title product following the general procedure outlined for 4-{2-[4-(4,4,5,5-tetramethyl-1,3,2-dioxaborolan-2-yl) phenoxy]ethyl}pyridine in Example 37, Step B. The title compound was obtained as an orange solid (221.5 mg, 71.7%) LC-MS m/z 286.4 (M+1). ¹H NMR (400 MHz, CHLOROFORM-d) δ ppm 1.37 (s, 12H) 2.41 (d, J=1.17 Hz, 3H) 6.81-6.92 (m, 1H) 7.88 (d, J=8.39 Hz, 2H) 8.00 (d, J=8.39 Hz, 2H).

Step B) (2R)-2-methyl-4-{4-[4-(5-methyl-1,3-oxazol-2-yl)phenyl]-2-oxopyridin-1(2H)-yl}-2-(methylsulfonyl)-N-(tetrahydro-2H-pyran-2-yloxy)butanamide (2R)-4-(4-Iodo-2-oxopyridin-1(2H)-yl)-2-methyl-2-(methylsulfonyl)-N-(tetrahydro-2H-pyran-2-yloxy)butanamide, which may be produced as in Preparation 2B, and 5-Methyl-2-[4-(4,4,5,5-tetramethyl-1,3,2-dioxaborolan-2-yl)phenyl]-1,3-oxazole were converted to the title compound following the general procedure outlined for (+/+4-[4-(1-benzofuran-2-yl)-2-oxopyridin-1(2H)-yl]-2-methyl-2-(methylsulfonyl)-N-(tetrahydro-2H-pyran-2-yloxy)butanamid in Example 33, step A. The title compound was obtained as a white solid (121 mg, 61%) LC-MS m/z 514.7 (M−1).

Step C) (2R)—N-hydroxy-2-methyl-4-{4-[4-(5-methyl-1,3-oxazol-2-yl)phenyl]-2-oxopyridin-1(2H)-yl}-2-(methylsulfonyl)butanamide (2R)-2-methyl-4-{4-[4-(5-methyl-1,3-oxazol-2-yl)phenyl]-2-oxopyridin-1(2H)-yl}-2-(methylsulfonyl)-N-(tetrahydro-2H-pyran-2-yloxy)butanamide was converted to the title compound following the general procedure outlined for (+/+4-[4-(1-benzofuran-2-yl)-2-oxopyridin-1(2H)-yl]-N-hydroxy-2-methyl-2-(methylsulfonyl)butanamide, in Example 33, Step B The title compound was obtained as an off-white solid (56 mg, 68%). LC-MS m/z 446.5 (M+1). $^1$H NMR (400 MHz, DMSO-$d_6$) δ ppm 1.58 (s, 3H) 2.07-2.23 (m, 1H) 2.36-2.48 (m, 4H) 3.11 (s, 3H) 3.65-3.86 (m, 1H) 4.03-4.19 (m, 1H) 6.67-6.74 (m, 1H) 6.78 (d, J=1.95 Hz, 1H) 7.04 (d, J=1.17 Hz, 1H) 7.80 (d, J=7.23 Hz, 1H) 7.89 (d, J=8.59 Hz, 2H) 8.01 (d, J=8.59 Hz, 2H) 11.15 (br. s., 1H)

Example 39

(2R)—N-hydroxy-2-methyl-2-(methylsulfonyl)-4-[2-oxo-4-(4-pyrimidin-2-ylphenyl)pyridin-1(2H)-yl]butanamide

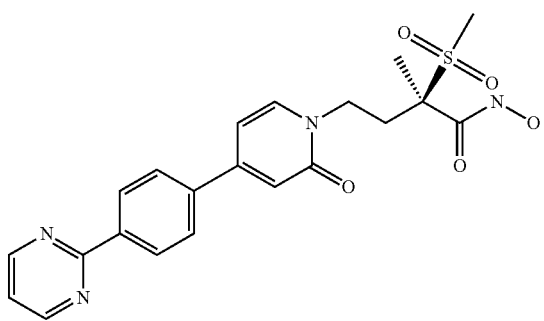 [SMILES: C[C@@](CCn1ccc(-c2ccc(-c3ncccn3)cc2)cc1=O)(C(=O)NO)S(C)(=O)=O]

Step A) 2-[4-(4,4,5,5-Tetramethyl-1,3,2-dioxaborolan-2-yl)phenyl]pyrimidine 2-(4-Bromophenyl)pyrimidine was converted to the title product following the general procedure outlined for 4-{2-[4-(4,4,5,5-tetramethyl-1,3,2-dioxaborolan-2-yl)phenoxy]ethyl}pyridine in Example 37, Step B. The title compound was obtained as an orange solid (242.8 mg, 59.3%) LC-MS m/z 283.4 (M+1). $^1$H NMR (400 MHz, CHLOROFORM-d) δ ppm 1.38 (s, 12H) 7.21 (t, J=4.88 Hz, 1H) 7.27 (s, 1H) 7.95 (d, J=8.39 Hz, 2H) 8.45 (d, J=8.59 Hz, 2H) 8.84 (d, J=4.88 Hz, 2H)

Step B) (2R)-2-methyl-2-(methylsulfonyl)-4-[2-oxo-4-(4-pyrimidin-2-ylphenyl)pyridin-1(2H)-yl]-Netrahydro-2H-pyran-2-yloxy)butanamide (2R)-4-(4-iodo-2-oxopyridin-1(2H)-yl)-2-methyl-2-(methylsulfonyl)-N-(tetrahydro-2H-pyran-2-yloxy)butanamide which may be produced as in Preparation 2B and 2-[4-(4,4,5,5-tetramethyl-1,3,2-dioxaborolan-2-yl)phenyl]pyrimidine were converted to the title compound following the general procedure outlined for (+/−)-4-[4-(1-benzofuran-2-yl)-2-oxopyridin-1(2H)-yl]-2-methyl-2-(methylsulfonyl)-N-(tetrahydro-2H-pyran-2-yloxy)butanamide in Example 33, Step A. The title compound was obtained as a yellow solid (166 mg, 78.6%) LC-MS m/z 525.7 (M−1).

Step C) (2R)—N-hydroxy-2-methyl-2-(methylsulfonyl)-4-[2-oxo-4-(4-pyrimidin-2-ylphenyl)pyridin-1(2H)-yl]butanamide (2R)-2-Methyl-2-(methylsulfonyl)-4-[2-oxo-4-(4-pyrimidin-2-ylphenyl)pyridin-1(2H)-yl]-Netrahydro-2H-pyran-2-yloxy)butanamide was converted to the title compound following the general procedure outlined for (+/−)-4-[4-(1-benzofuran-2-yl)-2-oxopyridin-1(2H)-yl]-N-hydroxy-2-methyl-2-(methylsulfonyl)butanamide in Example 33, Step B. The title compound was obtained as an off-white solid (76 mg, 55%). LC-MS m/z 443.5 (M+1). $^1$H NMR (400 MHz, DMSO-$d_6$) δ ppm 1.59 (s, 3H) 2.14-2.25 (m, 1H) 2.38-2.48 (m, 1H) 3.09 (s, 3H) 3.71-3.83 (m, 1H) 4.04-4.20 (m, 1H) 6.68-6.78 (m, 1H) 6.80 (d, J=2.15 Hz, 1H) 7.49 (t, J=4.88 Hz, 1H) 7.80 (d, J=7.02 Hz, 1H) 7.90 (d, J=8.59 Hz, 2H) 8.49 (d, J=8.59 Hz, 2H) 8.95 (d, J=4.88 Hz, 2H) 11.16 (s, 1H).

Example 40

(2R)—N-hydroxy-2-methyl-2-(methylsulfonyl)-4-{2-oxo-4-[4-(2H-1,2,3-triazol-2-yl)phenyl]pyridin-1(2H)-yl}butanamide

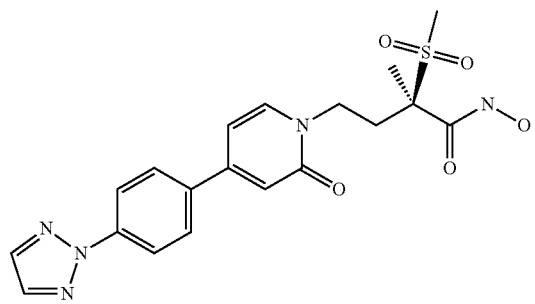 [SMILES: C[C@@](CCn1ccc(-c2ccc(-n3nccn3)cc2)cc1=O)(C(=O)NO)S(C)(=O)=O]

Step A) 2-[4-(4,4,5,5-Tetramethyl-1,3,2-dioxaborolan-2-yl)phenyl]-2H-1,2,3-triazole 2-(4-Bromophenyl)-2H-1,2,3-triazole was converted to the title product following the general procedure outlined for 4-{2-[4-(4,4,5,5-tetramethyl-1,3,2-dioxaborolan-2-yl)phenoxy]ethyl}pyridine in Example 37, Step B. The title compound was obtained as an orange solid (240.6 mg, 78%) LC-MS m/z 272.4 (M+1). $^1$H NMR (400 MHz, CHLOROFORM-d) δ ppm 1.37 (s, 12H) 7.83 (s, 2H) 7.94 (d, J=8.59 Hz, 2H) 8.10 (d, J=8.59 Hz, 2H).

Step B) (2R)-2-methyl-2-(methylsulfonyl)-4-{2-oxo-4-[4-(2H-1,2,3-triazol-2-yl)phenyl]pyridin-1(2H)-yl}-N-(tetrahydro-2H-pyran-2-yloxy)butanamide (2R)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2A, and 2-[4-(4,4,5,5-tetramethyl-1,3,2-dioxaborolan-2-yl)phenyl]-2H-1,2,3-triazole were converted to the title compound following the general procedure outlined for (+/−)-4-[4-(1-benzofuran-2-yl)-2-oxopyridin-1(2H)-yl]-2-methyl-2-(methylsulfonyl)-N-(tetrahydro-2H-pyran-2-yloxy)butanamide in Example 33, Step A. The title compound was obtained as a white solid (101 mg, 48.8%) LC-MS m/z 514.7 (M−1).

Step C) (2R)—N-hydroxy-2-methyl-2-(methylsulfonyl)-4-{2-oxo-4-[4-(2H-1,2,3-triazol-2-yl)phenyl]pyridin-1(2H)-yl}butanamide (2R)-2-methyl-2-(methylsulfonyl)-4-{2-oxo-4-[4-(2H-1,2,3-triazol-2-yl)phenyl]pyridin-1(2H)-yl}-N-(tetrahydro-2H-pyran-2-yloxy)butanamide was converted to the title compound following the procedure outlined for (+/−)-4-[4-(1-Benzofuran-2-yl)-2-oxopyridin-1(2H)-yl]-N-hydroxy-2-methyl-2-(methylsulfonyl)butanamide in Example 33, Step B. The title compound was obtained as an off-white solid (63.7 mg, 74%). LC-MS m/z 432.5 (M+1). $^1$H NMR (400 MHz, DMSO-d$_6$) δ ppm 1.58 (s, 3H) 2.09-2.25 (m, 1H) 2.34-2.47 (m, 1H) 3.11 (s, 3H) 3.70-3.82 (m, 1H) 4.04-4.19 (m, 1H) 6.68-6.73 (m, 1H) 6.78 (d, J=2.15 Hz, 1H) 7.79 (d, J=7.22 Hz, 1H) 7.95 (d, J=8.78 Hz, 2H) 8.12 (d, J=8.59 Hz, 2H) 8.17 (s, 2H) 11.15 (br. s., 1H).

Example 41

2R)-4-[4-(4-fluorophenyl)-2-oxopyridin-1(2H)-yl]-N-hydroxy-2-methyl-2-(methylsulfonyl)-butanamide

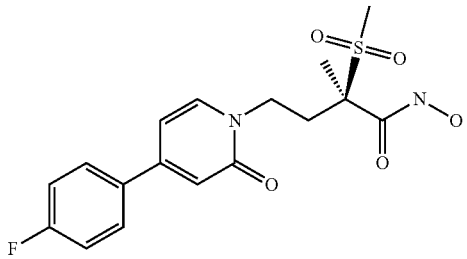 [SMILES: C[C@@](CCn1ccc(-c2ccc(F)cc2)cc1=O)(C(=O)NO)S(C)(=O)=O]

Step A) (2R)-4-[4-(4-fluorophenyl)-2-oxopyridin-1 (2H)-yl]-2-methyl-2-(methylsulfonyl)-N-(tetrahydro-2H-pyran-2-yloxy)butanamide Pd EnCat™ (200 mg, 0.06 mmol) was added to a mixture of potassium carbonate (250 mg, 1.81 mmol), (4-fluorophenyl)boronic acid (84 mg, 0.602 mmol), and (2R)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2 B, (300 mg, 0.602 mmol) in dioxane:water (5.5 mL, 10:1 mixture) in a 25 mL round bottom flask. The flask was heated overnight at 80° C. The reaction was cooled to ambient temperature and filtered through celite and washed with ethyl acetate (20 mL). The crude material was concentrated, and purified by chromatography on silica gel (gradient: 100:0 dichloromethane:methanol to 95:5 dichloromethane:methanol) to provide title compound as a viscous, foamy oil. Yield: 257 mg, 91.5%. MS (APCI) m/z 467.6 (M+H) $^1$H NMR (400 MHz, CHLOROFORM-d) δ ppm 1.54-1.65 (m, 3H) 1.68 (d, J=2.34 Hz, 3H) 1.71-1.99 (m, 3H) 2.32-2.44 (m, 1H) 2.44-2.57 (m, 1H) 3.18 (d, J=2.93 Hz, 3H) 3.54-3.66 (m, 1H) 3.97-4.10 (m, 1H) 4.11-4.25 (m, 1H) 4.25-4.38 (m, 1H) 5.16 (d, J=15.81 Hz, 1H) 6.48 (dd, J=6.93, 1.27 Hz, 1H) 6.76 (s, 1H) 7.12 (t, J=8.59 Hz, 2H) 7.39 (d, J=7.02 Hz, 1H) 7.47-7.57 (m, 2H) 12.15 (d, J=7.42 Hz, 1H)

Step B) (2R)-4-[4-(4-fluorophenyl)-2-oxopyridin-1 (2H)-yl]-N-hydroxy-2-methyl-2-(methylsulfonyl) butanamide A solution of 1.0 M aqueous HCl (2.76 mL) was added slowly to a solution of (2R)-4-[4-(4-fluorophenyl)-2-oxopyridin-1(2H)-yl]-2-methyl-2-(methylsulfonyl)-N-(tetrahydro-2H-pyran-2-yloxy)butanamide (257 mg, 0.55 mmol) in 2-propanol (15 mL) at room temperature. The reaction was allowed to stir at room temperature overnight. After 18 hours the reaction was concentrated to afford a brown solid. Crude material was triturated in ethyl acetate (50 mL) for 1 hour; the solid was collected via filtration and washed with hexanes (20 mL). The solid was allowed to dry on the filter under high vacuum to afford an off-white solid. Yield 153 mg, 73%. MS (APCI) m/z 383.6 (M+H), 1H NMR (400 MHz, DMSO-d$_6$) δ ppm 1.55 (s, 3H) 2.08-2.19 (m, 1H) 2.34-2.44 (m, 1H) 3.08 (s, 3H) 3.64-3.80 (m, 1H) 4.04-4.13 (m, 1H) 6.62 (dd, J=7.02, 2.15 Hz, 1H) 6.67 (d, J=1.95 Hz, 1H) 7.20-7.41 (m, 2H) 7.64-7.84 (m, 3H) 11.12 (br. s., 1H)

Example 42

(2R)-4-[4-(3-fluorophenyl)-2-oxopyridin-1(2H)-yl]-N-hydroxy-2-methyl-2-(methylsulfonyl)butanamide

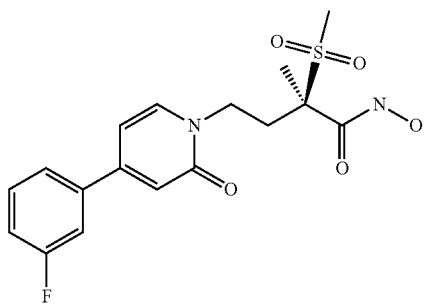 [SMILES: C[C@@](CCn1ccc(-c2cccc(F)c2)cc1=O)(C(=O)NO)S(C)(=O)=O]

Step A) (2R)-4-[4-(3-fluorophenyl)-2-oxopyridin-1 (2H)-yl]-2-methyl-2-(methylsulfonyl)-N-(tetrahydro-2H-pyran-2-yloxy)butanamide The title compound was produced following the general method of Example 41, Step A, using (3-fluorophenyl)boronic acid (84 mg, 0.602 mmol). The crude product was purified by chromatography on silica gel (elution solvent: ethyl acetate) to provide title compound as a viscous, foamy oil. Yield: 125 mg, 44.5%. MS (APCI) m/z 489.6 (M+Na) 1H NMR (400 MHz, CHLOROFORM-d) δ ppm 1.54-1.65 (m, 3H) 1.67-1.71 (m, 3H) 1.71-1.97 (m, 3H) 2.32-2.44 (m, 1H) 2.45-2.58 (m, 1H) 3.19 (d, J=3.32 Hz, 3H) 3.53-3.70 (m, 1H) 3.98-4.07 (m, 1H) 4.12-4.25 (m, 1H) 4.27-4.40 (m, 1H) 5.11-5.21 (m, 1H) 6.49 (dd, J=6.83, 1.76 Hz, 1H) 6.79 (s, 1H) 7.08-7.16 (m, 1H) 7.20-7.28 (m, 1H) 7.29-7.36 (m, 1H) 7.37-7.44 (m, 2H) 12.10 (d, J=6.05 Hz, 1H)

Step B) (2R)-4-[4-(3-fluorophenyl)-2-oxopyridin-1 (2H)-yl]-N-hydroxy-2-methyl-2-(methylsulfonyl) butanamide Title compound was produced using the general methodology of Example 41, Step B affording an off-white solid. Yield 55 mg, 54%. MS (APCI) m/z 383.5 (M+H). $^1$H NMR (400 MHz, DMSO-d$_6$) δ ppm 1.55 (s, 3H) 2.14 (td, J=12.05, 5.17 Hz, 1H) 2.40 (td, J=12.24, 4.78 Hz, 1H) 3.08 (s, 3H) 3.73 (td, J=11.95, 4.78 Hz, 1H) 4.02-4.14 (m, 1H) 4.17-4.42 (m, 1H) 6.65 (dd, J=7.12, 2.05 Hz, 1H) 6.74 (d, J=1.95 Hz, 1H) 7.21-7.33 (m, 1H) 7.43-7.63 (m, 3H) 7.75 (d, J=7.22 Hz, 1H) 11.11 (br. s., 1H)

Example 43

(2R)-4-[4-(2-fluorophenyl)-2-oxopyridin-1(2H)-yl]-N-hydroxy-2-methyl-2-(methylsulfonyl)butanamide

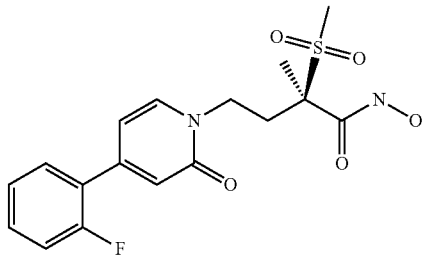 [SMILES: C[C@@](CCn1ccc(-c2ccccc2F)cc1=O)(C(=O)NO)S(C)(=O)=O]

Step A) (2R)-4-[4-(2-fluorophenyl)-2-oxopyridin-1(2H)-yl]-2-methyl-2-(methylsulfonyl)-N-(tetrahydro-2H-pyran-2-yloxy)butanamide Title compound was produced by following the general method of Example 41, Step A, using (2-fluorophenyl)boronic acid (84 mg, 0.602 mmol). The crude material was purified by chromatography on silica gel (elution solvent: ethyl acetate) to provide title compound as a viscous, foamy oil. Yield: 180 mg, 64.1%. MS (APCI) m/z 489.6 (M+Na) 1H NMR (400 MHz, CHLOROFORM-d) δ ppm 1.49-1.66 (m, 3H) 1.69 (d, J=2.34 Hz, 3H) 1.71-1.97 (m, 3H) 2.28-2.45 (m, 1H) 2.45-2.59 (m, 1H) 3.19 (d, J=2.93 Hz, 3H) 3.54-3.70 (m, 1H) 3.92-4.07 (m, 1H) 4.12-4.24 (m, 1H) 4.28-4.39 (m, 1H) 5.10-5.21 (m, 1H) 6.50 (d, J=7.02 Hz, 1H) 6.79 (s, 1H) 7.10-7.17 (m, 1H) 7.18-7.24 (m, 1H) 7.34-7.43 (m, 3H) 12.15 (d, J=7.42 Hz, 1H)

Step B) (2R)-4-[4-(2-fluorophenyl)-2-oxopyridin-1(2H)-yl]-N-hydroxy-2-methyl-2-(methylsulfonyl)butanamide Title compound was produced using the general methodology of Example 41, Step B affording an off-white solid. Yield 71 mg, 48%. MS (APCI) m/z 383.5 (M+H). $^1$H NMR (400 MHz, DMSO-$d_6$) δ ppm 1.55 (s, 3H) 2.05-2.21 (m, 1H) 2.35-2.45 (m, 1H) 3.08 (s, 3H) 3.73 (td, J=12.15, 4.59 Hz, 1H) 4.10 (td, J=11.90, 5.07 Hz, 1H) 4.16-4.34 (m, 1H) 6.46 (dt, J=6.98, 1.88 Hz, 1H) 6.55 (s, 1H) 7.23-7.36 (m, 2H) 7.42-7.52 (m, 1H) 7.56 (td, J=7.90, 1.56 Hz, 1H) 7.73 (d, J=7.02 Hz, 1H) 11.10 (br. s., 1H)

Example 44

(2R)-4-[4-(2,3-difluoro-4-methoxyphenyl)-2-oxopyridin-1(2H)-yl]-N-hydroxy-2-methyl-2-(methylsulfonyl)butanamide

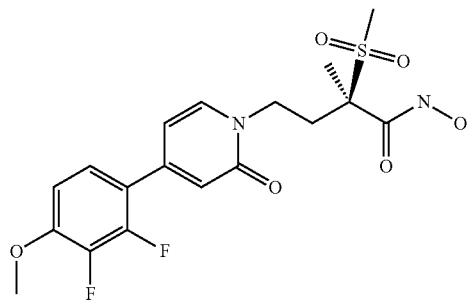 [SMILES: COc1ccc(-c2ccn(CC[C@](C)(C(=O)NO)S(C)(=O)=O)c(=O)c2)c(F)c1F]

Step A) (2R)-4-[4-(2,3-difluoro-4-methoxyphenyl)-2-oxopyridin-1(2H)-yl]-2-methyl-2-(methylsulfonyl)-N-(tetrahydro-2H-pyran-2-yloxy)butanamide Title compound was produced by following the general method of Example 41, Step A, using (2,3-difluoro-4-methoxyphenyl)boronic acid (113 mg, 0.602 mmol. The resulting crude material was purified by chromatography on silica gel (elution solvent: ethyl acetate) to provide title compound as a viscous, foamy oil. Yield: 132 mg, 42.6%. MS (APCI) m/z 515.5 (M+H) 1H NMR (400 MHz, CHLOROFORM-d) δ ppm 1.54-1.66 (m, 3H) 1.68 (d, J=2.34 Hz, 3H) 1.71-1.97 (m, 3H) 2.30-2.44 (m, 1H) 2.45-2.58 (m, 1H) 3.18 (d, J=3.12 Hz, 3H) 3.54-3.68 (m, 1H) 3.92 (s, 3H) 3.99-4.08 (m, 1H) 4.11-4.23 (m, 1H) 4.26-4.40 (m, 1H) 5.10-5.21 (m, 1H) 6.42-6.53 (m, 1H) 6.75 (s, 1H) 6.77-6.86 (m, 1H) 7.05-7.17 (m, 1H) 7.37 (d, J=7.02 Hz, 1H) 12.10 (d, J=7.61 Hz, 1H)

Step B) (2R)-4-[4-(2,3-difluoro-4-methoxyphenyl)-2-oxopyridin-1(2H)-yl]-N-hydroxy-2-methyl-2-(methylsulfonyl)butanamide A solution of 1.0 M aqueous HCl (2.76 mL) was added slowly to a solution of (2R)-4-[4-(2,3-difluoro-4-methoxyphenyl)-2-oxopyridin-1(2H)-yl]-2-methyl-2-(methylsulfonyl)-N-(tetrahydro-2H-pyran-2-yloxy)butanamide (132 mg, 0.26 mmol) in 1,4-dioxane (15 mL) at room temperature. The reaction was allowed to stir at room temperature overnight. After 18 hours the reaction was concentrated to 25% of the original volume, resulting in a white precipitate. The precipitate was filtered via Buchner funnel and washed with hexanes (20 mL) to afford a white solid. Yield 45 mg, 41%. MS (APCI) m/z 431.1 (M+H). $^1$H NMR (400 MHz, DMSO-$d_6$) δ ppm 1.55 (s, 3H) 2.14 (td, J=12.20, 4.88 Hz, 1H) 2.35-2.45 (m, 1H) 3.08 (s, 3H) 3.72 (td, J=12.05, 4.78 Hz, 1H) 3.90 (s, 3H) 4.09 (td, J=11.90, 5.27 Hz, 1H) 6.46 (dt, J=7.02, 1.85 Hz, 1H) 6.54 (s, 1H) 7.03-7.17 (m, 1H) 7.37 (td, J=8.63, 2.24 Hz, 1H) 7.72 (d, J=7.22 Hz, 1H) 9.22 (br. s., 1H) 11.10 (s, 1H)

Example 45

(2R)-4-[4-(3-chloro-2-fluorophenyl)-2-oxopyridin-1(2H)-yl]-N-hydroxy-2-methyl-2-(methylsulfonyl)butanamide

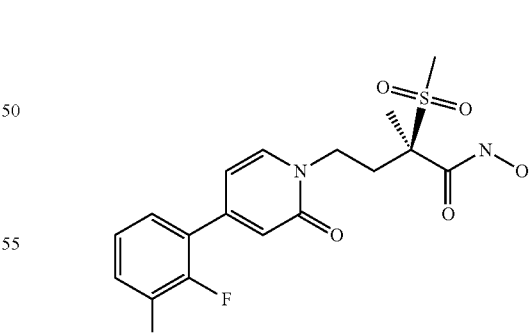

Step A) (2R)-4-[4-(3-chloro-2-fluorophenyl)-2-oxopyridin-1(2H)-yl]-2-methyl-2-(methylsulfonyl)-N-(tetrahydro-2H-pyran-2-yloxy)butanamide Title compound was produced by following the general method of Example 41, Step A, using (3-chloro-2-fluorophenyl)boronic acid (105 mg, 0.602 mmol). The crude material was purified by chromatography on silica gel (elution solvent: ethyl acetate) to provide title compound as a viscous, foamy oil. Yield: 137 mg, 45.4%. MS (APCI (type)) m/z 523.5 (M+Na). $^1$H NMR (400 MHz, CHLOROFORM-d) δ ppm 1.55-1.66 (m, 3H) 1.70 (d, J=2.34 Hz, 3H) 1.73-1.98 (m, 3H) 2.33-2.45 (m, 1H) 2.47-2.63 (m, 1H) 3.20 (d, J=3.71 Hz, 3H) 3.55-3.72 (m, 1H) 3.99-4.11 (m, 1H) 4.12-4.25 (m, 1H) 4.30-4.41 (m, 1H) 5.11-5.23 (m, 1H) 6.45-6.51 (m, 1H) 6.78 (d, J=0.78 Hz, 1H) 7.13-7.20 (m, 1H) 7.26-7.33 (m, 1H) 7.40 (d, J=7.02 Hz, 1H) 7.43-7.50 (m, 1H) 12.04 (d, J=4.29 Hz, 1H)

Step B) (2R)-4-[4-(3-chloro-2-fluorophenyl)-2-oxopyridin-1(2H)-yl]-N-hydroxy-2-methyl-2-(methylsulfonyl)butanamide Title compound was produced using the general methodology of Example 44, Step B. Yield 64 mg, 56%. MS (APCI) m/z 417.5 (M+H). $^1$H NMR (400 MHz, DMSO-d$_6$) δ ppm 1.55 (s, 3H) 2.14 (td, J=12.05, 4.98 Hz, 1H) 2.33-2.45 (m, 1H) 3.08 (s, 3H) 3.74 (td, J=11.71, 4.68 Hz, 1H) 4.10 (td, J=11.85, 4.98 Hz, 1H) 6.47 (d, J=7.22 Hz, 1H) 6.57 (s, 1H) 7.31 (t, J=7.81 Hz, 1H) 7.52 (t, J=6.93 Hz, 1H) 7.66 (d, J=14.83 Hz, 1H) 7.75 (d, J=6.83 Hz, 1H) 9.22 (br. s., 1H) 11.09 (s, 1H)

Example 46

(2R)-4-[4-(2,3-dichlorophenyl)-2-oxopyridin-1(2H)-yl]-N-hydroxy-2-methyl-2-(methylsulfonyl)butanamide

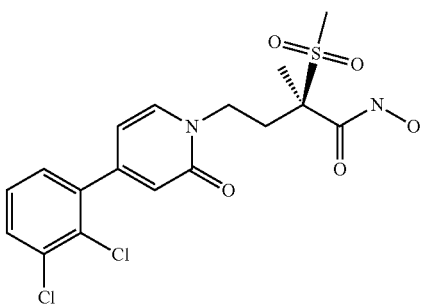 [SMILES: C[C@@](CCn1ccc(-c2cccc(Cl)c2Cl)cc1=O)(C(=O)NO)S(C)(=O)=O]

Step A) (2R)-4-[4-(2,3-dichlorophenyl)-2-oxopyridin-1(2H)-yl]-2-methyl-2-(methylsulfonyl)-N-(tetrahydro-2H-pyran-2-yloxy)butanamide Title compound was produced by following the general method of Example 41, Step A, using (2,3-dichlorophenyl) boronic acid (115 mg, 0.602 mmol). The resulting crude material was purified by chromatography on silica gel (elution solvent: ethyl acetate) to provide title compound as a viscous, foamy oil. Yield: 142 mg, 45.6%. MS (APCI (type)) m/z 539.5 (M+Na). 1H NMR (400 MHz, CHLOROFORM-d) δ ppm 1.53-1.67 (m, 3H) 1.68-1.73 (m, 3H) 1.73-1.98 (m, 3H) 2.36-2.48 (m, 1H) 2.48-2.61 (m, 1H) 3.20 (d, J=4.49 Hz, 3H) 3.57-3.73 (m, 1H) 3.96-4.09 (m, 1H) 4.12-4.25 (m, 1H) 4.27-4.49 (m, 1H) 5.03-5.32 (m, 1H) 6.21-6.42 (m, 1H) 6.62 (d, J=1.76 Hz, 1H) 7.00-7.19 (m, 1H) 7.21-7.29 (m, 1H) 7.38 (d, J=7.02 Hz, 1H) 7.51 (dd, J=8.00, 1.56 Hz, 1H) 12.03 (s, 1H)

Step B) (2R)-4-[4-(2,3-dichlorophenyl)-2-oxopyridin-1(2H)-yl]-N-hydroxy-2-methyl-2-(methylsulfonyl)butanamide Title compound was produced using the general methodology of Example 44, Step B. Yield 30 mg, 25%. MS (APCI) m/z 433.4 (M+H). $^1$H NMR (400 MHz, DMSO-d$_6$) δ ppm 1.55 (s, 3H) 2.10-2.21 (m, 1H) 2.31-2.42 (m, 1H) 3.08 (s, 3H) 3.74 (td, J=12.00, 4.88 Hz, 1H) 4.10 (td, J=11.85, 4.78 Hz, 1H) 6.34 (dd, J=7.02, 1.95 Hz, 1H) 6.40 (d, J=1.95 Hz, 1H) 7.33-7.39 (m, 1H) 7.40-7.48 (m, 1H) 7.69 (dd, J=7.90, 1.66 Hz, 1H) 7.73 (d, J=7.02 Hz, 1H) 9.22 (s, 1H) 11.09 (s, 1H)

Example 47

(2R)—N-hydroxy-2-methyl-2-(methylsulfonyl)-4-{2-oxo-4-[4-(tetrahydro-2H-pyran-4-yl)phenyl]pyridin-1(2H)-yl}butanamide

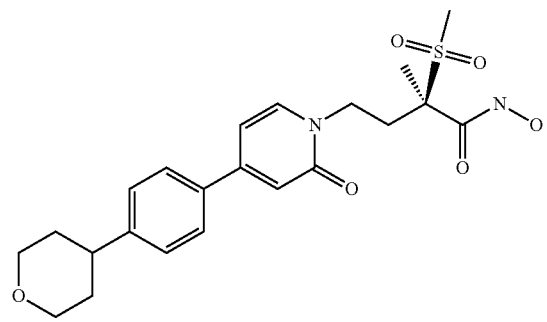 [SMILES: C[C@@](CCn1ccc(-c2ccc(C3CCOCC3)cc2)cc1=O)(C(=O)NO)S(C)(=O)=O]

Step A) 4-[4-(4,4,5,5-tetramethyl-1,3,2-dioxaborolan-2-yl)phenyl]tetrahydro-2H-pyran To a solution of 4-(4-bromophenyl)tetrahydro-2H-pyran (250 mg, 1.04 mmol) in dioxane (7 mL) was added 4,4,4',4',5,5,5',5'-octamethyl-2,2'-bi-1,3,2-dioxaborolane (290 mg, 1.14 mmol) and potassium acetate (210 mg, 2.07 mmol), followed by PdCl$_2$(dppf) (80.1 mg, 0.104 mmol, 10 mol %). The reaction mixture was stirred at 80° C. for overnight. The reaction was cooled to room temperature then added 5 mL of water and 10 mL of ethyl acetate. The aqueous layer was extracted with ethyl acetate (10 mL×3) and the combined organics were dried with sodium sulfate, filtered and concentrated. The residue was purified by chromatography on silica gel (Gradient: 0% to 100% ethyl acetate in heptane) to give the title compound as a solid (33.8%). $^1$H NMR (400 MHz, DMSO-d$_6$) δ ppm 1.29 (s, 1H) 1.28 (s, 11H) 1.64 (br. s., 4H) 2.77 (br. s., 1 h) 3.42 (br. s., 2H) 3.92 (br. s., 2H) 7.26 (d, J=8.01 Hz, 2H) 7.61 (d, J=8.20 HZ, 2H).

Step B) (2R)-2-methyl-2-(methylsulfonyl)-4-{2-oxo-4-[4-(tetrahydro-2H-pyran-4-yl)phenyl]pyridin-1(2H)-yl}-N-(tetrahydro-2H-pyran-2-yloxy)butanamide To a flask of 4-[4-(4,4,5,5-tetramethyl-1,3,2-dioxaborolan-2-yl)phenyl]tetrahydro-2H-pyran (98.3 mg, 0.341 mmol) and (2R)-4-(4-iodo-2-oxopyridin-1(2H)-yl)-2-methyl-2-(methylsulfonyl)-N-(tetrahydro-2H-pyran-2-yloxy)butanamide, which may be produced as in Preparation 2B, (170 mg, 0.341 mmol) was added Pd(II)Encat (113 mg, 0.034 mmol, 10 mol %) followed by dioxane (5.0 mL) and 2.0 M potassium carbonate (0.511 mL). The reaction mixture was stirred for overnight at 80° C. The reaction mixture was cooled and poured onto celite. The filtered solution was concentrated under reduced pressure. The residue was purified by chromatography on silica gel (Gradient: 0% to 100% ethyl acetate in heptane) to give the title compound as a glass (82 mg, 45%). LCMS m/z 533.0 (M+1). $^1$H NMR (400 MHz, METHANOL-$d_4$) δ ppm 1.61 (br. s., 2H) 1.73 (d, J=7.23 Hz, 3H) 1.75-1.89 (m, 1H) 1.75-1.89 (m, 6H) 2.40 (dddd, J=13.35, 10.86, 7.91, 5.18 Hz, 1H) 2.54-2.68 (m, 1H) 2.82-2.93 (m, 1H) 3.10-3.15 (m, 3H) 3.54-3.64 (m, 3H) 3.91-4.02 (m, 1H) 4.02-4.07 (m, 2H) 4.14-4.24 (m, 1H) 4.24-4.36 (m, 1H) 5.05 (d, J=2.34 Hz, 1H) 6.74-6.81 (m, 2H) 7.39 (m, J=8.40 Hz, 2H) 7.65 (m, J=8.20 Hz, 2H) 7.71 (dd, J=6.74, 5.76 Hz, 1H) 7.71 (dd, J=6.74, 5.76 Hz, 1H).

Step C) (2R)—N-hydroxy-2-methyl-2-(methylsulfonyl)-4-{2-oxo-4-[4-(tetrahydro-2H-pyran-4-yl)phenyl]pyridin-1(2H)-yl}butanamide To a solution of (2R)-2-methyl-2-(methylsulfonyl)-4-{2-oxo-4-[4-(tetrahydro-2H-pyran-4-yl)phenyl]pyridin-1(2H)-yl}-N-(tetrahydro-2H-pyran-2-yloxy)butanamide (82 mg, 0.15 mmol) in 2-propanol (1.5 mL) was added 1.0 N hydrochloric acid (0.77 mL). The solution was stirred for 1 h. The reaction was concentrated, the residue was triturated with 2-propanol as a white suspension at 50° C. for 30 minutes. A white solid was collected by filtration (75%). LCMS m/z 449.0 (M+1). $^1$H NMR (400 MHz, DMSO-$d_6$) δ ppm 1.57 (s, 3H) 1.65-1.74 (m, 4H) 2.11-2.21 (m, 1H) 2.37-2.47 (m, 1H) 2.83 (tt, J=10.40, 5.42 Hz, 1H) 3.11 (s, 3H) 3.39-3.49 (m, 2H) 3.74 (td, J=12.01, 4.69 Hz, 1H) 3.92-3.99 (m, 2H) 4.11 (td, J=11.91, 5.08 Hz, 1H) 6.65 (dd, J=7.03, 2.15 Hz, 1H) 6.69 (d, J=2.15 Hz, 1H) 7.37 (m, 2H) 7.67 (m, 2H) 7.74 (d, J=7.23 Hz, 1H) 9.27 (br. s., 1H) 11.19 (s, 1H).

Example 48

(2R)—N-hydroxy-4-[4-{4-[(2-methoxyethyl)thio]phenyl}-2-oxopyridin-1(2H)-yl]-2-methyl-2-(methylsulfonyl)butanamide

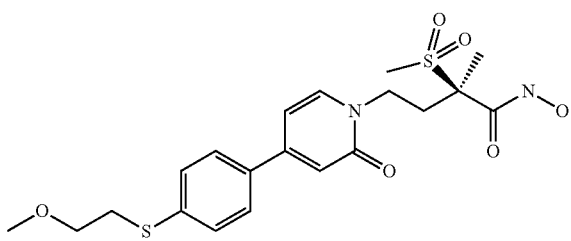 [SMILES: COCCSc1ccc(-c2ccn(CC[C@](C)(C(=O)NO)S(C)(=O)=O)c(=O)c2)cc1]

Step A) 2-{4-[(2-Methoxyethyl)thio]phenyl}-4,4,5,5-tetramethyl-1,3,2-dioxaborolane The title compound was produced by following the general methodology of Example 47, Step A, using 1-bromo-4-[(2-methoxyethyl)thio]benzene (250 mg, 1.01 mmol.) in place of 4-(4-bromophenyl)tetrahydro-2H-pyran. The title compound was obtained an oil (67.5%). $^1$H NMR (400 MHz, DMSO-$d_6$) δ ppm 1.28 (s, 12H) 3.18 (t, J=6.45 Hz, 2H) 3.25 (s, 3H) 3.52 (t, J=6.45 Hz, 2H) 7.31 (d, J=8.40 Hz, 2H) 7.31 (d, J=4.88 Hz, 1H) 7.58 (d, J=8.40 Hz, 2H)

Step B) (2R)-4-[4-{4-[(2-methoxyethyl)thio]phenyl}-2-oxopyridin-1(2H)-yl]-2-methyl-2-(methylsulfonyl)-N-(tetrahydro-2H-pyran-2-yloxy)butanamide The title compound was produced by following the general methodology of Example 47, Step B, giving the title compound as a solid (66.8%). LCMS m/z 539.0 (M+1).

Step C) (2R)—N-hydroxy-4-[4-{4-[(2-methoxyethyl)thio]phenyl}-2-oxopyridin-1(2H)-yl]-2-methyl-2-(methylsulfonyl)butanamide The title compound was produced by following the general methodology of Example 47, Step C, producing a white solid that was collected by filtration (64%). LCMS m/z 455.0 (M+1). $^1$H NMR (400 MHz, DMSO-d6) δ ppm 1.57 (s, 3H) 2.16 (ddd, J=12.65, 6.20, 5.96 Hz, 1H) 3.11 (s, 3H) 3.22 (t, J=6.45 Hz, 2H) 3.26 (s, 3H) 3.54 (t, J=6.45 Hz, 2H) 3.74 (td, J=12.01, 5.08 Hz, 1H) 4.11 (td, J=11.91, 5.08 Hz, 1H) 6.67 (dd, J=7.13, 2.05 Hz, 1H) 6.71 (d, J=1.95 Hz, 1H) 7.41 (d, J=8.59 Hz, 2H) 7.68 (d, J=8.59 Hz, 2H) 7.76 (d, J=7.03 Hz, 1H)

Example 49A (2R)-4-[4-(4-chloro-2,3-difluorophenyl)-2-oxopyridin-1(2H)-yl]-N-hydroxy-2-methyl-2-(methylsulfonyl)butanamide

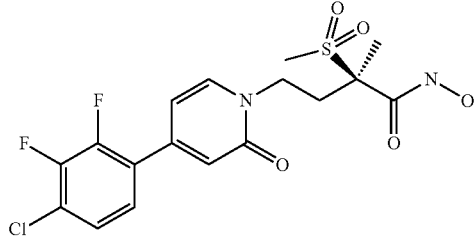 [SMILES: C[C@@](CCn1ccc(-c2ccc(Cl)c(F)c2F)cc1=O)(C(=O)NO)S(C)(=O)=O]

Step A: 2-(4-chloro-2,3-difluorophenyl)-4,4,5,5-tetramethyl-1,3,2-dioxaborolane

To a solution of 1-bromo-4-chloro-2,3-difluorobenzene (720 mg, 3.17 mmol) in tetrahydrofuran (10 mL) was added i-propylmagesiumchloride (1.90 mL, 3.80 mmol) at 0° C. The reaction mixture was stirred at 0° C. for 1 h. Then 2-isopropoxy-4,4,5,5-tetramethyl-1,3,2-dioxa-borolane (0.98 mL, 4.75 mmol) in tetrahydrofuran (5.0 mL) was added. The reaction mixture was allowed to warm up to room temperature and stirred at RT for 1 h. The mixture was used directly in the next step.

Step B: (2R)-4-[4-(4-chloro-2,3-difluorophenyl)-2-oxopyridin-1(2H)-yl]-2-methyl-2-(methylsulfonyl) butanoic acid Into the THF solution of 2-(4-chloro-2,3-difluorophenyl)-4,4,5,5-tetramethyl-1,3,2-dioxaborolane (771 mg, 2.81 mmol) was added 1.0 M $K_3PO_4$ (7.02 mL), ethyl (2R)-4-(4-iodo-2-oxopyridin-1(2H)-yl)-2-methyl-2-(methylsulfonyl) butanoate (1000 mg, 2.34 mmol) and Pd(II)dppf. DCM (90 mg, 0.117 mmol, 5 mol %). The reaction mixture was stirred for 1 h at 65° C. To the reaction mixture was then added a solution of LiOH (168 mg, 7.02 mmol) in water (7.5 mL). The reaction mixture was stirred for 45 min at 55° C. The reaction mixture was treated with 1N NaOH (4 mL) and the aqueous layer was separated and adjusted to a pH of 2 with 3 N HCl. A precipitate formed and was collected by filtration and washed with EtOAc to give the title compound as an off-white solid (0.88 g, 89.6%) LCMS m/z 420.0 (M+1). $^1$H NMR ppm 1.58 (s, 3H) 2.20 (ddd, J=13.12, 10.68, 4.88 Hz, 1H) 2.40-2.48 (m, 1H) 3.17 (s, 3H) 3.95 (ddd, J=12.54, 10.88, 5.66 Hz, 1H) 4.10 (ddd, J=12.63, 10.78, 4.88 Hz, 1H) 6.47 (dt, J=7.02, 1.85 Hz, 1H) 6.58-6.61 (m, 1H) 7.42-7.49 (m, 1H) 7.52-7.58 (m, 1H) 7.81 (d, J=7.02 Hz, 1H).

Step C: (2R)-4-[4-(4-chloro-2,3-difluorophenyl)-2-oxopyridin-1(2H)-yl]-2-methyl-2-(methylsulfonyl)-N-(tetrahydro-2H-pyran-2-yloxy)butanamide To a suspension of (2R)-4-[4-(4-chloro-2,3-difluorophenyl)-2-oxopyridin-1(2H)-yl]-2-methyl-2-(methylsulfonyl) butanoic acid (4500 mg, 10.7 mmol) in Me-THF (450 mL) was added N-methyl morpholine (1.80 mL, 16.1 mmol) and 2-chloro-4,6-dimethoxy-1,3,5-triazine (2520 mg, 13.9 mmol). The reaction mixture was stirred at room temperature for 1 h. To the mixture was added O-(tetrahydro-2H-pyran-2-yl)hydroxylamine (1630 mg, 13.9 mmol) and the resulting mixture was stirred at room temperature for 1 h. The reaction mixture was washed with water and passed through pad of sodium sulfate, celite and silica gel. The pad was washed with ethyl acetate. The combined organic solution was concentrated under reduced pressure to give the title compound as a solid in quantitative yield. LCMS m/z 519.0 (M+1). $^1$H NMR (400 MHz, DMSO-$d_6$) δ ppm 1.48-1.57 (m, 3H) 1.59 (d, J=3.90 Hz, 3H) 1.64-1.74 (m, 3H) 2.15-2.26 (m, 1H) 2.39-2.49 (m, 1H) 3.10 (d, J=6.44 Hz, 3H) 3.46-3.58 (m, 1H) 3.70-3.83 (m, 1H) 4.03 (d, J=7.02 Hz, 1H) 4.07-4.21 (m, 1H) 4.95-5.01 (m, 1H) 6.48-6.53 (m, 1H) 6.61-6.64 (m, 1H) 7.42-7.49 (m, 1H) 7.51-7.59 (m, 1H) 7.79 (dd, J=10.83, 7.12 Hz, 1H), H—N wasn't observed. $^{19}$F NMR (376 MHz, DMSO-$d_6$) ppm –138.09 (dd, J=22.56, 7.52 Hz)-139.10 (dd, J=22.56, 7.52 Hz)

Step D: (2R)-4-[4-(4-chloro-2,3-difluorophenyl)-2-oxopyridin-1(2H)-yl]-N-hydroxy-2-methyl-2-(methylsulfonyl)butanamide To a heterogeneous mixture of (2R)-4-[4-(4-chloro-2,3-difluorophenyl)-2-oxopyridin-1(2H)-yl]-2-methyl-2-(methylsulfonyl)-N-(tetrahydro-2H-pyran-2-yloxy)butanamide (14500 mg, 26.94 mmol) in Ethanol (50 mL) and water (100 mL) was added a solution of PPTS (pyridinium p-touluenesulfonate) (7090 mg, 27.9 mmol). The mixture was stirred overnight at 70° C. and a solid formed. The solid was collected via filtration and dried to furnish the title compound as a white solid (5.7 g, 46.9%). The filtrate was concentrated to half the volume and more desired product formed and was collected via filtration to provide additional title compound (3.3 g, 27.1%). LCMS m/z 435.0 (M+1). $^1$H NMR (400 MHz, DMSO-$d_6$) δ ppm 1.55 (s, 3H) 2.06-2.20 (m, 1H) 2.36-2.45 (m, 1H) 3.08 (s, 3H) 3.67-3.81 (m, 1H) 4.10 (ddd, J=12.20, 11.32, 4.78 Hz, 1H) 6.47 (dt, J=7.17, 1.98 Hz, 1H) 6.57-6.62 (m, 1H) 7.39-7.47 (m, 1H) 7.49-7.57 (m, 1H) 7.77 (d, J=7.22 Hz, 1H) 9.23 (br. s., 1H) 11.08 (s, 1H) $^{19}$F NMR (376 MHz, DMSO-$d_6$) δ ppm –138.08 (dd, J=22.56, 7.52 Hz)-139.09 (dd, J=22.56, 7.52 Hz).

Example 49B

Alternative preparation of (2R)-4-[4-(4-chloro-2,3-difluorophenyl)-2-oxopyridin-1(2H)-yl]-N-hydroxy-2-methyl-2-(methylsulfonyl)butanamide The title compound was made via a sequential procedure comprised of borylation, Suzuki coupling and THP removal. This one pot method could readily be applied to other compounds of the invention.

To a THF solution of 4-chloro-2,3-difluorophenyl bromide (1.0 mmol, 227 mg in 3 mL) at 0° C. was added 1.1 eq. i-PrMgBr (2.0 M in THF, 0.55 mL) slowly over 5 min. The resulting mixture was stirred at 0° C. for 30 min. To the reaction mixture was added 2-isopropoxy-4,4,5,5-tetramethyl-1,3,2-dioxaborolane (1.1 mmol, 204 mg) under $N_2$. The resulting mixture was stirred at 0° C. for 5 min and then RT for 30 min. LCMS indicated all bromide starting material was consumed. In a separate flask was added (2R)-4-(4-iodo-2-oxopyridin-1(2H)-yl)-2-methyl-2-(methylsulfonyl)-N-(tetrahydro-2H-pyran-2-yloxy)butanamide (T6), which may be produced as in Preparation 2 B, (1.0 mmol, 500 mg), $K_2CO_3$ (3.0 mmol, 420 mg), 3 mL DMF and 0.3 mL water. The boronate rxn mixture was then added into this flask. The mixture was deoxygenated by bubbling $N_2$ through for 10 min. Pd EnCat™ (0.15 equiv., 0.15 mmol, 460 mg) was added and bubbled with $N_2$ for an additional 5 mins. The reaction mixture was stirred at 80° C. for 16 h under $N_2$ and turned into a black dry solid. LCMS indicated 54% coupled product, m/z 519.3 (M+1), 435.2 (M+1–THP) and 25% coupled product without THP m/z 435.2 (M+1). To the mixture was added 8 mL DCM and 12 mL trifluoroacetic acid. Mixture stirred at RT for 1 h. LCMS indicated complete THP deprotection. The mixture was concentrated on the rotavap. The residue was treated with 6 mL DMSO, loaded onto a 5 g C18 pre-column, and purified using a 25 g C18 column with 0 to 80% ACN in water with 0.1% formic acid at a flow rate of 25 mL/min in 50 CV. The combined fractions furnished an off white solid, 257 mg (59%).

Example 50

(2R)—N-hydroxy-2-methyl-2-(methylsulfonyl)-4-[2-oxo-4-(2,3,4-trifluorophenyl)pyridin-1(2H)-yl]butanamide

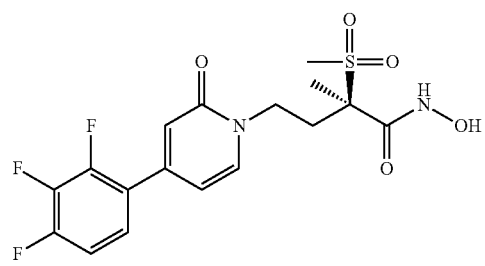 [SMILES: C[C@@](CCn1ccc(-c2ccc(F)c(F)c2F)cc1=O)(C(=O)NO)S(C)(=O)=O]

The title compound was produced by following the general methodology of Example 21, Step A through C using 2,3,4-trifluorophenylboronic acid instead of (2-Fluoro-4-methoxyphenyl)boronic acid with comparable yields. MS (LCMS) m/z 419.0 (M+1). $^1$H NMR (400 MHz, DMSO-$d_6$) δ ppm 1.54 (s, 3H) 2.09-2.18 (m, 1H) 2.37-2.45 (m, 1H) 3.07 (s, 3H)

3.68-3.78 (m, 1H) 4.04-4.14 (m, 1H) 6.43-6.48 (m, 1H) 6.57 (s, 1H) 7.36-7.49 (m, 2H) 7.76 (d, J=7.08 Hz, 1H) 9.21 (br. s., 1H) 11.08 (s, 1H).

Example 51

4-[4-(Benzyloxy)-2-oxopyridin-1(2H)-yl]-N-hydroxy-2-methyl-2-(methylsulfonyl)butanamide

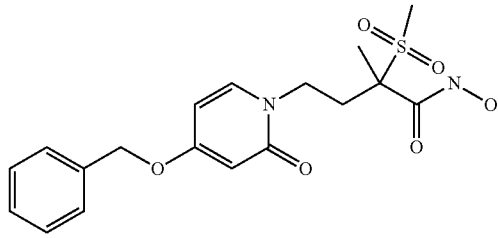 [SMILES: CC(CCn1ccc(OCc2ccccc2)cc1=O)(C(=O)NO)S(C)(=O)=O]

Step A) 4-[4-(Benzyloxy)-2-oxopyridin-1(2H)-yl]-2-methyl-2-(methylsulfonyl) butanoate To a solution of ethyl 4-bromo-2-methyl-2-(methylsulfonyl)butanoate (345 mg, 1.20 mmol) and 4-(benzyloxy)pyridin-2-ol (201 mg, 1.00 mmol) in tetrahydrofuran (10 mL) was added cesium carbonate (652 mg, 2.00) at ambient temperature. The resulting mixture was stirred at 50° C. overnight. The mixture was allowed to cool to ambient temperature and filtered through a celite pad. The pad was washed with ethyl acetate; the filtrates were combined and concentrated to a crude residue. The material was purified via filtration through a silica gel pad and eluted with heptanes/ethyl acetate. The desired fractions were isolated and the solvent removed via rotary evaporation affording ethyl 4-[4-(benzyloxy)-2-oxopyridin-1(2H)-yl]-2-methyl-2-(methylsulfonyl)butanoate as a white solid. 302.2 mg. $^1$H NMR (CD$_3$OD) 7.47, (1H, d), 7.41-7.29 (5H, m), 6.15-6.13, (1H, dd), 5.96 (1H, d), 5.07 (2H, s), 4.20-4.12 (2H, m), 4.00-3.93 (1H, m), 3.47 (1H, q), 3.21 (3H, s), 2.60-2.53 (1H, m), 2.32-2.25 (1H, M), 3.20 (3H, s), 1.26 (3H, t) ppm.

Step B) 4-[4-(Benzyloxy)-2-oxopyridin-1(2H)-yl]-2-methyl-2-(methylsulfonyl) butanoic acid To a solution of ethyl ethyl 4-[4-(benzyloxy)-2-oxopyridin-1(2H)-yl]-2-methyl-2-(methylsulfonyl)butanoate (740 mg, 1.82 mmol) in tetrahyrofuran/methanol/water (4:1:1, 18.2 mL) was added lithium hydroxide monohydrate (152 mg, 3.63 mmol). The mixture was stirred at ambient temperature overnight. The mixture was diluted with aqueous HCl (1N in water) and extracted with ether 2×. The combined organic extracts were washed with water, dried over magnesium sulfate, filtered and concentrated to dryness to afford 4-[4-(benzyloxy)-2-oxopyridin-1(2H)-yl]-2-methyl-2-(methylsulfonyl)butanoic acid as a solid. 674.9 mg.

LCMS: (M+1) 380

Step C) 4-[4-(Benzyloxy)-2-oxopyridin-1(2H)-yl]-2-methyl-2-(methylsulfonyl)-N-(tetrahydro-2H-pyran-2-yloxy)butanamide To a solution of 4-[4-(benzyloxy)-2-oxopyridin-1(2H)-yl]-2-methyl-2-(methylsulfonyl)butanoic acid (670 mg, 1.77 mmol) in methylene chloride (18 mL) at ambient temperature was added 1, (3-dimethylaminopropyl)-3-ethylcarbodiimide hydrochloride (474 mg, 2.47 mmol), 1-hydroxy benzotriazole monohydrate (487 mg, 3.18 mmol), triethylamine (443 uL, 3.18 mmol) and O-tetrahydro-2H-pyran-2-yl-hydroxylamine (310 mg, 2.65 mmol). The resulting mixture was stirred at ambient temperature overnight. The mixture was diluted with methylene chloride and water. The phases were separated and the aqueous layer was extracted with methylene chloride two times. The organic extracts were combined and dried over magnesium sulfate, filtered and concentrated to a crude residue. The crude residue was purified via silica gel chromatography eluting with methylene chloride and methanol. The fractions containing desired product were combined and concentrated to afford 4-[4-(benzyloxy)-2-oxopyridin-1(2H)-yl]-2-methyl-2-(methylsulfonyl)-N-(tetrahydro-2H-pyran-2-yloxy)butanamide as an oil. 536.3 mg

LCMS: (M−1) 477.3

Step D) 4-[4-(Benzyloxy)-2-oxopyridin-1(2H)-yl]-N-hydroxy-2-methyl-2-(methylsulfonyl)butanamide 4-[4-(Benzyloxy)-2-oxopyridin-1(2H)-yl]-2-methyl-2-(methylsulfonyl)-N-(tetrahydro-2H-pyran-2-yloxy)butanamide (536.3 mg, 1.12 mmol) was dissolved in methylene chloride (5 mL) at ambient temperature. To this solution was added HCl (4M in 1,4-dioxane, 8.41 mL, 30 mmol) and the slurry was stirred at RT for 15 minutes. Methanol (1 mL) was added followed by silica gel and the mixture was concentrated to dryness. The crude material purified via silica gel chromatography eluting with methylene chloride/methanol to afford title compound as a solid 117.8 mg. LCMS: (M+1) 395.3 $^1$H NMR (CD$_3$OD) 7.51 (1H, d, J=7.62 Hz), 7.42-7.32 (5H, m), 6.18 (1H, dd, J=7.42, J=2.73), 5.09 (2H, s), 4.21-4.13 (1H, m), 3.85-3.77 (1H, m), 3.08 (3H, s), 2.53-2.45 (1H, m), 2.32-2.25 (1H, m), 1.65 (3H, s) ppm.

Example 52

N-Hydroxy-2-methyl-4-(3-methyl-2-oxo-4-phenylpyridin-1(2H)-yl)-2-(methylsulfonyl)butanamide

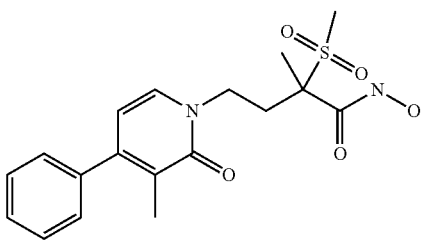 [SMILES: Cc1c(-c2ccccc2)ccn(CCC(C)(C(=O)NO)S(C)(=O)=O)c1=O]

Step A) 4-Iodo-3-methylpyridin-2(1H)-one

To a solution of 2-fluoro-4-iodo-3-methylpyridine (1.68 g, 7.09 mmol) in 1,4-dioxane/water (1:1, 5.2 mL) was added concentrated HCl (5.5 mL). The resulting clear solution was heated to 100° C. After 1 h, the reaction mixture was allowed to cool to ambient temperature and was stirred overnight, during which time a precipate formed. The mixture was filtered and dried to a constant weight to afford 4-iodo-3-methylpyridin-2(1H)-one as a yellow solid 1.47 g.

Step B) 4-(4-Iodo-3-methyl-2-oxopyridin-1(2H)-yl)-2-methyl-2-(methylsulfonyl) butanoate To a solution of ethyl 4-bromo-2-methyl-2-(methylsulfonyl)butanoate (2.08 g, 7.25 mmol) and 4-iodo-3-methylpyridin-2(1H)-one (1.42 g, 6.04 mmol) in tetrahydrofuran (60.4 mL) was added cesium carbonate (4.06 g, 12.1) at ambient temperature. The resulting mixture was stirred at 50° C. overnight. The mixture was allowed to cool to ambient temperature and filtered through a celite pad. The pad was washed with ethyl acetate and the filtrate was concentrated to a crude residue. The material was purified via filtration through a silica gel pad, eluting with heptanes/ethyl acetate. The desired fractions were isolated, the solvent removed via rotary evaporation affording ethyl 4-(4-iodo-3-methyl-2-oxopyridin-1 (2H)-yl)-2-methyl-2-(methylsulfonyl)butanoate as an oil. 1.97 g
LCMS: (M+1) 442

Step C) Ethyl 2-methyl-4-(3-methyl-2-oxo-4-phenylpyridin-1(2H)-yl)-2-(methylsulfonyl)butanoate Water (1 mL) was added to a suspension of potassium carbonate (392 mg, 2.84 mg), phenylboronic acid (76.1 mg, 0.624 mmol), and ethyl 4-(4-iodo-3-methyl-2-oxopyridin-1 (2H)-yl)-2-methyl-2-(methylsulfonyl)butanoate (250 mg, 0.567 mmol) in 1,4-dioxane (5 mL) at ambient temperature. To this mixture was added Pd EnCat™ (154 mg, 0.06 mmol) and the mixture was stirred at 80° C. overnight. The mixture was cooled to ambient temperature, filtered, diluted with ethyl acetate and washed with water. To the organic extract was added silica gel and the mixture was concentrated to dryness. The material was purified via silica gel chromatography eluting with ethyl acetate/heptanes to afford ethyl 2-methyl-4-(3-methyl-2-oxo-4-phenylpyridin-1(2H)-yl)-2-(methylsulfonyl)butanoate as an oil. 118.3 mg
LCMS: (M+1) 392.3

Step D) 2-Methyl-4-(3-methyl-2-oxo-4-phenylpyridin-1(2H)-yl)-2-(methylsulfonyl) butanoic acid To a solution of ethyl 2-methyl-4-(3-methyl-2-oxo-4-phenylpyridin-1(2H)-yl)-2-(methylsulfonyl)butanoate (118.3 mg, 0.313 mmol) in tetrahydrofuran/methanol/water (4:1:1, 3.13 mL) was added lithium hydroxide monohydrate (26.3 mg, 0.626 mmol). The mixture was stirred at ambient temperature overnight. The mixture was diluted with aqueous HCl (1N in water) and extracted with ethyl acetate 2×. The combined organic extracts were dried over magnesium sulfate, filtered and concentrated to dryness to afford 2-methyl-4-(3-methyl-2-oxo-4-phenylpyridin-1(2H)-yl)-2-(methylsulfonyl)butanoic acid as a solid. 109.4 mg.
LCMS: (M+1) 364.3

Step E) 2-methyl-4-(3-methyl-2-oxo-4-phenylpyridin-1(2H)-yl)-2-(methylsulfonyl)-N-(tetrahydro-2H-pyran-2-yloxy)butanamide To a solution of 2-methyl-4-(3-methyl-2-oxo-4-phenylpyridin-1(2H)-yl)-2-(methylsulfonyl)butanoic acid (109.4 mg, 0.301 mmol) in methylene chloride (3 mL) at ambient temperature was added 1-(3-dimethylaminopropyl)-3-ethylcarbodiimide hydrochloride (80.7 mg, 0.421 mmol), 1-hydroxy benzotriazole monohydrate (83 mg, 0.542 mmol), triethyl amine (75 uL, 0.542 mmol) and O-tetrahydro-2H-pyran-2-yl-hydroxylamine (53 mg, 0.452 mmol). The resulting mixture was stirred at ambient temperature overnight. The mixture was diluted with methylene chloride and washed successively with sat. aqueous sodium bicarbonate, aqueous HCl (1N) and water. The organic extracts were dried over magnesium sulfate, filtered and concentrated to a crude residue. The crude residue was purified via silica gel chromatography eluting with methylene chloride and methanol. The fractions containing the desired product were combined and concentrated to afford 2-methyl-4-(3-methyl-2-oxo-4-phenylpyridin-1(2H)-yl)-2-(methylsulfonyl)-N-(tetrahydro-2H-pyran-2-yloxy)butanamide as a solid. 137.3 mg
LCMS: (M−1) 477.3

Step F) N-hydroxy-2-methyl-4-(3-methyl-2-oxo-4-phenylpyridin-1(2H)-yl)-2-(methylsulfonyl)butanamide 2-methyl-4-(3-methyl-2-oxo-4-phenylpyridin-1(2H)-yl)-2-(methylsulfonyl)-N-(tetrahydro-2H-pyran-2-yloxy)butanamide (137 mg, 0.296 mmol) was dissolved in methylene chloride (2 mL) at ambient temperature. To this solution was added HCl (4M in 1,4-dioxane, 2.22 mL, 8.88 mmol) and the slurry was stirred at ambient temperature for 15 minutes. Methanol (1 mL) was added followed by silica gel and the mixture was concentrated to dryness. Crude material was purified via silica gel chromatography eluting with methylene chloride/methanol to afford N-hydroxy-2-methyl-4-(3-methyl-2-oxo-4-phenylpyridin-1(2H)-yl)-2-(methylsulfonyl) butanamide as a solid. 65.8 mg
LCMS: (M+1) 379.3
$^1$H NMR (CD$_3$OD) 7.52 (1H, d, J=7.03 Hz), 7.47-7.38 (3H, m), 7.33-7.30 (2H, m), 6.32 (1H, d, J=6.83), 4.34-4.27 (1H, m), 3.95-3.88 (1H, m), 3.10 (3H, s), 2.61-254 (1H, m), 2.41-2.34 (1H, m), 2.03 (3H, s), 1.70 (3H, s) ppm.

Example 53

4-(4-Cyclohexyl-2-oxopyridin-1(2H)-yl)-2-methyl-2-(methylsulfonyl)-N-(tetrahydro-2H-pyran-2-yloxy) butanamide

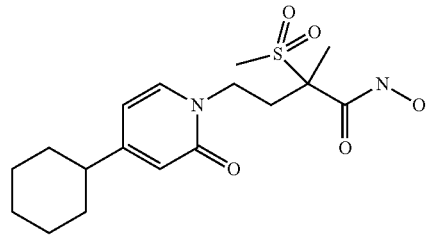 [SMILES: CC(CCn1ccc(C2CCCCC2)cc1=O)(C(=O)NO)S(C)(=O)=O]

Step A) 4-(4-Cyclohexyl-2-oxopyridin-1(2H)-yl)-2-methyl-2-(methylsulfonyl)-N-(tetrahydro-2H-pyran-2-yloxy)butanamide A solution of cyclohexylmagnesium bromide (1.0M sol in THF, 1.6 mL, 1.56 mmol) was added to a suspension of copper (I) bromide-DMS complex in 6 mL THF at −78° C. under N$_2$. The mixture was warmed to room temperature until a dark colored solution was observed (ca 15 min) then re-cooled to −78° C. A suspension of 4-(4-iodo-2-oxopyridin-1 (2H)-yl)-2-methyl-2-(methylsulfonyl)-N-(tetrahydro-2H-pyran-2-yloxy)butanamide, which may be produced as in Preparation 2A (249 mg, 0.5 mmol) in THF (6 mL) was added to the mixture. The resulting mixture was stirred at −78° C.

for 2 hours then warmed to room temperature. The reaction mixture was quenched with sat. aq. NH$_4$Cl (6 mL) and diluted with water (60 mL) and extracted with ethyl acetate (2×60 mL). The combined organics were washed with water 100 mL and brine 100 mL, and dried over sodium sulfate, filtered and concentrated in vacuo to furnish 300 mg crude oil. The crude material was purified by chromatography on silica gel (gradient: 100:0 heptanes:ethyl acetate to 0:100 heptane:ethyl acetate) to afford a clear oil (274 mg, 96%) as a mixture of unreacted starting material and title compound.

Step B) 4-(4-Cyclohexyl-2-oxopyridin-1(2H)-yl)-N-hydroxy-2-methyl-2-(methylsulfonyl)butanamide A 4.0 M solution of HCl in 1,4-dioxane (3.3 mL) was added slowly to a solution of the 4-(4-cyclohexyl-2-oxopyridin-1 (2H)-yl)-2-methyl-2-(methylsulfonyl)-N-(tetrahydro-2H-pyran-2-yloxy)butanamide (220 mg, 0.14 mmol) in dichloromethane (5 mL) followed by methanol (1 mL) at room temperature. The reaction was concentrated in vacuo and the title compound was purified using reverse phase chromatography (Gradient used with formic acid modifier (0.05%), 95:5 water:acetonitrile to 5:95 water:acetonitrile). Gradient time 6 minutes. Furnished a white solid (105 mg, 58.6%) MS (LC/MS) m/z 371.6 (M+1)

Example 54

2-Ethyl-N-hydroxy-2-(methylsulfonyl)-4-(2-oxo-4-phenylpyridin-1(2H)-yl)butanamide

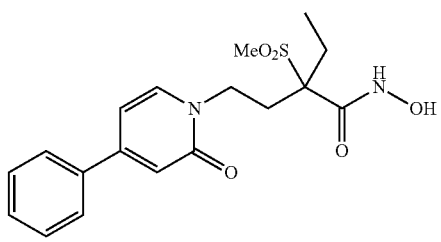 [SMILES: CCC(CCn1ccc(-c2ccccc2)cc1=O)(C(=O)NO)S(C)(=O)=O]

Step A) Ethyl 2-(methylsulfonyl)butanoate

Ethyl(methylsulfonyl)acetate (0.79 mL, 5.8 mmol, 1.0 equiv) was added dropwise via syringe to a mixture of sodium hydride (0.25 g 60% in mineral oil, 6.1 mmol, 1.1 equiv) in DMF (20 mL) at room temperature. The mixture was allowed to stir for 30 min, after which time 1-iodoethane (0.48 mL, 5.8 mmol, 1.0 equiv) was added. The reaction was allowed to stir overnight. A solution of saturated ammonium chloride (10 mL) and water (10 mL) were added, and the resulting mixture was extracted with diethyl ether (1×25 mL). The organic phase was separated, washed with water (1×10 mL), brine (1×5 mL), dried over anhydrous magnesium sulfate, and concentrated under reduced pressure. The crude material was purified by flash chromatography (2:1-0:1 heptane/ethyl acetate) to provide a white solid (0.29 g, 26%). MS (LCMS) m/z 195.4 (M+1). $^1$H NMR (400 MHz, CHLOROFORM-d) δ ppm 1.05 (t, J=7.41 Hz, 3H) 1.33 (t, J=7.12 Hz, 3H) 1.99-2.25 (m, 2H) 2.99 (s, 3H) 3.66 (dd, J=10.54, 3.90 Hz, 1H) 4.30 (q, J=7.22 Hz, 2H).

Step B) Ethyl 4-bromo-2-ethyl-2-(methylsulfonyl)butanoate

Sodium hydride (66 mg, 1.6 mmol, 1.05 equiv) was added to a solution of the ethyl 2-(methylsulfonyl)butanoate (0.29 g, 1.5 mmol, 1.0 equiv) in DMF (5 mL) at room temperature. After 30 min, 1,2-dibromopropane (0.42 g, 2.2 mmol, 1.5 equiv) was added, and the reaction was allowed to stir overnight. Water (5 mL) was added, and the resulting mixture was extracted with diethyl ether (1×20 mL). The organic phase was separated, washed with brine (1×5 mL), dried over anhydrous magnesium sulfate, filtered and concentrated under reduced pressure. The crude material was purified by flash chromatography on silica gel (2:1-1:1 heptane/ethyl acetate) to provide a colorless oil (0.17 g, 37%). $^1$H NMR (400 MHz, CHLOROFORM-d) δ ppm 1.03 (t, J=7.51 Hz, 3H) 1.33 (t, J=7.12 Hz, 3H) 1.97-2.23 (m, 2H) 2.54 (ddd, J=14.63, 12.20, 5.17 Hz, 1H) 2.76 (ddd, J=14.63, 12.10, 4.68 Hz, 1H) 3.06 (s, 3H) 3.50-3.61 (m, 1H) 3.69 (ddd, J=12.20, 9.76, 4.59 Hz, 1H) 4.31 (q, J=7.02 Hz, 2H).

Step C) Ethyl 2-ethyl-2-(methylsulfonyl)-4-(2-oxo-4-phenylpyridin-1(2H)-yl)butanoate Cesium carbonate (0.71 g, 2.2 mmol, 4.0 equiv) was added to a solution of the 4-phenylpyridin-2-ol (0.10 g, 0.58 mmol, 1.05 equiv) and ethyl 4-bromo-2-ethyl-2-(methylsulfonyl) butanoate (0.17 g, 0.55 mmol, 1.0 equiv) in tetrahydrofuran (5 mL). The resulting mixture was heated to 55° C. and allowed to stir for 3 days. The reaction was diluted with ethyl acetate (20 mL), filtered through a pad of Celite, and concentrated under reduced pressure. The crude material was purified by flash chromatography on silica gel (4:1-0:1 heptane/ethyl acetate) to provide a light yellow oil (43 mg, 20%). $^1$H NMR (400 MHz, CHLOROFORM-d) δ ppm 1.15 (t, J=7.42 Hz, 3H) 1.33 (t, J=7.13 Hz, 3H) 2.07-2.19 (m, 1H) 2.26-2.36 (m, 1H) 2.44 (ddd, J=14.89, 11.18, 4.98 Hz, 1H) 2.59-2.71 (m, 1H) 3.15 (s, 3H) 4.19-4.37 (m, 4H) 6.45 (dd, J=7.03, 1.56 Hz, 1H) 6.72-6.78 (m, 1H) 7.38-7.48 (m, 4H) 7.53-7.60 (m, 2H).

Step D) 2-Ethyl-2-(methylsulfonyl)-4-(2-oxo-4-phenylpyridin-1(2H)-yl)butanoic acid Potassium hydroxide (37 mg, 0.66 mmol, 6.0 equiv) was added to a solution of ethyl 2-ethyl-2-(methylsulfonyl)-4-(2-oxo-4-phenylpyridin-1(2H)-yl)butanoate (43 mg, 0.11 mmol, 1.0 equiv) in 2:2:1 tetrahydrofuran-methanol-water (2.5 mL) at 0° C. The reaction was allowed to warm to room temperature and stir overnight. The reaction was concentrated under reduced pressure to provide a wet residue that was diluted with water (5 mL) and acidified (to pH=2) with 1.0 hydrochloric acid. The resulting white precipitate was filtered, washed with water, and dried under reduced pressure to provide the title compound (34 mg, 85%). $^1$H NMR (400 MHz, CHLOROFORM-d) δ ppm 1.09 (t, J=7.52 Hz, 3H) 1.42 (s, 3H) 1.93-2.07 (m, 1H) 2.23-2.37 (m, 2H) 2.55 (d, J=5.66 Hz, 1H) 3.25 (s, 3H) 4.10-4.24 (m, 2H) 4.47-4.59 (m, 2H) 6.63-6.67 (m, 1H) 6.90 (d, J=1.95 Hz, 1H) 7.44-7.50 (m, 4H) 7.54-7.62 (m, 2H).

Step E) 2-Ethyl-2-(methylsulfonyl)-4-(2-oxo-4-phenylpyridin-1(2H)-yl)-N-(tetrahydro-2H-pyran-2-yloxy)butanamide Diisopropylethylamine (35 uL, 0.2 mmol, 2.1 equiv) and 1-hydroxyl benzotriazole monohydrate (27 mg, 0.18 mmol, 1.9 equiv) were added sequentially to a solution of 2-ethyl-2-(methylsulfonyl)-4-(2-oxo-4-phenylpyridin-1(2H)-yl)butanoic acid (34 mg, 0.09 mmol, 1.0 equiv) in dichloromethane (2 mL) at room temperature. After 30 min, 0-(tetrahydro-2H-pyran-2-yl)hydroxylamine (15 mg, 0.12 mmol, 1.3 equiv) and N-(3-dimethylaminopropyl)-N'-ethylcarbodiimide hydrochloride (26 mg, 0.13 mmol, 1.4 equiv) were added, and the reaction was allowed to stir overnight. Water (2 mL) was added, the organic phase was separated, dried over anhydrous magnesium sulfate, and concentrated under reduced pressure. The crude material was purified by flash chromatography (1:1-0:1 heptane/ethyl acetate) to provide a colorless oil (45 mg, 100%). MS (LCMS) m/z 461.8 (M−1).

Step F) 2-Ethyl-N-hydroxy-2-(methylsulfonyl)-4-(2-oxo-4-phenylpyridin-1(2H)-yl)butanamide A solution of hydrochloric acid (0.5 mL, 4.0 M in 1,4-dioxane) was added dropwise to a solution of 2-ethyl-2-(methylsulfonyl)-4-(2-oxo-4-phenylpyridin-1(2H)-yl)-N-(tetrahydro-2H-pyran-2-yloxy)butanamide (45 mg, 0.1 mmol) in dichloromethane (0.5 mL) and methanol (0.1 mL) at 0° C. After 2 h, the reaction was concentrated under reduced pressure. The resulting residue was triturated with diethyl ether, filtered, washed with heptane, and dried under reduced pressure to provide an off-white solid (10 mg, 27%). MS (LCMS) m/z 379.5 (M+1). $^1$H NMR (400 MHz, CDCl$_3$) δ ppm 0.97 (t, J=7.5 Hz, 3H), 1.86-1.95 (m, 1H), 2.31-2.45 (m, 3H), 3.29 (s, 3H), 3.99-4.08 (m 1H), 4.53-4.63 (m, 1H), 6.69 (br d, J=5.6 Hz, 1H), 6.99 (br s, 1H), 7.44-7.49 (m, 4H), 7.55-7.60 (m, 2H).

Example 55

(2R)-4-(3-fluoro-2-oxo-4-phenylpyridin-1(2H)-yl)-N-hydroxy-2-methyl-2-(methylsulfonyl)butanamide

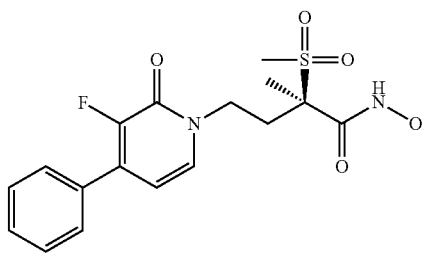 [SMILES: C[C@@](CCn1ccc(-c2ccccc2)c(F)c1=O)(C(=O)NO)S(C)(=O)=O]

Step A) 3-Fluoro-4-iodopyridin-2(1H)-one 2,3-Difluoro-4-iodopyridine (300 mg, 1.24 mmol) was suspended in acetic acid:water (2:1, 15 mL). The mixture was heated to reflux and stirred at this temperature overnight. Reaction was concentrated to dryness, and triturated in water (10 mL) for 30 min. The solid was collected via filtration, washed with water (2×10 mL), and pentane (2×20 mL) and dried under vacuum to afford the title compound as a white solid (354 mg, 71.4%). LC-MS m/z 342.0 (M+1). $^1$H NMR (400 MHz, METHANOL-d$_4$) δ ppm 6.56-6.82 (m, 1H) 6.83-7.18 (m, 1H).

Step B) Ethyl (2R)-4-(3-fluoro-4-iodo-2-oxopyridin-1(2H)-yl)-2-methyl-2-(methylsulfonyl)butanoate Cesium carbonate (1.50 g, 4.60 mmol) was added to a solution of 3-fluoro-4-iodopyridin-2(1H)-one (354 mg, 1.48 mmol) and ethyl 4-bromo-2-methyl-2-(methylsulfonyl)butanoate (595 mg, 2.07 mmol in THF (25 mL). The resulting suspension was heated to 50° C. and stirred overnight. The reaction was heated to 70° C. and stirred at this temperature overnight. The reaction was filtered through celite (~1 inch), and the filter pad was washed with ethyl acetate (2×30 ml). The combined filtrates were concentrated and the crude was purified via flash chromatography on an Analogix SF15-24g column and an eluant of ethyl acetate in heptane (50-100%) to afford the title compounds as a clear gum (366 mg, 55.5%). LC-MS m/z 445.9 (M+1). $^1$H NMR (400 MHz, CHLOROFORM-d) δ ppm 1.35 (t, J=7.12 Hz, 3H) 1.76 (s, 3H) 2.43-2.56 (m, 2H) 3.11 (s, 3H) 3.97-4.10 (m, 1H) 4.20-4.38 (m, 3H) 6.50 (dd, 1H) 6.75-6.98 (m, 1H).

Step C) Ethyl (2R)-4-(3-fluoro-2-oxo-4-phenylpyridin-1(2H)-yl)-2-methyl-2-(methylsulfonyl)butanoate Pd EnCat™ (172 mg, 0.067 mmol) was added to a mixture of potassium carbonate (298 mg, 2.16 mmol), phenylboronic acid (132 mg, 1.08 mmol), and ethyl (2R)-4-(3-fluoro-4-iodo-2-oxopyridin-1(2H)-yl)-2-methyl-2-(methylsulfonyl)butanoate (288 mg, 0.647 mmol) in 1,4-dioxane:water (10 ml, 4:1) in a 20 ml vial. The vial was sealed and the reaction was heated to 80° C. and allowed to stir overnight at that temperature. The reaction was allowed to cool to RT, filtered and the catalyst was washed with methanol (20 mL) and dichloromethane (20 mL). The combined filtrates were concentrated and the crude product was purified via flash chromatography using an Analogix SF15-12g column and an eluant of ethyl acetate in heptane (60-100%) to afford the title compound as a white solid (131 mg, 51.2%). LC-MS m/z 396.1 (M+1). $^1$H NMR (400 MHz, CHLOROFORM-d) δ ppm 1.36 (t, J=7.12 Hz, 3H) 1.79 (s, 3H) 2.46-2.67 (m, 2H) 3.14 (s, 3H) 3.99-4.16 (m, 1H) 4.22-4.44 (m, 3H) 6.24-6.39 (m, 1H) 7.10-7.22 (m, 1H) 7.38-7.55 (m, 3H) 7.54-7.63 (m, 2H).

Step D) (2R)-4-(3-Fluoro-2-oxo-4-phenylpyridin-1(2H)-yl)-2-methyl-2-(methylsulfonyl)butanoic acid Potassium hydroxide (120 mg, 2.14 mmol) was added to a solution of ethyl (2R)-4-(3-fluoro-2-oxo-4-phenylpyridin-1(2H)-yl)-2-methyl-2-(methylsulfonyl)butanoate (131 mg, 0.33 mmol) in THF:methanol:water (2:2:1, 10 mL) and the reaction was stirred at RT overnight. The reaction was concentrated, and the residue was dissolved in aqueous 1N sodium hydroxide (20 mL), washed with ethyl acetate (3×20 mL), acidified using concentrated HCl, and extracted with ethyl acetate (3×50 mL). The combined organics were dried (MgSO$_4$), filtered, and concentrated to afford the title compound as a white solid (88.4 mg, 72.7%). LC-MS m/z 383.0 (M+1). $^1$H NMR (400 MHz, DMSO-d$_6$) δ ppm 1.59 (s, 3H) 2.13-2.30 (m, 1H) 3.17 (s, 3H) 3.93-4.23 (m, 2H) 6.43 (t, J=6.93 Hz, 1H) 7.44-7.56 (m, 3H) 7.57-7.66 (m, 3H).

Step E) (2R)-4-(3-Fluoro-2-oxo-4-phenylpyridin-1(2H)-yl)-2-methyl-2-(methylsulfonyl)-N-(tetrahydro-2H-pyran-2-yloxy)butanamide (2R)-4-(3-Fluoro-2-oxo-4-phenylpyridin-1(2H)-yl)-2-methyl-2-(methylsulfonyl)butanoic acid (88.4 mg, 0.241 mmol) was dissolved in anhydrous DCM (5 ml) and treated with Hunig's Base (93 uL, 0.54 mmol) followed by HOBt (78 mg, 0.51 mmol) and the solution was stirred at RT for 30 minutes. The mixture was then treated with THP-ONH$_2$ (46 mg, 0.39 mmol) followed by EDCI (71 mg, 0.37 mmol) and the reaction was allowed to stir at RT. The reaction was concentrated in vacuo and the crude product was purified via flash chromatography using an Analogix SF10-8g column and an eluant of ethyl acetate in heptane (50-100%) to afford the title compound as a yellow solid (110 mg, 97.9%).

LC-MS m/z 465.0 (M−1).

Step F) (2R)-4-(3-Fluoro-2-oxo-4-phenylpyridin-1(2H)-yl)-N-hydroxy-2-methyl-2-(methylsulfonyl)butanamide Pyrinium p-toluenesulfonate (20 mg, 0.080 mmol) was added to a solution of (2R)-4-(3-fluoro-2-oxo-4-phenylpyridin-1(2H)-yl)-2-methyl-2-(methylsulfonyl)-N-(tetrahydro-2H-pyran-2-yloxy)butanamide (110 mg, 0.236 mmol) in ethanol (5 ml) and heated at reflux for 3 hours. The solution was cooled to RT, and upon cooling, a solid precipitated. The solid was collected via filtration and washed with ethanol (5 mL), heptane (10 mL), and ether (10 mL). The solid was dried under vacuum to afford the title compound as a yellow solid (38.4 mg, 42.6%). LC-MS m/z 383.0 (M+1). $^1$H NMR (400 MHz, DMSO-$d_6$) δ ppm 1.60 (s, 3H) 2.10-2.26 (m, 1H) 3.11 (s, 3H) 3.70-3.94 (m, 1H) 4.07-4.30 (m, 1H) 6.46 (t, J=6.93 Hz, 1H) 7.46-7.57 (m, 3H) 7.59-7.65 (m, 3H)

Example 56

(2R)-4-(5-fluoro-2-oxo-4-phenylpyridin-1(2H)-yl)-N-hydroxy-2-methyl-2-(methylsulfonyl)butanamide

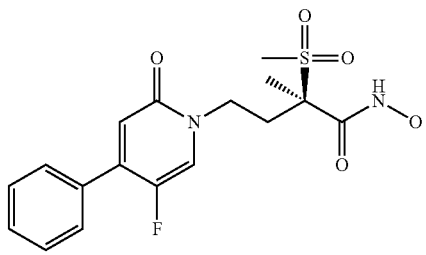 [SMILES: C[C@@](CCn1cc(F)c(-c2ccccc2)cc1=O)(C(=O)NO)S(C)(=O)=O]

Step A) 2,5-difluoro-4-iodopyridine n-Butyllithium (2.5 M in hexanes, 18.6 mL, 46.5 mmol) was added to a solution of diisopropylamine (6.51 mL, 46.1 mmol) in anhydrous tetrahydrofuran (85 mL) at −78° C. and stirred at this temperature for 1 hour. A solution of 2,5-difluoropyridine (5.0 g, 43 mmol) in anhydrous THF (12 mL) was added dropwise via cannula and the reaction was stirred at −78° C. for 3 hours. After this time, iodine (12.1 g, 47.8 mmol) in tetrahydrofuran (50 mL) was added dropwise via cannula to the reaction at −78° C. and stirred at this temperature for 1 hour after complete addition. Water (100 mL) was added to the reaction and the temperature was allowed to come to RT. The reaction was extracted with diethyl ether (3×100 mL). The combined organics were washed with brine (100 mL), dried (MgSO$_4$), filtered and concentrated. The crude was purified via flash chromatography using an Analogix SF40-80g column and an eluant of ethyl acetate in heptane (0-10%) to afford the title compound as a yellow solid (4.60 g, 44%). LC-MS m/z 242.0 (M+1). $^1$H NMR (400 MHz, CHLOROFORM-d) δ ppm 7.39 (t, J=3.71 Hz, 1H) 7.96 (d, J=1.56 Hz, 1H).

Step B) 5-Fluoro-4-iodopyridin-2(1H)-one 2,5-Difluoro-4-iodopyridine (500 mg, 2.08 mmol) was suspended in acetic acid:water (2:1, 30 mL). The mixture was heated to reflux and stirred at this temperature overnight. The reaction was concentrated to dryness to afford the title compound as a yellow solid (491 mg, 99.0%). $^1$H NMR (400 MHz, DMSO-$d_6$) δ ppm 7.02 (d, J=5.07 Hz, 1H) 7.69 (d, J=2.34 Hz, 1H).

Step C) Ethyl (2R)-4-(5-fluoro-4-iodo-2-oxopyridin-1(2H)-yl)-2-methyl-2-(methylsulfonyl)butanoate Cesium carbonate (2.01 g, 6.16 mmol) was added to a solution of the 5-fluoro-4-iodopyridin-2(1H)-one (491 mg, 2.06 mmol) and ethyl 4-bromo-2-methyl-2-(methylsulfonyl)butanoate (767 mg, 2.67 mmol in THF (30 mL). The resulting suspension was heated to reflux and stirred at this temperature overnight. The reaction was filtered through celite (~1 inch), and the filter pad was washed with ethyl acetate (2×30 ml). The combined filtrates were concentrated and the crude was purified via flash chromatography on an Analogix SF15-12g column and an eluant of ethyl acetate in heptane (30-100%) to afford the title compound as a white gum (319 mg, 34.9%). LC-MS m/z 446.0 (M+1). $^1$H NMR (400 MHz, CHLOROFORM-d) δ ppm 1.35 (t, J=7.12 Hz, 3H) 1.75 (s, 3H) 2.40-2.58 (m, 2H) 3.10 (s, 3H) 3.87-3.99 (m, 1H) 4.16-4.25 (m, 1H) 4.29 (q, J=7.22 Hz, 2H) 7.15 (d, J=5.85 Hz, 1H) 7.20 (d, J=3.32 Hz, 1H).

Step D) Ethyl (2R)-4-(5-fluoro-2-oxo-4-phenylpyridin-1(2H)-yl)-2-methyl-2-(methylsulfonyl)butanoate Pd EnCat™ (95 mg, 0.037 mmol) was added to a mixture of potassium carbonate (312 mg, 2.26 mmoll), phenylboronic acid (131 mg, 1.07 mmol), and ethyl (2R)-4-(5-fluoro-4-iodo-2-oxopyridin-1(2H)-yl)-2-methyl-2-(methylsulfonyl)butanoate (319 mg, 0.716 mmol) in dioxane:water (10 ml, 4:1) in a 20 mL vial equipped with a stir bar. The reaction was heated to 90° C. and allowed to stir overnight at that temperature. The reaction was allowed to cool to RT, filtered and the catalyst was washed with methanol (10 ml) and dichloromethane (10 ml). The filtrate was concentrated to afford a crude solid. The crude was purified via flash chromatography using an Analogix SF15-12 column and an eluant of ethyl acetate in heptane (50-100%) and methanol in ethyl acetate (0-5%) to afford the title compound as a yellowish white solid (250 mg, 64.8%). LC-MS m/z 396.1 (M+1). $^1$H NMR (400 MHz, DMSO-$d_6$) δ ppm 1.23 (t, J=7.12 Hz, 3H) 1.62 (s, 3H) 2.15-2.32 (m, 1H) 2.53-2.66 (m, 1H) 3.16 (s, 3H) 3.89-4.06 (m, 2H) 4.07-4.26 (m, 2H) 6.50 (d, J=7.61 Hz, 0H) 7.20-8.12 (m, 6H).

Step E) (2R)-4-(5-Fluoro-2-oxo-4-phenylpyridin-1(2H)-yl)-2-methyl-2-(methylsulfonyl)butanoic acid Ethyl(2R)-4-(5-fluoro-2-oxo-4-phenylpyridin-1(2H)-yl)-2-methyl-2-(methylsulfonyl)butanoate was converted to the title product following the procedure for the preparation of (2R)-4-(3-fluoro-2-oxo-4-phenylpyridin-1(2H)-yl)-2-methyl-2-(methylsulfonyl)butanoic acid as described in Example 55, Step D. The title compound was obtained as a white solid (171 mg, 73.6%). $^1$H NMR (400 MHz, DMSO-$d_6$) δ ppm 1.58 (s, 3H) 2.09-2.31 (m, OH) 2.39-2.63 (m, 1H) 3.17 (s, 3H) 3.83-4.19 (m, 2H) 6.49 (d, J=7.61 Hz, 1H) 7.41-7.68 (m, 5H) 8.06 (d, J=6.63 Hz, 1H).

Step F) ((2R)-4-(5-fluoro-2-oxo-4-phenylpyridin-1(2H)-yl)-2-methyl-2-(methylsulfonyl)-N-(tetrahydro-2H-pyran-2-yloxy)butanamide (2R)-4-(5-Fluoro-2-oxo-4-phenylpyridin-1(2H)-yl)-2-methyl-2-(methylsulfonyl)butanoic acid was converted to the title product following the procedure for the preparation of (2R)-4-(3-fluoro-2-oxo-4-phenylpyridin-1(2H)-yl)-2-methyl-2-(methylsulfonyl)-N-(tetrahydro-2H-pyran-2-yloxy) butanamide as described in Example 55, Step E. The title compound was obtained as a white solid (197 mg, 90.9%) LC-MS m/z 465.0 (M−1).

Step G) (2R)-4-(5-fluoro-2-oxo-4-phenylpyridin-1(2H)-yl)-N-hydroxy-2-methyl-2-(methylsulfonyl)butanamide Pyridinium p-toluenesulfonate (22 mg, 0.088 mmol) was added to a solution of (2R)-4-(5-fluoro-2-oxo-4-phenylpyridin-1(2H)-yl)-2-methyl-2-(methylsulfonyl)-N-(tetrahydro-2H-pyran-2-yloxy)butanamide (197 mg, 0.422 mmol). The solution was heated to reflux in ethanol (10 ml) and stirred at this temperature until complete. The solution was cooled to RT, and the volatiles were removed in vacuo. The solid was triturated in ethanol (5 mL), collected via filtration, then washed with ethanol (3×5 mL), hexanes (10 mL), and ether (3×10 mL). The solid was dried under vacuum to afford a white solid (85.1 g, 76.4%). LC-MS m/z 383.1 (M+1). $^1$H NMR (400 MHz, DMSO-d$_6$) δ ppm 1.58 (s, 3H) 2.11-2.23 (m, 0H) 2.41-2.55 (m, 1H) 3.12 (s, 3H) 3.73-3.84 (m, 1H) 3.99-4.11 (m, 1H) 6.53 (d, J=7.61 Hz, 1H) 7.41-7.73 (m, 5H) 8.04 (d, J=6.44 Hz, 1H) 9.24 (s, 1H) 11.10 (s, 1H).

Example 57

2-(ethylsulfonyl)-N-hydroxy-2-methyl-4-(2-oxo-4-phenylpyridin-1(2H)-yl)butanamide

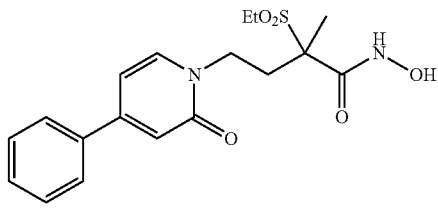

The title compound was prepared following analogous procedures described wherein sodium ethyl sulfinate was used instead sodium methyl sulfinate for the preparation of 1A to provide 2-ethanesulfonyl-propionic acid ethyl ester. The title compound may then be produced by following the general methodology of Example 11. MS (LCMS) m/z 379.5 (M+1). $^1$H NMR (400 MHz, METHANOL-d$_4$) δ ppm 1.33 (t, J=7.51 Hz, 3H) 1.72 (s, 3H) 2.34-2.46 (m, 0H) 2.62-2.73 (m, 0H) 3.29-3.33 (m, 2H) 4.02-4.13 (m, 1H) 4.33-4.44 (m, 1H) 6.98 (s, 1H) 7.03 (d, J=7.42 Hz, 1H) 7.47-7.54 (m, 3H) 7.68-7.75 (m, 2H) 7.91 (d, J=7.02 Hz, 1H).

Example 58

(2R)—N-hydroxy-4-{4-[4-(4-methoxy-2H-1,2,3-triazol-2-yl)phenyl]-2-oxopyridin-1(2H)-yl}-2-methyl-2-(methylsulfonyl)butanamide

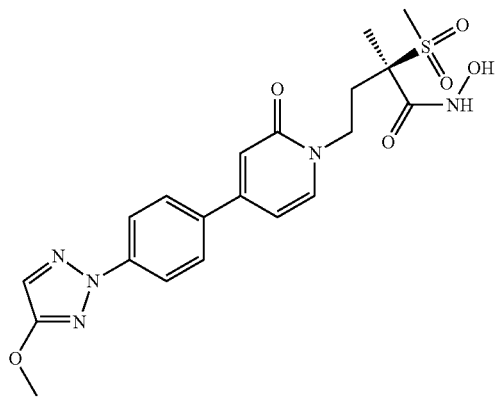 [SMILES: COc1cnn(-c2ccc(-c3ccn(CC[C@](C)(C(=O)NO)S(C)(=O)=O)c(=O)c3)cc2)n1]

Step A) 2-(4-bromophenyl)-2H-1,2,3-triazole 1-oxide

Water (20 ml) was added to a flask containing glyoxal (2.0 g, 14 mmol). Hydroxylamine.HCl (958 mg, 13.8 mmol) and sodium carbonate (1.53 g, 14.5 mmol) were added in one portion to the glyoxal flask (CO$_2$ evolution observed). The reaction mixture was stirred at RT for 20 minutes (reaction mixture turned yellow). Methanol (40 ml) was added to the reaction mixture and 4-bromophenyl hydrazine.HCl (3.1 g, 13.8 mmole) was added portionwise under ice cooling. The reaction mixture was then stirred at rt for 30 min. Copper (II) sulfate.hexahydrate (20 g, 78 mmol) was added to the reaction mixture. A water:pyridine (1:1) mixture (200 ml) was added then heated at 90° C. for 16 hours. The reaction mixture was cooled and adjusted to pH=3 with 6N HCl (approx 200 ml). The mixture was filtered through celite to remove insolubles. The celite was washed with additional ethyl acetate (1000 ml). The organic layer was separated and the product extracted additionally from the aqueous layer with EtOAc (3×250). The organic phases were combined, dried over potassium carbonate, filtered and concentrated to approximately half the volume. This material was then filtered through a silica pad (approx 6 in). Silica was washed with an additional 300 ml of ethyl acetate. The solvent was then concentrated in vacuo. The crude material was purified by chromatography on silica gel (4:1 heptane:EtOAc to 3:1 heptane:EtOAc). Concentrated fractions furnished a light tan solid (1.0 g, 30% TY). MS (LC/MS) m/z 240.1 (M+1). $^1$H NMR (400 MHz, CHLOROFORM-d) δ ppm 7.47 (d, J=0.98 Hz, 1H) 7.65-7.69 (m, 2H) 7.73 (d, J=0.78 Hz, 1H) 7.86-7.90 (m, 2H)

Step B) 2-(4-bromophenyl)-2H-1,2,3-triazol-4-yl acetate

Acetyl chloride (4.71 ml, 63 mmol) was added to a flask containing 2-(4-bromophenyl)-2H-1,2,3-triazole 1-oxide (500 mg, 2.08 mmol) and was stirred at RT for 16 hours. Acetyl chloride was removed in vacuo and ethyl acetate (30 ml) was added and concentrated (2×) to furnish a light brown solid (520 mg, 90%). MS (LC/MS) m/z 282.1 (M+1). $^1$H NMR (400 MHz, CHLOROFORM-d) δ ppm 2.39 (s, 3H) 7.57-7.63 (m, 2H) 7.84 (s, 1H) 7.87-7.93 (m, 2H)

Step C) 2-(4-bromophenyl)-2H-1,2,3-triazol-4-ol 2-(4-bromophenyl)-2H-1,2,3-triazol-4-yl acetate (520 mg, 1.84 mmol) was treated with methanol (10 ml) and water (10 ml) followed by 1,4-dioxane (5 ml). The resulting solution was treated with lithium hydroxide (265 mg, 11.1 mmol). The reaction mixture was stirred at RT for 36 hours. 1N HCl (40 ml) was added to the reaction mixture and the product was extracted with ethyl acetate (3×100 ml). The combined organic phases were dried over potassium carbonate, filtered, and concentrated. The crude material was purified by chromatography on silica gel (4:1 heptane:EtOAc 1:4 heptane:EtOAc) to furnish a light tan solid (440 mg, 98% TY). MS (LC/MS) m/z 240.21 (M+1). $^1$H NMR (400 MHz, CHLOROFORM-d) δ ppm 7.33 (s, 1H) 7.58 (d, J=8.98 Hz, 2H) 7.78 (d, J=8.98 Hz, 2H).

Step D) 2-(4-bromophenyl)-4-methoxy-2H-1,2,3-triazole 2-(4-bromophenyl)-2H-1,2,3-triazol-4-ol (200 mg, 0.833 mmol) was weighed into a 20 ml vial equipped with a septa cap. THF (10.0 ml) was added. To this was added cesium carbonate (814 mg, 2.5 mmol), followed by the addition of methyl iodide (65.8 uL, 1.04 mmol) via syringe. The reaction was heated at 60° C. for 16 hours. Water (20 ml) was added and the product was extracted with ethyl acetate (2×75 ml). Organic phases were combined, dried over potassium carbonate, filtered and concentrated to furnish a light tan solid (190 mg, 89% TY). $^1$H NMR (400 MHz, CHLOROFORM-d) δ ppm 4.04 (s, 3H) 7.30 (s, 1H) 7.56 (d, J=8.98 Hz, 2H) 7.84 (d, J=8.98 Hz, 2H)

Step E) 4-methoxy-2-[4-(4,4,5,5-tetramethyl-1,3,2-dioxaborolan-2-yl)phenyl]-2H-1,2,3-triazole Potassium acetate (220 mg, 2.24 mmol) was added to 2-(4-bromophenyl)-4-methoxy-2H-1,2,3-triazole (190 mg, 0.748 mmol), bis(pinacolato)diboron (228 mg, 0.898 mmol) and Pd(dppf)Cl$_2$.DCM complex (185 mg, 0.224 mmol) in a 20 ml vial equipped with a septa cap. The vial was evacuated and backfilled with nitrogen 3×. To this was added 1,4-dioxane (8 ml). The reaction mixture was heated at 80° C. for 16 hours. The reaction mixture was filtered through celite (approx 2 inches). The celite was washed with additional ethyl acetate (150 ml). The filtrate was concentrated in vacuo and the crude material was purified by chromatography on silica gel (9:1 heptane:1EtOAc to 2:4 heptane:EtOAc) to furnish a light tan solid (145 mg, 65% TY). MS (LC/MS) m/z 302.3 (M+1). $^1$H NMR (400 MHz, CHLOROFORM-d) δ ppm 1.37 (s, 12H) 4.06 (s, 3H) 7.31 (s, 1H) 7.90 (s, 2H) 7.95 (s, 2H).

Step F) (2R)-4-{4-[4-(4-methoxy-2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide Pd EnCat (98 mg, 0.03 mmol) was added to a mixture of potassium carbonate (171 mg, 1.24 mmol), 4-methoxy-2-[4-(4,4,5,5-tetramethyl-1,3,2-dioxaborolan-2-yl)phenyl]-2H-1,2,3-triazole (138 mg, 0.457 mmol) and (2R)-4-(4-iodo-2-oxopyridin-1(2H)-yl)-2-methyl-2-(methylsulfonyl)-N-(tetrahydro-2H-pyran-2-yloxy)butanamide which may be produced as in Preparation 2B(T6) (190 mg, 0.381 mmol) in dioxane:water (6 ml, 5:1 mix) in a 20 ml vial. The reaction was cooled and filtered through celite (approx 1 inch). The celite was washed with additional methanol (100 ml). The filtrate was concentrated in vacuo and the crude material was purified by chromatography on silica gel (4:1 heptane:EtOAc to 100% EtOAc to 85% EtOAc:15% methanol) to furnish a light tan gum (120 mg, 58% TY). MS (LC/MS) m/z 546.2 (M+1). $^1$H NMR (400 MHz, METHANOL-d$_4$) δ ppm 1.28 (s, 1H) 1.57-1.70 (m, 2H) 1.68-1.81 (m, 3H) 1.78-1.92 (m, 3H) 2.36-2.50 (m, 1H) 2.55-2.72 (m, 1H) 3.09-3.21 (m, 3H) 3.56-3.70 (m, 1H) 4.07 (s, 3H) 4.12 (d, J=7.22 Hz, 2H) 4.15-4.25 (m, 1H) 4.25-4.42 (m, 1H) 5.01-5.14 (m, 1H) 6.76-6.85 (m, 1H) 6.87 (s, 1H) 7.49 (s, 1H) 7.68-7.80 (m, 1H) 7.85 (d, J=9.17 Hz, 2H) 8.08 (d, J=8.98 Hz, 2H)

Step G) (2R)—N-hydroxy-4-{4-[4-(4-methoxy-2H-1,2,3-triazol-2-yl)phenyl]-2-oxopyridin-1(2H)-yl}-2-methyl-2-(methylsulfonyl)butanamide To (2R)-4-{4-[4-(4-methoxy-2H-1,2,3-triazol-2-yl)phenyl]-2-oxopyridin-1(2H)-yl}-2-methyl-2-(methylsulfonyl)-N-(tetrahydro-2H-pyran-2-yloxy)butanamide (120 mg, 0.22 mmol) was added dioxane (2 ml), dichloromethane (2 ml), and water (1 ml). The reaction flask was cooled externally with ice then treated with a 4.0M sol of HCl in dioxane (0.55 ml). The reaction mixture was stirred for 15 minutes then concentrated under reduced pressure. IPA (10 ml) was added and concentrated to azeotrope any remaining water to furnish a tan solid (80 mg, 80% TY). MS (LC/MS) m/z 462.3 (M+1). $^1$H NMR (400 MHz, METHANOL-d$_4$) δ ppm 1.74 (s, 3H) 2.34-2.51 (m, 1H) 2.55-2.81 (m, 1H) 3.13 (s, 3H) 3.96-4.06 (m, 1H) 4.07 (s, 3H) 4.26-4.45 (m, 1H) 6.84-7.00 (m, 2H) 7.49 (s, 1H) 7.75-7.93 (m, 3H) 8.09 (d, J=8.78 Hz, 2H)

Example 59

(2R)-4-[4-{4-[(6-methoxypyridin-3-yl)methoxy]phenyl}-2-oxopyridin-1(2H)-yl]-2-methyl-2-(methylsulfonyl)-N-(tetrahydro-2H-pyran-2-yloxy)butanamide

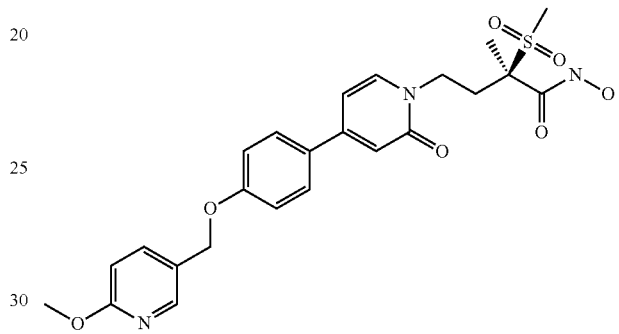

Step A: (6-methoxypyridin-3-yl)methanol

Sodium borohydride (11.30 g, 299 mmol) was added to a solution of the methyl 6-methoxynicotinate (5.00 g, 29.9 mmol) in ethanol (100 mL) at 0° C. The reaction was allowed to warm to room temperature and stirred for 3 days. The reaction was cooled to 0° C. and quenched by slow addition of 1N HCl until pH 4.0. The reaction mixture was concentrated to remove ethanol. The remaining aqueous solution was washed with ethyl acetate (2×), then neutralized with saturated aqueous sodium bicarbonate, then extracted with ethyl acetate (3×). The organic layers were combined, washed with brine, dried (Na$_2$SO$_4$), filtered and concentrated. The crude material was purified by silica chromatography (hexanes/ethyl acetate 1:1, 3:7) to give a clear oil. Mass/Yield –3.9 g/94% TLC (hexanes/ethyl acetate=1:1) Rf=0.22, UV active. $^1$H NMR (400 MHz, CHLOROFORM-d) δ ppm 3.91 (s, 3H) 4.61 (s, 2H) 6.68-6.77 (m, 1H) 7.49-7.68 (m, 1H) 8.09 (s, 1H).

Step B:
5-[(4-bromophenoxy)methyl]-2-methoxypyridine

4-Bromophenol (1.37 g, 7.90 mmol) was added to a solution of (6-methoxypyridin-3-yl)methanol (1.0 g, 7.16 mmol) in THF (100 mL). Triphenylphosphine (1.88 g, 7.19 mmol) was added followed by triethylamine (0.727 g, 7.19 mmol). The resulting solution was cooled to 0° C. and DIAD (1.45 g, 7.19 mmol) was added by drop-wise addition and was maintained at 0° C. for 30 minutes, then warmed to room temperature and stirred for two days. The reaction was quenched by addition of water and extracted with ether (2×100 mL). The organic layer was washed with water (2×100 mL) then brine (1×100 mL), dried (MgSO$_4$), filtered and concentrated to give a yellow oil. The crude material was purified by flash column chromatography on a Biotage SNAP cartridge Kp-sil 100 g column (hexanes/ethyl acetate 9:1) to give a white solid. Mass/Yield—1.78 g/84% TLC (hexanes/ethyl acetate=8:2) Rf=0.12, UV active. LCMS MS ES+ 294.4/296.4. $^1$H NMR (400 MHz, CHLOROFORM-d) δ ppm 3.93 (s, 3H) 4.93 (s, 2H) 6.72-6.78 (m, 1H) 6.81-6.86 (m, 2H) 7.33-7.42 (m, 2H) 7.58-7.65 (m, 1H) 8.18 (s, 1H).

Step C 2-methoxy-5-{[4-(4,4,5,5-tetramethyl-1,3,2-dioxaborolan-2-yl)phenoxy]methyl}pyridine A solution of the 5-[(4-bromophenoxy)methyl]-2-methoxypyridine (0.50 g, 1.70 mmol), bis(pinacolato)diborane (0.518 g, 2.04 mmol), potassium acetate (0.698 g, 7.12 mmol) and palladium dppf (69.4 mg, 0.085 mmol) in 1,4-dioxane (10 mL) was heated to reflux overnight. After 18 hours the reaction was cooled to room temperature then concentrated. The residue was partitioned between ether and water, an emulsion was removed by filtration through celite eluting with ether. The layers in the filtrate were separated. The organic layer was washed with water (2×) then brine (1×). The organic layer was dried (Na$_2$SO$_4$), filtered and concentrated. The crude material was purified by silica chromatography (hexanes/ethyl acetate 9:1) to give a white solid. Mass/Yield –285 mg/50% LCMS MS ES +342.6. $^1$H NMR (400 MHz, CHLOROFORM-d) δ ppm 1.32 (s, 12H) 3.93 (s, 3H) 4.99 (s, 2H) 6.72-6.78 (m, 1H) 6.91-6.98 (m, 2H) 7.61-7.69 (m, 1H) 7.71-7.79 (m, 2H) 8.20 (s, 1H)

Step D (2R)-4-[4-{4-[(6-methoxypyridin-3-yl)methoxy]phenyl}-2-oxopyridin-1(2H)-yl]-2-methyl-2-(methylsulfonyl)-N-(tetrahydro-2H-pyran-2-yloxy)butanamide Water (1.0) was added to a suspension of potassium carbonate (222 mg, 1.61 mmol), (2R)-4-(4-iodo-2-oxopyridin-1(2H)-yl)-2-methyl-2-(methylsulfonyl)-N-(tetrahydro-2H-pyran-2-yloxy)butanamide, T6, (400 mg, 0.803 mmol), which may be produced as in Preparation 2B and 2-methoxy-5-{[4-(4,4,5,5-tetramethyl-1,3,2-dioxaborolan-2-yl)phenoxy]methyl}pyridine (274 mg, 0.803 mmol) in 1,4-dioxane (10 mL). Pd EnCat™ (218 mg, 0.085 mmol) was added and the resulting suspension was heated to 100° C. for 2 hours. The reaction mixture was cooled to room temperature, then diluted with ethyl acetate (50 mL) and filtered through celite and washed with ethyl acetate (50 mL). The filtrate was concentrated in vacuo and the residue was partitioned between ethyl acetate 1:1 saturated brine/water. The layers were separated and the aqueous layer was extracted with ethyl acetate (2×). The organic layers were combined, dried (Na$_2$SO$_4$), filtered and concentrated. The crude material was purified by silica chromatography (hexanes/ethyl acetate 1:1-05:95) to give a white solid. Mass/Yield –254 mg/54% LCMS (MS ES–) 584.8. $^1$H NMR (400 MHz, DMSO-d$_6$) δ ppm 1.04 (s, 0H) 1.51 (br. s., 1H) 1.53-1.58 (m, 3H) 1.67 (br. s., 2H) 2.10-2.25 (m, 1H) 2.34-2.43 (m, 1H) 3.07 (s, 3H) 3.28 (s, 2H) 3.44-3.53 (m, 1H) 3.65-3.75 (m, 1H) 3.89 (s, 3H) 4.00-4.16 (m, 2H) 4.95 (s, 1H) 5.09 (s, 2H) 6.58-6.67 (m, 2H) 6.78-6.85 (m, 1H) 7.10 (s, 2H) 7.59-7.68 (m, 2H) 7.69-7.74 (m, 1H) 7.74-7.82 (m, 1H) 8.26 (s, 1H) 11.60 (s, 1H)

Step E: (2R)—N-hydroxy-4-[4-{4-[(6-methoxypyridin-3-yl)methoxy]phenyl}-2-oxopyridin-1(2H)-yl]-2-methyl-2-(methylsulfonyl)butanamide HCl (1.0 N in water, 2.09 mL) was added to a solution of the (2R)-4-[4-{4-[(6-methoxypyridin-3-yl)methoxy]phenyl}-2-oxopyridin-1(2H)-yl]-2-methyl-2-(methylsulfonyl)-N-(tetrahydro-2H-pyran-2-yloxy)butanamide (245 mg, 0.418 mmol) in IPA (5.0 mL) for 1 hour. The reaction mixture was concentrated and the residue was triturated with IPA to afford a white suspension at 50° C. for 30 minutes. A white solid was collected by filtration. Yield 215 mg/95% LCMS MS ES– 500.1. $^1$H NMR (400 MHz, DMSO-d$_6$) δ ppm 1.54 (s, 3H) 2.07-2.23 (m, 1H) 2.33-2.43 (m, 1H) 3.08 (s, 3H) 3.64-3.79 (m, 1H) 3.83 (s, 3H) 4.00-4.12 (m, 1H) 5.09 (s, 3H) 6.57-6.67 (m, 2H) 6.80-6.88 (m, 1H) 7.05-7.12 (m, 2H) 7.64-7.73 (m, 3H) 7.78 (s, 1H) 8.26 (s, 1H).

Example 60

(2R)-4-[4-{4-[difluoro(trans-4-hydroxycyclohexyl)methoxy]phenyl}-2-oxopyridin-1(2H)-yl]-N-hydroxy-2-methyl-2-(methylsulfonyl)butanamide

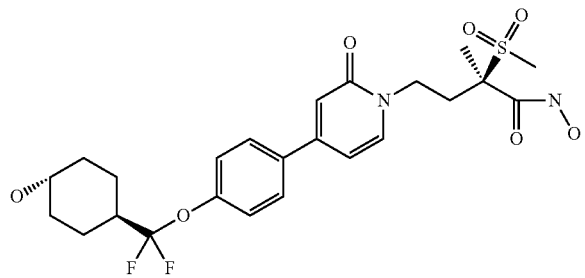 [SMILES: C[C@@](CCn1ccc(-c2ccc(OC(F)(F)[C@H]3CC[C@H](O)CC3)cc2)cc1=O)(C(=O)NO)S(C)(=O)=O]

Step A 8-[1,3]Dithian-2-ylidene-1,4-dioxa-spiro[4,5]decane

The title compound can be made following the procedure described in Eur. J. Org. Chem. 2008, 3479-34871, except that 4-dioxaspiro[4.5]decan-8-one was used as the ketone substrate. The resulting product was purified via silica gel chromatography (10% ethyl acetate 90% heptane to 100% ethyl acetate over 45 minutes. Isolated (6000 mg, ~100%). LCMS 259.2 $^1$H NMR (400 MHz, CHLOROFORM-d) δ ppm 1.67 (s, 4H) 2.12 (qq, 2H) 2.57-2.63 (m, 4H) 2.83-2.89 (m, 4H) 3.93-3.96 (m, 4H)

Step B: 8-((4-bromophenoxy)difluoromethyl)-1,4-dioxaspiro[4.5]decane

Trifluoromethanesulfonic acid (0.681 mL, 7.82 mmoles) was added dropwise to a stirred solution of 8-[1,3]dithian-2-ylidene-1,4-dioxa-spiro[4,5]decane (2000 mg, 7.740 mmoles) in 25 mL of dichloromethane at –22° C. The solution was allowed to warm to room temperature and stirred for 30 minutes The black reaction mixture was cooled to –72° C. and a solution of 4-bromo-phenol (2010 mg, 11.6 mmoles) and triethylamine (1.90 mL, 13.6 mmoles) in 25 mL of dichloromethane was added (solution turned red). The reaction was allowed to stir for an hour at –72° C., before NEt3.3HF (6.31 mL, 38.7 mmoles) was added. After 5 minutes a suspension of DBH (1,3-dibromo-5,5-dimethylhydanthoin) (11.1 g, 38.7 mmoles) in 25 mL's of dichloromethane was added in portions over 30 minutes (solution turned greenish/black). The solution was stirred for an additional hour, then warmed to 0° C. and poured into a solution of 1N NaOH. The organic layer was separated, washed with water, dried over sodium sulfate, filtered and concentrated in vacuo. The crude material was purified via silica gel chromatography and was eluted with 20% ethyl acetate 80% heptane to 100% ethyl acetate for 45 minutes. The isolated product was taken on directly to the next step. (2.811 g, 24.9%).

Step C: 4-[(4-bromo-phenoxy)-difluoro-methyl]-cyclohexanone

4 N HCl (4.23 mL, 16.9 mmoles) was added to a solution of 8-((4-bromophenoxy)difluoromethyl)-1,4-dioxaspiro[4.5]decane (1230 mg, 3.387 mmoles) in acetone (11.3 mL, 0.3M) and was allowed to stir overnight at room temperature. The reaction mixture was concentrated onto silica gel and purified via chromatography (9:1 heptane:ethyl acetate to 3:7 heptane:EtOAc over 40 minutes followed by 100% EtOAc for 10 minutes) afforded the desired material (1081 mg, 97.13%). $^1$H NMR (400 MHz, METHANOL-$d_4$) δ ppm 1.27 (br. s., 2H) 1.39-1.51 (m, 2H) 1.96-2.10 (m, 5H) 3.32-3.38 (m, 0H) 3.47-3.55 (m, 1H) 7.05-7.13 (m, 2H) 7.45-7.53 (m, 2H)

Step D: trans-4-[(4-bromophenoxy)(difluoro)methyl]cyclohexanol

To a stirred solution of 4-[(4-bromo-phenoxy)-difluoromethyl]-cyclohexanone (1050 mg, 3.290 mmoles) in ethanol (16.4 mL, 0.2M) was added NaBH$_4$ (249 mg, 6.58 mmoles) 0° C. The solution was stirred at 0° C. for 20 minutes and then warmed to room temperature for 20 minutes. The reaction was quenched with 1N HCl to a pH of ~7, and extracted three times with ethyl acetate. The organics where combined, dried over magnesium sulfate, filtered and concentrated. Cis/trans isomers were then separated by chiral purification. Isolated 260 mg of trans isomer (24%). $^1$H NMR (400 MHz, METHANOL-$d_4$) δ ppm 1.39 (s, 2H) 1.51-1.65 (m, 2H) 1.83-1.96 (m, 2H) 2.01-2.21 (m, 2H) 2.38-2.47 (m, 1H) 7.03-7.14 (m, 2H) 7.41-7.58 (m, 2H)

Step E: (2R)-4-[4-{4-[difluoro(trans-4-hydroxycyclohexyl)methoxy]phenyl}-2-oxopyridin-1(2H)-yl]-2-methyl-2-(methylsulfonyl)-N-(tetrahydro-2H-pyran-2-yloxy)butanamide (2R)-4-(4-(5,5-dimethyl-1,3,2-dioxaborinan-2-yl)-2-oxopyridin-1(2H)-yl)-2-methyl-2-(methylsulfonyl)-N-(tetrahydro-2H-pyran-2-yloxy)butanamide, T8, (240 mg, 0.495 mmoles), which may be produced as in Preparation 3, trans-4-[(4-bromophenoxy)(difluoro)methyl]cyclohexanol (159 mg, 0.495 mmoles), potassium carbonate (274 mg, 1.98 mmoles), and dioxane (3 mL, 0.2 M) were added to a 5 mL microwave vial followed by the addition of water and Pd EnCat™ (128 mg, 0.05 mmole, loading factor 0.39 mmol/g). The reaction mixture was irradiated at 120° C. for 45 minutes. The crude material was filtered through a thin film of celite and was rinsed with ethyl acetate then the filtrate was concentrated in vacuo. The material was purified via silica gel chromatography (15% EtOAc 85% heptane to 100% ethyl acetate over 45 minutes and then 5% MeOH 95% ethyl acetate for an additional 5 minutes). Isolated 290 mg title compound (95.6%) LCMS ES– 611.8

Step F: (2R)-4-[4-{4-[difluoro(trans-4-hydroxycyclohexyl)methoxy]phenyl}-2-oxopyridin-1(2H)-yl]-N-hydroxy-2-methyl-2-(methylsulfonyl)butanamide To a stirred solution of (2R)-4-[4-{4-[difluoro(trans-4-hydroxycyclohexyl)methoxy]phenyl}-2-oxopyridin-1(2H)-yl]-2-methyl-2-(methylsulfonyl)-N-(tetrahydro- 2H-pyran-2-yloxy)butanamide (280 mg, 0.473 mM) in 2.3 mL of dichloromethane was added a solution of 4 M HCl in dioxane (0.120 mL, 0.473 mM). The reaction mixture was allowed to stir for 20 minutes before being treated with 0.5 mL of MeOH. Reaction was concentrated in vacuo and purified by reverse phase (Shimadzu) prep HPLC 35 mg, (14%). LCMS 529.1 $^1$H NMR (400 MHz, METHANOL-$d_4$) δ ppm 1.30 (br. s., 2H) 1.40-1.54 (m, 2H) 1.64-1.74 (m, 3H) 1.99-2.14 (m, 4H) 2.31-2.42 (m, 1H) 2.51-2.67 (m, 1H) 3.09 (s, 3H) 3.45-3.62 (m, 1H) 3.87-4.02 (m, 1H) 4.23-4.34 (m, 1H) 6.70-6.75 (m, 1H) 6.78 (s, 1H) 7.21-7.33 (m, 2H) 7.65-7.74 (m, 3H)

Example 61

(2R)—N-hydroxy-4-[4-{4-[4-(hydroxymethyl)piperidin-1-yl]phenyl}-2-oxopyridin-1(2H)-yl]-2-methyl-2-(methylsulfonyl)butanamide

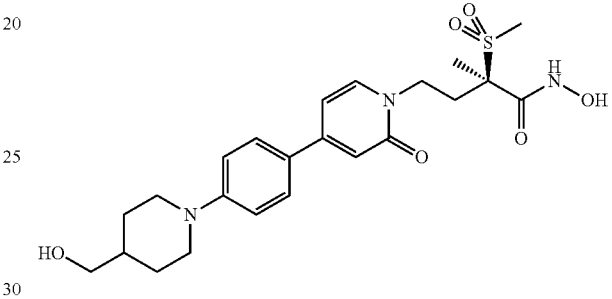

Step A)
[1-(4-bromo-phenyl)-piperidin-4-yl]-methanol

A mixture of 1-bromo-4-iodo-benzene (2.5 g, 8.8 mmol), piperidine-4-yl-methanol (2.0 g, 17.7 mmol), potassium phosphate (3.8 g, 17.7 mmol) and copper (I) iodide (3.8 g, 17.7 mmol) in N,N-dimethyl ethanolamine (8.4 mL) was heated to 55° C. for 48 hours. The mixture was allowed to cool to ambient temperature, water was added and the mixture was extracted with ether 2×. The combined organic extracts were washed with water 3×. The organic extract was dried over magnesium sulfate, filtered and concentrated to a crude residue. The residue was dissolved in methylene chloride and passed through a silica gel pad. The pad was eluted ethyl acetate/heptanes (3:7) to ethyl acetate/heptanes (6:4) and the filtrate was concentrated in vacuo to afford [1-(4-bromo-phenyl)-piperidin-4-yl]-methanol as a white solid. (2.4 g)

Step B) {1-[4-(4,4,5,5-tetramethyl-[1,3,2]dioxaborolan-2-yl)-phenyl]-piperidin-4-yl}-methanol

[1-(4-Bromo-phenyl)piperidin-4-yl]-methanol (380 mg, 1.41 mmol), was dissolved in 1,4-dioxane (10 mL, degassed with nitrogen). Bis(pinacolato)diborane (428 mg, 1.69 mmol), potassium acetate (414 mg, 4.22 mmol) and palladium dichloride dppf (115 mg, 0.141 mmol) were added at ambient temperature. The resulting mixture was stirred at 90° C. overnight. A further portion of bis(pinacolato)diborane (358 mg, 1.41 mmol) was added and the mixture was stirred at 90° C. overnight. The mixture was cooled to ambient temperature, filtered thought a pad of celite, rinsed with ethyl acetate and the filtrate was concentrated to a crude residue. The residue was absorbed onto silica gel and purified via flash column chromatography (gradient: 100% heptanes to 2:8 ethyl acetate/heptanes to 1:1 ethyl acetate/heptanes). The fractions containing desired product were combined and concentrated to afford {1-[4-(4,4,5,5-tetramethyl-[1,3,2]dioxaborolan-2-yl)-phenyl]-piperidin-4-yl}-methanol (399 mg)

Step C: (R)-4-{4-[4-(4-Hydroxymethyl-piperidin-1-yl)-phenyl]-2-oxo-2H-pyridin-1-yl}-2-methanesulfonyl-2-methyl-N-(tetrahydro-pyran-2-yloxy)-butyramide Water (1 mL, degassed with nitrogen) was added to a mixture of potassium carbonate (277 mg, 2.0 mmol), (R)-4-(4-iodo-2-oxo-2H-pyridin-1-yl)-2-methanesulfonyl-2-methyl-N-(tetrahydro-pyran-2-yloxy)-butyramide (200 mg, 0.4 mmol), which may be produced as in Preparation 2B, and {1-[4-(4,4,5,5-tetramethyl-[1,3,2]dioxaborolan-2-yl)-phenyl]-piperidin-4-yl}-methanol (153 mg, 0.48 mmol) in 1,4-dioxane (4 mL, degassed with nitrogen) at ambient temperature. To this mixture was added PdEncat (103 mg, 0.04 mmol, 0.39 mmol/g load) and the mixture was heated to 80° C. overnight. The mixture was cooled to ambient temperature and filtered through a pad of celite. The pad was rinsed with ethyl acetate and the filtrate was concentrated to a crude residue. The residue was purified via combiflash companion. The desired fractions were collected, combined and concentrated in vacuo to afford (R)-4-{4-[4-(4-Hydroxymethyl-piperidin-1-yl)-phenyl]-2-oxo-2H-pyridin-1-yl}-2-methanesulfonyl-2-methyl-N-(tetrahydro-pyran-2-yloxy)-butyramide. (85.1 mg)

Step D: (R)—N-Hydroxy-4-{4-[4-(4-hydroxymethyl-piperidin-1-yl)-phenyl]-2-oxo-2H-pyridin-1-yl}-2-methanesulfonyl-2-methyl-butyramide (R)-4-{4-[4-(4-hydroxymethyl-piperidin-1-yl)-phenyl]-2-oxo-2H-pyridin-1-yl}-2-methanesulfonyl-2-methyl-N-(tetrahydro-pyran-2-yloxy)-butyramide (85.1 mg, 0.152 mmol) was dissolved in methylene chloride (5 mL) at ambient temperature. To this solution was added 4M HCl in 1,4-dioxane (0.304 mL, 1.22 mmol) and methanol (1 ml). The resulting solution was stirred at ambient temperature for 45 minutes. The solution was concentrated to a crude residue in vacuo. To the residue was added ethyl acetate (10 ml) and the resulting slurry was stirred overnight at ambient temperature. The slurry was filtered and washed with ethyl acetate/heptanes (1:1). The solid was dried in vacuo to afford (R)—N-Hydroxy-4-{4-[4-(4-hydroxymethyl-piperidin-1-yl)-phenyl]-2-oxo-2H-pyridin-1-yl}-2-methanesulfonyl-2-methyl-butyramide hydrochloride as an off-white solid. (72.7 mg). LCMS: M+1 478.6. $^1$H NMR (CD$_3$OD, 400 MHZ) dppm, 7.82 (2H, d), 7.79 (1H, d), 6.84 (1H, d), 6.80-6.77 (1H, dd), 4.35-4.28 (1H, m), 4.00-3.93 (1H, m), 3.79-3.72 (4H, m), 3.55 (2H, d), 3.09 (3H, s), 2.64-2.56 (1H, m), 2.40-2.33 (1H, m), 2.16-2.13 (2H, d), 2.00-1.92 (1H, m), 1.87-1.76 (2H, m), 1.70 (3H, s).

Example 62

N-hydroxy-4-[4-{4[(1E)-N-methoxyethanimidoyl]phenyl}-2-oxopyridin-1(2H)-yl]-2-methyl-2-(methylsulfonyl)butanamide

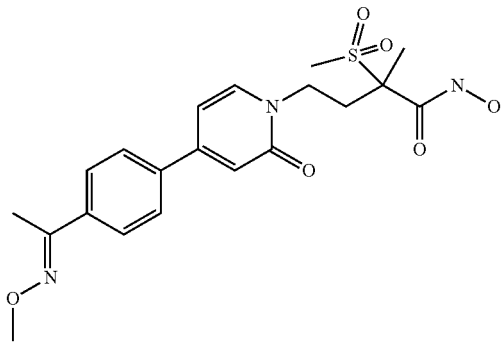 [SMILES: CO/N=C(\C)c1ccc(-c2ccn(CCC(C)(C(=O)NO)S(C)(=O)=O)c(=O)c2)cc1]

Step A: 4-[4-(4-Acetylphenyl)-2-oxopyridin-1(2H)-yl]-N-hydroxy-2-methyl-2-(methylsulfonyl)butanamide 4-Acetylphenylboronic acid was converted to the title product following the general procedure outlined for (2R)-4-[4-(2-fluoro-4-methylphenyl)-2-oxopyridin-1(2H)-yl]-2-methyl-2-(methylsulfonyl)-N-(tetrahydro-2H-pyran-2-yloxy)butanamide in Example 13. $^1$H NMR (400 MHz, DMSO-d$_6$) δ ppm 1.58 (s, 3H) 2.17 (ddd, J=12.83, 11.56, 5.07 Hz, 1H) 2.40-2.49 (m, 1H) 2.62 (s, 3H) 3.11 (s, 3H) 3.77 (td, J=11.95, 4.78 Hz, 1H) 4.13 (td, J=11.90, 5.07 Hz, 1H) 6.70 (dd, J=7.22, 2.15 Hz, 1H) 6.79 (d, J=2.15 Hz, 1H) 7.81 (d, J=7.03 Hz, 1H) 7.87 (d, J=8.39 Hz, 2H) 8.04 (d, J=8.59 Hz, 2H) 11.14 (br. s., 1H).

Step B: N-Hydroxy-4-[4-{4-[(1E)-N-methoxyethanimidoyl]phenyl}-2-oxopyridin-1(2H)-yl]-2-methyl-2-(methylsulfonyl)butanamide A suspension of 4-[4-(4-acetylphenyl)-2-oxopyridin-1(2H)-yl]-N-hydroxy-2-methyl-2-(methylsulfonyl)butanamide (105 mg, 0.258 mmol), O-methylhydroxylamine hydrochloride (86.2 mg, 1.03 mmol) and sodium acetate (107 mg, 1.03 mmol) in ethanol (10 mL, 0.025M) was heated in an oil bath at 70° C. for 3 hours. The volatiles were removed by rotary evaporation. The remaining material was redissolved in 1.5 mL DMSO and run on Shimadzu HPLC 30×100 mm reverse phase column. The material was eluted with 20-35% acetonitrile in water with 0.1% ammonium hydroxide modifier. The gradient was run for 8 min then held at 35% for an additional two minutes. The desired material eluted at about 30% acetonitrile. This solution was concentrated down by rotary evaporation yielding 90.7 mg (80.7%) of the title compound a white solid. LC/MS m/z 436 (M+1). $^1$H NMR (500 MHz, DMSO-d$_6$) δ ppm 1.57 (s, 3H) 2.13-2.21 (m, 1H) 2.21 (s, 3H) 2.39-2.48 (m, 1H) 3.11 (s, 3H) 3.70-3.81 (m, 1H) 3.94 (s, 3H) 4.12 (td, J=11.90, 5.00 Hz, 1H) 6.68 (dd, J=7.20, 1.83 Hz, 1H) 6.75 (d, J=1.95 Hz, 1H) 7.71-7.82 (m, 5H) 9.27 (br. s., 1H) 11.14 (br. s., 1H)

Example 63

N-Hydroxy-4-[4-{4-[3-(hydroxymethyl)isoxazol-5-yl]-3-methylphenyl}-2-oxopyridin-1(2H)-yl]-2-methyl-2-(methylsulfonyl)butanamide

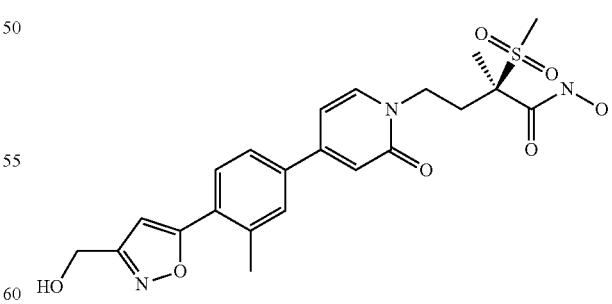

Step A: 5-(4-bromo-2-methylphenyl)-3-[(tetrahydro-2H-pyran-2-yloxy)methyl]isoxazole To a flask containing a solution of 4-bromo-1-ethynyl-2-methylbenzene (875 mg, 4.49 mmol) (may be prepared according to the procedures in *Journal of Chemical Research* (2007), 12 728-732) in toluene (20 mL), was added 2-(2-nitroethoxy)tetrahydro-2H-pyran (1.34 g, 7.63 mmol), phenyl isocyanate (1.82 g, 15.3 mmol), and triethylamine (1.50 mL, 10.8 mmol). The reaction was heated at 100° C. and stirred under nitrogen overnight. The reaction was cooled, quenched with methanol and filtered. The filtrate was evaporated in vacuo onto silica gel. Chromatography on silica gel with a heptane-ethyl acetate gradient (0-35% ethyl acetate) eluted 5-(4-bromo-2-methylphenyl)-3-[(tetrahydro-2H-pyran-2-yloxy)methyl]isoxazole as an orange oil (581 mg, 36.8%). ¹H NMR (400 MHz, CHLOROFORM-d) δ ppm 1.57-1.71 (m, 4H) 1.73-1.82 (m, 1H) 1.82-1.91 (m, 1H) 2.51 (s, 3H) 3.56-3.62 (m, 1H) 3.89-3.96 (m, 1H) 4.69 (d, J=12.88 Hz, 1H) 4.76-4.79 (m, 1H) 4.86 (d, J=12.88 Hz, 1H) 6.51 (s, 1H) 7.42-7.46 (m, 1H) 7.48 (d, J=1.56 Hz, 1H) 7.59 (d, J=8.20 Hz, 1H).

Step B: 5-[2-Methyl-4-(4,4,5,5-tetramethyl-1,3,2-dioxaborolan-2-yl)phenyl]-3-[(tetrahydro-2H-pyran-2-yloxy)methyl]isoxazole 5-(4-Bromo-2-methylphenyl)-3-[(tetrahydro-2H-pyran-2-yloxy)methyl]isoxazole was converted to the title product following the procedure outlined for (+/−)-2-[(cis-4-{[4-(4,4,5,5-tetramethyl-1,3,2-dioxaborolan-2-yl)phenoxy]methyl}cyclohexyl)oxy]tetrahydro-2H-pyran in Example 8, step D. The title compound was isolated as an orange oil, 473 mg, 71.9%. ¹H NMR (400 MHz, CHLOROFORM-d) δ ppm 1.37 (s, 12H) 1.53-1.71 (m, 4H) 1.73-1.82 (m, 1H) 1.82-1.93 (m, 1H) 2.54 (s, 3H) 3.55-3.63 (m, 1H) 3.89-3.96 (m, 1H) 4.69 (d, J=12.69 Hz, 1H) 4.78 (t, J=3.51 Hz, 1H) 4.86 (d, J=12.89 Hz, 1H) 6.55 (s, 1H) 7.71-7.76 (m, 3H).

Step C: (2R)-4-[4-{4-[3-(hydroxymethyl)isoxazol-5-yl]-3-methylphenyl}-2-oxopyridin-1(2H)-yl]-2-methyl-2-(methylsulfonyl)-N-(tetrahydro-2H-pyran-2-yloxy)butanamide 5-[2-Methyl-4-(4,4,5,5-tetramethyl-1,3,2-dioxaborolan-2-yl)phenyl]-3-[(tetrahydro-2H-pyran-2-yloxy)methyl]isoxazole was converted to the title product following the procedure outlined for (2R)-2-methyl-2-(methylsulfonyl)-4-[2-oxo-4-(4-{[cis-4-(tetrahydro-2H-pyran-2-yloxy)cyclohexyl]methoxy}phenyl)pyridin-1(2H)-yl]-Netrahydro-2H-pyran-2-yloxy)butanamide in Example 8 step E. Isolated crude yellow foam, 488 mg, 110% (impure). LCMS 642 (M−1)

Step D: N-Hydroxy-4-[4-{4-[3-(hydroxymethyl)isoxazol-5-yl]-3-methylphenyl}-2-oxopyridin-1(2H)-yl]-2-methyl-2-(methylsulfonyl)butanamide (2R)-4-[4-{4-[3-(hydroxymethyl)isoxazol-5-yl]-3-methylphenyl}-2-oxopyridin-1(2H)-yl]-2-methyl-2-(methylsulfonyl)-N-(tetrahydro-2H-pyran-2-yloxy)butanamide was converted to title product following the procedure outlined for (2R)—N-hydroxy-4-[4-{4-[(cis-4-hydroxycyclohexyl)methoxy]phenyl}-2-oxopyridin-1(2H)-yl]-2-methyl-2-(methylsulfonyl)butanamide in Example 8, step F. Isolated title compound as a tan solid, 256.5 mg, 77.3%. ¹H NMR (400 MHz, METHANOL-d₄) δ ppm 1.73 (s, 3H) 2.37-2.45 (m, 1H) 2.60 (s, 3H) 2.62-2.70 (m, 1H) 3.11 (s, 3H) 3.99-4.08 (m, 1H) 4.33-4.41 (m, 1H) 4.72 (s, 2H) 6.76 (s, 1H) 6.96 (s, 2H) 7.67 (dd, J=8.20, 1.56 Hz, 1H) 7.72 (s, 1H) 7.86 (d, J=8.20 Hz, 2H). LCMS 476 (M+1).

Example 64

(2R)—N-Hydroxy-2-methyl-2-(methylsulfonyl)-4-[2-oxo-4-(3-phenylazetidin-1-yl)pyridin-1(2H)-yl]butanamide

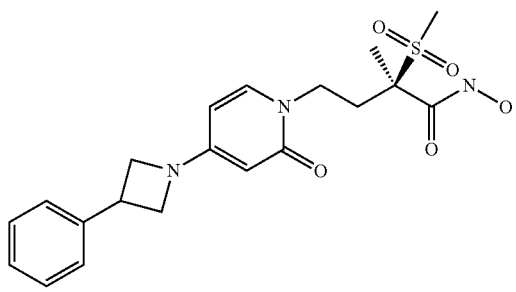 [SMILES: C[C@@](CCn1ccc(N2CC(c3ccccc3)C2)cc1=O)(C(=O)NO)S(C)(=O)=O]

Step A: 2(R)-2-Methyl-2-(methylsulfonyl)-4-[2-oxo-4-(3-phenylazetidin-1-yl)pyridin-1(2H)-yl]-Netrahydro-2H-pyran-2-yloxy)butanamide (2R)-4-(4-iodo-2-oxopyridin-1(2H)-yl)-2-methyl-2-(methylsulfonyl)-N-(tetrahydro-2H-pyran-2-yloxy)butanamide, T6, which may be produced as in Preparation 2B (309 mg, 0.620 mmol), 3-phenylazetidine (185 mg, 1.39 mmol), potassium tert-butoxide (209 mg, 1.86 mmol), and tris(dibenzylideneacetone)dipalladium(0) (26 mg, 0.025 mmol) and ±BINAP (23 mg, 0.037 mmol) were combined into a flask, placed under vacuum and opened to nitrogen. Deoxygenated 1,2-dimethoxyethane (3.0 mL) and triethylamine (43 uL, 0.310 mmol) were added and the reaction was placed on vacuum and opened to nitrogen three times and then heated at 80° C. under nitrogen overnight. The reaction was cooled, diluted with dichloromethane and methanol and evaporated in vacuo onto silica gel. Chromatography on silica gel with a dichloromethane-methanol gradient (1%-20%) eluted (2R)-2-methyl-2-(methylsulfonyl)-4-[2-oxo-4-(3-phenylazetidin-1-yl)pyridin-1(2H)-yl]-Netrahydro-2H-pyran-2-yloxy)butanamide as a yellow oil (192 mg, 61.7%). LCMS 504 (M+1).

Step B: (2R)—N-Hydroxy-2-methyl-2-(methylsulfonyl)-4-[2-oxo-4-(3-phenylazetidin-1-yl)pyridin-1(2H)-yl]butanamide (2R)-2-methyl-2-(methylsulfonyl)-4-[2-oxo-4-(3-phenylazetidin-1-yl)pyridin-1(2H)-yl]-Netrahydro-2H-pyran-2-yloxy)butanamide was converted to title product following the procedure outlined for (2R)—N-hydroxy-4-[4-{4-[(cis-4-hydroxycyclohexyl)methoxy]phenyl}-2-oxopyridin-1(2H)-yl]-2-methyl-2-(methylsulfonyl)butanamide in Example 8, step F. Isolated title compound as a white solid, 55.0 mg, 34.8%. ¹H NMR (400 MHz, METHANOL-d₄) δ ppm 1.67 (s, 3H) 2.23-2.38 (m, 1H) 2.41-2.55 (m, 1H) 3.10 (s, 3H) 3.70-3.87 (m, 1H) 3.95-4.05 (m, 3H) 4.07-4.21 (m, 1H)

4.35-4.48 (m, 2H) 5.28-5.34 (m, 1H) 5.82-5.93 (m, 1H) 7.21-7.30 (m, 1H) 7.33-7.38 (m, 3H) 7.38-7.46 (m, 2H). LCMS 420 (M+1)

Example 65

(2R)—N-Hydroxy-2-methyl-2-(methylsulfonyl)-4-[2-oxo-4-(phenylethynyl)pyridin-1(2H)-yl]butanamide

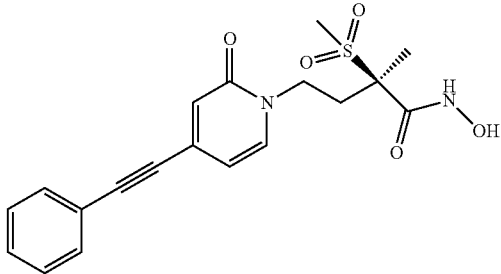 [SMILES: C[C@@](CCn1ccc(C#Cc2ccccc2)cc1=O)(C(=O)NO)S(C)(=O)=O]

Step A: (2R)-2-methyl-2-(methylsulfonyl)-4-(2-oxo-4-(phenylethynyl)pyridin-1(2H)-yl)-N-(tetrahydro-2H-pyran-2-yloxy)butanamide (2R)-4-(4-iodo-2-oxopyridin-1(2H)-yl)-2-methyl-2-(methylsulfonyl)-N-(tetrahydro-2H-pyran-2-yloxy)butanamide, T6, which may be produced as in Preparation 2B (200 mg, 0.401 mmol) was dissolved in tetrahydrofuran (5 mL) and diisopropylethylamine (2 ml) at room temperature. The solution was degassed with nitrogen over a 5 minute period. Palladium tetrakis (23.3 mg, 0.020 mmol), copper iodide (7.80 mg, 0.040 mmol), and phenylacetylene (49.1 mg, 0.481 mmol) were added to the reaction. The reaction was allowed to stir at room temperature for 3 hours under a nitrogen atmosphere. The reaction was diluted with ethyl acetate (200 ml) and was extracted with a saturated aqueous solution of ammonium chloride (100 ml). The organic layer was washed with brine, dried over sodium sulfate, and evaporated in vacuo. The crude material was purified via silica chromatography, using 50%-100% [ethyl acetate/hexanes] as the gradient elution solvent. The target fractions were combined and concentrated in vacuo to afford a viscous, colorless oil that crystallized upon standing. Yield 107 mg, 57%. MS (APCI) m/z 471.5 (M–H) $^1$H NMR (400 MHz, CHLOROFORM-d) δ ppm 1.57-1.65 (m, 2H) 1.69 (d, J=1.95 Hz, 3H) 1.71-1.98 (m, 4H) 2.30-2.42 (m, 1H) 2.43-2.55 (m, 1H) 3.19 (d, J=3.32 Hz, 3H) 3.56-3.69 (m, 1H) 3.97-4.06 (m, 1H) 4.13-4.25 (m, 1H) 4.26-4.36 (m, 1H) 5.16 (dt, J=16.00, 2.63 Hz, 1H) 6.34 (dd, J=7.02, 1.76 Hz, 1H) 6.75 (s, 1H) 7.29 (d, J=7.02 Hz, 1H) 7.34-7.40 (m, 3H) 7.52 (dd, J=7.32, 1.85 Hz, 2H) 12.00 (br. s., 1H)

Step B: (R)—N-hydroxy-2-methyl-2-(methylsulfonyl)-4-(2-oxo-4-(phenylethynyl)pyridin-1(2H)-yl) butanamide A solution of 1.0 M aqueous HCl (10 ml) was added slowly to a solution of (2R)-2-methyl-2-(methylsulfonyl)-4-(2-oxo-4-(phenylethynyl)pyridin-1(2H)-yl)-N-(tetrahydro-2H-pyran-2-yloxy)butanamide (107 mg, 0.226 mmol) in 1,4-dioxane (20 mL) at room temperature. The reaction mixture was allowed to stir at room temperature overnight. After 18 hours the reaction was concentrated to low volume then redissolved in methanol (20 ml) and concentrated in vacuo to afford a light-yellow solid. Yield 71 mg, 81%. MS (APCI) m/z 389.4 (M+H), $^1$H NMR (400 MHz, DMSO-d$_6$) δ ppm 1.46 (none, 3H) 1.53 (s, 3H) 2.03-2.17 (m, 1H) 2.33-2.45 (m, 1H) 3.07 (s, 3H) 3.71 (td, J=11.90, 4.88 Hz, 1H) 3.96-4.14 (m, 1H) 6.35 (dd, J=6.93, 1.85 Hz, 1H) 6.56 (d, J=1.76 Hz, 1H) 7.36-7.48 (m, 3H) 7.51-7.61 (m, 2H) 7.69 (d, J=7.02 Hz, 1H) 11.05 (br. s., 1H)

Example 66

4-[4-(3-Cyclohexylpropoxy)-2-oxopyridin-1(2H)-yl]-N-hydroxy-2-methyl-2-(methylsulfonyl)butanamide

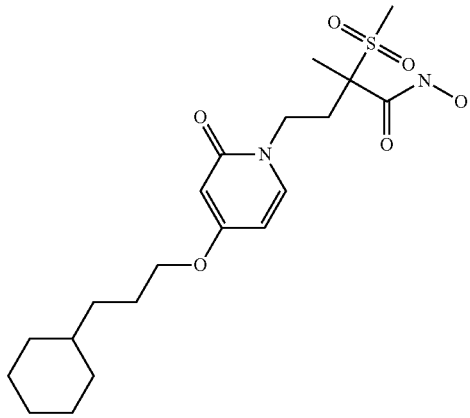 [SMILES: CC(CCn1ccc(OCCCC2CCCCC2)cc1=O)(C(=O)NO)S(C)(=O)=O]

Step A: ethyl 4-(4-hydroxy-2-oxopyridin-1(2H)-yl)-2-methyl-2-(methylsulfonyl)butanoate Ethyl 4-[4-(benzyloxy)-2-oxopyridin-1(2H)-yl]-2-methyl-2-(methylsulfonyl)butanoate (2.4 g, 5.9 mmol) which may be prepared by the same method disclosed in Example 51, step A, was dissolved in ethanol (100 ml) and cooled with a dry ice/acetone bath. To the cooled solution was added Pearlman's catalyst (2.0 g) and cyclohexene (9.0 ml, 88.4 mmol) then heated to 85° C. for 3 hours. The reaction mixture was cooled to RT and filtered through celite (approx 2 inches) to remove catalyst. The celite was washed with an additional 100 ml of ethanol. The filtrate was then concentrated under reduced pressure and the residue was dried under vacuum to afford a light gray solid. (1.75 g, 94%). MS (LC/MS) m/z 318.1 (M+1) $^1$H NMR (400 MHz, DMSO-d$_6$) δ ppm 1.22 (t, J=7.02 Hz, 3H) 1.56 (s, 3H) 2.02-2.26 (m, 1H) 2.33-2.48 (m, 1H) 3.14 (s, 3H) 3.67-3.84 (m, 1H) 3.84-4.02 (m, 1H) 4.13 (dd, J=7.02, 4.49 Hz, 2H) 5.55 (d, J=2.54 Hz, 1H) 5.85 (dd, J=7.42, 2.54 Hz, 1H) 7.48 (d, J=7.42 Hz, 1H)

Step B: 4-[4-(3-cyclohexylpropoxy)-2-oxopyridin-1(2H)-yl]-2-methyl-2-(methylsulfonyl)butanoic acid Ethyl 4-(4-hydroxy-2-oxopyridin-1(2H)-yl)-2-methyl-2-(methylsulfonyl)butanoate (285 mg, 0.898 mmol) was weighed into a 20 ml septa cap vial with THF (10 ml) added. To this was added 3-cyclohexyl-1-propanol (0.191 ml, 1.26 mmol), followed by triphenylphosphine (330 mg, 1.21 mmol). The reaction mixture was stirred at RT for 20 minutes and then DIAD (0.248 ml, 1.26 mmol) was added. The reaction mixture was stirred for 72 hours at RT, was then diluted with ethyl acetate (100 ml) and washed with saturated sodium bicarbonate (50 ml). The product was re-extracted with ethyl acetate (100 ml). The organic phases were combined, dried over sodium sulfate, filtered and concentrated in vacuo. The residue was dissolved in dioxane (6 ml) and ethanol (6 ml). To this was added a 2.0M aqueous solution of LiOH (2.6 ml, 5.3 mmol). The reaction mixture was stirred at RT overnight, then was diluted with 30 ml of water and washed with ethyl acetate (2×50 ml) to remove any TPPO. The aqueous phase was adjusted to pH-2 with 1N HCl (10 ml) and the product was extracted with ethyl acetate (3×50 ml). The organic phases were combined, dried over sodium sulfate, filtered and concentrated to provide the title compound as a white solid (190 mg, 51%). MS (LC/MS) m/z 414.1 (M+1) $^1$H NMR (400 MHz, METHANOL-$d_4$) δ ppm 0.81-1.08 (m, 2H) 1.16-1.44 (m, 6H) 1.72 (s, 9H) 2.01 (s, 1H) 2.29-2.47 (m, 1H) 2.48-2.68 (m, 1H) 3.18 (s, 3H) 4.04 (s, 2H) 4.07-4.17 (m, 1H) 4.22-4.37 (m, 1H) 5.97-6.12 (m, 1H) 6.25-6.36 (m, 1H) 7.57-7.73 (m, 1H)

Step C: 4-[4-(3-cyclohexylpropoxy)-2-oxopyridin-1 (2H)-yl]-2-methyl-2-(methylsulfonyl)-N-(tetrahydro-2H-pyran-2-yloxy)butanamide 4-[4-(3-Cyclohexylpropoxy)-2-oxopyridin-1(2H)-yl]-2-methyl-2-(methylsulfonyl)butanoic acid (190 mg, 0.451 mmol) and CDMT (95.6 mg, 0.539 mmol) were charged into a flask. The flask was flushed with nitrogen and 2-MeTHF (10 ml) was added, followed by NMM (64 uL, 0.581 mmol). The reaction mixture was stirred at RT for 1 hour. O-(tetrahydro-2H-pyran-2-yl)hydroxylamine (64 mg, 0.539 mmol) was added to the reaction mixture and stirred for 16 hours at RT. Water (25 ml) was added, the layers were separated and the aqueous layer was extracted with EtOAc (3×50 ml). The organic layers were combined and dried over sodium sulfate, filtered and concentrated in vacuo. Crude material was purified by chromatography on silica gel (70% heptane:30% ethyl acetate to 100% ethyl acetate) to afford a white solid (220 mg, 79%). MS (LC/MS) m/z 511.1 (M−1) $^1$H NMR (400 MHz, METHANOL-$d_4$) δ ppm 0.93 (t, J=7.02 Hz, 3H) 1.12-1.42 (m, 9H) 1.49-1.99 (m, 10H) 2.25-2.43 (m, 1H) 2.45-2.64 (m, 1H) 3.12 (d, J=5.07 Hz, 3H) 3.51-3.68 (m, 2H) 3.82-4.03 (m, 4H) 4.08-4.26 (m, 2H) 5.03-5.14 (m, 1H) 5.94 (d, J=2.54 Hz, 1H) 6.07-6.21 (m, 1H) 7.45-7.60 (m, 1H).

Step D: 4-[4-(3-cyclohexylpropoxy)-2-oxopyridin-1 (2H)-yl]-N-hydroxy-2-methyl-2-(methylsulfonyl) butanamide 4-[4-(3-Cyclohexylpropoxy)-2-oxopyridin-1(2H)-yl]-2-methyl-2-(methylsulfonyl)-N-(tetrahydro-2H-pyran-2-yloxy)butanamide (220 mg, 0.429 mmole) was dissolved in dioxane (4 ml), DCM (4 ml) and water (2 ml). To this was added a 4.0M solution of HCl in dioxane (1.0 ml, 4.29 mmole) and was stirred at RT for 1 hour. The reaction mixture was concentrated in vacuo and azeotroped with IPA (2×5 ml) to afford a white solid (100 mg, 54.4%). MS (LC/MS) m/z 429.1 (M+1) $^1$H NMR (400 MHz, METHANOL-$d_4$) δ ppm 0.83-1.06 (m, 3H) 1.19-1.40 (m, 6H) 1.41 (s, 2H) 1.64-1.90 (m, 4H) 2.31-2.41 (m, 1H) 2.61-2.79 (m, 1H) 3.08 (s, 3H) 3.60 (s, 1H) 3.63-3.71 (m, 1H) 3.86-3.99 (m, 2H) 4.04 (s, 1H) 4.11 (d, J=8.00 Hz, 3H) 4.25-4.41 (m, 1H) 6.29 (s, 1H) 6.53-6.68 (m, 1H) 7.83-7.93 (m, 1H)

Example 67

(2R)—N-Hydroxy-2-methyl-2-(methylsulfonyl)-4-(2-oxo-1'-pyrimidin-2-yl-1',2',3',6'-tetrahydro-4,4'-bipyridin-1(2H)-yl)butanamide

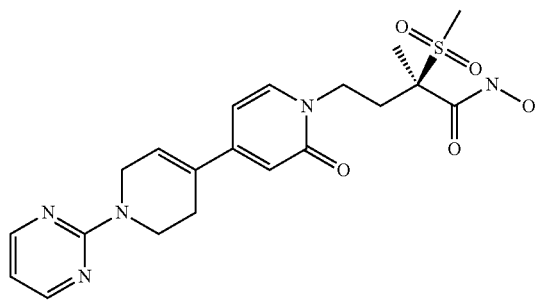 [SMILES: C[C@@](CCn1ccc(C2=CCN(c3ncccn3)CC2)cc1=O)(C(=O)NO)S(C)(=O)=O]

Step A: 2-[4-(4,4,5,5-tetramethyl-1,3,2-dioxaborolan-2-yl)-3,6-dihydropyridin-1(2H)-yl]pyrimidine To a flask containing 1-pyrimidin-2-yl-1,2,3,6-tetrahydropyridin-4-yl trifluoromethanesulfonate (300 mg, 0.970 mmol) (may be prepared according to the procedures in PCT Int Appl 2006124897), bis(pinacolato)diboron (296 mg, 1.16 mmol), potassium acetate (288 mg, 2.91 mmol), 1,1'-bis-(diphenylphosphino)ferrocene (16 mg, 0.029 mmol) and [1,1'-bis-(diphenylphosphino)ferrocene]-dichloropalladium (II) dichloromethane complex (71 mg, 0.097 mmol) was added deoxygenated 1,4-dioxane (5.0 ml). The reaction was placed under vacuum and opened to nitrogen three times and then heated at 80° C. under nitrogen overnight. The reaction was cooled and purified directly by chromatography on silica gel with 6:1 heptane-ethyl acetate to give 2-[4-(4,4,5,5-tetramethyl-1,3,2-dioxaborolan-2-yl)-3,6-dihydropyridin-1 (2H)-yl]pyrimidine as a yellow solid (210 mg, 75.4%). $^1$H NMR (400 MHz, CHLOROFORM-d) δ ppm 1.29 (s, 12H) 2.25-2.44 (m, 2H) 3.89 (t, J=5.66 Hz, 2H) 4.24-4.29 (m, 1H) 6.42-6.54 (m, 1H) 6.58-6.69 (m, 1H) 8.21-8.40 (m, 2H). LCMS: 288.4 M+1.

Step B: (2R)-2-methyl-2-(methylsulfonyl)-4-(2-oxo-1'-pyrimidin-2-yl-1',2',3',6'-tetrahydro-4,4'-bipyridin-1(2H)-yl)-N-(tetrahydro-2H-pyran-2-yloxy)butanamide (2R)-4-(4-iodo-2-oxopyridin-1(2H)-yl)-2-methyl-2-(methylsulfonyl)-N-(tetrahydro-2H-pyran-2-yloxy)butanamide, T6, which may be produced as in Preparation 2B (310 mg, 0.622 mmol), 2-[4-(4,4,5,5-tetramethyl-1,3,2-dioxaborolan-2-yl)-3,6-dihydropyridin-1(2H)-yl]pyrimidine (210 mg, 0.731 mmol), potassium carbonate (430 mg, 3.11 mmol), and Pd EnCat™ (159 mg, 0.062 mmol) were combined into a flask, placed under vacuum and opened to nitrogen. Deoxygenated 1,4-dioxane (4.0 mL) and water (1.0 mL) were added and the reaction was placed on vacuum and opened to nitrogen three times and then heated at 80° C. under nitrogen for 16 hours. The reaction mixture was cooled, diluted with ethyl acetate and filtered through celite. The filtrate was concentrated onto silica gel in vacuo. Chromatography on silica gel with a dichloromethane-methanol gradient (1%-20%) afforded (2R)-2-methyl-2-(methylsulfonyl)-4-(2-oxo-1'-pyrimidin-2-yl-1',2',3',6'-tetrahydro-4,4'-bipyridin-1(2H)-yl)-N-(tetrahydro-2H-pyran-2-yloxy)butanamide as a brown oil (140 mg, 42.5%). LCMS 530 (M−1).

Step C: (2R)—N-Hydroxy-2-methyl-2-(methylsulfonyl)-4-(2-oxo-1'-pyrimidin-2-yl-1',2',3',6'-tetrahydro-4,4'-bipyridin-1(2H)-yl)butanamide (2R)-2-methyl-2-(methylsulfonyl)-4-(2-oxo-1'-pyrimidin-2-yl-1',2',3',6'-tetrahydro-4,4'-bipyridin-1(2H)-yl)-N-(tetrahydro-2H-pyran-2-yloxy)butanamide (140 mg, 0.253 mmol) was converted to title product following the procedure outlined for (2R)—N-hydroxy-4-[4-{4-[(cis-4-hydroxycyclohexyl)methoxy]phenyl}-2-oxopyridin-1(2H)-yl]-2-methyl-2-(methylsulfonyl)butanamide in Example 8, step F. Isolated title compound as an off white solid (94.8 mg 80.5%). $^1$H NMR (400 MHz, METHANOL-d$_4$) δ ppm 1.70 (s, 3H) 2.29-2.42 (m, 1H) 2.55-2.67 (m, 1H) 2.68-2.78 (m, 2H) 3.10 (s, 3H) 3.93-4.04 (m, 1H) 4.17 (t, J=5.76 Hz, 2H) 4.26-4.37 (m, 1H) 4.49-4.55 (m, 2H) 6.62 (br. s., 1H) 6.67 (s, 1H) 6.74-6.85 (m, 1H) 7.07 (t, J=5.37 Hz, 1H) 7.75 (d, J=7.81 Hz, 1H) 8.67 (d, J=5.46 Hz, 2H). LCMS: 448 (M+1).

Examples 68-A to 68-U

The following compounds can be made following the procedures described herein. Products are typically derived from a Suzuki-Miyaura cross coupling with optional deprotection of a terminal hydroxamic acid protecting group. Methods used to describe the synthesis of the precursors or coupling partners such as boronic acids or esters are known to those skilled in the art.

TABLE 3

| Example number | IUPAC NAME | Retention Time | Mass ion[1] | Purity | NMR |
|---|---|---|---|---|---|
| E68-A | (2R)-N-hydroxy-2-methyl-2-(methylsulfonyl)-4-[4-(2-naphthyl)-2-oxopyridin-1(2H)-yl]butanamide | | 415 | 100 | 1H NMR (400 MHz, METHANOL-d4) d ppm 1.74 (s, 3 H) 2.31-2.55 (m, 1 H) 2.64-2.83 (m, 1 H) 3.10 (s, 3 H) 3.96-4.24 (m, 1 H) 4.30-4.59 (m, 1 H) 7.17 (d, J = 1.95 Hz, 1 H) 7.29 (m, 1 H) 7.52-7.63 (m, 2 H) 7.78-7.86 (m, 1 H) 7.89-7.96 (m, 1 H |
| E68-B | (2R)-4-[4-(4-chloro-3-fluorophenyl)-2-oxopyridin-1(2H)-yl]-N-hydroxy-2-methyl-2-(methylsulfonyl)butanamide | | 415 (m − 1) | | $^1$H NMR (400 MHz, DMSO-d$_6$) d ppm 1.57 (s, 3 H) 2.11-2.21 (m, 1 H) 2.38-2.48 (m, 1 H) 3.11 (s, 3 H) 3.76 (td, J = 11.95, 4.78 Hz, 1 H) 4.11 (td, J = 11.81, 5.07 Hz, 1 H) 6.69 (dd, J = 7.12, 2.05 Hz, 1 H) 6.80 (d, J = 1.95 Hz, 1 H) 7.60-7.65 (m, 1 H) 7.67-7. |
| E68-C | (2R)-4-[4-(3,4-dichlorophenyl)-2-oxopyridin-1(2H)-yl]-N-hydroxy-2-methyl-2-(methylsulfonyl)butanamide | | 433 | 100 | $^1$H NMR (400 MHz, DMSO-d$_6$) d ppm 1.57 (s, 3 H) 2.16 (td, J = 12.20, 5.07 Hz, 1 H) 2.38-2.48 (m, 1 H) 3.10 (s, 3 H) 3.76 (td, J = 11.90, 4.88 Hz, 1 H) 4.12 (td, J = 11.85, 4.98 Hz, 1 H) 6.70 (dd, J = 7.12, 2.05 Hz, 1 H) 6.80 (d, J = 1.95 Hz, 1 H) 7.74 (d, J = 0.98 Hz |
| E68-D | (2R)-N-hydroxy-2-methyl-2-(methylsulfonyl)-4-{2-oxo-4-[4-(1,3-thiazol-2-yl)phenyl]pyridin-1(2H)-yl}butanamide | 0.48 | 448 | 100 | 1H NMR (400 MHz, DMSO-d$_6$) d ppm 1.58 (s, 3 H) 2.18 (td, J = 12.05, 4.98 Hz, 1 H) 2.40-2.48 (m, 1 H) 3.11 (s, 3 H) 3.77 (td, J = 12.15, 5.37 Hz, 1 H) 4.08-4.19 (m, 1 H) 6.72 (dd, J = 7.22, 2.15 Hz, 1 H) 6.79 (d, J = 2.15Hz, 1 H) 7.80 (d, J = 7.22Hz, 1 H) 7.84 |
| E68-E | (2R)-4-[4-(2-chloro-3-methylphenyl)-2-oxopyridin-1(2H)-yl]-N-hydroxy-2-methyl-2-(methylsulfonyl)butanamide | 0.55 | 413 | 100 | $^1$H NMR (400 MHz, DMSO-d$_6$) d ppm 1.55 (s, 3 H) 2.15 (td, J = 12.20, 5.07 Hz, 1 H) 2.37 (s, 3 H) 2.38-2.45 (m, 1 H) 3.08 (s, 3 H) 3.74 (td, J = 12.00, 4.68 Hz, 1 H) 4.10 (td, J = 11.90, 5.07 Hz, 1 H) 6.30 (dd, J = 7.02, 1.95 Hz, 1 H) 6.35 (d, J = 1.76 Hz, 1 H) 7.21 |
| E68-F | (2R)-N-hydroxy-4-[4-(4-isoxazol-3-ylphenyl)-2-oxopyridin-1(2H)-yl]-2-methyl-2-(methylsulfonyl)butanamide | 0.46 | 432 | 100 | 1H NMR (400 MHz, DMSO-d$_6$) d ppm 1.58 (s, 3 H) 2.11-2.23 (m, 1 H) 2.38-2.46 (m, 1 H) 3.11 (s, 3 H) 3.71-3.82 (m, 1 H) 4.06-4.21 (m, 1 H) 6.72 (dd, J = 7.02, 2.15 Hz, 1 H) 6.80 (d, J = 2.15 Hz, 1 H) 7.24 (d, J = 1.76 Hz, 1 H) 7.79 )d, J = 7.03 Hz, 1 H) 7.89 |
| E68-G | (2R)-N-hydroxy-2-methyl-2-(methylsulfonyl)-4-[2-oxo-4-(4-propionylphenyl)pyridin-1(2H)-yl]butanamide | 0.47 | 421 | 94 | $^1$H NMR (400 MHz, DMSO-d$_6$) d ppm 1.07 (t, J = 7.22 Hz, 3 H) 1.55 (s, 3 H) 2.09-2.21 (m, 1 H) 2.36-2.45 (m, 1 H) 3.05 (q, 2 H) 3.08 (s, 3 H) 3.74 (td, J = 12.10, 4.49 Hz, 1 H) 4.05-4.15 (m, 1 H) 6.67 (dd, J = 7.02, 2.15 Hz, 1 H) 6.76 (d, J = 1.95 Hz, 1 H) 7.7 |

TABLE 3-continued

| Example number | IUPAC NAME | Retention Time | Mass ion[1] | Purity | NMR |
|---|---|---|---|---|---|
| E68-H | (2R)-N-hydroxy-4-{4-[4-(cis-3-hydroxy-3-methylcyclobutyl)phenyl]-2-oxopyridin-1(2H)-yl}-2-methyl-2-(methylsulfonyl)butanamide | 0.45 | 449 | 100 | $^1$H NMR (400 MHz, DMSO-d$_6$) d ppm 1.31 (s, 3 H) 1.54 (s, 3 H) 2.02-2.19 (m, 3 H) 2.26-2.44 (m, 3 H) 2.93-3.07 (m, 1 H) 3.08 (s, 3 H) 3.71 (td, J = 12.00, 4.68 Hz, 1 H) 4.03-4.14 (m, 1 H) 5.01 (s, 1 H) 6.61 (dd, J = 7.12, 2.05 Hz, 1 H) 6.66 (d, J = 2.15 Hz |
| E68-I | (2R)-N-hydroxy-2-methyl-2-(methylsulfonyl)-4-{2-oxo-4-[4-(trifluoromethyl)phenyl]pyridin-1(2H)-yl}butanamide | 0.56 | 433 | 100 | $^1$H NMR (400 MHz, DMSO-d6) d ppm 1.58 (s, 3 H) 2.17 (ddd, J = 12.83, 11.56, 4.88 Hz, 1 H) 2.41-2.48 (m, 1 H) 3.11 (s, 3 H) 3.78 (td, J = 11.90, 4.88 Hz, 1 H) 4.13 (td, J = 11.85, 4.98 Hz, 1 H) 6.69 (dd, J = 7.12, 2.05 Hz, 1 H) 6.79 (d, J = 1.95 Hz, 1 H) 7.80-7.8 |
| E68-J | (2R)-N-hydroxy-2-methyl-4-{3-methyl-2-oxo-4-[4-(2H-1,2,3-triazol-2-yl)phenyl]pyridin-1(2H)-yl}-2-(methylsulfonyl)butanamide | 0.52 | 446 | 100 | 1H NMR (400 MHz, DMSO-d6) d ppm 1.59 (s, 3 H) 2.01 (s, 3 H) 2.20 (td, J = 12.29, 4.88 Hz, 1 H) 2.44 (td, J = 12.05, 4.59 Hz, 1 H) 3.12 (s, 3 H) 3.78 (td, J = 11.90, 4.68 Hz, 2 H) 4.16 (td, J = 11.76, 4.98 Hz, 1 H) 6.27 (d, J = 6.83 Hz, 1 H) 7.57 (d, J = 8.78 Hz, 2 H) |
| E68-K | (2R)-4-(4-cyclohex-1-en-1-yl-2-oxopyridin-1(2H)-yl)-N-hydroxy-2-methyl-2-(methylsulfonyl)butanamide | | 369 | | $^1$H NMR (400 MHz, METHANOL-d4) d ppm 1.54 (s, 14 H) 1.60-1.66 (m, 8 H) 1.69-1.77 (m, 9 H) 2.09-2.15 (m, 8 H) 2.21-2.29 (m, 9 H) 2.36 (dd, 4 H) 2.74 (dd, 4 H) 3.04 (s, 13 H) 4.11 (dd, 4 H) 4.21 (dd, 4 H) 5.97-6.01 (m, 4 H) 7.51-7.54 (m, 4 H) 7.5 |
| E68-L | (2R)-4-(4-cyclohept-1-en-1-yl-2-oxopyridin-1(2H)-yl)-N-hydroxy-2-methyl-2-(methylsulfonyl)butanamide | | 383 | | $^1$H NMR (400 MHz, CHLOROFORM-d) d ppm 1.50 (br. s., 1 H) 1.51-1.55 (m, 1 H) 1.55-1.58 (m, 1 H) 1.67 (s, 3 H) 1.74-1.80 (m, 1 H) 1.78-1.81 (m, 1 H) 1.82-1.89 (m, 1 H) 2.17-2.28 (m, 1 H) 2.26-2.31 (m, 1 H) 2.31-2.36 (m, 1 H) 2.38-2.42 (m, 1 |
| E68-M | (2R)-N-hydroxy-4-[4-{4-[(3-hydroxycyclobutyl)methyl]phenyl}-2-oxopyridin-1(2H)-yl]-2-methyl-2-(methylsulfonyl)butanamide | 0.43 | 449 | 100 | 1H NMR (400 MHz, METHANOL-d4) d ppm 1.19 (t, 2 H) 1.55-1.70 (m, 2 H) 1.72 (s, 3 H) 1.96-2.13 (m, 1 H) 2.33-2.46 (m, 3 H) 2.53-2.66 (m, 1 H) 2.73-2.84 (m, 2 H) 3.13 (s, 3 H) 3.56-3.68 (m, 1 H) 3.88-3.99 (m, 1 H) 3.99-4.11 (m, 1 H) 4.23-4. |
| E68-N | (2R)-N-hydroxy-4-[4-{6-[(1S)-1-hydroxyethyl]-2-naphthyl}-2-oxopyridin-1(2H)-yl]-2-methyl-2-(methylsulfonyl)butanamide | 0.45 | 459 | 100 | 1H NMR (400 MHz, DMSO-d6) d ppm 1.34-1.52 (m, 3 H) 1.60 (s, 3 H) 2.13-2.30 (m, 1 H) 2.38-2.49 (m, 1 H) 3.13 (s, 3 H) 3.69-3.91 (m, 1 H) 4.04-4.24 (m, 1 H) 4.85-5.02 (m, 1 H) 5.34 (d, J = 4.10 Hz, 1 H) 6.81-6.85 (m, 1 H) 6.87 (d, J = 1.95 Hz, 1 H |
| E68-O | N-hydroxy-4-[4-(6-hydroxy-5,6,7,8-tetrahydronaphthalen-2-yl)-2-oxopyridin-1(2H)-yl-2-methyl-2-(methylsulfonyl)butanamide | 0.36 | 435 | 100 | $^1$H NMR (400 MHz, DMSO-d$_6$) ppm 1.54 (s, 3 H) 1.59-1.69 (m, 2 H) 1.81-1.98 (m, 1 H) 2.03-2.23 (m, 1 H) 2.28-2.40 (m, 2 H) 2.61-2.79 (m, 2 H) 2.82-2.97 (m, 2 H) 3.08 (s, 3 H) 3.58-3.79 (m, 1 H) 4.01-4.17 (m, 1 H) 4.74-4.82 (m, 1 H) 6.52 - |
| E68-P | (2R)-N-hydroxy-2-methyl-2-(methylsulfonyl)-4-[2-oxo-4-(5-phenyl-2-thienyl)pyridin-1(2H)-yl]butanamide | 0.61 | 447 | 100 | 1H NMR (400 MHz, DMSO-d6) d ppm 1.57 (s, 3 H) 2.09-2.26 (m, 2 H) 2.38-2.48 (m, 1 H) 3.11 (s, 3 H) 3.64-3.83 (m, 1 H) 4.05-4.17 (m, 1 H) 6.66 (s, 1 H) 6.67 - 6.71 (m, 1 H) 7.31-7.42 (m, 1 H) 7.46 (s, 2 H) 7.62 (d, J = 3..90 Hz, 1 H) 7.70-7.76 {m, |
| E68-Q | N-hydroxy-4-{4-[4-(1-hydroxyethyl)phenyl]-2-oxopyridin-1(2H)-yl}-2-methyl-2-(methylsulfonyl)butanamide | 0.29 | 409 | 100 | $^1$H NMR (400 MHz, DMSO-d$_6$) d ppm 1.29 (s, 3 H) 1.47 (s, 3 H) 2.08-2.21 (m, 1 H) 2.24-2.37 (m, 1 H) 3.02 (s, 3 H) 3.64-3.73 (m, 1 H) 4.07-4.17 (m, 1 H) 4.66-4.76 (m, 1 H) 5.19 (br. s., 1 H) 6.53-6.62 (m, 2 H) 7.34-7.43 (m, 2 H) 7.56-7.66 (m, 3 H) |

TABLE 3-continued

| Example number | IUPAC NAME | Retention Time | Mass ion[1] | Purity | NMR |
|---|---|---|---|---|---|
| E68-R | N-hydroxy-2-methyl-4-[4-(1-methyl-1H-indol-2-yl)-2-oxopyridin-1(2H)-y1]-2-(methylsulfonyl)butanamide | 0.51 | 418 | 100 | 1H NMR (400 MHz, METHANOL-d4) d ppm 1.74 (s, 3 H) 2.36-2.50 (m, 1 H) 2.68 (s, 1 H) 3.14 (s, 3 H) 3.86 (s, 3 H) 3.90-4.14 (m, 1 H) 4.22-4.44 (m, 1 H) 6.65-6.76 (m, 2 H) 6.80 (s, 1 H) 7.03-7.17 (m, 1 H) 7.23-7.35 (m, 1 H) 7.46 (d, J = 8.39 Hz, 1H |
| E68-S | 4-[4-(2-cyclopentylethoxy)-2-oxopyridin-1(2H)-yl]-N-hydroxy-2-methyl-2-(methylsulfonyl)butanamide | | 401 | | 1H NMR (400 MHz, METHANOL-d4) d ppm 1.09-1.33 (m, 2 H) 1.49-1.64 (m, 2 H) 1.62-1.75 (m, 5 H) 1.75-1.92 (m, 4 H) 1.91-2.07 (m, 1 H) 2.25-2.42 (m, 1 H) 2.45-2.62 (m, 1 H) 3.12 (s, 3 H) 3.76-3.95 (m, 1 H) 4.04 (t, J = 6.54 Hz, 2 H) 4.13-4.29 |
| E68-T | N-hydroxy-2-methyl-2-(methylsulfonyl)-4-[2-oxo-4-(2-phenylethoxy)pyridin-1(2H)-yl]ibutanamide | | 409 | | 1H NMR (400 MHz, METHANOL-d4) d ppm 1.69 (s, 3 H) 2.24-2.41 (m, 1 H) 2.61-2.76 (m, 1 H) 3.07 (s, 3 H) 3.13 (t, J = 6.63 Hz, 2 H) 3.87-3.99 (m, 1 H) 4.04 (s, 1 H) 4.26-4.41 (m, 2 H) 6.28 (d, J = 2.73 Hz, 1 H) 6.51-6.63 (m, 1 H) 7.16-7.27 (m, 1 H) 7 |
| E68-U | 4-[4-(4-acetylphenyl)-2-oxopyridin-1(2H)-yl]-N-hydroxy-2-methyl-2-(methylsulfonyl)butanamide | 0.31 | 407 | 100 | $^1$H NMR (400 MHz, DMSO-d$_6$) d ppm 1.58 (s, 3 H) 2.17 (ddd, J = 12.83, 11.56, 5.07 Hz, 1 H) 2.40-2.49 (m, 1 H) 2.62 (s, 3 H) 3.11 (s, 3 H) 3.77 (td, J = 11.95, 4.78 Hz, 1 H) 4.13 (td, J = 11.90, 5.07 Hz, 1 H) 6.70 (dd, J = 7.22, 2.15 Hz, 1 H) 6.79 (d, J = 2.15 Hz, 1 |

Foot note[1]Mass Spec.-See Method A as described in Table 5 infra.

Biological Examples

In order to assess the compounds biological activity, selected in-vitro assays were conducted on selected compounds. One of the assays measured the compounds ability to disrupt the synthesis of lipopolysaccharide, LPS, which is a component of the outer membrane of Gram-negative bacteria. Disruption of this synthesis is lethal to the bacteria. The assay determined the compound's ability to inhibit LpxC, which is the first enzyme in the biosynthetic pathway for LPS (measured as $IC_{50}$). Additionally, MICs (minimal inhibitory concentrations) were determined for several bacteria. The specific protocols are described below:

A) $IC_{50}$ Assay, LpxC Enzyme from *P. aeruginosa* (Labeled as PA LpxC Enzyme $IC_{50}$):

$IC_{50}$ determination in the LpxC enzyme assay was carried out in a similar manner to that described by Malikzay et al in the 2006 Poster, Screening LpxC (UDP-3-O—(R-3-hydroxymyristoyl)-GlcNAc deacetylase) using BioTrove RapidFire HTS Mass Spectrometry (aNew Lead Discovery and bInflammation and Infectious Disease, cStructural Chemistry, Schering-Plough Research Institute, Kenilworth, N.J. 07033, (BioTrove, Inc. 12 Gill St., Suite 4000, Woburn, Mass. 01801). Briefly, *Pseudomonas aeruginosa* LpxC enzyme (0.1 nM) purified from *E. coli*-overexpressing bacteria was incubated at 25° C. in a final volume of 50 ul containing 0.5 uM UDP-3-O—(R-3-hydroxydecanoyl)-N-acetylglucosamine, 1 mg/mL BSA, and 50 mM sodium phosphate buffer, pH 8.0 in the presence and absence of inhibitor compound. At the end of 1 hour, 5 ul of 1N HCl was added to stop the enzyme reaction; the plates were centrifuged, and then processed with the BioTrove Rapidfire HTMS Mass Spectrometry System. A no-enzyme control was used in calculating the $IC_{50}$ values from the percent conversion values.

B) MIC Determinations:

The in vitro antibacterial activity of compounds described in the Examples was evaluated by minimum inhibitory concentration (MIC) testing according to Clinical and Laboratory Standards Institute (CLSI, formerly NCCLS) guidelines. See: Clinical and Laboratory Standards Institute. Methods for Dilution Antimicrobial Susceptibility Tests for Bacteria that Grow Aerobically; Approved Standard-Seventh Edition. CLSI document M7-A7 [ISBN 1-56238-587-9]. Clinical and Laboratory Standards Institute, 940 West Valley Road, Suite 1400, Wayne, Pa. 19087-1898 USA, 2006; also Clinical and Laboratory Standards Institute. Performance Standards for Antimicrobial Susceptibility Testing; Eighteenth Informational Supplement. CLSI document M100-S18 [ISBN1-56238-653-0]. Clinical and Laboratory Standards Institute.

The following bacterial strains were used in these MIC determinations:

1) *Pseudomonas aeruginosa* UI-18: Wild-type, labeled as PA-7 in Tables 4, and 5;

2) *Acinetobacter baumanii/haemolyticus*: Multidrug-resistant clinical isolate labeled as AB-3167 in Tables 4 and 5;

3) *Escherichia coli* EC-1: VOGEL, mouse virulent labeled as EC-1 in Tables 4 and 5;

4) *Klebsiella pneumoniae*: Ciprofloxacin-resistant isolate, expresses extended-spectrum beta-lactamases (ESBL), clinical isolate, labeled as KP-3700 in Tables 4, and 5.

Table 4 below shows the results that were obtained with the final products described in Examples 1-69U. If a particular table is left blank, then the data is not available at the current time.

Column 1 corresponds to the Example number, column 2 provides the IUPAC name, column 3 provides the results from the LpxC enzyme assay described above, and columns 4-7 provide the MIC data as described above.

TABLE 4

| Example | Name-IUPAC | PA: IC50 | AB-3167 | EC-1 | KP-3700 | PA-7 |
|---|---|---|---|---|---|---|
| 1 | (2R)-N-hydroxy-2-methyl-2-(methylsulfonyl)-4-{2-oxo-4-[4-(1H-pyrazol-1-yl)phenyl]pyridin-1(2H)-yl}butanamide | 0.000184 | >64.0 | 0.5 | 2 | 2 |
| 2 | (2R)-N-hydroxy-2-methyl-2-(methylsulfonyl)-4-{2-oxo-4-[(E)-2-phenylvinyl]pyridin-1(2H)-yl}butanamide | 0.000414 | 64 | 0.5 | 1 | 2 |
| 3 | (2R)-N-hydroxy-2-methyl-2-(methylsulfonyl)-4-[2-oxo-4-(2-phenylethyl)pyridin-1(2H)-yl]butanamide | 0.000037 | 64 | 1 | 2 | 4 |
| 4 | 4-[4-{4-[3-(4,4-difluoropiperidin-1-yl)propoxy]phenyl}-2-oxopyridin-1(2H)-yl]-N-hydroxy-2-methyl-2-(methylsulfonyl)butanamide | <0.00100 | >64.0 | 1 | 2 | 4 |
| 5 | (2R)-N-hydroxy-4-{4-[4-(cis-3-hydroxycyclobutyl) phenyl]-2-oxopyridin-1(2H)-yl}-2-methyl-2-(methylsulfonyl)butanamide | 0.000083 | >64.0 | 4 | 8 | 2 |
| 6 | N-hydroxy-4-{4-[4-(3-hydroxycyclobutyl)phenyl]-2-oxopyridin-1(2H)-yl}-2-methyl-2-(methylsulfonyl) butanamide | 0.000272 | >64.0 | 4 | 16 | 4 |
| 7 | (2R)-N-hydroxy-4-[4-{4-[(4-hydroxycyclohexyl)oxy]phenyl}-2-oxopyridin-1(2H)-yl]-2-methyl-2-(methylsulfonyl)butanamide | 0.00022 | 64 | 1 | >64.0 | 2 |
| 8 | (2R)-N-hydroxy-4-[4-{4-[(cis-4-hydroxycyclohexyl)methoxy]phenyl}-2-oxopyridin-1(2H)-yl]-2-methyl-2-(methylsulfonyl)butanamide | 0.000187 | >64.0 | 0.5 | 2 | 1 |
| 9 | (2R)-N-hydroxy-4-[4-{4-[(trans-4-hydroxycyclohexyl)methoxy]phenyl}-2-oxopyridin-1(2H)-yl]-2-methyl-2-(methylsulfonyl)butanamide | 0.000122 | 32 | 0.25 | 2 | 1 |
| 10 | (2R)-4-[4-{2-fluoro-4-[(trans-4-hydroxycyclohexyl)methoxy]phenyl}-2-oxopyridin-1(2H)-yl]-N-hydroxy-2-methyl-2-(methylsulfonyl)butanamide | 0.000154 | >64.0 | 0.25 | 2 | 1 |
| 10-A | (2R)-N-hydroxy-4-[4-{4-[(4-hydroxy-4-methylcyclohexyl)oxy]phenyl}-2-oxopyridin-1(2H)-yl]-2-methyl-2-(methylsulfonyl) butanamide | 0.000201 | >64.0 | 0.25 | 2 | 1 |
| 10-B | (2R)-N-hydroxy-4-[4-{4-[(3-hydroxy-3-methylcyclobutyl) methoxy]phenyl}-2-oxopyridin-1(2H)-yl]-2-methyl-2-(methylsulfonyl)butanamide | 0.000106 | >64.0 | 0.5 | 4 | 1 |
| 10-C | (2R)-4-{4-[4-(3-cyanopropoxy)phenyl]-2-oxopyridin-1(2H)-yl}-N-hydroxy-2-methyl-2-(methylsulfonyl)butanamide | 0.0000118 | >64.0 | 0.5 | 2 | 1 |
| 10-D | (2R)-N-hydroxy-4-[4-(4-{[3-(hydroxymethyl)cyclobutyl]methoxy}phenyl)-2-oxopyridin-1(2H)-yl]-2-methyl-2-(methylsulfonyl)butanamide | 0.0000755 | >64.0 | 0.25 | 2 | 1 |
| 10-E | N-hydroxy-4-[4-{4-[(4-hydroxy-4-methylpentyl)oxy]phenyl}-2-oxopyridin-1(2H)-yl]-2-methyl-2-(methylsulfonyl) butanamide | | >64.0 | 0.5 | 8 | 2 |
| 10-F | N-hydroxy-4-[4-(4-{[3-(hydroxymethyl)cyclobutyl]oxy}phenyl)-2-oxopyridin-1(2H)-yl]-2-methyl-2-(methylsulfonyl)butanamide | | 64 | 0.5 | 4 | 2 |
| 10-G | (2R)-N-hydroxy-4-[4-{4-[(4-hydroxy-4-methylcyclohexyl)oxy]phenyl}-2-oxopyridin-1(2H)-yl]-2-methyl-2-(methylsulfonyl) butanamide | 0.000376 | 64 | 0.5 | 4 | 2 |
| 10-H | (2R)-N-hydroxy-4-[4-(4-{[3-(1-hydroxy-1-methylethyl)cyclobutyl]oxy}phenyl)-2-oxopyridin-1(2H)-yl]-2-methyl-2-(methylsulfonyl)butanamide | 0.0000443 | >64.0 | 1 | 8 | 2 |
| 10-I | (2R)-4-[4-{3-fluoro-4-[(4-hydroxy-4-methylcyclohexyl)oxy]phenyl}-2-oxopyridin-1(2H)-yl]-N-hydroxy-2-methyl-2-(methylsulfonyl)butanamide | 0.000305 | >64.0 | 0.5 | 8 | 2 |
| 10-J | N-hydroxy-4-{4-[4-(2-hydroxy-2-methylpropoxy)phenyl]-2-oxopyridin-1(2H)-yl}-2-methyl-2-(methylsulfonyl)butanamide | | >64.0 | 4 | 16 | 8 |
| 10-K | (2R)-4-[4-{4-[(3,4-dihydroxy-4-methylpentyl)oxy]phenyl}-2-oxopyridin-1(2H)-yl]-N-hydroxy-2-methyl-2-(methylsulfonyl)butanamide | >0.100 | >64.0 | 8 | 64 | 8 |

TABLE 4-continued

| Example | Name-IUPAC | PA: IC50 | AB-3167 | EC-1 | KP-3700 | PA-7 |
|---|---|---|---|---|---|---|
| 10-L | (2R)-4-[4-{2-fluoro-4-[(cis-4-hydroxycyclohexyl)methoxy]phenyl}-2-oxopyridin-1(2H)-yl]-N-hydroxy-2-methyl-2-(methylsulfonyl)butanamide | 0.0000508 | >64.0 | 0.25 | 2 | 1 |
| 11 | (2R)-N-hydroxy-2-methyl-2-(methylsulfonyl)-4-(2-oxo-4-phenylpyridin-1(2H)-yl)butanamide | 0.000264 | 64 | 8 | 8 | 1 |
| 12 | (2R)-4-[4-(2-fluoro-4-hydroxy-3-methylphenyl)-2-oxopyridin-1(2H)-yl]-N-hydroxy-2-methyl-2-(methylsulfonyl)butanamide | | >64.0 | 16 | 32 | 16 |
| 13 | (2R)-4-[4-(2-fluoro-4-methylphenyl)-2-oxopyridin-1(2H)-yl]-N-hydroxy-2-methyl-2-(methylsulfonyl)butanamide | 0.0000746 | >64.0 | 0.5 | 1 | 0.5 |
| 14 | (2R)-4-[4-(2,3-difluorophenyl)-2-oxopyridin-1(2H)-yl]-N-hydroxy-2-methyl-2-(methylsulfonyl)butanamide | 0.0000255 | >64.0 | 0.5 | 1 | 0.5 |
| 15 | (2R)-4-[4-(4-chlorophenyl)-2-oxopyridin-1(2H)-yl]-N-hydroxy-2-methyl-2-(methylsulfonyl)butanamide | 0.0000402 | >64.0 | 0.5 | 1 | 0.5 |
| 16 | (2R)-N-hydroxy-2-methyl-4-[4-(4-methylphenyl)-2-oxopyridin-1(2H)-yl]-2-(methylsulfonyl)butanamide | 0.0000673 | >64.0 | 0.5 | 1 | 0.5 |
| 17 | (2R)-N-hydroxy-4-[4-(4-methoxyphenyl)-2-oxopyridin-1(2H)-yl]-2-methyl-2-(methylsulfonyl)butanamide | 0.0000186 | >64.0 | 0.5 | 1 | 0.5 |
| 18 | (2R)-4-[4-(2,3-dihydro-1,4-benzodioxin-6-yl)-2-oxopyridin-1(2H)-yl]-N-hydroxy-2-methyl-2-(methylsulfonyl)butanamide | 0.0003 | >64.0 | >64.0 | 2 | 1 |
| 19 | (2R)-N-hydroxy-2-methyl-4-[4-(2-methyl-1H-indol-5-yl)-2-oxopyridin-1(2H)-yl]-2-(methylsulfonyl)butanamide | 0.000169 | >64.0 | 1 | 4 | 2 |
| 20 | (2R)-4-[4-(4-chloro-2-fluorophenyl)-2-oxopyridin-1(2H)-yl]-N-hydroxy-2-methyl-2-(methylsulfonyl)butanamide | 0.000132 | >64.0 | 0.25 | 0.5 | 0.25 |
| 21 | (2R)-4-[4-(2-fluoro-4-methoxyphenyl)-2-oxopyridin-1(2H)-yl]-N-hydroxy-2-methyl-2-(methylsulfonyl)butanamide | 0.000085 | 32 | 0.125 | 0.25 | 0.25 |
| 22 | (2R)-N-hydroxy-2-methyl-4-{4-[4-(2-methylpyrimidin-4-yl)phenyl]-2-oxopyridin-1(2H)-yl}-2-(methylsulfonyl)butanamide | 0.000432 | >64.0 | 2 | 8 | 4 |
| 23 | (2R)-N-hydroxy-2-methyl-2-(methylsulfonyl)-4-[2-oxo-4-(2,3,6-trifluorophenyl)pyridin-1(2H)-yl]butanamide | 0.000393 | >64.0 | 2 | 64 | 2 |
| 24 | (2R)-N-hydroxy-2-methyl-4-{4-[4-(1-methyl-1H-pyrazol-5-yl)phenyl]-2-oxopyridin-1(2H)-yl}-2-(methylsulfonyl)butanamide | 0.000336 | >64.0 | 1 | 8 | 2 |
| 25 | (2R)-N-hydroxy-2-methyl-4-{4-[4-(2-methyl-1,3-oxazol-4-yl)phenyl]-2-oxopyridin-1(2H)-yl}-2-(methylsulfonyl)butanamide | 0.000298 | >64.0 | 1 | 2 | 2 |
| 26 | (2R)-N-hydroxy-2-methyl-4-{4-[4-(5-methyl-1,2,4-oxadiazol-3-yl)phenyl]-2-oxopyridin-1(2H)-yl}-2-(methylsulfonyl)butanamide | 0.037 | | | | |
| 27 | (2R)-N-hydroxy-2-methyl-4-{4-[4-(2-methylpyrimidin-5-yl)phenyl]-2-oxopyridin-1(2H)-yl}-2-(methylsulfonyl)butanamide | 0.000256 | >64.0 | 16 | 32 | 4 |
| 28 | (2R)-4-{4-[4-(difluoromethoxy)-2-fluorophenyl]-2-oxopyridin-1(2H)-yl]-N-hydroxy-2-methyl-2-(methylsulfonyl)butanamide | 0.0000364 | >64.0 | 0.25 | 1 | 0.5 |
| 29 | N-hydroxy-2-methyl-2-(methylsulfonyl)-4-{2-oxo-4-[4-(pyridin-2-yloxy)phenyl]pyridin-1(2H)-yl}butanamide | <0.00100 | >64.0 | 0.5 | 2 | 4 |
| 30 | N-hydroxy-4-{4-[4-(3-hydroxypropoxy)phenyl]-2-oxopyridin-1(2H)-yl}-2-methyl-2-(methylsulfonyl) butanamide | 0.000152 | >64.0 | 2 | 16 | 4 |
| 31 | N-hydroxy-4-{4-[4-(3-hydroxypropyl)phenyl]-2-oxopyridin-1(2H)-yl}-2-methyl-2-(methylsulfonyl)butanamide | 0.000267 | >64.0 | 8 | 16 | 4 |
| 32 | (2R)-N-hydroxy-4-{4-{4-[2-(3-hydroxycyclobutyl)ethoxy]phenyl}-2-oxopyridin-1(2H)-yl]-2-methyl-2-(methylsulfonyl)butanamide | 0.0000118 | >64.0 | 0.25 | 1 | 1 |
| 33 | 4-[4-(1-benzofuran-2-yl)-2-oxopyridin-1(2H)-yl]-N-hydroxy-2-methyl-2-(methylsulfonyl)butanamide | 0.000625 | >64.0 | 1 | 4 | 2 |

TABLE 4-continued

| Example | Name-IUPAC | PA: IC50 | AB-3167 | EC-1 | KP-3700 | PA-7 |
|---|---|---|---|---|---|---|
| 34 | N-hydroxy-4-[4-(6-methoxy-2-naphthyl)-2-oxopyridin-1(2H)-yl]-2-methyl-2-(methylsulfonyl)butanamide | 0.000094 | 8 | <0.0600 | 0.5 | 1 |
| 35 | N-hydroxy-2-methyl-2-(methylsulfonyl)-4-[2-oxo-4-(4-pyridin-4-ylphenyl)pyridin-1(2H)-yl]butanamide | 0.000107 | >64.0 | 0.5 | 4 | 2 |
| 36 | N-hydroxy-2-methyl-2-(methylsulfonyl)-4-(2-oxo-4-quinolin-7-ylpyridin-1(2H)-yl)butanamide | 0.000912 | >64.0 | 4 | 8 | 8 |
| 37 | N-hydroxy-2-methyl-2-(methylsulfonyl)-4-{2-oxo-4-[4-(2-pyridin-4-ylethoxy)phenyl]pyridin-1(2H)-yl}butanamide | 0.000055 | >64.0 | 0.5 | 2 | 4 |
| 38 | (2R)-N-hydroxy-2-methyl-4-{4-[4-(5-methyl-1,3-oxazol-2-yl)phenyl]-2-oxopyridin-1(2H)-yl}-2-(methylsulfonyl)butanamide | 0.0000233 | >64.0 | 0.06 | 0.125 | 0.5 |
| 39 | (2R)-N-hydroxy-2-methyl-2-(methylsulfonyl)-4-[2-oxo-4-(4-pyrimidin-2-ylphenyl)pyridin-1(2H)-yl]butanamide | 0.000142 | >64.0 | 0.5 | 1 | 2 |
| 40 | (2R)-N-hydroxy-2-methyl-2-(methylsulfonyl)-4-{2-oxo-4-[4-(2H-1,2,3-triazol-2-yl)phenyl]pyridin-1(2H)-yl}butanamide | 0.0000482 | >64.0 | 0.03 | 0.06 | 0.25 |
| 41 | (2R)-4-[4-(4-fluorophenyl)-2-oxopyridin-1(2H)-yl]-N-hydroxy-2-methyl-2-(methylsulfonyl)butanamide | 0.0000322 | >64.0 | 1 | 4 | 0.5 |
| 42 | (2R)-4-[4-(3-fluorophenyl)-2-oxopyridin-1(2H)-yl]-N-hydroxy-2-methyl-2-(methylsulfonyl)butanamide | 0.0000569 | >64.0 | 2 | 4 | 1 |
| 43 | (2R)-4-[4-(2-fluorophenyl)-2-oxopyridin-1(2H)-yl]-N-hydroxy-2-methyl-2-(methylsulfonyl)butanamide | 0.00011 | >64.0 | 1 | 2 | 0.5 |
| 44 | (2R)-4-[4-(2,3-difluoro-4-methoxyphenyl)-2-oxopyridin-1(2H)-yl]-N-hydroxy-2-methyl-2-(methylsulfonyl)butanamide | 0.000166 | >64.0 | 0.015 | 2 | 1 |
| 45 | (2R)-4-[4-(3-chloro-2-fluorophenyl)-2-oxopyridin-1(2H)-yl]-N-hydroxy-2-methyl-2-(methylsulfonyl)butanamide | 0.000112 | >64.0 | 0.25 | 0.5 | 0.5 |
| 46 | (2R)-4-[4-(2,3-dichlorophenyl)-2-oxopyridin-1(2H)-yl]-N-hydroxy-2-methyl-2-(methylsulfonyl)butanamide | 0.000107 | >64.0 | 0.25 | 0.5 | 0.5 |
| 47 | (2R)-N-hydroxy-2-methyl-2-(methylsulfonyl)-4-{2-oxo-4-[4-(tetrahydro-2H-pyran-4-yl)phenyl]pyridin-1(2H)-yl}butanamide | 0.000352 | >64.0 | 0.5 | 4 | 2 |
| 48 | (2R)-N-hydroxy-4-[4-{4-[(2-methoxyethyl)thio]phenyl}-2-oxopyridin-1(2H)-yl]-2-methyl-2-(methylsulfonyl)butanamide | 0.0000561 | >64.0 | 0.25 | 1 | 1 |
| 49 | (2R)-4-[4-(4-chloro-2,3-difluorophenyl)-2-oxopyridin-1(2H)-yl]-N-hydroxy-2-methyl-2-(methylsulfonyl)butanamide | 0.000133 | >64.0 | 0.125 | 0.25 | 0.25 |
| 50 | (2R)-N-hydroxy-2-methyl-2-(methylsulfonyl)-4-[2-oxo-4-(2,3,4-trifluorophenyl)pyridin-1(2H)-yl]butanamide | 0.000133 | 64 | 0.5 | 1 | 0.5 |
| 51 | 4-[4-(benzyloxy)-2-oxopyridin-1(2H)-yl]-N-hydroxy-2-methyl-2-(methylsulfonyl)butanamide | | >64.0 | 16 | 32 | 16 |
| 52 | N-hydroxy-2-methyl-4-(3-methyl-2-oxo-4-phenylpyridin-1(2H)-yl)-2-(methylsulfonyl)butanamide | | >64.0 | 2 | 4 | 4 |
| 53 | 4-(4-cyclohexyl-2-oxopyridin-1(2H)-yl)-N-hydroxy-2-methyl-2-(methylsulfonyl)butanamide | | >64.0 | 16 | 64 | 8 |
| 54 | 2-ethyl-N-hydroxy-2-(methylsulfonyl)-4-(2-oxo-4-phenylpyridin-1(2H)-yl)butanamide | | 64 | 16 | >64.0 | 16 |
| 55 | (2R)-4-(3-fluoro-2-oxo-4-phenylpyridin-1(2H)-yl)-N-hydroxy-2-methyl-2-(methylsulfonyl)butanamide | 0.000606 | >64.0 | 8 | 8 | 1 |
| 56 | (2R)-4-(5-fluoro-2-oxo-4-phenylpyridin-1(2H)-yl)-N-hydroxy-2-methyl-2-(methylsulfonyl)butanamide | 0.000455 | >64.0 | 4 | 4 | 1 |
| 57 | 2-(ethylsulfonyl)-N-hydroxy-2-methyl-4-(2-oxo-4-phenylpyridin-1(2H)-yl)butanamide | | 16 | 8 | 16 | 64 |
| 58 | (2R)-N-hydroxy-4-{4-[4-(4-methoxy-2H-1,2,3-triazol-2-yl)phenyl]-2-oxopyridin-1(2H)-yl}-2-methyl-2-(methylsulfonyl)butanamide | 0.000125 | >64.0 | 0.03 | 0.25 | 0.5 |
| 59 | (2R)-N-hydroxy-4-[4-(4-{[(6-methoxypyridin-3-yl)oxy]methyl}phenyl)-2-oxopyridin-1(2H)-yl]-2-methyl-2-(methylsulfonyl)butanamide | 0.0000864 | >64.0 | 0.25 | 0.5 | 1 |

TABLE 4-continued

| Example | Name-IUPAC | PA: IC50 | AB-3167 | EC-1 | KP-3700 | PA-7 |
|---|---|---|---|---|---|---|
| 60 | (2R)-4-[4-{4-[difluoro(trans-4-hydroxycyclohexyl)methoxy]phenyl}-2-oxopyridin-1(2H)-yl]-N-hydroxy-2-methyl-2-(methylsulfonyl)butanamide | 0.0000838 | 32 | 0.125 | 1 | 1 |
| 61 | (2R)-N-hydroxy-4-[4-{4-[4-(hydroxymethyl)piperidin-1-yl]phenyl}-2-oxopyridin-1(2H)-yl]-2-methyl-2-(methylsulfonyl)butanamide | 0.000454 | >64.0 | 64 | 8 | 2 |
| 62 | N-hydroxy-4-[4-{4-[(1E)-N-methoxyethanimidoyl]phenyl}-2-oxopyridin-1(2H)-yl]-2-methyl-2-(methylsulfonyl)butanamide | | >64.0 | 0.5 | 2 | 4 |
| 63 | N-hydroxy-4-[4-{4-[3-(hydroxymethyl)isoxazol-5-yl]-3-methylphenyl}-2-oxopyridin-1(2H)-yl]-2-methyl-2-(methylsulfonyl)butanamide | | >64.0 | 2 | 16 | 4 |
| 64 | (2R)-N-hydroxy-2-methyl-2-(methylsulfonyl)-4-[2-oxo-4-(3-phenylazetidin-1-yl)pyridin-1(2H)-yl]butanamide | 0.00078 | >64.0 | 8 | 16 | 8 |
| 65 | (2R)-N-hydroxy-2-methyl-2-(methylsulfonyl)-4-[2-oxo-4-(phenylethynyl)pyridin-1(2H)-yl]butanamide | 0.000239 | 64 | 0.125 | 0.25 | 0.5 |
| 66 | 4-[4-(3-cyclohexylpropoxy)-2-oxopyridin-1(2H)-yl]-N-hydroxy-2-methyl-2-(methylsulfonyl)butanamide | 0.0035 | 2 | 1 | 4 | 8 |
| 67 | (2R)-N-hydroxy-2-methyl-2-(methylsulfonyl)-4-(2-oxo-1'-pyrimidin-2-yl-1',2',3',6'-tetrahydro-4,4'-bipyridin-1(2H)-yl)butanamide | 0.00301 | >64.0 | 8 | 16 | 8 |
| 68-A | (2R)-N-hydroxy-2-methyl-2-(methylsulfonyl)-4-[4-(2-naphthyl)-2-oxopyridin-1(2H)-yl]butanamide | 0.000156 | >64.0 | 0.06 | 0.5 | 0.5 |
| 68-B | (2R)-4-[4-(4-chloro-3-fluorophenyl)-2-oxopyridin-1(2H)-yl]-N-hydroxy-2-methyl-2-(methylsulfonyl)butanamide | 0.0000886 | >64.0 | 0.5 | 2 | 0.5 |
| 68-C | (2R)-4-[4-(3,4-dichlorophenyl)-2-oxopyridin-1(2H)-yl]-N-hydroxy-2-methyl-2-(methylsulfonyl)butanamide | 0.000119 | >64.0 | 0.125 | 0.5 | 0.5 |
| 68-D | (2R)-N-hydroxy-2-methyl-2-(methylsulfonyl)-4-{2-oxo-4-[4-(1,3-thiazol-2-yl)phenyl]pyridin-1(2H)-yl}butanamide | 0.000176 | >64.0 | 0.06 | 0.125 | 0.5 |
| 68-E | (2R)-4-[4-(2-chloro-3-methylphenyl)-2-oxopyridin-1(2H)-yl]-N-hydroxy-2-methyl-2-(methylsulfonyl)butanamide | 0.000433 | 64 | 0.25 | 0.5 | 0.5 |
| 68-F | (2R)-N-hydroxy-4-[4-(4-isoxazol-3-ylphenyl)-2-oxopyridin-1(2H)-yl]-2-methyl-2-(methylsulfonyl)butanamide | 0.000118 | >64.0 | 0.25 | 0.5 | 0.5 |
| 68-G | (2R)-N-hydroxy-2-methyl-2-(methylsulfonyl)-4-[2-oxo-4-(4-propionylphenyl)pyridin-1(2H)-yl]butanamide | 0.0000135 | >64.0 | 0.5 | 2 | 1 |
| 68-H | (2R)-N-hydroxy-4-{4-[4-(cis-3-hydroxy-3-methylcyclobutyl)phenyl]-2-oxopyridin-1(2H)-yl}-2-methyl-2-(methylsulfonyl)butanamide | 0.000205 | >64.0 | 2 | 8 | 1 |
| 68-I | (2R)-N-hydroxy-2-methyl-2-(methylsulfonyl)-4-{2-oxo-4-[4-(trifluoromethyl)phenyl]pyridine-1(2H)-yl}butanamide | 0.0000256 | >64.0 | 1 | 4 | 1 |
| 68-J | (2R)-N-hydroxy-2-methyl-4-{3-methyl-2-oxo-4-[4-(2H-1,2,3-triazol-2-yl)phenyl]pyridin-1(2H)-yl}-2-(methylsulfonyl)butanamide | 0.000298 | >64.0 | 0.125 | 0.125 | 1 |
| 68-K | (2R)-4-(4-cyclohex-1-en-1-yl-2-oxopyridin-1(2H)-yl)-N-hydroxy-2-methyl-2-(methylsulfonyl)butanamide | | >64.0 | 4 | 8 | 1 |
| 68-L | (2R)-4-(4-cyclohept-1-en-1-yl-2-oxopyridin-1(2H)-yl)-N-hydroxy-2-methyl-2-(methylsulfonyl)butanamide | | >64.0 | 2 | 8 | 1 |
| 68-M | (2R)-N-hydroxy-4-[4-{4-[(3-hydroxycyclobutyl)methyl]phenyl}-2-oxopyridin-1(2H)-yl]-2-methyl-2-(methylsulfonyl)butanamide | 0.0000856 | >64.0 | 0.5 | 4 | 2 |
| 68-N | (2R)-N-hydroxy-4-[4-{6-[(1S)-1-hydroxyethyl]-2-naphthyl}-2-oxopyridin-1(2H)-yl]-2-methyl-2-(methylsulfonyl)butanamide | 0.0000824 | >64.0 | 0.5 | 4 | 2 |

TABLE 4-continued

| Example | Name-IUPAC | PA: IC50 | AB-3167 | EC-1 | KP-3700 | PA-7 |
|---|---|---|---|---|---|---|
| 68-O | N-hydroxy-4-[4-(6-hydroxy-5,6,7,8-tetrahydronaphthalen-2-yl)-2-oxopyridin-1(2H)-yl]-2-methyl-2-(methylsulfonyl)butanamide | | >64.0 | 16 | 64 | 8 |
| 68-P | (2R)-N-hydroxy-2-methyl-2-(methylsulfonyl)-4-[2-oxo-4-(5-phenyl-2-thienyl)pyridin-1(2H)-yl]butanamide | 0.000263 | >64.0 | 0.06 | 0.5 | 8 |
| 68-Q | N-hydroxy-4-{4-[4-(1-hydroxyethyl)phenyl]-2-oxopyridin-1(2H)-yl}-2-methyl-2-(methylsulfonyl)butanamide | | >64.0 | 64 | >64.0 | 16 |
| 68-R | N-hydroxy-2-methyl-4-[4-(1-methyl-1H-indol-2-yl)-2-oxopyridin-1(2H)-yl]-2-(methylsulfonyl)butanamide | | >64.0 | 4 | 4 | 8 |
| 68-S | 4-[4-(2-cyclopentylethoxy)-2-oxopyridin-1(2H)-yl]-N-hydroxy-2-methyl-2-(methylsulfonyl)butanamide | 0.00894 | 64 | 16 | 64 | 32 |
| 68-T | (2R)-4-(4-cyclohex-1-en-1-yl-2-oxopyridin-1(2H)-yl)-N-hydroxy-2-methyl-2-(methylsulfonyl)butanamide | | >64.0 | 4 | 8 | 1 |
| 68-U | N-hydroxy-2-methyl-2-(methylsulfonyl)-4-[2-oxo-4-(2-phenylethoxy)pyridin-1(2H)-yl]butanamide | 0.0332 | >64.0 | 32 | 64 | 64 |
| 68-V | 4-[4-(4-acetylphenyl)-2-oxopyridin-1(2H)-yl]-N-hydroxy-2-methyl-2-(methylsulfonyl)butanamide | | >64.0 | 4 | 8 | 4 |

Examples 69 to 488

The following compounds can be made following the general procedures outlined in Examples 1-68 in above. Products are typically derived from a Suzuki-Miyaura cross coupling with optional deprotection of a terminal hydroxamic acid protecting group. Methods used to describe the synthesis of the precursors or coupling partners such as boronic acids or esters are known to those skilled in the art.

In Table 5 below, column 2 provides the IUPAC name, column's 3-7 provide in-vitro biological data generated in the same manner as in Table 4, columns 8 and 10 provide the retention times and mass spectra generated via LCMS, using either Method A or B as described below. Data is not currently available for all compounds, as indicated by a blank cell in Table 5.

The LCMS retention times (LCMS-RT) reported in column 9 were generated in the following manner:

1) Acidic-Labelled as "$^a$" in Column 9
Gradients:
0.05% TFA 95__5 to 5__95 Water_ACN
Flow rate: 1.3 mL/min
Column dimensions: Acquity UPLC BEH C18 1.7 μm 2.1×30 mm.
Run time: 1.1 minutes 2) Basic-Labelled as "$^b$" in column 9
Gradients:
Solvent A: 0.06% NH4OH (in water)
Solvent B: 0.06% NH4OH (in acetonitrile)

| Time (min) | % A | % B |
|---|---|---|
| 0 | 95 | 5 |
| 0.4 | 95 | 5 |
| 3.2 | 5 | 95 |
| 3.5 | 5 | 95 |
| 4.0 | 95 | 5 |

Flow rate: 2 mL/min
Column dimensions: Not currently available
Run time: 4 minutes

TABLE 5

| Example Number | IUPACNAME | PA: IC50 | AB-3167: | EC-1 | KP-3700 | PA-7 | Retention Time | Method | MASS |
|---|---|---|---|---|---|---|---|---|---|
| 69 | 4-{4-[4-(1,1-difluoro-2-hydroxyethyl)phenyl]-2-oxopyridin-1(2H)-yl}-N-hydroxy-2-methyl-2-(methylsulfonyl)butanamide | 0.00133 | 64 | 4 | >64.0 | 16 | 0.32 | a | 445.1 |
| 70 | 4-[4-(3-fluoro-4-hydroxyphenyl)-2-oxopyridin-1(2H)-yl]-N-hydroxy-2-methyl-2-(methylsulfonyl)butanamide | 0.00397 | >64.0 | >64.0 | >64.0 | >64.0 | 0.29 | a | 399 |
| 71 | N-hydroxy-2-methyl-2-(methylsulfonyl)-4-{4-[4-(3-morpholin-4-ylpropoxy)phenyl]-2-oxopyridin-1(2H)-yl}butanamide | 0.000699 | >64.0 | 2 | 8 | 4 | 0.26 | a | 508.1 |
| 72 | N-hydroxy-4-{4-[4-(hydroxymethyl)phenyl]-2-oxopyridin-1(2H)-yl}-2-methyl-2-(methylsulfonyl)butanamide | 0.00164 | >64.0 | >64.0 | >64.0 | 16 | 0.26 | a | 395 |
| 73 | 4-[4-(4-glycoloylphenyl)-2-oxopyridin-1(2H)-yl]-N-hydroxy-2-methyl-2-(methylsulfonyl)butanamide | 0.00163 | >64.0 | >64.0 | >64.0 | 64 | 0.27 | a | 423.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 74 | N-hydroxy-2-methyl-2-(methylsulfonyl)-4-{2-oxo-4-[4-(2-pyrrolidin-1-ylethoxy)phenyl]pyridin-1(2H)-yl}butanamide | 0.00316 | >64.0 | >64.0 | >64.0 | >64.0 | 0.26 | a | 478.1 |
| 75 | N-hydroxy-4-{4-[4-(4-hydroxybutoxy)phenyl]-2-oxopyridin-1(2H)-yl}-2-methyl-2-(methylsulfonyl)butanamide | 0.0000945 | >64.0 | 2 | 4 | 4 | 0.33 | a | 453.2 |
| 76 | 4-{4-[3-fluoro-4-(2-hydroxyethoxy)phenyl]-2-oxopyridin-1(2H)-yl}-N-hydroxy-2-methyl-2-(methylsulfonyl)butanamide | 0.000599 | >64.0 | 16 | 64 | 32 | 0.29 | a | 443.1 |
| 77 | N-hydroxy-2-methyl-2-(methylsulfonyl)-4-{2-oxo-4-[4-(3-piperidin-1-ylpropoxy)phenyl]pyridin-1(2H)-yl}butanamide | 0.0033 | >64.0 | 64 | >64.0 | 64 | | | |
| 78 | N-hydroxy-2-methyl-2-(methylsulfonyl)-4-{2-oxo-4-[4-(3-pyrrolidin-1-ylpropoxy)phenyl]pyridin-1(2H)-yl}butanamide | 0.00416 | >64.0 | >64.0 | >64.0 | >64.0 | | | |
| 79 | N-hydroxy-4-[4-(1H-indol-5-yl)-2-oxopyridin-1(2H)-yl]-2-methyl-2-(methylsulfonyl)butanamide | 0.000241 | >64.0 | 4 | 8 | 4 | | | |
| 80 | N-hydroxy-4-[4-{4-[(1E)-N-hydroxyethanimidoyl]phenyl}-2-oxopyridin-1(2H)-yl]-2-methyl-2-(methylsulfonyl)butanamide | 0.0004 | >64.0 | 8 | 16 | 32 | 0.31 | a | 422.1 |
| 81 | N-hydroxy-2-methyl-2-(methylsulfonyl)-4-{2-oxo-4-[4-(3-thiomorpholin-4-ylpropoxy)phenyl]pyridin-1(2H)-yl}butanamide | 0.000572 | >64.0 | 2 | 4 | 4 | 0.28 | a | 524.2 |
| 82 | 4-[4-{4-[3-(1,1-dioxidothiomorpholin-4-yl)propoxy]phenyl}-2-oxopyridin-1(2H)-yl]-N-hydroxy-2-methyl-2-(methylsulfonyl)butanamide | 0.00111 | >64.0 | 8 | 64 | 32 | 0.26 | a | 556.2 |
| 83 | N-hydroxy-4-[4-{4-[3-(4-hydroxypiperidin-1-yl)propoxy]phenyl}-2-oxopyridin-1(2H)-yl]-2-methyl-2-(methylsulfonyl)butanamide | 0.00157 | >64.0 | 32 | >64.0 | 16 | 0.25 | a | 522.2 |
| 84 | N-hydroxy-4-[4-{4-[3-(3-hydroxyazetidin-1-yl)propoxy]phenyl}-2-oxopyridin-1(2H)-yl]-2-methyl-2-(methylsulfonyl)butanamide | 0.00345 | >64.0 | >64.0 | >64.0 | 32 | 0.25 | a | 494.2 |
| 85 | 4-{4-[2-fluoro-4-(2-hydroxyethoxy)phenyl]-2-oxopyridin-1(2H)-yl}-N-hydroxy-2-methyl-2-(methylsulfonyl)butanamide | 0.000468 | >64.0 | 16 | 64 | 16 | 0.29 | a | 443.1 |
| 86 | N-hydroxy-2-methyl-2-(methylsulfonyl)-4-[2-oxo-4-{4-[3-(3-oxopiperazin-1-yl)propoxy]phenyl}pyridin-1(2H)-yl]butanamide | 0.00118 | >64.0 | 16 | >64.0 | 32 | 0.24 | a | 521.2 |
| 87 | N-hydroxy-2-methyl-4-{4-[4-[3-(4-methylpiperazin-1-yl)propoxy]phenyl]-2-oxopyridin-1(2H)-yl]-2-(methylsulfonyl)butanamide | 0.00319 | >64.0 | 64 | >64.0 | 32 | | | |
| 88 | N-hydroxy-2-methyl-2-(methylsulfonyl)-4-{2-oxo-4-[4-(3-pyridin-3-ylpropoxy)phenyl]pyridin-1(2H)-yl}butanamide | 0.000141 | >64.0 | 0.25 | 2 | 2 | | | |
| 89 | N-hydroxy-2-methyl-2-(methylsulfonyl)-4-{2-oxo-4-[4-(3-pyridin-4-ylpropoxy)phenyl]pyridin-1(2H)-yl}butanamide | 0.000104 | >64.0 | 0.25 | 2 | 2 | | | |
| 90 | 4-[4-(2-fluoro-3-methoxyphenyl)-2-oxopyridin-1(2H)-yl]-N-hydroxy-2-methyl-2-(methylsulfonyl)butanamide | 0.000147 | >64.0 | 0.5 | 2 | 2 | | | |
| 91 | N-hydroxy-4-[4-(1H-indol-2-yl)-2-oxopyridin-1(2H)-yl]-2-methyl-2-(methylsulfonyl)butanamide | 0.000752 | >64.0 | 4 | 32 | 16 | | | |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 92 | N-hydroxy-2-methyl-2-(methylsulfonyl)-4-[2-oxo-4-{4-[3-(1H-1,2,4-triazol-1-yl)propoxy]phenyl}pyridin-1(2H)-yl]butanamide | 0.000689 | >64.0 | 8 | 32 | 16 | 0.3 | a | 490.1 |
| 93 | 4-[4-{4-[3-(3,3-difluoropyrrolidin-1-yl)propoxy]phenyl}-2-oxopyridin-1(2H)-yl]-N-hydroxy-2-methyl-2-(methylsulfonyl)butanamide | 0.000218 | >64.0 | 1 | 4 | 8 | 0.27 | a | 528.1 |
| 94 | N-hydroxy-2-methyl-2-(methylsulfonyl)-4-{4-[4-(2-morpholin-4-ylethoxy)phenyl]-2-oxopyridin-1(2H)-yl}butanamide | 0.000768 | >64.0 | 2 | 16 | 4 | | | |
| 95 | N-hydroxy-4-{4-[3-(hydroxymethyl)isoxazol-5-yl]phenyl}-2-oxopyridin-1(2H)-yl]-2-methyl-2-(methylsulfonyl)butanamide | 0.000237 | >64.0 | 8 | 16 | 8 | 0.3 | a | 462 |
| 96 | 4-[4-(2-fluoro-3-hydroxyphenyl)-2-oxopyridin-1(2H)-yl]-N-hydroxy-2-methyl-2-(methylsulfonyl)butanamide | 0.00127 | >64.0 | 64 | >64.0 | >64.0 | | | |
| 97 | N-hydroxy-4-[4-(4-hydroxyphenyl)-2-oxopyridin-1(2H)-yl]-2-methyl-2-(methylsulfonyl)butanamide | 0.00222 | >64.0 | >64.0 | >64.0 | >64.0 | 0.26 | a | 381.1 |
| 98 | N-hydroxy-2-methyl-2-(methylsulfonyl)-4-(2-oxo-4-phenylpyridin-1(2H)-yl)butanamide | 0.00412 | >64.0 | 64 | >64.0 | 32 | 0.35 | a | 365.1 |
| 99 | 4-[4-(4-acetyl-3-hydroxyphenyl)-2-oxopyridin-1(2H)-yl]-N-hydroxy-2-methyl-2-(methylsulfonyl)butanamide | 0.00149 | >64.0 | 8 | 16 | 16 | 0.44 | a | 423.1 |
| 100 | 4-[4-{4-[3-(3,3-difluoropiperidin-1-yl)propoxy]phenyl}-2-oxopyridin-1(2H)-yl]-N-hydroxy-2-methyl-2-(methylsulfonyl)butanamide | 0.000281 | >64.0 | 1 | 8 | 8 | 0.28 | a | 542.1 |
| 101 | N-hydroxy-2-methyl-2-(methylsulfonyl)-4-[4-(4-nitrophenyl)-2-oxopyridin-1(2H)-yl]butanamide | 0.000153 | >64.0 | 8 | 8 | 4 | 0.35 | a | 410 |
| 102 | N-hydroxy-2-methyl-4-[4-{4-[(methylamino)sulfonyl]phenyl}-2-oxopyridin-1(2H)-yl]-2-(methylsulfonyl)butanamide | 0.00492 | >64.0 | >64.0 | >64.0 | >64.0 | 0.28 | a | 458 |
| 103 | N-ethyl-3-fluoro-5-{1-[4-(hydroxyamino)-3-methyl-3-(methylsulfonyl)-4-oxobutyl]-2-oxo-1,2-dihydropyridin-4-yl}benzamide | >0.100 | >64.0 | >64.0 | >64.0 | >64.0 | 0.31 | a | 454.1 |
| 104 | N-hydroxy-2-methyl-4-{4-[4-(1-methyl-1H-imidazol-2-yl)phenyl]-2-oxopyridin-1(2H)-yl}-2-(methylsulfonyl)butanamide | 0.0111 | >64.0 | >64.0 | >64.0 | >64.0 | 0.22 | a | 445.1 |
| 105 | 4-[4-(5-chloro-2-ethoxyphenyl)-2-oxopyridin-1(2H)-yl]-N-hydroxy-2-methyl-2-(methylsulfonyl)butanamide | >0.100 | >64.0 | >64.0 | >64.0 | >64.0 | 0.43 | a | 443 |
| 106 | 4-[4-{4-[(dimethylamino)sulfonyl]phenyl}-2-oxopyridin-1(2H)-yl]-N-hydroxy-2-methyl-2-(methylsulfonyl)butanamide | 0.00297 | >64.0 | >64.0 | >64.0 | 64 | 0.32 | a | 472.1 |
| 107 | N-hydroxy-2-methyl-2-(methylsulfonyl)-4-[2-oxo-4-(3-thienyl)pyridin-1(2H)-yl]butanamide | 0.0023 | >64.0 | 32 | 64 | 16 | 0.33 | a | 371 |
| 108 | 4-[4-(5-amino-2-methylphenyl)-2-oxopyridin-1(2H)-yl]-N-hydroxy-2-methyl-2-(methylsulfonyl)butanamide | >0.100 | >64.0 | >64.0 | >64.0 | >64.0 | 0.22 | a | 394 |
| 109 | N-hydroxy-4-(4-isoquinolin-4-yl-2-oxopyridin-1(2H)-yl)-2-methyl-2-(methylsulfonyl)butanamide | 0.00733 | >64.0 | >64.0 | >64.0 | >64.0 | 0.22 | a | 416.1 |
| 110 | 4-[4-(3-aminophenyl)-2-oxopyridin-1(2H)-yl]-N-hydroxy-2-methyl-2-(methylsulfonyl)butanamide | 0.0111 | >64.0 | >64.0 | >64.0 | 64 | 0.2 | a | 380 |
| 111 | N-hydroxy-2-methyl-2-(methylsulfonyl)-4-{2-oxo-4-[3-(1H-pyrazol-1-yl)phenyl]pyridin-1(2H)-yl}butanamide | 0.0162 | >64.0 | >64.0 | >64.0 | >64.0 | 0.35 | a | 431.1 |
| 112 | 4-[4-(3-fluoro-5-methylphenyl)-2-oxopyridin-1(2H)-yl]-N-hydroxy-2-methyl-2-(methylsulfonyl)butanamide | 0.000679 | >64.0 | 4 | 16 | 4 | 0.39 | a | 397.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 113 | 4-{1-[4-(hydroxyamino)-3-methyl-3-(methylsulfonyl)-4-oxobutyl]-2-oxo-1,2-dihydropyridin-4-yl}-3-methylbenzamide | 0.0211 | >64.0 | >64.0 | >64.0 | >64.0 | 0.24 | a | 422.1 |
| 114 | 4-[4-(3-chlorophenyl)-2-oxopyridin-1(2H)-yl]-N-hydroxy-2-methyl-2-(methylsulfonyl)butanamide | 0.000589 | >64.0 | 2 | 8 | 4 | 0.39 | a | 399.1 |
| 115 | 4-[4-(3-amino-4-methylphenyl)-2-oxopyridin-1(2H)-yl]-N-hydroxy-2-methyl-2-(methylsulfonyl)butanamide | 0.00101 | >64.0 | 64 | 64 | 16 | 0.23 | a | 394 |
| 116 | 4-[6-(dimethylamino)-2'-oxo-3,4'-bipyridin-1'(2'H)-yl]-N-hydroxy-2-methyl-2-(methylsulfonyl)butanamide | 0.00699 | >64.0 | 16 | 32 | 64 | 0.2 | a | 409.1 |
| 117 | 4-[4-(5-fluoro-2-hydroxyphenyl)-2-oxopyridin-1(2H)-yl]-N-hydroxy-2-methyl-2-(methylsulfonyl)butanamide | 0.00472 | >64.0 | >64.0 | >64.0 | >64.0 | 0.32 | a | 399.1 |
| 118 | 4-[4-(3-furyl)-2-oxopyridin-1(2H)-yl]-N-hydroxy-2-methyl-2-(methylsulfonyl)butanamide | 0.0235 | >64.0 | >64.0 | >64.0 | 64 | 0.29 | a | 355.2 |
| 119 | 4-[4-(4-cyclohexylphenyl)-2-oxopyridin-1(2H)-yl]-N-hydroxy-2-methyl-2-(methylsulfonyl)butanamide | 0.000135 | 16 | 0.5 | 8 | 16 | 0.54 | a | 447.1 |
| 120 | N-hydroxy-4-[4-(2-methoxyphenyl)-2-oxopyridin-1(2H)-yl]-2-methyl-2-(methylsulfonyl)butanamide | 0.003 | >64.0 | 64 | >64.0 | 16 | 0.35 | a | 395.1 |
| 121 | 4-[4-(3-chloro-5-fluorophenyl)-2-oxopyridin-1(2H)-yl]-N-hydroxy-2-methyl-2-(methylsulfonyl)butanamide | 0.000583 | >64.0 | 8 | 32 | 16 | 0.4 | a | 417.1 |
| 122 | 4-[4-(4-fluoro-2-methylphenyl)-2-oxopyridin-1(2H)-yl]-N-hydroxy-2-methyl-2-(methylsulfonyl)butanamide | 0.000785 | >64.0 | 16 | 64 | 8 | 0.38 | a | 397.1 |
| 123 | 4-[4-(2,3-difluoro-4-methoxyphenyl)-2-oxopyridin-1(2H)-yl]-N-hydroxy-2-methyl-2-(methylsulfonyl)butanamide | 0.00022 | >64.0 | 2 | 8 | 2 | 0.37 | a | 431.1 |
| 124 | N-hydroxy-2-methyl-2-(methylsulfonyl)-4-(2-oxo-4-quinolin-3-ylpyridin-1(2H)-yl)butanamide | 0.000962 | >64.0 | 16 | 64 | 16 | 0.26 | a | 416.1 |
| 125 | N-hydroxy-2-methyl-2-(methylsulfonyl)-4-(2-oxo-4-quinolin-3-ylpyridin-1(2H)-yl)butanamide | 0.00196 | >64.0 | 16 | 64 | 32 | 0.26 | a | 416.1 |
| 126 | N,N-diethyl-4-{1-[4-(hydroxyamino)-3-methyl-3-(methylsulfonyl)-4-oxobutyl]-2-oxo-1,2-dihydropyridin-4-yl}benzamide | 0.00562 | >64.0 | >64.0 | >64.0 | >64.0 | 0.34 | a | 464.1 |
| 127 | 4-[4-(3-acetylphenyl)-2-oxopyridin-1(2H)-yl]-N-hydroxy-2-methyl-2-(methylsulfonyl)butanamide | 0.00312 | >64.0 | 16 | 64 | 32 | 0.32 | a | 407.1 |
| 128 | 4-[4-(7-chlorothieno[3,2-b]pyridin-2-yl)-2-oxopyridin-1(2H)-yl]-N-hydroxy-2-methyl-2-(methylsulfonyl)butanamide | 0.00203 | >64.0 | 32 | 64 | 64 | 0.36 | a | 455.9 |
| 129 | 4-{4-[4-(cyanomethyl)phenyl]-2-oxopyridin-1(2H)-yl}-N-hydroxy-2-methyl-2-(methylsulfonyl)butanamide | 0.000695 | >64.0 | 2 | 16 | 32 | 0.31 | a | 404.1 |
| 130 | N-hydroxy-2-methyl-2-(methylsulfonyl)-4-[2-oxo-4-(3,4,5-trifluorophenyl)pyridin-1(2H)-yl]butanamide | 0.000973 | >64.0 | 16 | 32 | 8 | 0.4 | a | 419.1 |
| 131 | N-hydroxy-2-methyl-2-(methylsulfonyl)-4-{2-oxo-4-[2-(2,2,2-trifluoroethoxy)phenyl]pyridin-1(2H)-yl}butanamide | >0.100 | >64.0 | >64.0 | >64.0 | >64.0 | 0.39 | a | 463 |
| 132 | 4-[4-(2-cyanophenyl)-2-oxopyridin-1(2H)-yl]-N-hydroxy-2-methyl-2-(methylsulfonyl)butanamide | 0.0451 | >64.0 | >64.0 | >64.0 | >64.0 | 0.31 | a | 390.1 |
| 133 | 4-[4-(3-acetamidophenyl)-2-oxopyridin-1(2H)-yl]-N-hydroxy-2-methyl-2-(methylsulfonyl)butanamide | 0.0768 | >64.0 | >64.0 | >64.0 | >64.0 | 0.28 | a | 422.1 |
| 134 | 4-[4-(3,4-difluorophenyl)-2-oxopyridin-1(2H)-yl]-N-hydroxy-2-methyl-2-(methylsulfonyl)butanamide | 0.000243 | >64.0 | 4 | 8 | 4 | 0.37 | a | 401.1 |
| 135 | 4-[4-(4-chloro-3-cyanophenyl)-2-oxopyridin-1(2H)-yl]-N-hydroxy-2-methyl-2-(methylsulfonyl)butanamide | 0.000536 | >64.0 | 16 | 64 | 16 | 0.37 | a | 424 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 136 | 4-{4-[4-(ethylsulfonyl)phenyl]-2-oxopyridin-1(2H)-yl}-N-hydroxy-2-methyl-2-(methylsulfonyl)butanamide | 0.00236 | >64.0 | >64.0 | >64.0 | 64 | 0.29 | a | 457 |
| 137 | 4-{4-[5-fluoro-2-(trifluoromethoxy)phenyl]-2-oxopyridin-1(2H)-yl}-N-hydroxy-2-methyl-2-(methylsulfonyl)butanamide | 0.0682 | >64.0 | >64.0 | >64.0 | >64.0 | 0.41 | a | 467 |
| 138 | 4-[4-(3,4-dimethoxyphenyl)-2-oxopyridin-1(2H)-yl]-N-hydroxy-2-methyl-2-(methylsulfonyl)butanamide | 0.00391 | >64.0 | 64 | >64.0 | 64 | 0.32 | a | 425.1 |
| 139 | N-hydroxy-4-{4-[4-(4-methoxyphenoxy)phenyl]-2-oxopyridin-1(2H)-yl}-2-methyl-2-(methylsulfonyl)butanamide | 0.000116 | 64 | 0.125 | 0.5 | 8 | 0.46 | a | 487 |
| 140 | 4-[4-(2-acetylphenyl)-2-oxopyridin-1(2H)-yl]-N-hydroxy-2-methyl-2-(methylsulfonyl)butanamide | >0.100 | >64.0 | >64.0 | >64.0 | >64.0 | 0.31 | a | 407.1 |
| 141 | 4-[4-(4-chlorophenyl)-2-oxopyridin-1(2H)-yl]-N-hydroxy-2-methyl-2-(methylsulfonyl)butanamide | 0.000161 | >64.0 | 1 | 4 | 1 | 0.52 | a | 399.1 |
| 142 | 4-[4-(4-chloro-3-fluorophenyl)-2-oxopyridin-1(2H)-yl]-N-hydroxy-2-methyl-2-(methylsulfonyl)butanamide | 0.0000468 | >64.0 | 1 | 2 | 1 | 0.53 | a | 417.1 |
| 143 | N-hydroxy-2-methyl-2-(methylsulfonyl)-4-{2-oxo-4-[3-(trifluoromethyl)phenyl]pyridin-1(2H)-yl}butanamide | 0.000584 | >64.0 | 4 | 16 | 8 | 0.41 | a | 433.1 |
| 144 | N-hydroxy-4-{4-[3-(hydroxymethyl)phenyl]-2-oxopyridin-1(2H)-yl}-2-methyl-2-(methylsulfonyl)butanamide | 0.0111 | >64.0 | >64.0 | >64.0 | >64.0 | 0.27 | a | 395.1 |
| 145 | N-hydroxy-2-methyl-2-(methylsulfonyl)-4-{2-oxo-4-[4-(trifluoromethoxy)phenyl]pyridin-1(2H)-yl}butanamide | 0.000326 | >64.0 | 1 | 4 | 2 | 0.43 | a | 449 |
| 146 | 4-{1-[4-(hydroxyamino)-3-methyl-3-(methylsulfonyl)-4-oxobutyl]-2-oxo-1,2-dihydropyridin-4-yl}-N-isopropylbenzamide | 0.00663 | >64.0 | >64.0 | >64.0 | >64.0 | 0.31 | a | 450.1 |
| 147 | 4-[4-(2,3-difluorophenyl)-2-oxopyridin-1(2H)-yl]-N-hydroxy-2-methyl-2-(methylsulfonyl)butanamide | 0.000198 | >64.0 | 2 | 4 | 1 | 0.36 | a | 401.1 |
| 148 | 4-[4-{3-[(dimethylamino)sulfonyl]phenyl}-2-oxopyridin-1(2H)-yl]-N-hydroxy-2-methyl-2-(methylsulfonyl)butanamide | 0.00761 | >64.0 | 64 | 64 | >64.0 | 0.33 | a | 472.1 |
| 149 | 4-[4-(5-cyano-2-thienyl)-2-oxopyridin-1(2H)-yl]-N-hydroxy-2-methyl-2-(methylsulfonyl)butanamide | 0.00081 | >64.0 | 16 | 32 | 16 | 0.31 | a | 396.1 |
| 150 | 4-[4-(5-chloro-2-fluorophenyl)-2-oxopyridin-1(2H)-yl]-N-hydroxy-2-methyl-2-(methylsulfonyl)butanamide | 0.000355 | >64.0 | 4 | 16 | 4 | 0.39 | a | 417 |
| 151 | 4-[4-(3-fluoro-4-methylphenyl)-2-oxopyridin-1(2H)-yl]-N-hydroxy-2-methyl-2-(methylsulfonyl)butanamide | 0.000253 | >64.0 | 2 | 4 | 2 | 0.52 | a | 397.1 |
| 152 | N-hydroxy-2-methyl-2-(methylsulfonyl)-4-[2-oxo-4-(1-propyl-1H-pyrazol-4-yl)pyridin-1(2H)-yl]butanamide | 0.0417 | >64.0 | >64.0 | >64.0 | >64.0 | 0.3 | a | 397 |
| 153 | 4-[4-(3-fluoro-2-methylphenyl)-2-oxopyridin-1(2H)-yl]-N-hydroxy-2-methyl-2-(methylsulfonyl)butanamide | 0.000617 | >64.0 | 32 | 64 | 8 | 0.39 | a | 397 |
| 154 | N-tert-butyl-1'-[4-(hydroxyamino)-3-methyl-3-(methylsulfonyl)-4-oxobutyl]-2'-oxo-1',2'-dihydro-3,4'-bipyridine-5-carboxamide | >0.100 | >64.0 | >64.0 | >64.0 | >64.0 | 0.3 | a | 465.1 |
| 155 | 4-[4-(2-chloro-4-fluorophenyl)-2-oxopyridin-1(2H)-yl]-N-hydroxy-2-methyl-2-(methylsulfonyl)butanamide | 0.000322 | >64.0 | 4 | 8 | 0.5 | 0.39 | a | 417.1 |
| 156 | N-hydroxy-2-methyl-2-(methylsulfonyl)-4-[2-oxo-4-(4-phenoxyphenyl)pyridin-1(2H)-yl]butanamide | 0.000481 | 32 | <0.0600 | 0.25 | 4 | 0.46 | a | 457.1 |
| 157 | 4-[4-(2-chloro-3-fluorophenyl)-2-oxopyridin-1(2H)-yl]-N-hydroxy-2-methyl-2-(methylsulfonyl)butanamide | 0.00035 | >64.0 | 4 | 8 | 2 | 0.38 | a | 417 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 158 | N-hydroxy-2-methyl-4-[4-(5-methyl-2-furyl)-2-oxopyridin-1(2H)-yl]-2-(methylsulfonyl)butanamide | 0.0591 | >64.0 | 64 | >64.0 | 64 | | a | |
| 159 | 4-[4-(2-fluorophenyl)-2-oxopyridin-1(2H)-yl]-N-hydroxy-2-methyl-2-(methylsulfonyl)butanamide | 0.000291 | >64.0 | 2 | 8 | 2 | 0.35 | a | 383.1 |
| 160 | 4-[4-{5-[(dimethylamino)sulfonyl]-2-methylphenyl}-2-oxopyridin-1(2H)-yl]-N-hydroxy-2-methyl-2-(methylsulfonyl)butanamide | >0.100 | >64.0 | >64.0 | >64.0 | >64.0 | 0.35 | a | 486.1 |
| 161 | 4-[4-(2,4-dimethoxyphenyl)-2-oxopyridin-1(2H)-yl]-N-hydroxy-2-methyl-2-(methylsulfonyl)butanamide | 0.00113 | >64.0 | 8 | 32 | 8 | 0.37 | a | 425.1 |
| 162 | N-hydroxy-2-methyl-4-[4-(2-methyl-3-oxo-2,3-dihydro-1H-isoindol-5-yl)-2-oxopyridin-1(2H)-yl]-2-(methylsulfonyl)butanamide | 0.0326 | >64.0 | >64.0 | >64.0 | >64.0 | 0.28 | a | 434.1 |
| 163 | 4-[4-(2,3-dichlorophenyl)-2-oxopyridin-1(2H)-yl]-N-hydroxy-2-methyl-2-(methylsulfonyl)butanamide | 0.0000992 | >64.0 | 0.5 | 1 | 1 | 0.42 | a | 432.9 |
| 164 | 4-[4-(2,3-dihydro-1-benzofuran-5-yl)-2-oxopyridin-1(2H)-yl]-N-hydroxy-2-methyl-2-(methylsulfonyl)butanamide | 0.00122 | >64.0 | 8 | 32 | 32 | 0.35 | a | 407 |
| 165 | 4-[4-(1-benzyl-1H-pyrazol-4-yl)-2-oxopyridin-1(2H)-yl]-N-hydroxy-2-methyl-2-(methylsulfonyl)butanamide | 0.0746 | >64.0 | >64.0 | >64.0 | >64.0 | 0.35 | a | 445.1 |
| 166 | 4-[4-(4-fluoro-2-methoxyphenyl)-2-oxopyridin-1(2H)-yl]-N-hydroxy-2-methyl-2-(methylsulfonyl)butanamide | 0.00117 | >64.0 | 16 | 32 | 8 | 0.37 | a | 413 |
| 167 | 4-[4-(5-acetyl-2-thienyl)-2-oxopyridin-1(2H)-yl]-N-hydroxy-2-methyl-2-(methylsulfonyl)butanamide | 0.000891 | >64.0 | 16 | 32 | 16 | 0.31 | a | 412.9 |
| 168 | N-hydroxy-4-(2-isopropoxy-2'-oxo-3,4'-bipyridin-1'(2'H)-yl)-2-methyl-2-(methylsulfonyl)butanamide | >0.100 | >64.0 | >64.0 | >64.0 | >64.0 | 0.38 | a | 424.1 |
| 169 | 4-[4-(3-cyanophenyl)-2-oxopyridin-1(2H)-yl]-N-hydroxy-2-methyl-2-(methylsulfonyl)butanamide | 0.00549 | >64.0 | >64.0 | >64.0 | 64 | 0.32 | a | 390 |
| 170 | N-hydroxy-4-[4-(4-methoxyphenyl)-2-oxopyridin-1(2H)-yl]-2-methyl-2-(methylsulfonyl)butanamide | 0.00039 | >64.0 | 1 | 2 | 1 | 0.45 | a | 395.1 |
| 171 | 4-[4-(5-fluoro-2-methylphenyl)-2-oxopyridin-1(2H)-yl]-N-hydroxy-2-methyl-2-(methylsulfonyl)butanamide | 0.00965 | >64.0 | 64 | >64.0 | 32 | 0.39 | a | 397 |
| 172 | N-hydroxy-2-methyl-4-{4-[3-(1-methyl-1H-imidazol-2-yl)phenyl]-2-oxopyridin-1(2H)-yl}-2-(methylsulfonyl)butanamide | 0.0841 | >64.0 | >64.0 | >64.0 | >64.0 | 0.28 | b | 445.1 |
| 173 | 4-[4-(5-fluoro-2-methoxyphenyl)-2-oxopyridin-1(2H)-yl]-N-hydroxy-2-methyl-2-(methylsulfonyl)butanamide | 0.0114 | >64.0 | 64 | >64.0 | 64 | 0.37 | a | 413 |
| 174 | 4-{4-[2,4-bis(trifluoromethyl)phenyl]-2-oxopyridin-1(2H)-yl}-N-hydroxy-2-methyl-2-(methylsulfonyl)butanamide | 0.0154 | >64.0 | 64 | >64.0 | >64.0 | 0.46 | a | 501 |
| 175 | 4-[4-(2-furyl)-2-oxopyridin-1(2H)-yl]-N-hydroxy-2-methyl-2-(methylsulfonyl)butanamide | 0.0066 | >64.0 | 64 | >64.0 | 16 | 0.3 | a | 355 |
| 176 | N-hydroxy-4-[4-(1H-indol-6-yl)-2-oxopyridin-1(2H)-yl]-2-methyl-2-(methylsulfonyl)butanamide | 0.000709 | >64.0 | 8 | 16 | 4 | 0.36 | a | 404 |
| 177 | N-ethyl-2-fluoro-4-{1-[4-(hydroxyamino)-3-methyl-3-(methylsulfonyl)-4-oxobutyl]-2-oxo-1,2-dihydropyridin-4-yl}benzamide | 0.00201 | >64.0 | >64.0 | >64.0 | 64 | 0.3 | a | 454 |
| 178 | N-hydroxy-2-methyl-4-[4-(3-methylphenyl)-2-oxopyridin-1(2H)-yl]-2-(methylsulfonyl)butanamide | 0.000473 | >64.0 | 4 | 8 | 2 | 0.39 | a | 379.1 |
| 179 | N-hydroxy-2-methyl-4-[4-(2-methyl-1-oxo-2,3-dihydro-1H-isoindol-5-yl)-2-oxopyridin-1(2H)-yl]-2-(methylsulfonyl)butanamide | 0.00418 | >64.0 | >64.0 | >64.0 | >64.0 | 0.26 | a | 434 |
| 180 | 4-[4-(3-fluoro-4-methoxyphenyl)-2-oxopyridin-1(2H)-yl]-N-hydroxy-2-methyl-2-(methylsulfonyl)butanamide | 0.000481 | >64.0 | 2 | 8 | 8 | 0.36 | a | 413.1 |
| 181 | 4-[6-(cyclohexylmethoxy)-2'-oxo-3,4'-bipyridin-1'(2'H)-yl]-N-hydroxy-2-methyl-2-(methylsulfonyl)butanamide | 0.000199 | 64 | 0.125 | 1 | 4 | 0.52 | a | 478.2 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 182 | N-hydroxy-4-(2-methoxy-2'-oxo-3,4'-bipyridin-1'(2'H)-yl)-2-methyl-2-(methylsulfonyl)butanamide | 0.0142 | >64.0 | >64.0 | >64.0 | 64 | 0.3 | a | 396 |
| 183 | N-hydroxy-2-methyl-2-(methylsulfonyl)-4-{2-oxo-4-[2-(trifluoromethyl)phenyl]pyridin-1(2H)-yl}butanamide | 0.00413 | >64.0 | 32 | >64.0 | 32 | 0.39 | a | 433 |
| 184 | 4-[4-(4-ethoxy-3-fluorophenyl)-2-oxopyridin-1(2H)-yl]-N-hydroxy-2-methyl-2-(methylsulfonyl)butanamide | 0.000223 | >64.0 | 0.5 | 2 | 2 | 0.39 | a | 427 |
| 185 | 4-(6-ethoxy-2'-oxo-3,4'-bipyridin-1'(2'H)-yl)-N-hydroxy-2-methyl-2-(methylsulfonyl)butanamide | 0.000388 | >64.0 | 2 | 4 | 4 | 0.33 | a | 410 |
| 186 | 4-[4-(2,4-difluorophenyl)-2-oxopyridin-1(2H)-yl]-N-hydroxy-2-methyl-2-(methylsulfonyl)butanamide | 0.000173 | >64.0 | 2 | 4 | 2 | 0.47 | a | 401.1 |
| 187 | 4-[4-(3-fluorophenyl)-2-oxopyridin-1(2H)-yl]-N-hydroxy-2-methyl-2-(methylsulfonyl)butanamide | 0.000658 | >64.0 | 8 | 16 | 2 | 0.36 | a | 383 |
| 188 | 4-{1-[4-(hydroxyamino)-3-methyl-3-(methylsulfonyl)-4-oxobutyl]-2-oxo-1,2-dihydropyridin-4-yl}-N-methylbenzamide | 0.0104 | >64.0 | >64.0 | >64.0 | >64.0 | 0.25 | a | 422.1 |
| 189 | N-hydroxy-2-methyl-2-(methylsulfonyl)-4-(2-oxo-4-quinolin-8-ylpyridin-1(2H)-yl)butanamide | 0.0038 | >64.0 | >64.0 | >64.0 | 64 | 0.26 | a | 416 |
| 190 | N-hydroxy-2-methyl-4-[4-(4-methylphenyl)-2-oxopyridin-1(2H)-yl]-2-(methylsulfonyl)butanamide | 0.000281 | >64.0 | 1 | 4 | 1 | 0.5 | a | 379.1 |
| 191 | N-hydroxy-4-{4-[2-(methoxymethyl)phenyl]-2-oxopyridin-1(2H)-yl}-2-methyl-2-(methylsulfonyl)butanamide | >0.100 | >64.0 | >64.0 | >64.0 | >64.0 | 0.35 | a | 409 |
| 192 | 4-[4-(4-fluorophenyl)-2-oxopyridin-1(2H)-yl]-N-hydroxy-2-methyl-2-(methylsulfonyl)butanamide | 0.00078 | >64.0 | 8 | 8 | 2 | 0.36 | a | 383 |
| 193 | 4-[4-(4-fluoro-3-methylphenyl)-2-oxopyridin-1(2H)-yl]-N-hydroxy-2-methyl-2-(methylsulfonyl)butanamide | 0.0000495 | >64.0 | 2 | 8 | 2 | 0.4 | a | 397 |
| 194 | 4-[4-(5-cyano-1-methyl-1H-pyrrol-2-yl)-2-oxopyridin-1(2H)-yl]-N-hydroxy-2-methyl-2-(methylsulfonyl)butanamide | 0.0166 | >64.0 | >64.0 | >64.0 | >64.0 | 0.32 | a | 393.1 |
| 195 | 4-[4-(2,5-dimethoxyphenyl)-2-oxopyridin-1(2H)-yl]-N-hydroxy-2-methyl-2-(methylsulfonyl)butanamide | 0.0565 | >64.0 | >64.0 | >64.0 | >64.0 | 0.36 | a | 425.1 |
| 196 | 4-[4-(2,5-difluorophenyl)-2-oxopyridin-1(2H)-yl]-N-hydroxy-2-methyl-2-(methylsulfonyl)butanamide | 0.000763 | >64.0 | 8 | 16 | 4 | 0.36 | a | 401 |
| 197 | 4-[4-(2-fluorobiphenyl-4-yl)-2-oxopyridin-1(2H)-yl]-N-hydroxy-2-methyl-2-(methylsulfonyl)butanamide | 0.000115 | 16 | 0.25 | 0.5 | 2 | 0.47 | a | 459 |
| 198 | 4-[4-(4-cyanophenyl)-2-oxopyridin-1(2H)-yl]-N-hydroxy-2-methyl-2-(methylsulfonyl)butanamide | 0.000456 | >64.0 | 16 | 32 | 8 | 0.32 | a | 390 |
| 199 | 4-[4-(4-butylphenyl)-2-oxopyridin-1(2H)-yl]-N-hydroxy-2-methyl-2-(methylsulfonyl)butanamide | 0.0000867 | 32 | 0.125 | 0.5 | 2 | 0.5 | a | 421 |
| 200 | N-hydroxy-4-(6-methoxy-2-methyl-2'-oxo-3,4'-bipyridin-1'(2'H)-yl)-2-methyl-2-(methylsulfonyl)butanamide | 0.00365 | >64.0 | 32 | 64 | 16 | 0.27 | a | 410.1 |
| 201 | N-hydroxy-2-methyl-4-[4-(2-methylphenyl)-2-oxopyridin-1(2H)-yl]-2-(methylsulfonyl)butanamide | 0.00612 | >64.0 | 32 | 64 | 16 | 0.38 | a | 379.1 |
| 201 | 3-fluoro-5-{1-[4-(hydroxyamino)-3-methyl-3-(methylsulfonyl)-4-oxobutyl]-2-oxo-1,2-dihydropyridin-4-yl}-N-methylbenzamide | >0.100 | >64.0 | >64.0 | >64.0 | >64.0 | 0.29 | a | 440.1 |
| 203 | N-hydroxy-2-methyl-4-[4-(5-methyl-1-phenyl-1H-pyrazol-4-yl)-2-oxopyridin-1(2H)-yl]-2-(methylsulfonyl)butanamide | 0.0304 | >64.0 | 64 | >64.0 | >64.0 | 0.36 | a | 445 |
| 204 | 4-[4-(2-chloro-5-hydroxyphenyl)-2-oxopyridin-1(2H)-yl]-N-hydroxy-2-methyl-2-(methylsulfonyl)butanamide | 0.0168 | >64.0 | 64 | >64.0 | >64.0 | 0.33 | a | 415 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 205 | 4-(2-ethoxy-2'-oxo-3,4'-bipyridin-1'(2'H)-yl)-N-hydroxy-2-methyl-2-(methylsulfonyl)butanamide | >0.100 | >64.0 | >64.0 | >64.0 | >64.0 | 0.34 | a | 410 |
| 206 | N-hydroxy-4-[4-(3-methoxyphenyl)-2-oxopyridin-1(2H)-yl]-2-methyl-2-(methylsulfonyl)butanamide | 0.000574 | 16 | 4 | 8 | 4 | 0.36 | a | 395 |
| 207 | 4-[4-(4-cyano-3-fluorophenyl)-2-oxopyridin-1(2H)-yl]-N-hydroxy-2-methyl-2-(methylsulfonyl)butanamide | 0.000756 | >64.0 | 16 | >64.0 | 16 | 0.34 | a | 408 |
| 208 | 4-[4-(4-fluoro-3-methoxyphenyl)-2-oxopyridin-1(2H)-yl]-N-hydroxy-2-methyl-2-(methylsulfonyl)butanamide | 0.00148 | >64.0 | 32 | 64 | 16 | 0.37 | a | 413 |
| 209 | N-hydroxy-2-methyl-4-(2'-methyl-2-oxo-4,4'-bipyridin-1(2H)-yl)-2-(methylsulfonyl)butanamide | 0.00428 | >64.0 | 64 | >64.0 | 32 | 0.16 | a | 380 |
| 210 | N-hydroxy-4-[4-(3-hydroxyphenyl)-2-oxopyridin-1(2H)-yl]-2-methyl-2-(methylsulfonyl)butanamide | 0.00151 | >64.0 | >64.0 | >64.0 | >64.0 | 0.29 | a | 381.1 |
| 211 | N-tert-butyl-2-fluoro-5-{1-[4-(hydroxyamino)-3-methyl-3-(methylsulfonyl)-4-oxobutyl]-2-oxo-1,2-dihydropyridin-4-yl}benzamide | 0.0486 | >64.0 | 64 | >64.0 | >64.0 | 0.39 | a | 482.1 |
| 212 | N-hydroxy-2-methyl-2-(methylsulfonyl)-4-[2-oxo-4-(3,4,5-trimethoxyphenyl)pyridin-1(2H)-yl]butanamide | >0.100 | >64.0 | >64.0 | >64.0 | >64.0 | 0.34 | a | 455 |
| 213 | N-hydroxy-4-[4-(2-hydroxyphenyl)-2-oxopyridin-1(2H)-yl]-2-methyl-2-(methylsulfonyl)butanamide | 0.015 | >64.0 | >64.0 | >64.0 | >64.0 | 0.3 | a | 381 |
| 214 | 4-[4-(3-chloro-4-fluorophenyl)-2-oxopyridin-1(2H)-yl]-N-hydroxy-2-methyl-2-(methylsulfonyl)butanamide | 0.000172 | >64.0 | 1 | 4 | 2 | 0.41 | a | 417 |
| 215 | N-hydroxy-4-(4-isoquinolin-5-yl-2-oxopyridin-1(2H)-yl)-2-methyl-2-(methylsulfonyl)butanamide | 0.00402 | >64.0 | >64.0 | >64.0 | 64 | 0.21 | a | 416.1 |
| 216 | 4-[4-(3,5-dichlorophenyl)-2-oxopyridin-1(2H)-yl]-N-hydroxy-2-methyl-2-(methylsulfonyl)butanamide | 0.00135 | >64.0 | 4 | 16 | 8 | 0.44 | a | 432.9 |
| 217 | N-hydroxy-2-methyl-2-(methylsulfonyl)-4-[2-oxo-4-(4-pentylphenyl)pyridin-1(2H)-yl]butanamide | 0.000341 | 8 | <0.0600 | 1 | 8 | 0.54 | a | 435.1 |
| 218 | N-hydroxy-2-methyl-2-(methylsulfonyl)-4-(2-oxo-4,4'-bipyridin-1(2H)-yl)butanamide | 0.00793 | >64.0 | >64.0 | >64.0 | 64 | 0.12 | a | 366 |
| 219 | N-hydroxy-2-methyl-2-(methylsulfonyl)-4-(2'-oxo-3,4'-bipyridin-1'(2'H)-yl)butanamide | 0.0599 | >64.0 | >64.0 | >64.0 | >64.0 | 0.13 | a | 366 |
| 220 | N-hydroxy-2-methyl-4-(6-methyl-2-oxo-4-phenylpyridin-1(2H)-yl)-2-(methylsulfonyl)butanamide | 0.0386 | >64.0 | >64.0 | >64.0 | >64.0 | 0.38 | a | 379.1 |
| 221 | 4-{4-[3-chloro-4-(3-morpholin-4-ylpropoxy)phenyl]-2-oxopyridin-1(2H)-yl}-N-hydroxy-2-methyl-2-(methylsulfonyl)butanamide | 0.00037 | >64.0 | 2 | 16 | 8 | 0.28 | a | 542.2 |
| 222 | N-hydroxy-2-methyl-4-{4-[3-methyl-4-(3-morpholin-4-ylpropoxy)phenyl]-2-oxopyridin-1(2H)-yl}-2-(methylsulfonyl)butanamide | 0.00036 | >64.0 | 2 | 16 | 8 | 0.28 | a | 522.2 |
| 223 | 4-{4-[3-fluoro-4-(3-morpholin-4-ylpropoxy)phenyl]-2-oxopyridin-1(2H)-yl}-N-hydroxy-2-methyl-2-(methylsulfonyl)butanamide | 0.000651 | >64.0 | 4 | 32 | 8 | 0.26 | a | 526.2 |
| 224 | N-hydroxy-4-{4-[4-(2-hydroxypropyl)phenyl]-2-oxopyridin-1(2H)-yl}-2-methyl-2-(methylsulfonyl)butanamide | 0.00122 | >64.0 | 32 | 64 | 8 | 0.31 | a | 423.1 |
| 225 | 4-{4-[2-chloro-4-(3-morpholin-4-ylpropoxy)phenyl]-2-oxopyridin-1(2H)-yl}-N-hydroxy-2-methyl-2-(methylsulfonyl)butanamide | 0.000496 | >64.0 | 8 | 32 | 16 | 0.28 | a | 542.1 |
| 226 | 4-{4-[2-fluoro-4-(3-morpholin-4-ylpropoxy)phenyl]-2-oxopyridin-1(2H)-yl}-N-hydroxy-2-methyl-2-(methylsulfonyl)butanamide | 0.000563 | >64.0 | 2 | 16 | 8 | 0.26 | a | 526.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 227 | N-hydroxy-4-{4-[3-methoxy-4-(3-morpholin-4-ylpropoxy)phenyl]-2-oxopyridin-1(2H)-yl}-2-methyl-2-(methylsulfonyl)butanamide | 0.00616 | >64.0 | 64 | >64.0 | 64 | 0.26 | a | 538.1 |
| 228 | N-hydroxy-2-methyl-4-{4-[2-methyl-4-(3-morpholin-4-ylpropoxy)phenyl]-2-oxopyridin-1(2H)-yl}-2-(methylsulfonyl)butanamide | 0.000756 | >64.0 | 8 | 32 | 16 | 0.27 | a | 522.1 |
| 229 | N-hydroxy-4-[4-{4-[(5-hydroxypentyl)oxy]phenyl}-2-oxopyridin-1(2H)-yl]-2-methyl-2-(methylsulfonyl)butanamide | 0.00021 | >64.0 | 0.25 | 2 | 2 | 0.34 | a | 467.1 |
| 230 | 4-{4-[4-(aminosulfonyl)phenyl]-2-oxopyridin-1(2H)-yl}-N-hydroxy-2-methyl-2-(methylsulfonyl)butanamide | 0.00897 | >64.0 | 64 | >64.0 | >64.0 | 0.24 | a | 444 |
| 231 | N-hydroxy-4-{4-[3-(2-hydroxypropyl)phenyl]-2-oxopyridin-1(2H)-yl}-2-methyl-2-(methylsulfonyl)butanamide | 0.0102 | >64.0 | >64.0 | >64.0 | >64.0 | 0.32 | a | 423.1 |
| 232 | 4-{4-[2-chloro-4-(2-hydroxyethoxy)phenyl]-2-oxopyridin-1(2H)-yl}-N-hydroxy-2-methyl-2-(methylsulfonyl)butanamide | 0.000339 | >64.0 | 16 | 32 | 16 | 0.3 | a | 459 |
| 233 | N-hydroxy-4-{4-[4-(2-hydroxyethoxy)-2,5-dimethylphenyl]-2-oxopyridin-1(2H)-yl}-2-methyl-2-(methylsulfonyl)butanamide | 0.0361 | >64.0 | >64.0 | >64.0 | >64.0 | 0.32 | a | 453.1 |
| 234 | 4-{4-[2,3-dichloro-4-(2-hydroxyethoxy)phenyl]-2-oxopyridin-1(2H)-yl}-N-hydroxy-2-methyl-2-(methylsulfonyl)butanamide | 0.00141 | >64.0 | 64 | 64 | 32 | 0.34 | a | 493 |
| 235 | N-hydroxy-4-{4-[4-(2-hydroxyethoxy)-3-methylphenyl]-2-oxopyridin-1(2H)-yl}-2-methyl-2-(methylsulfonyl)butanamide | 0.000618 | >64.0 | 8 | 32 | 8 | 0.31 | a | 439.1 |
| 236 | 4-{4-[3-chloro-4-(2-hydroxyethoxy)phenyl]-2-oxopyridin-1(2H)-yl}-N-hydroxy-2-methyl-2-(methylsulfonyl)butanamide | 0.000902 | >64.0 | 32 | 64 | 16 | 0.31 | a | 459 |
| 237 | N-hydroxy-4-{4-[4-(2-hydroxyethoxy)-2-methylphenyl]-2-oxopyridin-1(2H)-yl}-2-methyl-2-(methylsulfonyl)butanamide | 0.00349 | >64.0 | >64.0 | >64.0 | 32 | 0.29 | a | 439.1 |
| 238 | 4-{4-[3-chloro-4-(4-hydroxybutoxy)phenyl]-2-oxopyridin-1(2H)-yl}-N-hydroxy-2-methyl-2-(methylsulfonyl)butanamide | 0.000195 | >64.0 | 0.5 | 4 | 4 | 0.35 | a | 487 |
| 239 | 4-{4-[2-chloro-4-(4-hydroxybutoxy)phenyl]-2-oxopyridin-1(2H)-yl}-N-hydroxy-2-methyl-2-(methylsulfonyl)butanamide | 0.000247 | >64.0 | 1 | 2 | 4 | 0.35 | a | 487 |
| 240 | 4-{4-[3-fluoro-4-(4-hydroxybutoxy)phenyl]-2-oxopyridin-1(2H)-yl}-N-hydroxy-2-methyl-2-(methylsulfonyl)butanamide | 0.000115 | >64.0 | 1 | 8 | 4 | 0.33 | a | 471.1 |
| 241 | 4-{4-[2-fluoro-4-(4-hydroxybutoxy)phenyl]-2-oxopyridin-1(2H)-yl}-N-hydroxy-2-methyl-2-(methylsulfonyl)butanamide | | >64.0 | 2 | 8 | 2 | | | |
| 242 | N-hydroxy-4-{4-[4-(4-hydroxybutoxy)-3-methoxyphenyl]-2-oxopyridin-1(2H)-yl}-2-methyl-2-(methylsulfonyl)butanamide | 0.00132 | >64.0 | 32 | >64.0 | 64 | 0.31 | a | 483.1 |
| 243 | N-hydroxy-4-{4-[4-(4-hydroxybutoxy)-2-methylphenyl]-2-oxopyridin-1(2H)-yl}-2-methyl-2-(methylsulfonyl)butanamide | 0.000592 | >64.0 | 4 | 16 | 8 | 0.34 | a | 467.1 |
| 244 | 4-{4-[2,5-dichloro-4-(2-hydroxyethoxy)phenyl]-2-oxopyridin-1(2H)-yl}-N-hydroxy-2-methyl-2-(methylsulfonyl)butanamide | 0.00394 | >64.0 | 32 | 64 | >64.0 | 0.32 | a | 493 |
| 245 | N-hydroxy-4-{4-[4-(4-hydroxybutoxy)-2-methoxyphenyl]-2-oxopyridin-1(2H)-yl}-2-methyl-2-(methylsulfonyl)butanamide | | >64.0 | 64 | >64.0 | 64 | | | |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 246 | 4-{4-[3-chloro-4-(3-hydroxypropoxy)phenyl]-2-oxopyridin-1(2H)-yl}-N-hydroxy-2-methyl-2-(methylsulfonyl)butanamide | 0.0000842 | >64.0 | 2 | 8 | 4 | 0.33 | a | 473 |
| 247 | 4-{4-[3-fluoro-4-(3-hydroxypropoxy)phenyl]-2-oxopyridin-1(2H)-yl}-N-hydroxy-2-methyl-2-(methylsulfonyl)butanamide | 0.000416 | >64.0 | 4 | 16 | 8 | 0.31 | a | 457.1 |
| 248 | N-hydroxy-4-{4-[4-(3-hydroxypropoxy)-3-methylphenyl]-2-oxopyridin-1(2H)-yl}-2-methyl-2-(methylsulfonyl)butanamide | 0.000072 | >64.0 | 2 | 8 | 4 | 0.33 | a | 453.1 |
| 249 | N-hydroxy-4-{4-[4-(3-hydroxypropoxy)-3-methoxyphenyl]-2-oxopyridin-1(2H)-yl}-2-methyl-2-(methylsulfonyl)butanamide | 0.00432 | >64.0 | >64.0 | >64.0 | 64 | 0.29 | a | 469.1 |
| 250 | 4-{4-[2-fluoro-4-(3-hydroxypropoxy)phenyl]-2-oxopyridin-1(2H)-yl}-N-hydroxy-2-methyl-2-(methylsulfonyl)butanamide | 0.0000867 | >64.0 | 2 | 8 | 4 | 0.31 | a | 457.1 |
| 251 | 4-{4-[2-chloro-4-(3-hydroxypropoxy)phenyl]-2-oxopyridin-1(2H)-yl}-N-hydroxy-2-methyl-2-(methylsulfonyl)butanamide | 0.000195 | >64.0 | 2 | 4 | 4 | 0.33 | a | 473 |
| 252 | N-hydroxy-4-{4-[4-(3-hydroxypropoxy)-2-methylphenyl]-2-oxopyridin-1(2H)-yl}-2-methyl-2-(methylsulfonyl)butanamide | 0.000125 | >64.0 | 16 | 64 | 16 | 0.32 | a | 453.1 |
| 253 | N-hydroxy-4-{4-[4-(3-hydroxypropoxy)-2-methoxyphenyl]-2-oxopyridin-1(2H)-yl}-2-methyl-2-(methylsulfonyl)butanamide | 0.000236 | >64.0 | 16 | 64 | >64.0 | 0.31 | a | 469.1 |
| 254 | N-hydroxy-2-methyl-2-(methylsulfonyl)-4-(2-oxo-4-quinolin-6-ylpyridin-1(2H)-yl)butanamide | | >64.0 | 4 | 8 | 4 | | | |
| 255 | N-hydroxy-4-{4-[4-(2-hydroxy-2-methylpropyl)phenyl]-2-oxopyridin-1(2H)-yl}-2-methyl-2-(methylsulfonyl)butanamide | 0.00206 | >64.0 | 2 | 32 | 8 | 0.33 | a | 437.1 |
| 256 | N-hydroxy-2-methyl-4-[4-(2-methyl-1H-indol-5-yl)-2-oxopyridin-1(2H)-yl]-2-(methylsulfonyl)butanamide | 0.000212 | 64 | 1 | 4 | 4 | 0.35 | a | 418.1 |
| 257 | 4-[4-(2,3-dimethylphenyl)-2-oxopyridin-1(2H)-yl]-N-hydroxy-2-methyl-2-(methylsulfonyl)butanamide | 0.00055 | >64.0 | 4 | 8 | 2 | 0.41 | a | 393.1 |
| 258 | N-hydroxy-4-[4-(6-hydroxy-2-naphthyl)-2-oxopyridin-1(2H)-yl]-2-methyl-2-(methylsulfonyl)butanamide | 0.000156 | >64.0 | 1 | 4 | 2 | 0.42 | a | 431.1 |
| 259 | N-hydroxy-2-methyl-2-(methylsulfonyl)-4-[2-oxo-4-(4-pyridin-2-ylphenyl)pyridin-1(2H)-yl]butanamide | 0.000252 | >64.0 | 0.5 | 2 | 2 | 0.33 | a | 442.1 |
| 260 | N-hydroxy-4-(4-isoquinolin-6-yl-2-oxopyridin-1(2H)-yl)-2-methyl-2-(methylsulfonyl)butanamide | 0.000244 | >64.0 | 4 | 8 | 4 | 0.22 | a | 416.1 |
| 261 | N-hydroxy-4-(4-isoquinolin-7-yl-2-oxopyridin-1(2H)-yl)-2-methyl-2-(methylsulfonyl)butanamide | 0.000497 | >64.0 | 8 | 16 | 4 | 0.22 | a | 416.1 |
| 262 | N-hydroxy-4-{4-[3-(2-hydroxy-2-methylpropyl)phenyl]-2-oxopyridin-1(2H)-yl}-2-methyl-2-(methylsulfonyl)butanamide | 0.0117 | >64.0 | 64 | >64.0 | >64.0 | 0.34 | a | 437.1 |
| 263 | N-hydroxy-4-{4-[3-(2-hydroxyethyl)-1H-indol-5-yl]-2-oxopyridin-1(2H)-yl}-2-methyl-2-(methylsulfonyl)butanamide | 0.0211 | >64.0 | 8 | >64.0 | >64.0 | 0.28 | a | 448.1 |
| 264 | 4-[4-(2-fluoro-3-methylphenyl)-2-oxopyridin-1(2H)-yl]-N-hydroxy-2-methyl-2-(methylsulfonyl)butanamide | 0.0000564 | >64.0 | 0.5 | 2 | 0.5 | 0.39 | a | 397.1 |
| 265 | N-hydroxy-4-{4-[1-(2-hydroxyethyl)-1H-indol-5-yl]-2-oxopyridin-1(2H)-yl}-2-methyl-2-(methylsulfonyl)butanamide | 0.000386 | >64.0 | 4 | 32 | 16 | 0.31 | a | 448.2 |
| 266 | 4-[4-(3-chloro-2-methylphenyl)-2-oxopyridin-1(2H)-yl]-N-hydroxy-2-methyl-2-(methylsulfonyl)butanamide | 0.00035 | >64.0 | 4 | 8 | 4 | 0.42 | a | 413.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 267 | N-hydroxy-4-{4-[1-(3-hydroxypropyl)-1H-indol-5-yl]-2-oxopyridin-1(2H)-yl}-2-methyl-2-(methylsulfonyl)butanamide | 0.000418 | >64.0 | 2 | 16 | 8 | 0.33 | a | 462.2 |
| 268 | N-hydroxy-2-methyl-2-(methylsulfonyl)-4-{2-oxo-4-[4-(pyridin-4-ylmethoxy)phenyl]pyridin-1(2H)-yl}butanamide | 0.000143 | >64.0 | 1 | 4 | 2 | 0.3 | a | 472.1 |
| 269 | N-hydroxy-2-methyl-2-(methylsulfonyl)-4-{2-oxo-4-[4-(pyridin-3-ylmethoxy)phenyl]pyridin-1(2H)-yl}butanamide | 0.000205 | >64.0 | 0.5 | 2 | 2 | 0.31 | a | 472.1 |
| 270 | N-hydroxy-2-methyl-2-(methylsulfonyl)-4-{2-oxo-4-[4-(pyridin-2-ylmethoxy)phenyl]pyridin-1(2H)-yl}butanamide | 0.000115 | >64.0 | 1 | 2 | 2 | 0.33 | a | 472.1 |
| 271 | N-hydroxy-2-methyl-2-(methylsulfonyl)-4-{2-oxo-4-[4-(2-pyridin-3-ylethoxy)phenyl]pyridin-1(2H)-yl}butanamide | 0.000305 | >64.0 | 0.25 | 1 | 2 | 0.32 | a | 486.1 |
| 272 | N-hydroxy-2-methyl-2-(methylsulfonyl)-4-{2-oxo-4-[4-(2-pyridin-2-ylethoxy)phenyl]pyridin-1(2H)-yl}butanamide | 0.000246 | >64.0 | 0.5 | 2 | 2 | 0.31 | a | 486.1 |
| 273 | N-hydroxy-4-{4-[6-(2-hydroxyethoxy)-2-naphthyl]-2-oxopyridin-1(2H)-yl}-2-methyl-2-(methylsulfonyl)butanamide | 0.000429 | >64.0 | 0.5 | 4 | 4 | 0.42 | a | 475.2 |
| 274 | N-hydroxy-4-{4-[6-(3-hydroxypropoxy)-2-naphthyl]-2-oxopyridin-1(2H)-yl}-2-methyl-2-(methylsulfonyl)butanamide | 0.000102 | >64.0 | 0.25 | 2 | 2 | 0.43 | a | 489.1 |
| 275 | N-hydroxy-4-[4-(1H-indazol-5-yl)-2-oxopyridin-1(2H)-yl]-2-methyl-2-(methylsulfonyl)butanamide | 0.000802 | | | | | 0.32 | a | 405 |
| 276 | 4-[4-{4-[4-(aminosulfonyl)butoxy]-2-chlorophenyl}-2-oxopyridin-1(2H)-yl]-N-hydroxy-2-methyl-2-(methylsulfonyl)butanamide | 0.000925 | >64.0 | 16 | 32 | 32 | 0.42 | a | 550.1 |
| 277 | N-hydroxy-2-methyl-2-(methylsulfonyl)-4-[4-{4-[(5-morpholin-4-ylpentyl)oxy]phenyl}-2-oxopyridin-1(2H)-yl]butanamide | 0.000105 | >64.0 | 1 | 4 | 4 | 0.36 | a | 536.2 |
| 278 | 4-{4-[4'-(aminosulfonyl)biphenyl-4-yl]-2-oxopyridin-1(2H)-yl}-N-hydroxy-2-methyl-2-(methylsulfonyl)butanamide | 0.000533 | >64.0 | 2 | 32 | 16 | 0.41 | a | 520.1 |
| 279 | (2R)-N-hydroxy-4-{4-[4-(4-hydroxybutoxy)phenyl]-2-oxopyridin-1(2H)-yl}-2-methyl-2-(methylsulfonyl)butanamide | 0.0000616 | >64.0 | 0.5 | 4 | 1 | 0.41 | a | 453.2 |
| 280 | (2R)-N-hydroxy-4-[4-{4-[(5-hydroxypentyl)oxy]phenyl}-2-oxopyridin-1(2H)-yl]-2-methyl-2-(methylsulfonyl)butanamide | 0.0000603 | >64.0 | 0.25 | 1 | 0.5 | 0.45 | a | 467.2 |
| 281 | 4-[6-(4-fluorophenyl)-2'-oxo-3',4'-bipyridin-1'(2'H)-yl]-N-hydroxy-2-methyl-2-(methylsulfonyl)butanamide | 0.000824 | >64.0 | 0.5 | 4 | 8 | 0.46 | a | 460.1 |
| 282 | 4-[4-(4-bromo-3-fluorophenyl)-2-oxopyridin-1(2H)-yl]-N-hydroxy-2-methyl-2-(methylsulfonyl)butanamide | 0.0000933 | 64 | 0.5 | 1 | 1 | 0.52 | a | 461 |
| 283 | 4-[4-(4-bromo-2-fluorophenyl)-2-oxopyridin-1(2H)-yl]-N-hydroxy-2-methyl-2-(methylsulfonyl)butanamide | 0.000226 | >64.0 | 0.25 | 0.5 | 1 | 0.54 | a | 461 |
| 284 | N-hydroxy-2-methyl-4-(5-methyl-2-oxo-4-phenylpyridin-1(2H)-yl)-2-(methylsulfonyl)butanamide | 0.00892 | >64.0 | 32 | 64 | 64 | 0.47 | a | 379.1 |
| 285 | (2R)-N-hydroxy-4-(6-methoxy-2'-oxo-3,4'-bipyridin-1'(2'H)-yl)-2-methyl-2-(methylsulfonyl)butanamide | 0.000382 | >64.0 | 4 | 8 | 4 | 0.37 | a | 396.1 |
| 286 | N-hydroxy-4-[4-{4-[3-(hydroxymethyl)isoxazol-5-yl]-2-methylphenyl}-2-oxopyridin-1(2H)-yl]-2-methyl-2-(methylsulfonyl)butanamide | 0.000403 | >64.0 | 16 | 32 | 16 | 0.41 | a | 476.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 287 | N-hydroxy-2-methyl-2-(methylsulfonyl)-4-{2-oxo-4-[4-(pyridin-3-yloxy)phenyl]pyridin-1(2H)-yl}butanamide | 0.000197 | >64.0 | 0.5 | 4 | 4 | 0.4 | a | 458.1 |
| 288 | N-hydroxy-4-[4-(7-methoxy-2-naphthyl)-2-oxopyridin-1(2H)-yl]-2-methyl-2-(methylsulfonyl)butanamide | 0.000175 | 64 | 0.125 | 32 | 4 | 0.55 | a | 445.1 |
| 289 | N-hydroxy-2-methyl-2-(methylsulfonyl)-4-[4-{2-methyl-4-[3-(1H-1,2,4-triazol-1-yl)propoxy]phenyl}-2-oxopyridin-1(2H)-yl]butanamide | 0.000601 | >64.0 | 32 | 64 | 32 | 0.4 | a | 504.2 |
| 290 | 4-[4-{3-chloro-4-[3-(1H-1,2,4-triazol-1-yl)propoxy]phenyl}-2-oxopyridin-1(2H)-yl]-N-hydroxy-2-methyl-2-(methylsulfonyl)butanamide | 0.000282 | >64.0 | 16 | 64 | 16 | 0.41 | a | 524.1 |
| 291 | 4-[4-{2-chloro-4-[3-(1H-1,2,4-triazol-1-yl)propoxy]phenyl}-2-oxopyridin-1(2H)-yl]-N-hydroxy-2-methyl-2-(methylsulfonyl)butanamide | 0.000552 | >64.0 | 16 | 1 | 16 | 0.41 | a | 524.1 |
| 292 | 4-[4-{2,3-dichloro-4-[3-(1H-1,2,4-triazol-1-yl)propoxy]phenyl}-2-oxopyridin-1(2H)-yl]-N-hydroxy-2-methyl-2-(methylsulfonyl)butanamide | 0.000193 | >64.0 | 8 | 32 | 16 | 0.45 | a | 558.1 |
| 293 | N-hydroxy-2-methyl-2-(methylsulfonyl)-4-[4-{3-methyl-4-[3-(1H-1,2,4-triazol-1-yl)propoxy]phenyl}-2-oxopyridin-1(2H)-yl]butanamide | 0.000311 | 64 | 4 | 64 | 16 | 0.41 | a | 504.2 |
| 294 | N-hydroxy-2-(methylsulfonyl)-2-[2-(2-oxo-4-phenylpyridin-1(2H)-yl)ethyl]pentanamide | 0.055 | >64.0 | >64.0 | >64.0 | >64.0 | 0.52 | a | 393.1 |
| 295 | 4-[4-(2-fluoro-4-pyridin-3-ylphenyl)-2-oxopyridin-1(2H)-yl]-N-hydroxy-2-methyl-2-(methylsulfonyl)butanamide | 0.000133 | >64.0 | 1 | 2 | 8 | 0.31 | a | 460.1 |
| 296 | N-hydroxy-4-[4-(1H-indol-3-yl)-2-oxopyridin-1(2H)-yl]-2-methyl-2-(methylsulfonyl)butanamide | 0.00207 | >64.0 | 64 | >64.0 | 64 | 0.41 | a | 404 |
| 297 | 4-[4-(3-fluoro-4-pyridin-3-ylphenyl)-2-oxopyridin-1(2H)-yl]-N-hydroxy-2-methyl-2-(methylsulfonyl)butanamide | 0.000105 | 64 | 1 | 4 | 2 | 0.3 | a | 460 |
| 298 | 4-[4-(3-fluoro-4-pyridin-4-ylphenyl)-2-oxopyridin-1(2H)-yl]-N-hydroxy-2-methyl-2-(methylsulfonyl)butanamide | 0.0000733 | >64.0 | 0.5 | 4 | 4 | 0.29 | a | 460 |
| 299 | N-hydroxy-4-[4-(7-hydroxy-2-naphthyl)-2-oxopyridin-1(2H)-yl]-2-methyl-2-(methylsulfonyl)butanamide | 0.000238 | >64.0 | 1 | 8 | 4 | 0.43 | a | 431 |
| 300 | N-hydroxy-2-methyl-4-[4-(2-methylquinolin-6-yl)-2-oxopyridin-1(2H)-yl]-2-(methylsulfonyl)butanamide | 0.000599 | >64.0 | 4 | 16 | 8 | 0.26 | a | 430.1 |
| 301 | N-hydroxy-2-methyl-4-[4-(3-methylquinolin-6-yl)-2-oxopyridin-1(2H)-yl]-2-(methylsulfonyl)butanamide | 0.00111 | >64.0 | 4 | 16 | 16 | 0.28 | a | 430 |
| 302 | N-hydroxy-2-methyl-4-[4-(4-methylquinolin-6-yl)-2-oxopyridin-1(2H)-yl]-2-(methylsulfonyl)butanamide | 0.00225 | >64.0 | 64 | >64.0 | 16 | 0.26 | a | 430 |
| 303 | (2R)-4-[4-{2,3-dichloro-4-[2-(4-hydroxypiperidin-1-yl)ethoxy]phenyl}-2-oxopyridin-1(2H)-yl]-N-hydroxy-2-methyl-2-(methylsulfonyl)butanamide | 0.000809 | >64.0 | 32 | >64.0 | 16 | 0.34 | a | 576 |
| 304 | (2R)-4-{4-[2,3-dichloro-4-(2-morpholin-4-ylethoxy)phenyl]-2-oxopyridin-1(2H)-yl}-N-hydroxy-2-methyl-2-(methylsulfonyl)butanamide | 0.000397 | >64.0 | 4 | 32 | 16 | 0.35 | a | 562 |
| 305 | N-hydroxy-2-methyl-4-[4-(2-methylquinolin-7-yl)-2-oxopyridin-1(2H)-yl]-2-(methylsulfonyl)butanamide | 0.00768 | >64.0 | 16 | 64 | >64.0 | 0.27 | a | 430.1 |
| 306 | 4-[4-(7-fluoroisoquinolin-6-yl)-2-oxopyridin-1(2H)-yl]-N-hydroxy-2-methyl-2-(methylsulfonyl)butanamide | 0.000323 | >64.0 | 8 | 4 | 4 | 0.3 | a | 434.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 307 | 4-{4-[2-fluoro-3-(3-hydroxypropoxy)phenyl]-2-oxopyridin-1(2H)-yl}-N-hydroxy-2-methyl-2-(methylsulfonyl)butanamide | 0.000482 | >64.0 | 16 | 32 | 16 | 0.39 | a | 457.1 |
| 308 | N-hydroxy-2-methyl-4-[4-(3-methylquinolin-7-yl)-2-oxopyridin-1(2H)-yl]-2-(methylsulfonyl)butanamide | 0.000465 | >64.0 | 2 | 4 | 4 | 0.32 | a | 430.1 |
| 309 | N-hydroxy-4-{4-[6-(hydroxymethyl)-2-naphthyl]-2-oxopyridin-1(2H)-yl}-2-methyl-2-(methylsulfonyl)butanamide | 0.000294 | >64.0 | 1 | 4 | 4 | 0.41 | a | 445.1 |
| 310 | (2R)-N-hydroxy-4-{4-[4-(6-methoxypyridin-3-yl)phenyl]-2-oxopyridin-1(2H)-yl}-2-methyl-2-(methylsulfonyl)butanamide | 0.0000406 | >16.0 | 0.125 | 0.5 | 0.5 | 0.51 | a | 472.2 |
| 311 | (2R)-4-[4-{4-[(1-glycoloylpiperidin-4-yl)methoxy]phenyl}-2-oxopyridin-1(2H)-yl]-N-hydroxy-2-methyl-2-(methylsulfonyl)butanamide | 0.000149 | >64.0 | 1 | 8 | 4 | 0.42 | a | 536.2 |
| 312 | (2R)-4-[4-{4-[2-(1-glycoloylpiperidin-4-yl)ethoxy]phenyl}-2-oxopyridin-1(2H)-yl]-N-hydroxy-2-methyl-2-(methylsulfonyl)butanamide | 0.0000768 | 64 | 0.5 | 4 | 4 | 0.45 | a | 550.2 |
| 313 | (2R)-4-[4-{4-[3-(1-glycoloylpiperidin-4-yl)propoxy]phenyl}-2-oxopyridin-1(2H)-yl]-N-hydroxy-2-methyl-2-(methylsulfonyl)butanamide | 0.000239 | 64 | 0.5 | 2 | 4 | 0.48 | a | 564.2 |
| 314 | (2R)-N-hydroxy-4-{4-[6-(2-hydroxyethoxy)-2-naphthyl]-2-oxopyridin-1(2H)-yl}-2-methyl-2-(methylsulfonyl)butanamide | 0.000109 | >64.0 | 0.5 | 2 | 1 | 0.43 | a | 475.2 |
| 315 | (2R)-N-hydroxy-4-{4-[6-(hydroxymethyl)-2-naphthyl]-2-oxopyridin-1(2H)-yl}-2-methyl-2-(methylsulfonyl)butanamide | 0.000147 | >64.0 | 0.5 | 1 | 1 | 0.41 | a | 445.1 |
| 316 | (2R)-4-[4-(3-fluoroquinolin-6-yl)-2-oxopyridin-1(2H)-yl]-N-hydroxy-2-methyl-2-(methylsulfonyl)butanamide | 0.000247 | >64.0 | 4 | 4 | 2 | 0.43 | a | 434.1 |
| 317 | (2R)-4-[4-(3-fluoro-4-methoxyphenyl)-2-oxopyridin-1(2H)-yl]-N-hydroxy-2-methyl-2-(methylsulfonyl)butanamide | 0.000156 | >64.0 | 2 | 4 | 1 | 0.46 | a | 413.1 |
| 318 | (2R)-4-[4-{3-fluoro-4-[(trans-4-hydroxycyclohexyl)methoxy]phenyl}-2-oxopyridin-1(2H)-yl]-N-hydroxy-2-methyl-2-(methylsulfonyl)butanamide | 0.0000747 | >64.0 | 0.25 | 2 | 1 | 0.46 | a | 511.2 |
| 319 | (2R)-N-hydroxy-4-[4-{4-[(4-hydroxybutyl)thio]phenyl}-2-oxopyridin-1(2H)-yl]-2-methyl-2-(methylsulfonyl)butanamide | | >64.0 | 0.25 | 1 | 1 | | | |
| 320 | (2R)-4-[4-(4-acetyl-2-fluorophenyl)-2-oxopyridin-1(2H)-yl]-N-hydroxy-2-methyl-2-(methylsulfonyl)butanamide | 0.000162 | >64.0 | 1 | 8 | 2 | 0.42 | a | 425.1 |
| 321 | (2R)-4-[4-(2,4-difluorophenyl)-2-oxopyridin-1(2H)-yl]-N-hydroxy-2-methyl-2-(methylsulfonyl)butanamide | 0.000154 | >64.0 | 1 | 2 | 1 | 0.47 | a | 401.1 |
| 322 | (2R)-4-[4-(3-fluoro-4-methylphenyl)-2-oxopyridin-1(2H)-yl]-N-hydroxy-2-methyl-2-(methylsulfonyl)butanamide | 0.000116 | >64.0 | 0.5 | 2 | 0.5 | 0.51 | a | 397.1 |
| 323 | (2R)-4-[4-(2-fluoro-3-methylphenyl)-2-oxopyridin-1(2H)-yl]-N-hydroxy-2-methyl-2-(methylsulfonyl)butanamide | 0.0000948 | >64.0 | 0.25 | 1 | 0.5 | 0.52 | a | 397.1 |
| 324 | (2R)-4-{4-[2-fluoro-4-(4-hydroxybutoxy)-3-methylphenyl]-2-oxopyridin-1(2H)-yl}-N-hydroxy-2-methyl-2-(methylsulfonyl)butanamide | 0.0000758 | >64.0 | 0.25 | 1 | 2 | 0.47 | a | 485.2 |
| 325 | (2R)-4-[4-(4-fluoro-3-methylphenyl)-2-oxopyridin-1(2H)-yl]-N-hydroxy-2-methyl-2-(methylsulfonyl)butanamide | 0.0000335 | 64 | 0.5 | 2 | 0.5 | 0.5 | a | 397.1 |
| 326 | (2R)-4-[4-{2-fluoro-4-[(4-hydroxy-4-methylcyclohexyl)oxy]phenyl}-2-oxopyridin-1(2H)-yl]-N-hydroxy-2-methyl-2-(methylsulfonyl)butanamide | 0.000154 | >64.0 | 0.5 | 2 | 4 | 0.48 | a | 511.2 |
| 327 | (2R)-N-hydroxy-2-methyl-2-(methylsulfonyl)-4-[2-oxo-4-(2-oxo-1,2-dihydroquinolin-6-yl)pyridin-1(2H)-yl]butanamide | 0.00257 | >64.0 | 4 | >64.0 | >64.0 | 0.32 | a | 432.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 328 | (2R)-N-hydroxy-4-[4-(2-methoxyquinolin-6-yl)-2-oxopyridin-1(2H)-yl]-2-methyl-2-(methylsulfonyl)butanamide | 0.0000841 | >64.0 | 1 | 2 | 1 | 0.49 | a | 446.1 |
| 329 | (2R)-N-hydroxy-4-{4-[4-(4-hydroxypiperidin-1-yl)phenyl]-2-oxopyridin-1(2H)-yl}-2-methyl-2-(methylsulfonyl)butanamide | 0.000831 | >64.0 | 1 | 32 | 4 | 0.28 | a | 464.2 |
| 330 | (2R)-4-[4-(3,4-dihydro-2H-1,5-benzodioxepin-7-yl)-2-oxopyridin-1(2H)-yl]-N-hydroxy-2-methyl-2-(methylsulfonyl)butanamide | 0.000541 | >64.0 | 0.5 | 8 | 4 | 0.46 | a | 437.1 |
| 331 | (2R)-N-hydroxy-2-methyl-2-(methylsulfonyl)-4-[2'-oxo-6-(trifluoromethyl)-3,4'-bipyridin-1'(2'H)-yl]butanamide | 0.00629 | >64.0 | 0.25 | 64 | 32 | 0.44 | a | 434.1 |
| 332 | (2R)-4-[4-(4-ethoxyphenyl)-2-oxopyridin-1(2H)-yl]-N-hydroxy-2-methyl-2-(methylsulfonyl)butanamide | 0.0000755 | >64.0 | 64 | 0.5 | 0.5 | 0.5 | a | 409.1 |
| 333 | (2R)-4-{4-[4-(cyanomethoxy)phenyl]-2-oxopyridin-1(2H)-yl}-N-hydroxy-2-methyl-2-(methylsulfonyl)butanamide | 0.000307 | >64.0 | 16 | 64 | 8 | 0.42 | a | 420.1 |
| 334 | (2R)-4-[4-(3-chloro-4-methoxyphenyl)-2-oxopyridin-1(2H)-yl]-N-hydroxy-2-methyl-2-(methylsulfonyl)butanamide | 0.0000985 | >64.0 | 8 | 4 | 1 | 0.49 | a | 429.1 |
| 335 | (2R)-4-[4-(3,5-difluorophenyl)-2-oxopyridin-1(2H)-yl]-N-hydroxy-2-methyl-2-(methylsulfonyl)butanamide | 0.000502 | >64.0 | 1 | 8 | 2 | 0.48 | a | 401.1 |
| 336 | (2R)-4-[4-(3,5-dichlorophenyl)-2-oxopyridin-1(2H)-yl]-N-hydroxy-2-methyl-2-(methylsulfonyl)butanamide | 0.000345 | >64.0 | 4 | 16 | 8 | 0.57 | a | 433 |
| 337 | (2R)-4-{4-[3-fluoro-4-(piperidin-4-yloxy)phenyl]-2-oxopyridin-1(2H)-yl}-N-hydroxy-2-methyl-2-(methylsulfonyl)butanamide | 0.00221 | >64.0 | >64.0 | >64.0 | >64.0 | 0.32 | a | 482.2 |
| 338 | (2R)-4-{4-[4-(difluoromethoxy)phenyl]-2-oxopyridin-1(2H)-yl}-N-hydroxy-2-methyl-2-(methylsulfonyl)butanamide | 0.0000528 | >64.0 | 0.5 | 2 | 0.5 | 0.49 | a | 431.1 |
| 339 | (2R)-N-hydroxy-2-methyl-2-(methylsulfonyl)-4-[2-oxo-4-(1-oxo-2,3-dihydro-1H-inden-5-yl)pyridin-1(2H)-yl]butanamide | 0.000378 | >64.0 | 4 | 16 | 4 | 0.39 | a | 419.1 |
| 340 | (2R)-N-hydroxy-2-methyl-2-(methylsulfonyl)-4-{4-[4-(1,3-oxazol-5-yl)phenyl]-2-oxopyridin-1(2H)-yl}butanamide | 0.0000898 | >64.0 | 0.25 | 2 | 1 | 0.41 | a | 432.1 |
| 341 | (2R)-4-[4-(2-chlorophenyl)-2-oxopyridin-1(2H)-yl]-N-hydroxy-2-methyl-2-(methylsulfonyl)butanamide | 0.000431 | >64.0 | 4 | 4 | 2 | 0.48 | a | 399.1 |
| 342 | (2R)-4-[4-(2-chloro-4-methoxyphenyl)-2-oxopyridin-1(2H)-yl]-N-hydroxy-2-methyl-2-(methylsulfonyl)butanamide | >0.100 | >64.0 | 0.5 | 0.5 | 0.5 | 0.5 | a | 429.1 |
| 343 | (2R)-4-{4-[4-(2-cyano-2-methylpropyl)phenyl]-2-oxopyridin-1(2H)-yl}-N-hydroxy-2-methyl-2-(methylsulfonyl)butanamide | 0.000602 | >64.0 | 8 | 16 | 2 | 0.51 | a | 446.2 |
| 344 | (2R)-4-{4-[3-fluoro-4-(3-hydroxypropyl)phenyl]-2-oxopyridin-1(2H)-yl}-N-hydroxy-2-methyl-2-(methylsulfonyl)butanamide | 0.000272 | >64.0 | 4 | 8 | 2 | 0.41 | a | 441.2 |
| 345 | (2R)-N-hydroxy-4-[4-(4-methoxy-2-methylphenyl)-2-oxopyridin-1(2H)-yl]-2-methyl-2-(methylsulfonyl)butanamide | 0.000733 | >64.0 | 4 | 8 | 4 | 0.48 | a | 409.1 |
| 346 | (2R)-N-hydroxy-4-[4-(4-methoxy-3-methylphenyl)-2-oxopyridin-1(2H)-yl]-2-methyl-2-(methylsulfonyl)butanamide | 0.0000305 | >64.0 | 0.5 | 1 | 0.5 | 0.51 | a | 409.1 |
| 347 | (2R)-4-{4-[4-(2-cyanoethyl)phenyl]-2-oxopyridin-1(2H)-yl}-N-hydroxy-2-methyl-2-(methylsulfonyl)butanamide | 0.000222 | >64.0 | 64 | 64 | 4 | 0.42 | a | 418.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 348 | (2R)-4-[4-{3-fluoro-4-[(cis-4-hydroxycyclohexyl)methoxy]phenyl}-2-oxopyridin-1(2H)-yl]-N-hydroxy-2-methyl-2-(methylsulfonyl)butanamide | 0.0000632 | >64.0 | 0.25 | 4 | 1 | 0.49 | a | 511.2 |
| 349 | (2R)-4-[4-{3-fluoro-4-[(4-hydroxy-4-methylcyclohexyl)oxy]phenyl}-2-oxopyridin-1(2H)-yl]-N-hydroxy-2-methyl-2-(methylsulfonyl)butanamide | 0.000304 | >64.0 | 0.5 | 16 | 4 | 0.47 | a | 511.2 |
| 350 | (2R)-N-hydroxy-4-{4-[4-(2-hydroxy-1,1-dimethylethyl)phenyl]-2-oxopyridin-1(2H)-yl}-2-methyl-2-(methylsulfonyl)butanamide | 0.00121 | >64.0 | 16 | 64 | 16 | 0.44 | a | 437.2 |
| 351 | (2R)-N-hydroxy-4-{4-[4-(1-hydroxycyclobutyl)phenyl]-2-oxopyridin-1(2H)-yl}-2-methyl-2-(methylsulfonyl)butanamide | 0.000572 | >64.0 | 16 | 64 | 16 | 0.42 | a | 435.2 |
| 352 | (2R)-N-hydroxy-4-{4-[4-(1-methoxycyclobutyl)phenyl]-2-oxopyridin-1(2H)-yl}-2-methyl-2-(methylsulfonyl)butanamide | 0.000824 | >64.0 | 2 | 32 | 8 | 0.53 | a | 449.2 |
| 353 | (2R)-4-[4-(2,6-difluorophenyl)-2-oxopyridin-1(2H)-yl]-N-hydroxy-2-methyl-2-(methylsulfonyl)butanamide | 0.000247 | >64.0 | 4 | 16 | 1 | 0.45 | a | 401.1 |
| 354 | (2R)-4-{4-[2-fluoro-4-(trifluoromethoxy)phenyl]-2-oxopyridin-1(2H)-yl}-N-hydroxy-2-methyl-2-(methylsulfonyl)butanamide | 0.0000764 | >64.0 | 0.25 | 1 | 0.5 | 0.57 | a | 467.1 |
| 355 | (2R)-4-{4-[(cyanomethyl)thio]phenyl}-2-oxopyridin-1(2H)-yl]-N-hydroxy-2-methyl-2-(methylsulfonyl)butanamide | 0.000156 | >64.0 | 4 | 16 | 2 | 0.46 | a | 436.1 |
| 356 | (2R)-4-[4-{4-[(cyanomethyl)thio]-2-methylphenyl}-2-oxopyridin-1(2H)-yl]-N-hydroxy-2-methyl-2-(methylsulfonyl)butanamide | 0.000324 | >64.0 | 16 | 32 | 4 | 0.49 | a | 450.1 |
| 357 | (2R)-4-[4-{4-[(1-cyanoethyl)thio]phenyl}-2-oxopyridin-1(2H)-yl]-N-hydroxy-2-methyl-2-(methylsulfonyl)butanamide | 0.0000515 | >64.0 | 1 | 16 | 1 | 0.52 | a | 450.1 |
| 358 | (2R)-N-hydroxy-2-methyl-2-(methylsulfonyl)-4-{4-[2-methyl-4-(2H-1,2,3-triazol-2-yl)phenyl]-2-oxopyridin-1(2H)-yl}butanamide | 0.000166 | >64.0 | 0.25 | 0.25 | 1 | 0.51 | a | 446.1 |
| 259 | (2R)-N-hydroxy-4-{4-[6-(1-hydroxy-1-methylethyl)-2-naphthyl]-2-oxopyridin-1(2H)-yl}-2-methyl-2-(methylsulfonyl)butanamide | 0.00199 | >64.0 | 2 | 32 | 16 | 0.48 | a | 473.2 |
| 360 | (2R)-N-hydroxy-4-{4-{6-[(1S)-1-hydroxyethyl]-2-naphthyl}-2-oxopyridin-1(2H)-yl}-2-methyl-2-(methylsulfonyl)butanamide | 0.0000394 | >64.0 | 0.5 | 2 | 1 | 0.45 | a | 459.2 |
| 361 | (2R)-4-[4-(4-ethoxy-2-fluorophenyl)-2-oxopyridin-1(2H)-yl]-N-hydroxy-2-methyl-2-(methylsulfonyl)butanamide | 0.000502 | >64.0 | 0.5 | 2 | 2 | 0.54 | a | 427.1 |
| 362 | (2R)-4-{4-[4-(1-cyano-1-methylethyl)phenyl]-2-oxopyridin-1(2H)-yl}-N-hydroxy-2-methyl-2-(methylsulfonyl)butanamide | 0.000553 | >64.0 | 16 | 32 | 4 | 0.5 | a | 432.2 |
| 363 | (2R)-N-hydroxy-2-methyl-4-{4-[4-(1-methyl-1H-imidazol-2-yl)phenyl]-2-oxopyridin-1(2H)-yl}-2-(methylsulfonyl)butanamide | 0.00824 | >64.0 | 32 | >64.0 | 64 | 0.28 | a | 445.2 |
| 364 | (2R)-N-hydroxy-2-methyl-2-(methylsulfonyl)-4-{2-oxo-4-[4-(1H-1,2,3-triazol-1-yl)phenyl]pyridin-1(2H)-yl}butanamide | 0.000394 | >64.0 | 16 | 64 | 16 | 0.38 | a | 432.1 |
| 365 | (2R)-4-[4-(4-{[(4R)-4,5-dihydroxypentyl]oxy}phenyl)-2-oxopyridin-1(2H)-yl]-N-hydroxy-2-methyl-2-(methylsulfonyl)butanamide | 0.00026 | 64 | 4 | 32 | 4 | 0.38 | a | 483.2 |
| 366 | (2R)-4-{4-[4-(3,4-dihydroxybutoxy)phenyl]-2-oxopyridin-1(2H)-yl}-N-hydroxy-2-methyl-2-(methylsulfonyl)butanamide | 0.000566 | >64.0 | 16 | >64.0 | 16 | 0.35 | a | 469.2 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 367 | (2R)-N-hydroxy-4-{4-[4-(1H-imidazol-2-yl)phenyl]-2-oxopyridin-1(2H)-yl}-2-methyl-2-(methylsulfonyl)butanamide | 0.00715 | >64.0 | 8 | >64.0 | >64.0 | 0.29 | a | 431.1 |
| 368 | (2R)-N-hydroxy-2-methyl-4-{4-[4-(2-methyl-1H-imidazol-1-yl)phenyl]-2-oxopyridin-1(2H)-yl}-2-(methylsulfonyl)butanamide | 0.000343 | >64.0 | >64.0 | >64.0 | 16 | 0.29 | a | 445.2 |
| 369 | (2R)-N-hydroxy-2-methyl-4-{4-[4-(3-methyl-1H-pyrazol-5-yl)phenyl]-2-oxopyridin-1(2H)-yl}-2-(methylsulfonyl)butanamide | | >64.0 | 2 | 8 | 4 | | | |
| 370 | (2R)-N-hydroxy-2-methyl-4-{4-[4-(5-methylisoxazol-3-yl)phenyl]-2-oxopyridin-1(2H)-yl}-2-(methylsulfonyl)butanamide | 0.0000595 | >64.0 | 0.125 | 1 | 0.5 | 0.49 | a | 446.1 |
| 371 | (2R)-N-hydroxy-2-methyl-2-(methylsulfonyl)-4-{2-oxo-4-[4-(1H-1,2,4-triazol-1-yl)phenyl]pyridin-1(2H)-yl}butanamide | 0.000207 | >64.0 | 32 | 32 | 8 | 0.37 | a | 432.1 |
| 372 | (2R)-4-{4-[2-fluoro-4-(2H-1,2,3-triazol-2-yl)phenyl]-2-oxopyridin-1(2H)-yl}-N-hydroxy-2-methyl-2-(methylsulfonyl)butanamide | 0.0000916 | >64.0 | 0.06 | 0.125 | 2 | | | |
| 373 | (2R)-4-{4-[4-(4,5-dimethyl-2H-1,2,3-triazol-2-yl)phenyl]-2-oxopyridin-1(2H)-yl}-N-hydroxy-2-methyl-2-(methylsulfonyl)butanamide | 0.0000899 | >64.0 | 0.125 | 0.5 | 1 | 0.55 | a | 460.2 |
| 374 | (2R)-N-hydroxy-2-methyl-2-(methylsulfonyl)-4-[2-oxo-4-(4-pyridin-2-ylphenyl)pyridin-1(2H)-yl]butanamide | 0.0000573 | 16 | 0.25 | 0.5 | 1 | 0.34 | a | 442.1 |
| 375 | (2R)-N-hydroxy-2-methyl-4-{4-[4-(4-methylpyrimidin-2-yl)phenyl]-2-oxopyridin-1(2H)-yl}-2-(methylsulfonyl)butanamide | 0.000753 | >64.0 | 0.5 | 2 | 4 | 0.48 | a | 457.2 |
| 376 | (2R)-N-hydroxy-2-methyl-2-(methylsulfonyl)-4-{4-[4-(2-methyl-2H-tetrazol-5-yl)phenyl]-2-oxopyridin-1(2H)-yl}butanamide | | >64.0 | 0.5 | 2 | 2 | | | |
| 377 | (2R)-N-hydroxy-2-methyl-2-(methylsulfonyl)-4-{4-[4-(4-methyl-1H-1,2,3-triazol-1-yl)phenyl]-2-oxopyridin-1(2H)-yl}butanamide | 0.0004 | 32 | 8 | 32 | 8 | 0.41 | a | 446.1 |
| 378 | (2R)-N-hydroxy-2-methyl-2-(methylsulfonyl)-4-{4-[4-(5-methyl-1H-tetrazol-1-yl)phenyl]-2-oxopyridin-1(2H)-yl}butanamide | 0.00208 | >64.0 | 32 | >64.0 | 64 | 0.37 | a | 447.1 |
| 379 | (2R)-N-hydroxy-2-methyl-2-(methylsulfonyl)-4-{4-[4-(5-methyl-2H-tetrazol-2-yl)phenyl]-2-oxopyridin-1(2H)-yl}butanamide | 0.000178 | >64.0 | 0.5 | 2 | 2 | 0.47 | a | 447.1 |
| 380 | (2R)-N-hydroxy-4-[4-(4-isothiazol-4-ylphenyl)-2-oxopyridin-1(2H)-yl]-2-methyl-2-(methylsulfonyl)butanamide | 0.00022 | >64.0 | 0.5 | 4 | 1 | 0.49 | a | 448.1 |
| 381 | (2R)-N-hydroxy-4-{4-[6-(4-hydroxypiperidin-1-yl)-2-naphthyl]-2-oxopyridin-1(2H)-yl}-2-methyl-2-(methylsulfonyl)butanamide | 0.000661 | >64.0 | 1 | 16 | 16 | 0.34 | a | 514.2 |
| 382 | (2R)-4-{4-[4-(3,5-dimethyl-4H-1,2,4-triazol-4-yl)phenyl]-2-oxopyridin-1(2H)-yl}-N-hydroxy-2-methyl-2-(methylsulfonyl)butanamide | 0.0398 | >64.0 | >64.0 | >64.0 | >64.0 | 0.3 | a | 460.2 |
| 383 | (2R)-N-hydroxy-2-methyl-2-(methylsulfonyl)-4-{4-[4-(3-methyl-4H-1,2,4-triazol-4-yl)phenyl]-2-oxopyridin-1(2H)-yl}butanamide | 0.00385 | >64.0 | >64.0 | >64.0 | >64.0 | 0.3 | a | 446.1 |
| 384 | (2R)-4-{4-[4-(3,5-dimethyl-1H-1,2,4-triazol-1-yl)phenyl]-2-oxopyridin-1(2H)-yl}-N-hydroxy-2-methyl-2-(methylsulfonyl)butanamide | 0.00159 | >64.0 | 8 | 64 | 16 | 0.35 | a | 460.2 |
| 385 | (2R)-4-[4-(2-ethoxyquinolin-6-yl)-2-oxopyridin-1(2H)-yl]-N-hydroxy-2-methyl-2-(methylsulfonyl)butanamide | 0.0000468 | 4 | 0.06 | 0.5 | 0.5 | 0.55 | a | 460.2 |
| 386 | (2R)-4-[4-(2,4-dichlorophenyl)-2-oxopyridin-1(2H)-yl]-N-hydroxy-2-methyl-2-(methylsulfonyl)butanamide | | >64.0 | 2 | 2 | 2 | | | |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 387 | (2R)-N-hydroxy-4-{4-[4-(5-methoxypyrimidin-2-yl)phenyl]-2-oxopyridin-1(2H)-yl}-2-methyl-2-(methylsulfonyl)butanamide | 0.0000131 | >64.0 | 0.06 | 0.5 | 0.5 | 0.49 | a | 473.1 |
| 388 | (2R)-N-hydroxy-4-{4-[4-(1H-imidazol-1-yl)phenyl]-2-oxopyridin-1(2H)-yl}-2-methyl-2-(methylsulfonyl)butanamide | >0.00533 | >64.0 | 16 | >64.0 | 16 | 0.28 | a | 431.1 |
| 389 | (2R)-N-hydroxy-2-methyl-2-(methylsulfonyl)-4-{4-[4-(1,3-oxazol-4-yl)phenyl]-2-oxopyridin-1(2H)-yl}butanamide | 0.000187 | >64.0 | 1 | 2 | 1 | 0.44 | a | 432.1 |
| 390 | (2R)-N-hydroxy-4-[4-(4-isopropoxyphenyl)-2-oxopyridin-1(2H)-yl]-2-methyl-2-(methylsulfonyl)butanamide | 0.000485 | >64.0 | 0.25 | 0.5 | 0.5 | 0.56 | a | 423.2 |
| 391 | (2R)-N-hydroxy-2-methyl-2-(methylsulfonyl)-4-{2-oxo-4-[4-(trifluoromethoxy)phenyl]pyridin-1(2H)-yl}butanamide | 0.000378 | >64.0 | 0.25 | 1 | 0.5 | 0.58 | a | 449.1 |
| 392 | (2R)-4-[4-(2-chloro-5-fluorophenyl)-2-oxopyridin-1(2H)-yl]-N-hydroxy-2-methyl-2-(methylsulfonyl)butanamide | 0.00587 | >64.0 | 16 | 16 | 8 | 0.51 | a | 417.1 |
| 393 | (2R)-4-[4-(2-fluoro-4-methoxyphenyl)-3-methyl-2-oxopyridin-1(2H)-yl]-N-hydroxy-2-methyl-2-(methylsulfonyl)butanamide | 0.000214 | 64 | 0.5 | 1 | 1 | 0.53 | a | 427.1 |
| 394 | (2R)-4-[4-(4-chloro-2-fluorophenyl)-3-methyl-2-oxopyridin-1(2H)-yl]-N-hydroxy-2-methyl-2-(methylsulfonyl)butanamide | 0.000248 | >64.0 | 1 | 1 | 1 | 0.59 | a | 431.1 |
| 395 | (2R)-4-[4-(4-fluorophenyl)-3-methyl-2-oxopyridin-1(2H)-yl]-N-hydroxy-2-methyl-2-(methylsulfonyl)butanamide | 0.000325 | >64.0 | 1 | 4 | 2 | 0.53 | a | 397.1 |
| 396 | (2R)-4-[4-(4-chlorophenyl)-3-methyl-2-oxopyridin-1(2H)-yl]-N-hydroxy-2-methyl-2-(methylsulfonyl)butanamide | 0.000107 | >64.0 | 0.25 | 0.5 | 0.5 | 0.58 | a | 413.1 |
| 397 | (2R)-N-hydroxy-4-[4-(4-methoxyphenyl)-3-methyl-2-oxopyridin-1(2H)-yl]-2-methyl-2-(methylsulfonyl)butanamide | 0.000125 | 64 | 0.25 | 0.5 | 1 | 0.51 | a | 409.1 |
| 398 | (2R)-4-[4-(4-cyanophenyl)-3-methyl-2-oxopyridin-1(2H)-yl]-N-hydroxy-2-methyl-2-(methylsulfonyl)butanamide | 0.000349 | 64 | 4 | 8 | 2 | 0.46 | a | 404.1 |
| 399 | (2R)-4-{4-[4-(difluoromethoxy)phenyl]-3-methyl-2-oxopyridin-1(2H)-yl}-N-hydroxy-2-methyl-2-(methylsulfonyl)butanamide | 0.000119 | 64 | 0.5 | 1 | 1 | 0.55 | a | 445.1 |
| 400 | (2R)-N-hydroxy-2-methyl-2-(methylsulfonyl)-4-[2-oxo-4-(4-pyrimidin-4-ylphenyl)pyridin-1(2H)-yl]butanamide | 0.000338 | >64.0 | 1 | 4 | 2 | 0.4 | a | 443.1 |
| 401 | (2R)-N-hydroxy-2-methyl-2-(methylsulfonyl)-4-{4-[4-(1-oxido-2H-1,2,3-triazol-2-yl)phenyl]-2-oxopyridin-1(2H)-yl}butanamide | 0.00146 | >64.0 | 8 | 16 | 8 | 0.35 | a | 448.1 |
| 402 | (2R)-N-hydroxy-2-methyl-2-(methylsulfonyl)-4-[2-oxo-4-(4-pyridin-4-ylphenyl)pyridin-1(2H)-yl]butanamide | 0.000272 | >64.0 | 0.5 | 2 | 2 | 0.3 | a | 442.1 |
| 403 | (2R)-N-hydroxy-4-[4-{4-[2-(2-methoxyethoxy)ethoxy]phenyl}-2-oxopyridin-1(2H)-yl]-2-methyl-2-(methylsulfonyl)butanamide | 0.000582 | 64 | 1 | 8 | 4 | 0.45 | a | 483.2 |
| 404 | (2R)-4-[4-(2-ethoxypyrimidin-5-yl)-2-oxopyridin-1(2H)-yl]-N-hydroxy-2-methyl-2-(methylsulfonyl)butanamide | 0.0507 | >64.0 | >64.0 | >64.0 | >64.0 | 0.38 | a | 411.1 |
| 405 | (2R)-N-hydroxy-2-methyl-2-(methylsulfonyl)-4-{2-oxo-4-[4-(1,3-thiazol-4-yl)phenyl]pyridin-1(2H)-yl}butanamide | 0.000194 | >64.0 | 0.125 | 0.25 | 1 | 0.47 | a | 448.1 |
| 406 | (2R)-N-hydroxy-2-methyl-2-(methylsulfonyl)-4-{2-oxo-4-[4-(1,3-thiazol-5-yl)phenyl]pyridin-1(2H)-yl}butanamide | 0.000153 | >64.0 | 0.25 | 1 | 0.5 | 0.44 | a | 448.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 407 | (2R)-N-hydroxy-4-{4-[4-(4-hydroxy-2H-1,2,3-triazol-2-yl)phenyl]-2-oxopyridin-1(2H)-yl}-2-methyl-2-(methylsulfonyl)butanamide | 0.00263 | 64 | 16 | 64 | 32 | 0.41 | a | 448.1 |
| 408 | (2R)-N-hydroxy-4-[4-{4-[3-(hydroxymethyl)isoxazol-5-yl]phenyl}-2-oxopyridin-1(2H)-yl]-2-methyl-2-(methylsulfonyl)butanamide | 0.000657 | >64.0 | 8 | 16 | 8 | 0.39 | a | 462.1 |
| 409 | (2R)-4-[4-{2-(dimethylamino)pyrimidin-5-yl]phenyl}-2-oxopyridin-1(2H)-yl]-N-hydroxy-2-methyl-2-(methylsulfonyl)butanamide | 0.000196 | >64.0 | 0.5 | 2 | 2 | 0.45 | a | 486.2 |
| 410 | (2R)-N-hydroxy-4-{4-[4-(2-methoxypyrimidin-5-yl)phenyl]-2-oxopyridin-1(2H)-yl}-2-methyl-2-(methylsulfonyl)butanamide | 0.00015 | >64.0 | 0.5 | 2 | 1 | 0.45 | a | 473.2 |
| 411 | (2R)-N-hydroxy-4-[4-(4-isoxazol-5-ylphenyl)-2-oxopyridin-1(2H)-yl]-2-methyl-2-(methylsulfonyl)butanamide | 0.000165 | >64.0 | 0.5 | 1 | 0.5 | 0.45 | a | 432.1 |
| 412 | (2R)-4-[4-(4-cyano-2-fluorophenyl)-3-methyl-2-oxopyridin-1(2H)-yl]-N-hydroxy-2-methyl-2-(methylsulfonyl)butanamide | 0.00127 | >64.0 | 8 | 16 | 4 | 0.47 | a | 422.1 |
| 413 | (2R)-4-[4-(3-chloro-2-fluorophenyl)-3-methyl-2-oxopyridin-1(2H)-yl]-N-hydroxy-2-methyl-2-(methylsulfonyl)butanamide | 0.00125 | >64.0 | 2 | 2 | 2 | 0.56 | a | 431.1 |
| 414 | (2R)-4-[4-(2,3-dichlorophenyl)-3-methyl-2-oxopyridin-1(2H)-yl]-N-hydroxy-2-methyl-2-(methylsulfonyl)butanamide | 0.00192 | >64.0 | 2 | 4 | 8 | 0.58 | a | 447.1 |
| 415 | (2R)-4-{4-[4-(6-cyanopyridin-3-yl)phenyl]-2-oxopyridin-1(2H)-yl}-N-hydroxy-2-methyl-2-(methylsulfonyl)butanamide | | >64.0 | 1 | 4 | 2 | | | |
| 416 | (2R)-4-{4-[4-(4,5-dimethyl-1H-1,2,3-triazol-1-yl)phenyl]-2-oxopyridin-1(2H)-yl}-N-hydroxy-2-methyl-2-(methylsulfonyl)butanamide | 0.00194 | >64.0 | 64 | >64.0 | 32 | 0.42 | a | 460.2 |
| 417 | (2R)-N-hydroxy-2-methyl-2-(methylsulfonyl)-4-{4-[4-(1,2,4-oxadiazol-5-yl)phenyl]-2-oxopyridin-1(2H)-yl}butanamide | 0.0151 | >64.0 | 8 | >64.0 | 64 | 0.36 | a | 433.1 |
| 418 | (2R)-N-hydroxy-4-[6-(hydroxymethyl)-2'-oxo-3,4'-bipyridin-1'(2'H)-yl]-2-methyl-2-(methylsulfonyl)butanamide | >0.100 | >64.0 | >64.0 | >64.0 | 64 | 0.21 | a | 396.1 |
| 419 | (2R)-N-hydroxy-2-methyl-2-(methylsulfonyl)-4-{2-oxo-4-[4-(1,2,4-thiadiazol-5-yl)phenyl]pyridin-1(2H)-yl}butanamide | 0.000127 | >64.0 | 0.25 | 1 | 1 | 0.46 | a | 449.1 |
| 420 | (2R)-N-hydroxy-2-methyl-4-[1'-(5-methylpyrimidin-2-yl)-2-oxo-1',2',3',6'-tetrahydro-4,4'-bipyridin-1(2H)-yl]-2-(methylsulfonyl)butanamide | 0.00172 | >64.0 | 4 | 8 | 8 | 0.39 | a | 462.2 |
| 421 | (2R)-N-hydroxy-2-methyl-2-(methylsulfonyl)-4-{2-oxo-4-[4-(1H-tetrazol-1-yl)phenyl]pyridin-1(2H)-yl}butanamide | 0.000911 | >64.0 | >64.0 | >64.0 | 64 | 0.37 | a | 433.1 |
| 422 | (2R)-N-hydroxy-2-methyl-4-{4-[4-(6-methylpyridin-2-yl)phenyl]-2-oxopyridin-1(2H)-yl}-2-(methylsulfonyl)butanamide | 0.0012 | >64.0 | 0.5 | 2 | 4 | 0.33 | a | 456.2 |
| 423 | (2R)-N-hydroxy-2-methyl-2-(methylsulfonyl)-4-[2-oxo-4-(4-pyrimidin-5-ylphenyl)pyridin-1(2H)-yl]butanamide | | >64.0 | 1 | 8 | 4 | | | |
| 424 | (2R)-N-hydroxy-2-methyl-2-(methylsulfonyl)-4-{2-oxo-4-[4-(pyrimidin-2-yloxy)phenyl]pyridin-1(2H)-yl}butanamide | 0.000708 | >64.0 | 4 | 8 | 4 | 0.41 | a | 459.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 425 | (2R)-N-hydroxy-2-methyl-2-(methylsulfonyl)-4-[2-oxo-4-{4-[(5-propylpyrimidin-2-yl)oxy]phenyl}pyridin-1(2H)-yl]butanamide | <0.00100 | | | | | 0.55 | a | 501.2 |
| 426 | (2R)-4-{4-[4-(2-cyanophenoxy)phenyl]-2-oxopyridin-1(2H)-yl}-N-hydroxy-2-methyl-2-(methylsulfonyl)butanamide | 0.000193 | 32 | 0.25 | 1 | 1 | 0.56 | a | 482.1 |
| 427 | (2R)-4-[4-{4-[(3-cyanopyridin-2-yl)oxy]phenyl}-2-oxopyridin-1(2H)-yl]-N-hydroxy-2-methyl-2-(methylsulfonyl)butanamide | <0.00100 | >64.0 | 2 | 4 | 2 | 0.5 | a | 483.1 |
| 428 | (2R)-4-[4-{4-[(4-chloropyridin-2-yl)oxy]phenyl}-2-oxopyridin-1(2H)-yl]-N-hydroxy-2-methyl-2-(methylsulfonyl)butanamide | 0.000235 | >64.0 | 0.125 | 0.5 | 1 | 0.54 | a | 492.1 |
| 429 | (2R)-N-hydroxy-2-methyl-2-(methylsulfonyl)-4-{2-oxo-4-[4-(pyrazin-2-yloxy)phenyl]pyridin-1(2H)-yl}butanamide | <0.00100 | | | | | 0.44 | a | 459.1 |
| 430 | (2R)-4-[4-{4-[(5-chloropyridin-2-yl)oxy]phenyl}-2-oxopyridin-1(2H)-yl]-N-hydroxy-2-methyl-2-(methylsulfonyl)butanamide | 0.000305 | 64 | 0.125 | 0.5 | 2 | 0.59 | a | 492.1 |
| 431 | (2R)-4-[4-{4-[(3-cyano-4-methylpyridin-2-yl)oxy]phenyl}-2-oxopyridin-1(2H)-yl]-N-hydroxy-2-methyl-2-(methylsulfonyl)butanamide | 0.000444 | | | | | 0.54 | a | 497.1 |
| 432 | (2R)-N-hydroxy-2-methyl-4-[4-{4-[(4-methylpyridin-2-yl)oxy]phenyl}-2-oxopyridin-1(2H)-yl]-2-(methylsulfonyl)butanamide | <0.00100 | | | | | 0.51 | a | 472.2 |
| 433 | (2R)-4-{4-[4-(6,7-dihydro-5H-cyclopenta[d]pyrimidin-4-yloxy)phenyl]-2-oxopyridin-1(2H)-yl}-N-hydroxy-2-methyl-2-(methylsulfonyl)butanamide | | | | | | 0.47 | a | 499.2 |
| 434 | (2R)-4-[4-{4-[(5-chloropyrimidin-2-yl)oxy]phenyl}-2-oxopyridin-1(2H)-yl]-N-hydroxy-2-methyl-2-(methylsulfonyl)butanamide | <0.00100 | | | | | 0.51 | a | 493.1 |
| 435 | (2R)-N-hydroxy-2-methyl-4-[4-{4-[(3-methylpyrazin-2-yl)oxy]phenyl}-2-oxopyridin-1(2H)-yl]-2-(methylsulfonyl)butanamide | <0.00100 | | | | | 0.48 | a | 473.1 |
| 436 | (2R)-N-hydroxy-2-methyl-2-(methylsulfonyl)-4-{2-oxo-4-[4-(pyridin-2-yloxy)phenyl]pyridin-1(2H)-yl}butanamide | No Summarized Data | >64.0 | 0.5 | 1 | 2 | 0.54 | a | 458.1 |
| 437 | (2R)-4-{4-[4-(furo[3,2-c]pyridin-4-yloxy)phenyl]-2-oxopyridin-1(2H)-yl}-N-hydroxy-2-methyl-2-(methylsulfonyl)butanamide | 0.000683 | >64.0 | 0.25 | 0.5 | 4 | 0.54 | a | 498.1 |
| 438 | (2R)-4-[4-{4-[(3-cyano-6-methylpyridin-2-yl)oxy]phenyl}-2-oxopyridin-1(2H)-yl]-N-hydroxy-2-methyl-2-(methylsulfonyl)butanamide | 0.000998 | >64.0 | 4 | 16 | 8 | 0.54 | a | 497.1 |
| 439 | (2R)-N-hydroxy-4-[4-{4-[(1-isopropyl-1H-tetrazol-5-yl)oxy]phenyl}-2-oxopyridin-1(2H)-yl]-2-methyl-2-(methylsulfonyl)butanamide | 0.00105 | | | | | 0.5 | a | 491.2 |
| 440 | (2R)-4-[4-{4-[(3-chloropyridin-2-yl)oxy]phenyl}-2-oxopyridin-1(2H)-yl]-N-hydroxy-2-methyl-2-(methylsulfonyl)butanamide | 0.000325 | 64 | 0.06 | 0.5 | 2 | 0.58 | a | 492.1 |
| 441 | (2R)-4-[4-{4-[(3-cyano-4,6-dimethylpyridin-2-yl)oxy]phenyl}-2-oxopyridin-1(2H)-yl]-N-hydroxy-2-methyl-2-(methylsulfonyl)butanamide | <0.00100 | | | | | 0.57 | a | 511.2 |
| 442 | (2R)-4-[4-{4-[(2-cyanopyridin-3-yl)oxy]phenyl}-2-oxopyridin-1(2H)-yl]-N-hydroxy-2-methyl-2-(methylsulfonyl)butanamide | 0.000188 | >64.0 | 4 | 16 | 4 | 0.49 | a | 483.1 |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 443 | (2R)-N-hydroxy-2-methyl-4-[4-{4-[(5-methylpyrimidin-2-yl)oxy]phenyl}-2-oxopyridin-1(2H)-yl]-2-(methylsulfonyl)butanamide | <0.00316 | | | | | 0.45 | a | 473.1 |
| 444 | (2R)-N-hydroxy-2-methyl-2-(methylsulfonyl)-4-{2-oxo-4-[4-(quinolin-4-yloxy)phenyl]pyridin-1(2H)-yl}butanamide | 0.000259 | >64.0 | 0.125 | 1 | 2 | | a | |
| 445 | (2R)-4-{4-[4-(1,3-benzothiazol-2-yloxy)phenyl]-2-oxopyridin-1(2H)-yl}-N-hydroxy-2-methyl-2-(methylsulfonyl)butanamide | 0.000245 | >64.0 | 0.25 | 2 | 4 | | a | |
| 446 | (2R)-4-[4-{4-[(3-cyano-4-methoxypyridin-2-yl)oxy]phenyl}-2-oxopyridin-1(2H)-yl]-N-hydroxy-2-methyl-2-(methylsulfonyl)butanamide | 0.000374 | | | | | 0.51 | a | 513.1 |
| 447 | (2R)-N-hydroxy-2-methyl-4-[4-{4-[(2-methylpyridin-4-yl)oxy]phenyl}-2-oxopyridin-1(2H)-yl]-2-(methylsulfonyl)butanamide | 0.000358 | | | | | 0.35 | a | 472.1 |
| 448 | (2R)-4-[4-{4-[(5-fluoropyrimidin-2-yl)oxy]phenyl}-2-oxopyridin-1(2H)-yl]-N-hydroxy-2-methyl-2-(methylsulfonyl)butanamide | 0.000208 | | | | | 0.46 | a | 477.1 |
| 449 | (2R)-4-[4-{4-[(4,6-dimethylpyrimidin-2-yl)oxy]phenyl}-2-oxopyridin-1(2H)-yl]-N-hydroxy-2-methyl-2-(methylsulfonyl)butanamide | 0.00109 | | | | | 0.48 | a | 487.2 |
| 450 | (2R)-4-{4-[4-(1,2-benzisoxazol-3-yloxy)phenyl]-2-oxopyridin-1(2H)-yl]-N-hydroxy-2-methyl-2-(methylsulfonyl)butanamide | 0.000247 | 32 | 0.06 | 0.5 | 2 | 0.61 | a | 498.1 |
| 451 | (2R)-4-[4-(2,3-dichloro-5-fluorophenyl)-2-oxopyridin-1(2H)-yl]-N-hydroxy-2-methyl-2-(methylsulfonyl)butanamide | 0.00139 | 64 | 4 | 4 | 4 | 0.57 | a | 451 |
| 452 | (2R)-4-[4-(2,3-dichloro-4-methoxyphenyl)-2-oxopyridin-1(2H)-yl]-N-hydroxy-2-methyl-2-(methylsulfonyl)butanamide | 0.000996 | >64.0 | 4 | 4 | 2 | 0.55 | a | 463 |
| 453 | (2R)-N-hydroxy-2-methyl-2-(methylsulfonyl)-4-[2-oxo-4-(4-pyridazin-3-ylphenyl)pyridin-1(2H)-yl]butanamide | 0.00195 | >64.0 | 4 | 64 | 8 | 0.36 | a | 443.1 |
| 454 | (2R)-N-hydroxy-4-[4-(4-isoxazol-4-ylphenyl)-2-oxopyridin-1(2H)-yl]-2-methyl-2-(methylsulfonyl)butanamide | 0.00332 | >64.0 | 2 | 16 | 4 | 0.45 | a | 432.1 |
| 455 | (2R)-N-hydroxy-2-methyl-2-(methylsulfonyl)-4-{4-[4-(4-methyl-2H-1,2,3-triazol-2-yl)phenyl]-2-oxopyridin-1(2H)-yl}butanamide | 0.000169 | >64.0 | 0.06 | 0.125 | 1 | | a | |
| 456 | (2R)-N-hydroxy-2-methyl-4-{4-[4-(6-methylpyridin-3-yl)phenyl]-2-oxopyridin-1(2H)-yl}-2-(methylsulfonyl)butanamide | 0.000205 | >64.0 | 0.25 | 1 | 1 | 0.32 | a | 456.2 |
| 457 | (2R)-N-hydroxy-2-methyl-4-{4-[4-(5-methylpyrazin-2-yl)phenyl]-2-oxopyridin-1(2H)-yl}-2-(methylsulfonyl)butanamide | 0.00104 | >64.0 | 0.5 | 2 | 2 | 0.46 | a | 457.2 |
| 458 | (2R)-4-{4-[4-(5-chloropyrimidin-2-yl)phenyl]-2-oxopyridin-1(2H)-yl}-N-hydroxy-2-methyl-2-(methylsulfonyl)butanamide | 0.000155 | >64.0 | 0.06 | 0.5 | 0.5 | 0.57 | a | 477 |
| 459 | (2R)-4-[4-(3,5-difluoro-4-methoxyphenyl)-2-oxopyridin-1(2H)-yl]-N-hydroxy-2-methyl-2-(methylsulfonyl)butanamide | | >64.0 | 2 | 8 | 2 | | | |
| 460 | (2S)-4-[4-(2-fluoro-4-methoxyphenyl)-2-oxopyridin-1(2H)-yl]-N-hydroxy-2-methyl-2-(methylsulfonyl)butanamide | | | | | | | | |
| 461 | (2R)-N-hydroxy-2-methyl-4-{4-[4-(5-methylpyrimidin-2-yl)phenyl]-2-oxopyridin-1(2H)-yl}-2-(methylsulfonyl)butanamide | | >64.0 | 0.125 | 1 | 1 | | | |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 462 | (2R)-N-hydroxy-2-methyl-2-(methylsulfonyl)-4-{2-oxo-4-[4-(tetrahydrofuran-2-ylmethoxy)phenyl]pyridin-1(2H)-yl}butanamide | | >64.0 | 0.5 | 1 | 1 | | | |
| 463 | trans-4-[(4-{1-[(3R)-4-(hydroxyamino)-3-methyl-3-(methylsulfonyl)-4-oxobutyl]-2-oxo-1,2-dihydropyridin-4-yl}phenoxy)methyl]cyclohexyl dihydrogen phosphate | | | | | | | | |
| 464 | (2R)-4-[4-(4-butylphenyl)-2-oxopyridin-1(2H)-yl]-N-hydroxy-2-methyl-2-(methylsulfonyl)butanamide | 0.000166 | 8 | 0.03 | 0.25 | 1 | 0.67 | a | 421.2 |
| 465 | (2R)-N-hydroxy-2-methyl-2-(methylsulfonyl)-4-[2-oxo-4-(4-propylphenyl)pyridin-1(2H)-yl]butanamide | 0.000189 | 64 | 0.125 | 0.5 | 0.5 | 0.62 | a | 407.2 |
| 466 | (2R)-N-hydroxy-4-[4-(3-isopropylphenyl)-2-oxopyridin-1(2H)-yl]-2-methyl-2-(methylsulfonyl)butanamide | | 64 | 2 | 16 | 4 | | | |
| 467 | (2R)-4-[4-(4-cyano-3-methylphenyl)-2-oxopyridin-1(2H)-yl]-N-hydroxy-2-methyl-2-(methylsulfonyl)butanamide | 0.0000999 | >64.0 | 4 | 8 | 2 | | | |
| 468 | (2R)-N-hydroxy-4-[4-(3-methoxy-2-methylphenyl)-2-oxopyridin-1(2H)-yl]-2-methyl-2-(methylsulfonyl)butanamide | | >64.0 | 2 | 4 | 2 | | | |
| 469 | (2R)-N-hydroxy-2-methyl-2-(methylsulfonyl)-4-[2-oxo-4-(1-phenyl-1H-pyrazol-4-yl)pyridin-1(2H)-yl]butanamide | 0.0205 | | | | | | | |
| 470 | (2R)-N-hydroxy-4-{4-[3-(2-methoxyethyl)phenyl]-2-oxopyridin-1(2H)-yl}-2-methyl-2-(methylsulfonyl)butanamide | 0.0016 | >64.0 | 16 | 32 | 32 | | | |
| 471 | (2R)-N-hydroxy-2-methyl-2-(methylsulfonyl)-4-[2-oxo-4-(5-phenyl-1,3,4-thiadiazol-2-yl)pyridin-1(2H)-yl]butanamide | 0.00323 | | | | | | | |
| 472 | (2R)-4-[4-(4-cyano-2-methylphenyl)-2-oxopyridin-1(2H)-yl]-N-hydroxy-2-methyl-2-(methylsulfonyl)butanamide | | >64.0 | 32 | 64 | 8 | | | |
| 473 | (2R)-4-[4-(3-aminoisoquinolin-7-yl)-2-oxopyridin-1(2H)-yl]-N-hydroxy-2-methyl-2-(methylsulfonyl)butanamide | | >64.0 | 16 | 64 | 16 | | | |
| 474 | (2R)-N-hydroxy-2-methyl-2-(methylsulfonyl)-4-[2-oxo-4-(2-phenyl-1,3-oxazol-5-yl)pyridin-1(2H)-yl]butanamide | 0.00895 | >64.0 | 64 | >64.0 | 64 | | | |
| 475 | (2R)-4-[4-{3-[(1-cyanoethyl)thio]phenyl}-2-oxopyridin-1(2H)-yl]-N-hydroxy-2-methyl-2-(methylsulfonyl)butanamide | | >64.0 | 8 | 32 | 8 | | | |
| 476 | (2R)-4-[4-(3-cyano-4-methylphenyl)-2-oxopyridin-1(2H)-yl]-N-hydroxy-2-methyl-2-(methylsulfonyl)butanamide | 0.000932 | >64.0 | 16 | 64 | 8 | | | |
| 477 | (2R)-4-[4-(4-cyano-2-fluoro-5-methoxyphenyl)-2-oxopyridin-1(2H)-yl]-N-hydroxy-2-methyl-2-(methylsulfonyl)butanamide | 0.00192 | >64.0 | 64 | >64.0 | 32 | | | |
| 478 | methyl 3-(4-{1-[(3R)-4-(hydroxyamino)-3-methyl-3-(methylsulfonyl)-4-oxobutyl]-2-oxo-1,2-dihydropyridin-4-yl}phenyl)propanoate | 0.000129 | >64.0 | 2 | 4 | 1 | | | |
| 479 | (2R)-4-[4-(3-cyano-4-ethoxyphenyl)-2-oxopyridin-1(2H)-yl]-N-hydroxy-2-methyl-2-(methylsulfonyl)butanamide | 0.00461 | >64.0 | 64 | >64.0 | 16 | | | |
| 480 | (2R)-4-{4-[3-(difluoromethoxy)phenyl]-2-oxopyridin-1(2H)-yl}-N-hydroxy-2-methyl-2-(methylsulfonyl)butanamide | 0.00202 | >64.0 | 8 | 16 | 4 | | | |

TABLE 5-continued

| Example Number | IUPACNAME | PA: IC50 | AB-3167: | EC-1 | KP-3700 | PA-7 | Retention Time | Method | MASS |
|---|---|---|---|---|---|---|---|---|---|
| 481 | (2R)-N-hydroxy-2-methyl-2-(methylsulfonyl)-4-[2-oxo-4-(1-oxo-3,4-dihydro-1H-isochromen-7-yl)pyridin-1(2H)-yl]butanamide | 0.0236 | >64.0 | >64.0 | >64.0 | 64 | | | |
| 482 | (2R)-N-hydroxy-4-[4-(4-methoxyquinolin-6-yl)-2-oxopyridin-1(2H)-yl]-2-methyl-2-(methylsulfonyl)butanamide | 0.0213 | >64.0 | >64.0 | >64.0 | >64.0 | | | |
| 483 | (2R)-N-hydroxy-2-methyl-4-[4-(3-methyl-2-oxo-2,3-dihydro-1,3-benzothiazol-6-yl)-2-oxopyridin-1(2H)-yl]-2-(methylsulfonyl)butanamide | 0.000808 | >64.0 | 8 | 32 | 8 | | | |
| 484 | (2R)-N-hydroxy-2-methyl-4-[4-(4-methyl-2-oxo-1,2,3,4-tetrahydroquinolin-6-yl)-2-oxopyridin-1(2H)-yl]-2-(methylsulfonyl)butanamide | | >64.0 | >64.0 | >64.0 | >64.0 | | | |
| 485 | (2R)-4-[4-(3-aminoisoquinolin-6-yl)-2-oxopyridin-1(2H)-yl]-N-hydroxy-2-methyl-2-(methylsulfonyl)butanamide | 0.00129 | >64.0 | 64 | >64.0 | 32 | | | |
| 486 | (2R)-N-hydroxy-2-methyl-2-(methylsulfonyl)-4-[2-oxo-4-(3-oxo-1,3-dihydro-2-benzofuran-5-yl)pyridin-1(2H)-yl]butanamide | 0.0304 | >64.0 | >64.0 | >64.0 | >64.0 | | | |
| 487 | (2R)-4-{4-[4-(difluoromethoxy)-2,3-difluorophenyl]-2-oxopyridin-1(2H)-yl}-N-hydroxy-2-methyl-2-(methylsulfonyl)butanamide | 0.000178 | | | | | 0.59 | a | 467.3 |
| 488 | 4-[4-(3-cyclopentylpropoxy)-2-oxopyridin-1(2H)-yl]-N-hydroxy-2-methyl-2-(methylsulfonyl)butanamide | 0.0109 | 64 | 8 | 64 | 64 | 0.71 | a | 415.2 |

What is claimed is:

1. A compound of the formula:

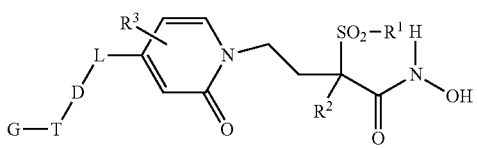

I or a pharmaceutically acceptable salt thereof, wherein
$R^1$ is methyl;
$R^2$ is methyl;
$R^3$ is hydrogen;
L is absent, or is selected from the group consisting of $C_1$-$C_6$ alkylene which may be optionally substituted, $C_2$-$C_6$ alkenylene, $C_2$-$C_6$ alkynylene, —$(CH_2)_p$—O—$(CH_2)_n$, and —$(CH_2)_p$—O—$(CH_2)_z$—O—$(CH_2)_n$—;
n is an integer ranging from 0 to 4;
p is an integer ranging from 0 to 4;
q is an integer ranging from 0 to 6;
z is an integer ranging from 1 to 4;
D is selected from the group consisting of:
  i) ($C_3$-$C_{10}$)cycloalkyl, optionally substituted,
  ii) ($C_6$-$C_{10}$)aryl, optionally substituted,
  iii) heteroaryl, optionally substituted,
  iv) heterocyclic, optionally substituted;
T is absent, or is —S—$(CH_2)_z$—O—$(CH_2)_n$, —O—$(CH_2)_z$—S—$(CH_2)_n$, —$(CH_2)_q$—, —$(CH_2)_n$—C(O)—$(CH_2)_p$—, —$(CH_2)_n$—O—$(CH_2)_p$—, —$(CH_2)_n$—S—$(CH_2)_p$, S—$C_1$-$C_6$ alkylene which may be optionally substituted, —O—$C_1$-$C_6$ alkylene which may be optionally substituted, —O—$(CH_2)_p$—C(O)—$(CH_2)_n$—, —$(CH_2)_p$—C(O)—$(CH_2)_q$—O—$(CH_2)_n$—, —O—$(CH_2)_z$—O—$(CH_2)_n$—, —O—$(CH_2)_z$—O—$(CH_2)_z$—O—$(CH_2)_n$—, —S—$(CH_2)_z$—S—$(CH_2)_n$—, —$(CH_2)_n$—SH, or —$(CH_2)_n$—OH, and;
G is absent, or is selected from the group consisting of:
  i) ($C_3$-$C_{10}$)cycloalkyl, optionally substituted;
  ii) ($C_6$-$C_{10}$)aryl optionally substituted;
  iii) heteroaryl, optionally substituted, and;
  iv) heterocyclic, optionally substituted.

2. A compound according to claim 1, or a pharmaceutically acceptable salt thereof in which said compound is the R-enantiomer.

3. A compound according to claim 1, or a pharmaceutically acceptable salt thereof in which L is absent.

4. A compound according to claim 1, or a pharmaceutically acceptable salt thereof in which G and T is absent.

5. A compound according to claim 1, or a pharmaceutically acceptable salt thereof in which D is ($C_6$-$C_{10}$)aryl optionally substituted.

6. A compound according to claim 4, or a pharmaceutically acceptable salt thereof in which D is optionally substituted phenyl.

7. A pharmaceutical composition comprising a compound according to claim 1, or a pharmaceutically acceptable salt thereof in admixture with at least one pharmaceutically acceptable excipient.

8. A method for treating bacterial infections comprising administering a compound according to claim 1, or a pharmaceutically acceptable salt thereof to a patient in need thereof.

9. A method of treating a bacterial infection in a patient, wherein the patient is a livestock animal or companion animal, the method comprising contacting the bacteria in the livestock animal or companion animal with a therapeutically effective amount of (2R)—N-hydroxy-2-methyl-2-(methylsulfonyl)-4-{2-oxo-4-[4-(2H-1,2,3-triazol-2-yl)phenyl]pyridine-1-(2H)-yl}butanamide, or a pharmaceutically acceptable salt thereof.

10. The method of claim 9 wherein the patient is a livestock animal.

11. The method of claim 9 wherein the patient is a companion animal.

12. The method according to claim 9 wherein the bacterial infection is a Gram-negative bacterial infection.

13. The method according to claim 9 wherein the Gram-negative bacterial infection is caused by a Gram-negative bacteria selected from the group consisting of *Acinetobacter baumannii, Acinetobacter* spp., *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia*, and *Pseudomonas aeruginosa.*

14. The method according to claim 9 wherein the bacterial infection is selected from the group consisting of nosocomial pneumonia, urinary tract infection, bacteremia, sepsis, skin infection, soft-tissue infection, intra-abdominal infection, lung infection, endocarditis, diabetic foot infection, osteomyelitis and central nervous system infection.

\* \* \* \* \*

UNITED STATES PATENT AND TRADEMARK OFFICE
CERTIFICATE OF CORRECTION

PATENT NO. : 9,018,384 B2
APPLICATION NO. : 14/447788
DATED : April 28, 2015
INVENTOR(S) : Matthew Frank Brown It is certified that error appears in the above-identified patent and that said Letters Patent is hereby corrected as shown below:

Title Page

Page 1 (item 63, Related U.S. Application Data) at line 3, Change "12/515,607," to --13/515,607,--.

In column 1 (page 2, item 56) at line 32, Under Other Publications, change "(toclizumab)" to --(tocilizumab)--.

In column 1 (page 2, item 56) at line 36, Under Other Publications, change "Medicinal Medicinal" to --Medicinal--.

In column 1 (page 2, item 56) at line 42, Under Other Publications, change "ISR" to --(ISR)--.

In column 2 (page 2, item 56) at line 5, Under Other Publications, change "Antiboitics" to --Antibiotics--.

In column 2 (page 2, item 56) at line 22, Under Other Publications, change "et l.," to --et al.,--.

Specification

In column 3 at line 63, Change "$C_1$-$C_6$lkyl" to --$C_1$-$C_6$ alkyl--.

In column 4 at line 4, Change ""($C_3$-$C_{10}$) cycloalkyl"" to --"($C_3$-$C_{10}$)cycloalkyl"--.

In column 4 at line 10, Change ""($C_3$-$C_{10}$) cycloalkyl"" to --"($C_3$-$C_{10}$)cycloalkyl"--.

In column 4 at line 11, Change "($C_3$-$C_{10}$) cycloalkyl" to --($C_3$-$C_{10}$)cycloalkyl--.

In column 5 at line 53, Change "($C_1$-$C_6$) alkyl," to --($C_1$-$C_6$)alkyl,--.

In column 8 at line 38, Change "(i.e" to --(i.e.--.

In column 8 at line 67, Change "wt/wt %." to --wt/wt %).--.

In column 12 at line 48, Change "carbonyliimidazole" to --carbonyldiimidazole--.

In column 13 at line 23, Change "i.e" to --i.e.--.

In column 13 at line 37, Change "organobornane" to --organoborane--.

Signed and Sealed this
Ninth Day of February, 2016

Michelle K. Lee
*Director of the United States Patent and Trademark Office*

CERTIFICATE OF CORRECTION (continued)
U.S. Pat. No. 9,018,384 B2

Specification

In column 13 at line 38, Change "etc.,)" to --etc.)--.

In column 13 at line 58, Change "i.e" to --i.e.--.

In column 14 at line 18, Change "Willamson/" to --Williamson/--.

In column 14 at line 39, Change "dimethyoxyethane" to --dimethyloxyethane--.

In column 15 at line 9, Change "malophilia." to --maltophilia.--.

In column 16 at line 1, Change "intravetricular" to --intraventricular--.

In column 16 at line 3, Change "accessibly" to --accessible--.

In column 16 at line 35, Change "polyvinylpyrollidone;" to --polyvinylpyrrolidone;--.

In column 16 at line 41, Change "will" to --well--.

In column 19 at line 12, Change "morphiline" to --morpholine--.

In column 24 at line 64, Change "$^1$NMR" to --$^1$H NMR--.

In column 25 at line 18, Change "$^1$NMR" to --$^1$H NMR--.

In column 27 at line 56, Change "Trisdibenzylidine" to --Trisdibenzylidene--.

In column 29 at line 17, Change "Netrahydro" to --N-(tetrahydro--.

In column 29 at line 33, Change "Netrahydro" to --N-(tetrahydro--.

In column 29 at line 59, Change "Netrahydro" to --N-(tetrahydro--.

In column 30 at line 27, Change "over night." to --overnight.--.

In column 31 at line 40, Change "(M+1)$^1$H" to --(M+1). $^1$H--.

In column 31 at line 50, Change "phenyl}" to --phenyl]--.

In column 31 at line 50, Change "yl]" to --yl}--.

In column 34 at line 42, Change "over night." to --overnight.--.

In column 36 at line 12, Change "methoxyl phenyl}" to --methoxy]phenyl}--.

In column 38 at lines 3-4, Change "Netrahydro" to --N-(tetrahydro--.

In column 38 at line 35, Change "Netrahydro" to --N-(tetrahydro--.

In column 39 at lines 37-38, Change "Netrahydro" to --N-(tetrahydro--.

In column 39 at line 49, Change "Netrahydro" to --N-(tetrahydro--.

In column 39 at line 59, Change "Netrahydro" to --N-(tetrahydro--.

In column 39 at line 64, Change "(M+1)$^1$H" to --(M+1). $^1$H--.

In column 41 at line 8, Change "Netrahydro" to --N-(tetrahydro--.

In column 41 at line 20, Change "2- (methylsulfonyl)" to --2-(methylsulfonyl)--.

In column 42 at line 5, Change "(M+1) $^1$H" to --(M+1). $^1$H--.

In columns 41-42 (NMR, Example Number 10-A, Table 2) at line 2, Change "d ppm" to --δ ppm--.

In columns 41-42 (Example Number 10-B, Table 2) at line 3, Change "yl[-2" to --yl]-2--.

CERTIFICATE OF CORRECTION (continued)
U.S. Pat. No. 9,018,384 B2

Specification

In columns 41-42 at line 2 (Example 10-C, Table 2), Change "y}-" to --yl}- --.

In columns 41-42 (NMR, Example 10-C, Table 2) at line 2, Change "d ppm" to --δ ppm--.

In columns 41-42 (NMR, Example 10-D, Table 2) at line 2, Change "d ppm" to --δ ppm--.

In columns 43-44 (NMR, Example 10-E, Table 2) at line 2, Change "d ppm" to --δ ppm--.

In columns 43-44 (NMR, Example 10-F, Table 2) at line 2, Change "d ppm" to --δ ppm--.

In columns 43-44 (NMR, Example 10-G, Table 2) at line 2, Change "d ppm" to --δ ppm--.

In columns 43-44 (NMR, Example 10-H, Table 2) at line 2, Change "d ppm" to --δ ppm--.

In columns 43-44 (NMR, Example 10-J, Table 2) at line 2, Change "d ppm" to --δ ppm--.

In columns 43-44 (NMR, Example 10-K, Table 2) at line 2, Change "d ppm" to --δ ppm--.

In column 46 at line 36, Change "compound" to --compound.--.

In column 48 at line 65, Change "(M+1) $^1$H" to --(M+1). $^1$H--.

In column 50 at line 64, Change "(M+1) $^1$H" to --(M+1). $^1$H--.

In column 52 at line 18, Change "(M+1) 1H" to --(M+1). $^1$H--.

In column 53 at line 10, Change "(M+1) 1H" to --(M+1). $^1$H--.

In column 53 at line 32, Change "(M+1) 1H" to --(M+1). $^1$H--.

In column 55 at line 18, Change "(d-6-DMSO) σ" to --(d6-DMSO) δ--.

In column 56 at line 39, Change "d ppm" to --δ ppm--.

In column 57 at line 6, Change "d ppm" to --δ ppm--.

In column 57 at line 37, Change "d ppm" to --δ ppm--.

In column 58 at line 6, Change "d ppm" to --δ ppm--.

In column 58 at line 36, Change "oxadiazole" to --oxadiazole.--.

In column 58 at line 38, Change "d ppm" to --δ ppm--.

In column 59 at line 6, Change "d ppm" to --δ ppm--.

In column 59 at lines 45-46, Change "chromotography" to --chromatography--.

In column 60 at line 24, Change "25%)" to --25%).--.

In column 60 at line 26, Change "d ppm" to --δ ppm--.

In column 62 at line 10, Change "(II)dichloromethane" to --(II) dichloromethane--.

In column 65 at line 38, Change "(II)dichloromethane" to --(II) dichloromethane--.

In column 65 at line 54, Change "Netrahydro" to --N-(tetrahydro--.

In column 66 at line 7, Change "Netrahydro" to --N-(tetrahydro--.

In column 66 at line 8, Change "89.1%." to --89.1%).--.

In column 66 at line 17, Change "Netrahydro" to --N-(tetrahydro--.

In column 68 at line 4, Change "butanamide" to --butanamide.--.

In column 68 at lines 38-39, Change "Netrahydro" to --N-(tetrahydro--.

CERTIFICATE OF CORRECTION (continued)
U.S. Pat. No. 9,018,384 B2

Specification

In column 68 at line 58, Change "Netrahydro" to --N-(tetrahydro--.

In column 69 at line 43, Change "bi-" to --bis- --.

In column 71 at line 18, Change "bi-" to --bis- --.

In column 72 at line 51, Change "(+/+4-[4" to --(+/-)-4-[4--.

In column 72 at line 53, Change "butanamid" to --butanamide--.

In column 72 at line 65, Change "(+/+4-[4" to --(+/-)-4-[4--.

In column 72 at line 67, Change "Step B" to --Step B.--.

In column 73 at lines 44-45, Change "Netrahydro" to --N-(tetrahydro--.

In column 73 at line 63, Change "Netrahydro" to --N-(tetrahydro--.

In column 78 at line 11, Change "(M+H) 1H" to --(M+H). $^1$H--.

In column 80 at line 41, Change "bi-" to --bis- --.

In column 82 at line 49, Change "propylmagesiumchloride" to --propylmagnesiumchloride--.

In column 83 at lines 53-54, Change "touluenesulfonate)" to --toluenesulfonate)--.

In column 85 at line 48, Change "ethyl ethyl" to --ethyl--.

In column 85 at line 50, Change "tetrahyrofuran" to --tetrahydrofuran--.

In column 86 at line 1, Change "1, (3" to --1,(3--.

In column 86 at line 65, Change "precipate" to --precipice--.

In column 90 at line 65, Change "0-" to --O- --.

In column 93 at line 5, Change "Pyrinium" to --Pyridium--.

In column 94 at line 26, Change "mmoll)," to --mmol),--.

In column 94 at line 46, Change "Ethyl(2R)" to --Ethyl (2R)--.

In column 94 at line 53, Change "(m, OH)" to --(m, 0H)--.

In column 97 at line 26, Change "heptane:1EtOAc" to --heptane:1 EtOAc--.

In column 100 at line 7, Change "ES- 500.1." to --ES-500.1.--.

In column 100 at lines 61-62, Change "dimethylhydanthoin)" to --dimethylhydantoin)--.

In column 101 at line 59, Change "ES- 611.8" to --ES-611.8--.

In column 102 at line 51, Change "phenyl)piperidin" to --phenyl)-piperdin--.

In column 103 at line 43, Change "dppm," to --δ ppm,--.

In column 103 at line 50, Change "{4[(1E)" to --{4-[(1E)--.

In column 105 at line 49, Change "Netrahydro" to --N-(tetrahydro--.

In column 106 at lines 29-30, Change "Netrahydro" to --N-(tetrahydro--.

In column 106 at line 49, Change "Netrahydro" to --N-(tetrahydro--.

In column 106 at line 59, Change "Netrahydro" to --N-(tetrahydro--.

In column 108 at line 52, Change "(M+1) $^1$H" to --(M+1). $^1$H--.

Specification

In column 109 at line 15, Change "(M+1) $^1$H" to --(M+1). $^1$H--.

In column 109 at line 64, Change "(M+1) $^1$H" to --(M+1). $^1$H--.

In columns 111-112 (NMR, Example number E68-A, Table 3) at line 2, Change "d ppm" to --δ ppm--.

In columns 111-112 (Example number E68-B, Table 3) at line 3, Change "yl]" to --yl]- --.

In columns 111-112 (NMR, Example number E68-B, Table 3) at line 1, Change "d ppm" to --δ ppm--.

In columns 111-112 (NMR, Example number E68-B, Table 3) at line 6, Change "d1" to --d,--.

In columns 111-112 (NMR, Example number E68-C, Table 3) at line 1, Change "d ppm" to --δ ppm--.

In columns 111-112 (NMR, Example number E68-D, Table 3) at lines 1-2, Change "d ppm" to --δ ppm--.

In columns 111-112 (NMR, Example number E68-E, Table 3) at line 1, Change "d ppm" to --δ ppm--.

In columns 111-112 (NMR, Example E68-F, Table 3) at lines 1-2, Change "d ppm" to --δ ppm--.

In columns 111-112 (NMR, Example number E68-F, Table 3) at line 7, Change "7.79 )d," to --7.79) d,--.

In columns 111-112 (Example number E68-G, Table 3) at line 7, Change "yl]ibutanamide" to --yl]butanamide--.

In columns 111-112 (NMR, Example number E68-G, Table 3) at line 1, Change "d ppm" to --δ ppm--.

In columns 113-114 (NMR, Example number E68-H, Table 3) at line 1, Change "d ppm" to --δ ppm--.

In columns 113-114 (NMR, Example number E68-I, Table 3) at line 1, Change "d ppm" to --δ ppm--.

In columns 113-114 (NMR, Example number E68-J, Table 3) at lines 1-2, Change "d ppm" to --δ ppm--.

In columns 113-114 (NMR, Example number E68-K, Table 3) at line 1, Change "d4)" to --d$_4$)--.

In columns 113-114 (NMR, Example number E68-K, Table 3) at line 2, Change "d ppm" to --δ ppm--.

In columns 113-114 (NMR, Example number E68-L, Table 3) at line 2, Change "d ppm" to --δ ppm--.

Specification

In columns 113-114 (NMR, Example number E68-M, Table 3) at line 2, Change "d ppm" to --δ ppm--.

In columns 113-114 (NMR, Example number E68-N, Table 3) at lines 1-2, Change "d ppm" to --δ ppm--.

In columns 113-114 (Example number E68-O, Table 3) at line 4, Change "y1)" to --yl)--.

In columns 113-114 (Example number E68-O, Table 3) at line 5, Change "yl" to --yl]--.

In columns 113-114 (NMR, Example number E68-P, Table 3) at lines 1-2, Change "d ppm" to --δ ppm--.

In columns 113-114 (NMR, Example number E68-Q, Table 3) at line 1, Change "d ppm" to --δ ppm--.

In columns 115-116 (Example number E68-R, Table 3) at line 4, Change "y1]-" to --yl]- --.

In columns 115-116 (NMR, Example number E68-R, Table 3) at line 2, Change "d ppm" to --δ ppm--.

In columns 115-116 (Example number E68-S, Table 3) at line 2, Change "d ppm" to --δ ppm--.

In columns 115-116 (Example number E68-T, Table 3) at line 6, Change "yl]ibutanamide" to --yl]butanamide--.

In columns 115-116 (NMR, Example number E68-T, Table 3) at line 2, Change "d ppm" to --δ ppm--.

In columns 115-116 (NMR, Example number E68-U, Table 3) at line 1, Change "d ppm" to --δ ppm--.

In column 115 at line 49, Change "et al" to --et al.--.

In column 116 at line 52, Change "baumanii" to --baumannii--.

In columns 117-118 (Example 5, Table 4) at line 2, Change "hydroxycyclobutyl) phenyl]" to --hydroxycyclobutyl)phenyl]--.

In columns 117-118 (Example 10-B, Table 4) at line 2, Change "methylcyclobutyl) methoxy]" to --methylcyclobutyl)methoxy]--.

Claims

In column 167 at line 57, In Claim 1, change "6" to --6;--.